(12) United States Patent
Vicker et al.

(10) Patent No.: US 8,003,783 B2
(45) Date of Patent: Aug. 23, 2011

(54) 17B-HYDROXYSTEROID DEHYDROGENASE INHIBITORS

(75) Inventors: Nigel Vicker, Slough (GB); Harshani Rithma Ruchiranani Lawrence, Slough (GB); Gillian Margaret Allan, Slough (GB); Christian Bubert, Slough (GB); Delphine Sophie Marion Fischer, Slough (GB); Atul Purohit, Slough (GB); Michael John Reed, Slough (GB); Barry Victor Lloyd Potter, Slough (GB)

(73) Assignee: Sterix Limited, Slough, Berkshire (GB)

( * ) Notice: Subject to any disclaimer, the term of this patent is extended or adjusted under 35 U.S.C. 154(b) by 1622 days.

(21) Appl. No.: 11/234,868

(22) Filed: Sep. 23, 2005

(65) Prior Publication Data
US 2006/0074060 A1    Apr. 6, 2006

Related U.S. Application Data

(63) Continuation-in-part of application No. PCT/GB2004/001234, filed on Mar. 22, 2004.

(51) Int. Cl.
*A61K 31/58* (2006.01)
*C07J 71/00* (2006.01)

(52) U.S. Cl. .......................... 540/49; 514/176

(58) Field of Classification Search ............. 540/49; 514/176
See application file for complete search history.

(56) References Cited

U.S. PATENT DOCUMENTS
3,047,568 A   7/1962   Kissman et al.
(Continued)

FOREIGN PATENT DOCUMENTS
DE   1 176 131   7/1961
(Continued)

OTHER PUBLICATIONS

Martin R. Tremblay, et al "Overview of a Rational Approach to Design Type I 17 β-Hydroxysteroid Dehydrogenase Inhibitors Without Estrogenic Activity: Chemical Synthesis and Biological Evaluation" 66(4) J. Steroid Biochem (1998): 179-191.

(Continued)

*Primary Examiner* — Barbara P. Badio
*Assistant Examiner* — Sara E Townsley
(74) *Attorney, Agent, or Firm* — Frommer Lawrence & Haug LLP; Sandra Kuzmich; Russell A. Garman

(57) ABSTRACT

There is provided a compound of Formula (III)

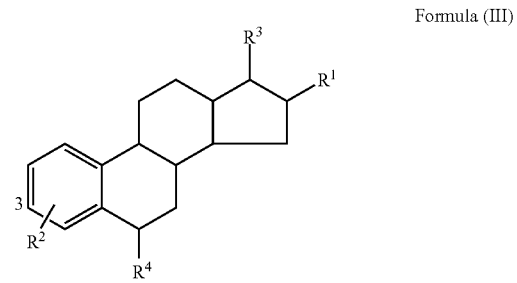

Formula (III)

wherein
$R^1$ is a selected from an alkyloxyalkyl group, a nitrile group, alkylaryl group, alkenylaryl group, alkylheteroaryl group, alkenylheteroaryl group, =N—O—alkyl or =N—O—H group, branched alkenyl, alkyl-alcohol group, amide or alkylamide or —CHO so that $R_1$ together with $R_3$ provide the enol tautomer or $R_1$ together with $R^3$ form a pyrazole, wherein (a) $R^4$ is =N—O-alkyl or =N—O—H group, (b) the pyrazole is substituted with one of alkyl-OH group, alkyl ester group, alkyloxyalkyl group, branched alkyl group, and an amide and/or (c) the 2-position is substituted with a group selected from —OH and —O-hydrocarbyl or a heteroaryl ring;
$R^2$ is selected from —OH and a sulphamate group; and
$R^3$ is selected from —OH or =O; wherein the ring system may be further substituted with one or more hydroxyl, alkyl, alkoxy, alkinyl or halo substituents.

19 Claims, 1 Drawing Sheet

U.S. PATENT DOCUMENTS

| | | | |
|---|---|---|---|
| 3,163,641 A | | 12/1964 | Christiansen et al. |
| 3,398,140 A | | 8/1968 | Clinton |
| 5,585,405 A | * | 12/1996 | Labrie et al. .................. 514/733 |
| 5,880,115 A | | 3/1999 | Li et al. |
| 6,046,186 A | | 4/2000 | Tanabe et al. |

FOREIGN PATENT DOCUMENTS

| | | |
|---|---|---|
| GB | 1033520 | 6/1966 |
| GB | 1096732 | 12/1967 |
| GB | 2331987 | 6/1999 |
| WO | WO 02/16392 | 2/2002 |
| WO | 02/32409 | 4/2002 |
| WO | WO 02/058634 | 8/2002 |

OTHER PUBLICATIONS

Maninder Minu, et al. "Synthesis and Biological Activity of 16-arylidene derivatives of Estrone and Estrone Methyl Ether" 42 (1) Indian Journal of Chemistry Section B (2003): 166-172.
Donald Poirier, et al. "A Multidetachable Sulfamate Linker Successfully Used in a Solid-Phase Strategy to Generate Libraries of Sulfamate and Phenol Derivatives" 12 Bioorganic & Medicinal Chemistry Letters (2002) 2833-2838.
Tremblay et al., "Synthesis of 16-(Bromoalkyl)-Estradiols having Inhibitory Effect on Human Placental Estradiol 17β-Hydroxysteroid Dehydrogenase (17β-HSD Type 1)", Bioorganic and Medicinal Chemistry, vol. 3, No. 5, pp. 505-523 (1995).
Liviu Constantin Ciobanu et al., "Nonsteroidal compounds designed to mimic potent steroid sulfatase inhibitors", Journal of Steroid Biochemistry & Molecular Biology, vol. 80, pp. 339-353, (2002).
Adamski, et al., Molecular cloning of a novel widely expressed human 80 kDa 17β-hydroxysteroid dehydrogenase IV, Biochem. J., 1995, vol. 311, p. 437-443.
Agnusdei D., et la. B. Ann. Endocrinol, 1999, vol. 60, No. 3, p. 242-246.
Appel et al., Uber das hydrazidosulpfamid, Chem. Ber., 1958, vol. 91, p. 1339-1341.
Breton, et al., The structure of a complex of human 17 β-hydroxysteroid dehydrogenase with oestradiol and NADP8 identifies two principal targets for the design of inhibitors, Structure (Lond.), 1996, vol. 4, p. 905-915.
Castiglione-Gertsch J. New aromatase inhibitors: more selectivity, less toxicity, unfortunately, the same activity, Eur. J. Cancer, 1996, vol. 32A, p. 393-395.
Claussner A. et al., J. Steroid. Biochem, 1992, vol. 41, p. 609-614.
Coldham et al., A possible mechanism for increased breast cell proliferation by progestins through increased reductive 17 β-hydroxysteroid dehydrogenase activity, Int. J. Cancer, 1990, vol. 45, p. 174-178.
Collins et al., The estrogenic and anti-oestrogenic activities of phytochemicals with the human estrogen receptor expressed in yeast, Steroids, 1997, vol. 62, p. 365-372.
Coulson C.J., Steroid biosynthesis and action, $2^{nd}$ edition, Molecular Mechanism of Drug Action, 1994, p. 95-122.
Deyashiki, et al., Molecular cloning and characterization of mouse oestradiol 17 β-dehydrogenase (A-specific), a member of the aldoketoreductase family, J. Biol. chem., 1995, vol. 270, p. 10461-10467.
Duncan, et al. Inhibition of oestrone sulphatase activity by estrone-3-methyl-thiophosphonate: a potential therapeutic agent in breast cancer, Cancer Res., 1993, vol. 53, p. 298-303.
Early Breast Cancer Trialists' Collaborative Group. Effects of adjuvant Tamoxifen and of cytotoxic therapy on mortality in early breast cancer, N. Eng. J. Med., 1988, vol. 319, p. 1681-1692.
Geissler et al., Male pseudohermaphroditism caused by mutation of testicular 17 β-hydroxysteroid dehydrogenase 3, Nat. Genet., 1994, vol. 7, p. 34-39.
Ghosh, et al., Structure of the human estrogenic 17 beta-hydroxysteroid dehydrogenase at 2.20A resolution, Structure, 1995, vol. 3, p. 503-513.
Gorski J., et al., Current models of steroid hormone action; a critique, Ann. Rev. Physiol., 1976, vol. 36, p. 425-450.
Gorski J., et al., Hormones receptors: studies on the interaction of estrogens with uterus, Recent Prog. Horm., Res., 1968, vol. 24, p. 45-80.
Gupta, et al., Synthesis and biological activity of some D-ring modified oestrone derivative, Ind. J. Chem. 1999, vol. 38B, p. 563-571.
Heer, et al., Uber Steroide, Marrianol-und Doisynoisaure, Uber oestrogene carbonsauren II. Heiv. Chim. Acta. 1945, vol. 28, p. 156-165.
Horiuchi, et al., Regioselective 2-Iodination of Estradiol, Estriol & Oestrone, J. Chem. Soc. Chem. Commun., 1982, p. 671-672.
Holli K., et al. Lumpectomy with or without postoperative radiotherapy for breast cancer with favourable prognostic features: results of a randomized study, Br. J. Cancer, 2001, vol. 84, No. 2, p. 164-169.
Horwitz K. B., et al., Nuclear mechanism of estrogen action: effects of oestradiol and anti-estrogens on estrogens receptors and nuclear receptor processing, J. Biol., Chem., 1978, vol. 253, p. 8185-8192.
Horwitz K.B. et al. Oestrogen control of progesterone receptor in human breast cancer; role of oestradiol and antiestrogen, Endocrinology, 1978, vol. 103, p. 1742-1751.
Jin J.-Z. et al., Human estrogenic 17 β-hydroxysteroid dehydrogenase : predominance of oestrone reduction and its induction by NADPH, Biochem, Biophys. Res., 1999, 259, p. 489-493.
Jordan V.C., The Strategic use of antiestrogens to control the development and growth of breast cancer, Cancer, 1992, vol. 70, p. 977-982.
Kaae S., et al., Does simple mastectomy followed by irradiation offer the survival comparable to radical procedures:, International Journal of Radiation Oncology, Biology, Physics, 1977, vol. 2, p. 1163-1166.
Labrie F, At the cutting edge, Intracrinology, Mol. Cell. Endocrinolo., 1991, 78, C113-118.
Lebail et al., Aromatase and 17β-hydroxysteroid dehydrogenase inhibition by flavinoids, Cancer Lett., 1998, vol. 133, p. 101-106.
Li P.-K. et al., Development of potent non-estrogenic oestrone sulphatase inhibitors, Steroids, 1998, 63, p. 425-432.
Lin et al., 3D structure of human estrogenic 17 β-HSD: binding with various steroids, J. Steroid. Biochem. Mol. Biol., 1999, vol. 69, p. 425-429.
Loev et al., Alkylphenols related to the poison ivy principle, An improved method of synthesis involving the Na-Butanol cleavage of benzyl ethers, J. Am. Chem. Soc., 1956, vol. 78 p. 6095-6101.
Makela, et al., Inhibition of 17 beta-hydroxysteroid oxidoreductase by flavonids in breast and prostate cancer cells, Proc. Soc. Exp, Biol. Med. 1998, vol. 217, p. 310-316.
Malini B., et al., Inhibition of steroid sulphatase activity by tricyclic coumarin sulfamates, J. Steroid Biochem. Molecular Biol., 2000, vol. 75, p. 253-258.
Matkovics, et al., Rearrangement of steroids, VII, Schmidt reaction and Beckmann rearrangement of oestrone and its derivatives, Acta Chim. Acad. Scien. Hung., 1974, vol. 80, p. 79-87.
Miller B.A., et al. (eds), Racial/Ethnic patterns of Cancer in the United States, 1988-1992, National Cancer Institute, 1996.
Miller W.R., Aromatase Inhibitors—where are we now?, Br. J. Cancer, 1996, vol. 73, p. 415-417.
Nicholls P.J., Breast Cancer Management: Science and Care Together, Pharm. J. 1997, vol. 259, p. 459-470.
Numazawa, et al., J. Chem. Soc. Chem. Commun., 1983, vol. 9 p. 533.
Okada et al., Efficient general method for sulfamoylation of a hydroxyl group, Tet. Lett., 2000, vol. 41, p. 7047-7051.
Peltoketo H., et al., Complete amino acid sequence of human placental 17β-hydroxysteroid dehydrogenase deduced from cDNA, FEBS Lett., 1988, vol. 239, No. 1, p. 73-77.
Peltoketo H., et al., 17β-hydroxysteroid dehydrogenase (HSD)/17-ketosteroid reductase (KSR) family, nomenclature and main characteristics of the 17 HSD/KSR enzymes, J. Mol. Endocrinol. 1999, vol. 23, No. 1, p. 1-11.
Penning T.M., Molecular endocrinology of hydroxysteroid dehydrogenases, Endocrine Reviews, 1997, vol. 18, p. 281-305.
Poulin R., et al., Stimulation of cell proliferation and estrogenic response by adrenal $C_{19}$ -?$^5$-steroids in the ZR-75-1 Human Breast Cancer Cell Line, Cancer Res., 1986, vol. 46, p. 4922-4937.
Powles T.J., Breast Cancer Res., 2000, vol. 2, p. 10-12.

Puranen et al., Origin of substrate specificity of human and rat 17β-hydroxysteroid dehydrogenase Type 1, using chimeric enzymes and site-directed substitutions, Endocrinology, 1997, vol. 139, p. 3532-3539.

Purohit A., et al., In vivo activity of 4-methylcoumarin-7-O-sulfamate, a non steroidal non estrogenic steroid sulphatase inhibitor, Cancer Res. 1996, vol. 56, p. 4950-4955.

Purohit A., et al., In vivo inhibition of estrone sulfatase activity and grow of nitrosomethylurea-induce mammary tumours by 667 COUMATE, Cancer Res. 2000, 60, p. 3394-3396.

Purohit A., et al., Inactivation of steroid sulfatase by an active site-directed inhibitor, estrone-3-O-sulfamate, Biochem, 1995, vol. 34, p. 11508-11514.

Purohit A., et al., Non-steroidal and steroidal sulfamates, new drugs for cancer therapy, Mol. Cell. Endocrinol, 2001, vol. 171, p. 129-135.

Purohit A., et al., In vivo inhibition of oestrone sulphatase and dehydroepiandrosterone sulphatase by estrone-3-O-sulfamate, Int. J. Cancer, 1995, vol. 63, p. 106-111.

Purohit A., et al., The effect of 2-methoxyestrone-3-O-sulphamate on the growth of breast cancer cells and induced mammary tumours, Int. J. Cancer, 2000, vol. 85, p. 584-589.

Regan, et al. 17- and 17-Aza-D-homosteroids, J. Am. Chem. Soc., 1956, vol. 78, p. 639-543.

Santner S.J. et al., In situ estrogen production via the oestrone sulphatase pathway in breast tumour relative importance vs the aromatase pathway, J. Clin. Endocrin. Metab., 1984, vol. 59, p. 29-33.

Saunders C.M. et at. Management of early breast cancer, Oncol. In Pract., 1994, vol. 3, p. 4-8.

Sexton M.J., et al., Selective estrogen receptor modulators: the ideal estrogen replacement: Prim. Care Update Ob/Gyns 2001, vol. 8, No. 1, p. 25-30.

Smith J.H., et al. Inhibitors of steroidogenesis as agents for the treatment of hormone-dependent breast cancer, Exp. Opin. Ther. Patents, 2001, vol. 11, p. 789-824.

Wakeling A.E., et al., Steroid pure antiestrogens, J. Endocrinol., 1987, vol. 112, R-7-R10.

Williams et al., X-ray crystal structure and mechanism of action of oestrone 2-O sulphamate, a synthetic active site-directed inhibitor of oestrone sulphatase by different mechanism, J. Steroid Biochem. Mol. Biol,, 1996, vol. 57, p. 79-88.

Woo et al., Heteroatom-substituted analogues of the active-site directed inhibitor estra-1,3,5, (10)-trien-17-one-3-sulphamate inhibit oestrone sulphatase by different mechanism, J. Steroid Biochem. Mol. Biol., 1996, vol. 57, p. 79-88.

Woo L.W.L, et al. Potent active site-directed inhibition of steroid sulphatase by tricyclic coumarin-based sulfamates, Chemistry & Biology, 2000, vol. 7, p. 773-791.

Woo L.W.L. et al., Steroidal and nonsteroidal sulfamates as potent inhibitors of steroid sulfamates as potent inhibitors of steroid sulphatase J. Med. Chem., 1998, vol. 41, p. 1068-1083.

Wu et al., Expression cloning and characterization of human 17 β-hydroxysteroid dehydrogenase type 2, a microsomal enzyme possessing 20α-hydroxysteroid dehydrogenase activity, J. Biol. Chem., 1993, vol. 268, p. 12964-12969.

* cited by examiner

17B-HYDROXYSTEROID DEHYDROGENASE INHIBITORS

REFERENCE TO RELATED APPLICATIONS

This application is a continuation-in-part of International Patent Application PCT/GB04/01234 filed Mar. 22, 2004 and published as WO 2004/085457 on Oct. 7, 2004 which claims priority to Great Britain Application Number 0306718.8 filed Mar. 24, 2003. Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of " have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. Patent law; namely, that these terms are closed ended.

FIELD OF INVENTION

The present invention relates to a compound. In particular the present invention provides compounds capable of inhibiting 17β-hydroxysteroid dehydrogenase (17β-HSD).

BACKGROUND TO THE INVENTION

Breast cancer is a devastating disease which remains to be a major cause of death for women in most Western countries. It is estimated to affect approximately 1 million women per year across the globe.[1]

Britain has one of the highest mortality rate for breast cancer in the world with over 35,000 women diagnosed each year accounting for nearly one in five of all cancer cases. It is estimated that 1 in 10 women living to the age of 85 in Britain will develop breast cancer during the course of her life. Although modern methods of treatment as well as an earlier detection of the disease have greatly improved survival rates, breast cancer remains the leading cause of death for women aged between 35-54.[2]

All women are at risk of breast cancer although a number of risk factors have been identified, most of them being related to women's hormonal and reproductive history as well as their family background of the disease. Women at higher risk are generally those with a strong family history of the disease, early onset of menarche, late onset of menopause or a first full-term pregnancy after the age of 30.[2]

In the earliest stages of a breast cancer, surgery appears to be the treatment of choice. In most of the cases, breast conserving surgical techniques, such as local incision of lump(s) in the breast(s), are involved rather than mastectomy. To prevent any recurrence of the disease, radiotherapy is often prescribed, particularly if breast conserving techniques have been involved.[3] It is also used to reduce large tumours to an operable size so that conservational surgery can be carried out.[4]

For advanced breast cancers, when the tumour has spread or recurred, the aim in the treatment is no longer to cure but to reach a palliative control. This is the case when metastases of the tumour have reached locations such as bones, skin, lymph, node or brain. The treatment varies depending on the hormonal status of the patient (whether it is a pre- or post-menopausal woman to be treated) and depending on the type of tumour. Certain tumours have indeed been proven to rely on estrogens for their growth and development, leading to what is called a Hormone Dependent Breast Cancer (HDBC, see I-9). While non HDBC are treated with chemotherapy, where the aim is to kill differentially tumour cells using a combination of cytotoxic agents,[5] HDBC are expected to respond to endocrine therapy.

The concept of hormone dependent tumours appeared in the early 1960s, when the model of estrogens action was first introduced.[6] In order for estrogens to regulate cell growth and function in humans, a specific protein, called the human Oestrogen Receptor (hER), must be present.[7] This protein, localised in the nucleus, interacts with estrogens resulting in the formation of a binding complex. This acts as a transcription factor by activating production of m-RNA from specific genes, one or more of which are probably essential for efficient tumour cell growth.

Patients with a measurable level of receptor protein are classified as oestrogen-receptor-positive (ER+) with opposition to oestrogen-receptor-negative (ER−). About 50% of pre-menopausal women and 75% of post-menopausal women fall into the ER+ group[8] where the development of breast cancers can be directly linked to the presence of estrogens. Endocrine therapy, where the use of drugs results in a deprivation of estrogenic stimulation to cells, has proven to be an effective approach to the treatment of HDBC. Originally, two classes of drugs, responding to different strategies, were developed: anti-oestrogens and aromatase inhibitors.

Anti-oestrogens, as antagonists of the oestrogen receptor, have been one of the first treatment considered for HDBC. Their action rely on their ability to bind competitively to the specific receptor protein hER, thus preventing access of endogenous estrogens to their specific binding site. Consequently, the natural hormone is unable to maintain tumour growth.

Of the anti-oestrogens commonly used in breast cancer therapy, tamoxifen (below) is the most widely used because of the very low toxicity profile of the molecule. Despite its non-steroidal skeleton, tamoxifen possesses a mixed agonist-antagonist activity that limits its therapeutic potential.[9] In addition, some form of drug resistance has been reported in patients after long-term tamoxifen treatment.[10]

Novel pure anti-oestrogenic drugs, such as ICI 164384 (below), have since been discovered but the loss of potency compared with that of tamoxifen suggested the need to design more highly potent targets.[11]

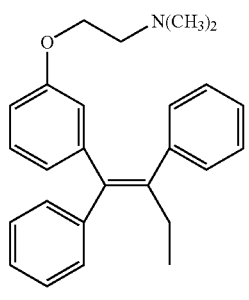
Tamoxifen

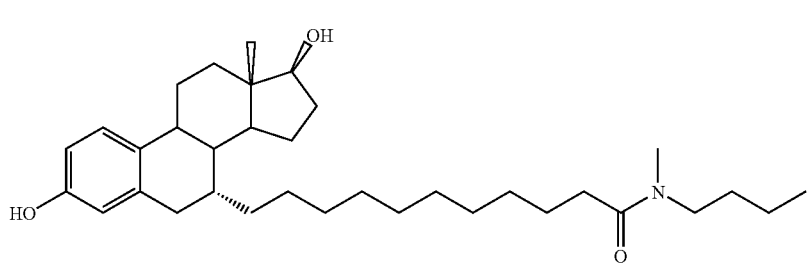
ICI 164384

For some years now, a new type of anti-oestrogen has emerged, combining oestrogen agonism on target tissues such as bone or liver and antagonism and/or minimal agonism in reproductive tissues such as breasts or uterus.[12] These compounds, designed as Selective Oestrogen Receptor Modulators (SERMs), are not only potentially effective in reducing a patient's risk of breast carcinoma but they have also been shown to increase bone mineral density and prevent osteoporosis in post-menopausal women. Raloxifen is the first of this class of compounds to be used clinically.[13] More SERMs are currently in clinical trials and these molecules might one day replace tamoxifen as the first line treatment for women with HDBC.

The use of therapeutic agents that inhibit one or several enzyme of the steroid biosynthesis pathway represents another important strategy to control of the development of oestrogen-dependent tumours.[14] The enzyme aromatase, which converts androgenic C19 steroids to estrogenic C18 steroids, has been the prime target for reducing oestrogen levels. This enzyme complex, which contains a cytochrome P450 haemoprotein, catalyses the aromatisation of the androgen A-ring with the subsequent loss of the C19 methyl group to yield estrogens.

Aminoglutethimide (below) was the first aromatase inhibitor used for the treatment of breast cancer. It however showed a number of undesirable side effects given its wide spectrum of inhibitory effects on other P450-dependant enzymes, and attempts to improve on the original structure have led to a number of non-steroidal compounds entering clinical trials.[15] The last generation developed compounds such as letrozole, which combine high potency and high selectivity for the enzyme, and are also better tolerated.

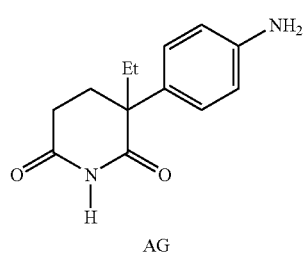
AG

-continued

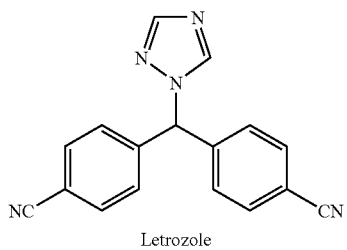
Letrozole

Structure of different types of aromatase inhibitors. Generation I: aminoglutethimide, AG; generation III, letrozole.

Traditionally, aromatase inhibitors are reserved as second line treatment for advanced HDBC patients whose diseases are no longer controlled by tamoxifen. However, because of the extreme good toxicity profile of some of the latest aromatase inhibitors, recent clinical trials have been conducted to assess their suitability as first line treatment for HDBC.

Strong evidence has emerged over the past decade, both biochemically and clinically, that the sole inhibition of the enzyme aromatase cannot afford an effective reduction of estrogenic stimulation to HDBC, the reason being that other pathways are involved in oestrogen biosynthesis. The sulphatase pathway is now considered to be the major route for breast tumour oestrogen synthesis since sulphatase activity was found to provide 10 fold more oestrone than the aromatase activity.[16]

In the sulphatase pathway, estrogens are synthesised from the highly available precursor oestrone-sulphate, via two enzymes (scheme below): oestrone sulphatase (STS) which hydrolyses oestrone-sulphate into oestrone, and 17β-hydroxysteroid dehydrogenase (17β-HSD) which reduces oestrone into oestradiol. These two enzymes represent the latest targets for oestrogen deprivation strategies.

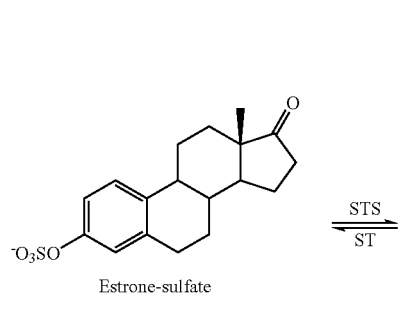
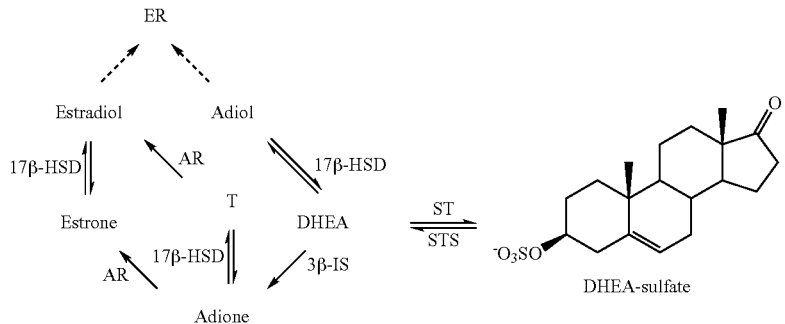

Origin of estrogens in normal and tumoral breast cells. AR, aromatase; ST: steroid sulfotransferase; STS, steroid sulphatase; 17β-HSD, 17β-hydroxysteroid dehydrogenase; 3β-IS, 3β-hydroxysteroid dehydrogenase $\Delta^5,\Delta^4$-isomerase; ER, oestrogen receptor.

Several potent inhibitors have been identified for oestrone sulphatase. They all share the common structural feature of an aromatic ring bearing a substituent that mimics the phenolic A-ring of the enzyme substrate, oestrone-sulphate. On the development of steroidal inhibitors, a wide variety of chemical groups have been introduced at C3, of which the 3-O-sulfamate was found to be the most potent for the oestrone molecule. The resulting compound, estrone-3-O-sulfamate (below) led to the identification of the aryl-O-sulphamate structure as an active pharmacophore required for potent inhibition of STS. EMATE was shown to inhibit steroid sulphatase activity in a time- and concentration-dependent manner[17] and was active in vivo on oral administration.[18] It was however revealed to be highly estrogenic which raised the need to design STS inhibitors devoid of agonist activity on hER.

To avoid the problems linked to an active steroid nucleus, non steroid-based inhibitors have been synthesised. Coumarin sulphamate such as 4-methylcoumarin-7-O-sulfamate (COUMATE, below), where the active pharmacophore is conserved, have been among the first inhibitors of that type to be identified.[19] Although COUMATE is less potent than EMATE, it has the advantage of being non estrogenic.[20] Some tricyclic coumarin-based sulphamates have also been developed and turned out to be much more potent than COUMATE, while retaining its non estrogenic characteristic.[21] 667COUMATE, which is some 3 times more potent than EMATE in vitro is now in pre-clinical development for clinical trials.[22]

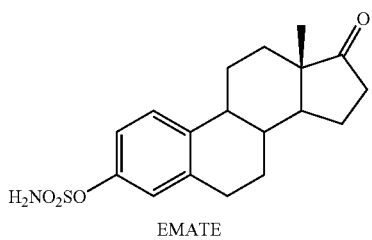

EMATE

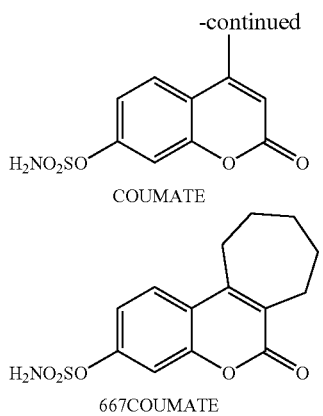

Structures of the steroid sulphatase inhibitors EMATE, COUMATE and 667COUMATE.

PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3-sulphamate and, preferably, oestrone-3-sulphamate (EMATE). It is known that EMATE is a potent E1-STS inhibitor as it displays more than 99% inhibition of E1-STS activity in intact MCF-7 cells at 0.1 mM. EMATE also inhibits the E1-STS enzyme in a time- and concentration-dependent manner, indicating that it acts as an active site-directed inactivator. Although EMATE was originally designed for the inhibition of E1-STS, it also inhibits dehydroepiandrosterone sulphatase (DHA-STS), which is an enzyme that is believed to have a pivotal role in regulating the biosynthesis of the oestrogenic steroid androstenediol. Also, there is now evidence to suggest that androstenediol may be of even greater importance as a promoter of breast tumour growth. EMATE is also active in vivo as almost complete inhibition of rat liver E1-STS (99%) and DHA-STS (99%) activities resulted when it is administered either orally or subcutaneously. In addition, EMATE has been shown to have a memory enhancing effect in rats. Studies in mice have suggested an association between DHA-STS activity and the regulation of part of the immune response. It is thought that this may also occur in humans. The bridging O-atom of the sulphamate moiety in EMATE is important for inhibitory activity. Thus, when the 3-O-atom is replaced by other heteroatoms as in oestrone-3-N-sulphamate and oestrone-3-S-sulphamate, these analogues are weaker non-time-dependent inactivators.

Although optimal potency for inhibition of E1-STS may have been attained in EMATE, it is possible that oestrone may be released during sulphatase inhibition and that EMATE and its oestradiol congener may possess oestrogenic activity.

17β-HSD, which catalyses the final step in estrogens and androgens biosynthesis, also appeared as a target for oestrogen deprivation strategies. This enzyme is responsible for the interconversion of the oxidised form (less active) and the reduced form (more active) of steroids. Its activity directly supports the growth and development of oestrogen dependent tumours since it preferably reduces oestrone into estradiol[25] and in a minor extend, via the conversion of the androgen DHEA into androstenediol (Adiol), which has recently been proven to have estrogenic properties and to be able to bind to the oestrogen receptor.[28]

17β-HSD belongs to a family of isoenzymes, 11 of which have been so far identified and cloned.[27] Each type has a selective substrate affinity and directional activity which means that selectivity of drug action has to be achieved. 17β-HSD type 1 is the isotype that catalyses the interconversion of oestrone and oestradiol.

Unlike STS inhibitors, only few 17β-HSD inhibitors have been reported. Most of the steroidal inhibitors for 17β-HSD type 1 have in common a D-ring modified structure. Oestradiol derivatives which contain a side-chain with a good leaving group at the 16α-position have been shown to be a potent class of inhibitors. In particular, 16α-(bromoalkyl)-estradiol[28] where the side-chains exhibit high reactivity towards nucleophilic amino-acids residues in the active site of the enzyme were found to be promising irreversible inhibitors. Analogues containing short bromoalkyl moieties at position 16 exhibited the highest activity with 16α-(Bromopropyl)-oestradiol, followed by 16α-(Bromobutyl)-oestradiol, the most potent of the series (3 and 4). They, however, turned out to be pure agonists of the oestrogen receptor.

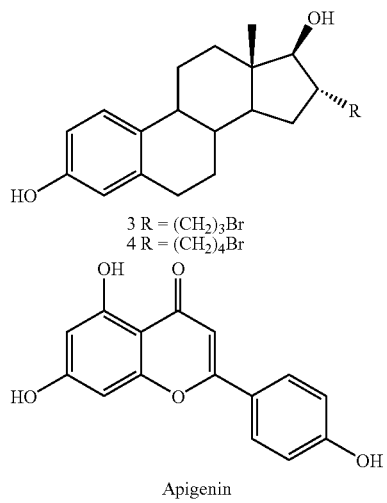

3 R = (CH$_2$)$_3$Br
4 R = (CH$_2$)$_4$Br

Apigenin

17β-HSD type 1 inhibitors: 16α-(bromopropyl)-oestradiol, 3; 16α-(bromopropyl)-oestradiol, 4 and a flavone derivative, apigenin.

In an attempt to eliminate the intrinsic oestrogenicity of potent inhibitors and possibly at the same time engineer anti-oestrogenic properties into the molecule, several 16α-(broadly)-oestradiol derivatives bearing the C7α-alkylamide side chain of the known anti-oestrogen ICI 164384 were synthesised.[21] However, rather poor inhibition of 17β-HSD type 1 was obtained, with estrogenic and anti-oestrogenic properties not completely abolished or introduced respectively.

In parallel, non-steroidal inhibitors of 17β-HSD type 1 have been designed. Flavonoids, which are structurally similar to estrogens, are able to bind to the oestrogen receptor with estrogenic or anti-estrogenic activities.[30] Their action on aromatase activity is well documented and in recent studies, they were found to reduce the conversion of oestrone into oestradiol catalysed by 17β-HSD type 1.[31] Flavone derivatives, such as apigenin emerged from a SAR study as a promising compounds with some inhibitory activity on 17β-HSD type 1 without being estrogenic at the inhibitory concentration.[32]

Ahmed et al (Biochem Biophys Res Commun 1999 Jan. 27;254(3):811-5) report on a structure-activity relationship study of steroidal and nonsteroidal inhibitors of STS.

Steroid dehydrogenases (DH) such as oestradiol 17β-hydroxysteroid dehydrogenases (E2HSD) have pivotal roles in regulating the availability of ligands to interact with the oestrogen receptor. E2HSD Type I reduces oestrone (E1) to the biologically active oestrogen, oestradiol (E2), while E2HSD Type II inactivates E2 by catalysing its oxidation to E1. Thus the identification of compounds having DH inhibitory activity, in particular, inhibitors of E2HSD Type I, could be of therapeutic value. in inhibiting the formation of E2.

SUMMARY ASPECTS OF THE PRESENT INVENTION

The present invention provides novel compounds which are capable of acting as effective 17β-hydroxysteroid dehydrogenase (17β-HSD) inhibitors. The present invention identifies that the compounds of the present application are effective 17β-hydroxysteroid dehydrogenase (17β-HSD) inhibitors.

As can be seen, two enzymes that are involved in the peripheral synthesis of oestrogens are the enzyme Oestradiol 17β-hydroxysteroid dehydrogenase and the enzyme oestrone sulphatase.

In situ synthesis of oestrogen is thought to make an important contribution to the high levels of oestrogens in tumours and therefore specific inhibitors of oestrogen biosynthesis are of potential value for the treatment of endocrine-dependent tumours.

Moreover, even though oestrogen formation in malignant breast and endometrial tissues via the sulphatase pathway makes a major contribution to the high concentration of oestrogens, there are still other enzymatic pathways that contribute to in vivo synthesis of oestrogen.

Thus, there is an urgent need to develop new therapies for the treatment of these cancers.

The present invention therefore seeks to overcome one or more of the problems associated with the prior art methods of treating breast and endometrial cancers.

In one aspect, therefore, the present invention provides a use of a compound for the preparation of a medicament that can or affect, such as substantially inhibit, the steroid dehydrogenase pathway—which pathway converts oestrone to and from oestradiol.

This aspect of the present invention is advantageous because by the administration of one type of compound it is possible to block the synthesis of oestradiol from oestrone. Hence, the present invention provides compounds that have considerable therapeutic advantages, particularly for treating breast and endometrial cancers.

The compounds of the present invention may comprise other substituents. These other substituents may, for example, further increase the activity of the compounds of the present invention and/or increase stability (ex vivo and/or in vivo).

DETAILED ASPECTS OF THE PRESENT INVENTION

Figure 1:
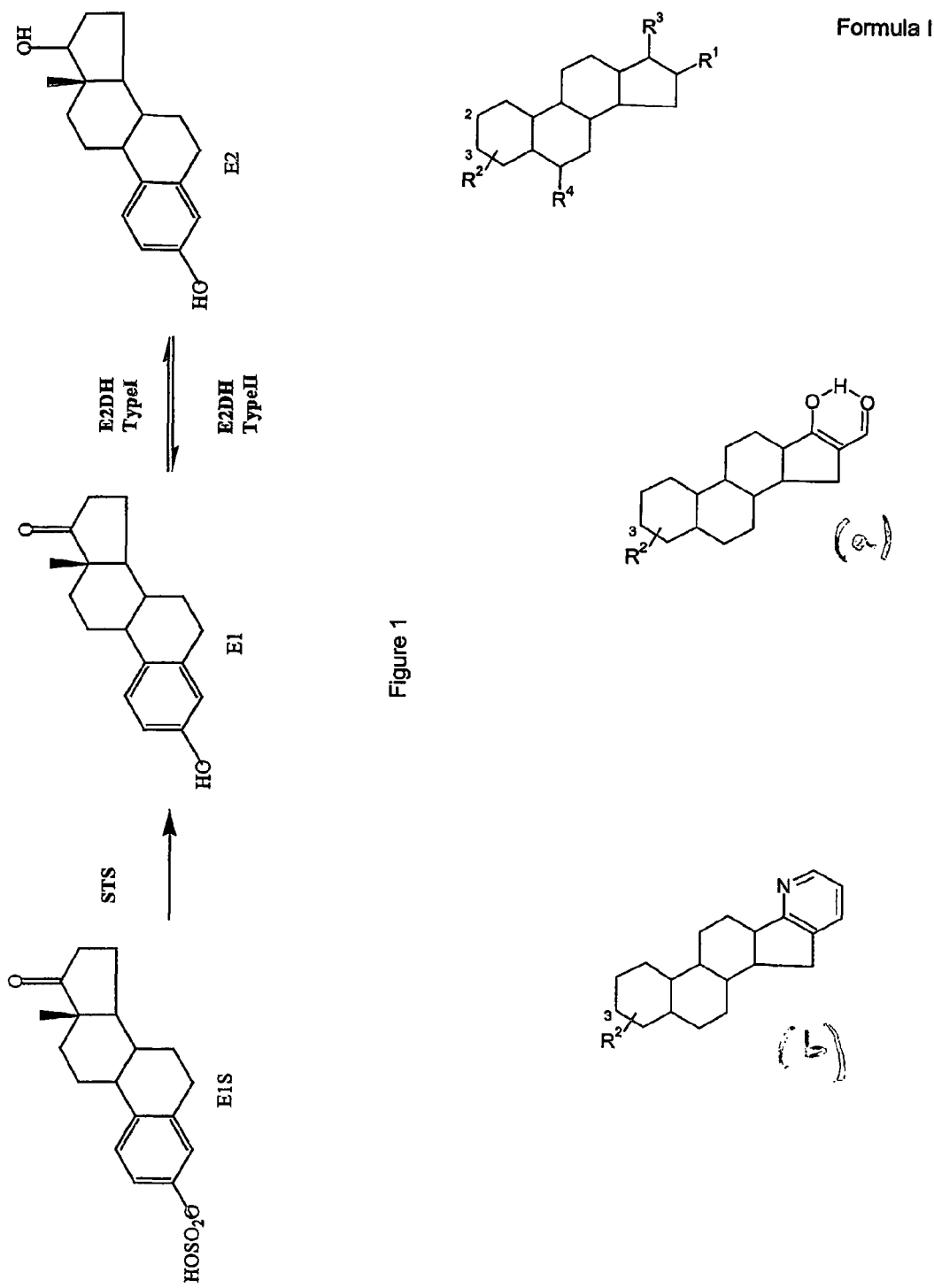
FIG. 1 shows some of the enzymes involved in the in situ synthesis of oestrone from oestrone sulphate, and oestradiol. "STS" denotes Oestrone Sulphatase, "E2DH Type I" denotes Oestradiol 17β-hydroxysteroid dehydrogenase Type I or Oestradiol 17β-hydroxysteroid dehydrogenase Type 1, 3, 5 and/or 7 and "E2DH Type II" denotes Oestradiol 17β-hydroxysteroid dehydrogenase Type II or Oestradiol 17β-hydroxysteroid dehydrogenase Type 2 and/or 8.

According to one aspect of the present invention, there is provided a compound having Formula I

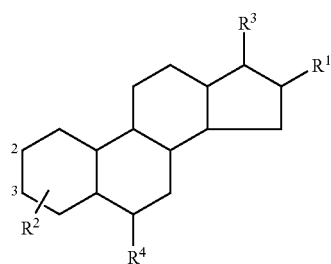

Formula I wherein
(I) $R^1$ is a selected from
  (i) an alkyloxyalkyl group
  (ii) a nitrile group, and wherein $R^2$ is capable of forming a hydrogen bond
  (iii) alkylaryl group, wherein the aryl group is substituted by other than a C1-10 group
  (iv) alkenylaryl group wherein the aryl group is substituted
  (v) alkylheteroaryl group, wherein when heteroaryl group comprises only C and N in the ring, the aryl group is substituted by other than a methyl group
  (vi) alkenylheteroaryl group
  (vii) =N—O-alkyl or =N—O—H group.
  (viii) branched alkenyl
  (ix) alkyl-alcohol group
  (x) amide or alkylamide wherein (a) the alkyl of the alkylamide is —CH$_2$— or —CH$_2$CH$_2$—, (b) the amide is di-substituted and/or (c) the amide is substituted with at least one of alkylheterocycle group, alkenylheterocycle group, alkylheteroaryl group, alkenylheteroaryl group, heteroaryl group, alkylamine group, alkyloxyalkyl group, alkylaryl group, straight or branched alkyl group,
  (xi) —CHO so that $R_1$ together with $R_3$ provide the enol tautomer

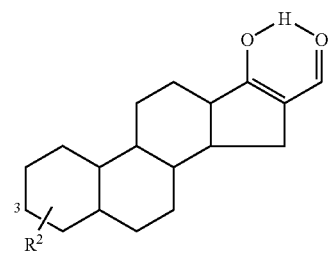

OR $R_1$ together with $R^3$ form
  (xii) a pyrazole wherein (a) $R^4$ is =N—O-alkyl or =N—O—H group, (b) the pyrazole is substituted with one of alkyl-OH group, alkyl ester group, alkyloxyalkyl group, branched alkyl group, and an amide and/or (c) the 2 position is substituted with a group selected from —OH and —O-hydrocarbyl
  (xiii) a heteroaryl ring to provide a compound of the formula

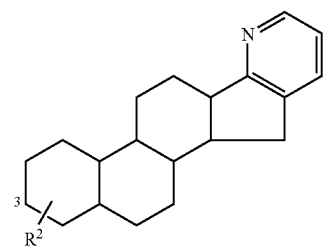

(II) $R^2$ is selected from
  groups capable of forming a hydrogen bond, a sulphamate group, a phosphonate group, a thiophosphonate group, a sulphonate group and a sulphonamide group; and
(III) $R^3$ is selected from
  —OH, =O, or a —C(=O)— mimetic According to one aspect of the present invention, there is provided use of a compound in the manufacture of a medicament for use in the therapy of a condition or disease associated with 17β-hydroxysteroid dehydrogenase (17β-HSD), wherein the compound is of Formula I

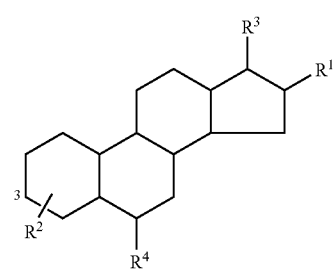

Formula I wherein
(I) $R^1$ is a selected from
  (i) an alkyloxyalkyl group
  (ii) a nitrile group
  (iii) alkylaryl group, wherein the aryl group is substituted by other than a methyl group
  (iv) alkenylaryl group
  (v) alkylheteroaryl group, wherein when heteroaryl group comprises only C and N in the ring, the aryl group is substituted by other than a methyl group (vi) alkenylheteroaryl group
(vii) =N—O-alkyl or =N—O—H group
(viii) carboxylic acid esters wherein (a) R³ is =O and/or (b) the ester is selected from —CO₂X, —CH₂CO₂X, and —CH₂CH₂CO₂X, wherein X is a hydrocarbyl group
(ix) CO₂H or alkyl-CO₂H group, wherein alkyl is CH₂ or CH₂CH₂ group
(x) branched alkenyl
(xi) alkyl-alcohol group or alkenyl-alcohol group
(xii) amide or alkylamide wherein (a) the alkyl of the alkylamide is —CH₂— or —CH₂CH₂—, (b) the amide is di-substituted and/or (c) the amide is substituted with at least one of alkylheterocycle group, alkenylheterocycle group, alkylheteroaryl group, alkenylheteroaryl group, heteroaryl group, alkylamine group, alkyloxyalkyl group, alkylaryl group, straight or branched alkyl group,
(xiv) —CHO so that R₁ together with R₃ provide the enol tautomer

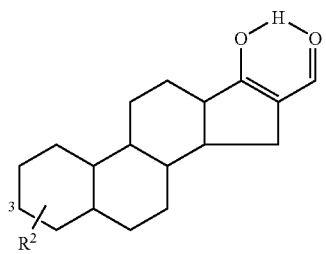

OR R₁ together with R³ form
(xii) a pyrazole wherein (a) R⁴ is =N—O-alkyl or =N—O—H group, (b) the pyrazole is substituted and/or (c) the 2 position is substituted with a group selected from —OH and —O-hydrocarbyl.
(xiii) a heteroaryl ring to provide a compound of the formula

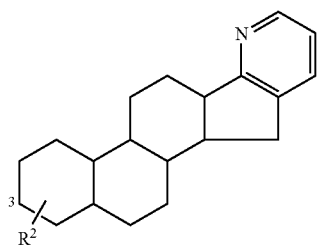

(II) R² is selected from
groups capable of forming a hydrogen bond, a sulphamate group, a phosphonate group, a thiophosphonate group, a sulphonate group and a sulphonamide group; and
(III) R³ is selected from
—OH, =O, or a —C(=O) mimetic According to one aspect of the present invention, there is provided use of a compound in the manufacture of a medicament for use in the therapy of a condition or disease associated with 17β-hydroxysteroid dehydrogenase (17β-HSD), wherein the compound is of Formula I

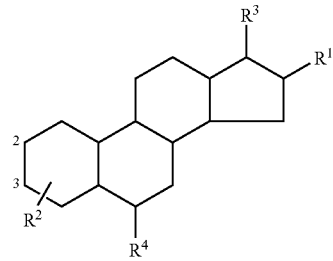

Formula I wherein
(I) R¹ is a selected from
(i) an alkyloxyalkyl group
(ii) a nitrile group, and wherein R² is capable of forming a hydrogen bond
(iii) alkylaryl group, wherein the aryl group is substituted by other than a C1-10 group
(iv) alkenylaryl group wherein the aryl group is substituted
(v) alkylheteroaryl group, wherein when heteroaryl group comprises only C and N in the ring, the aryl group is substituted by other than a methyl group
(vi) alkenylheteroaryl group
(vii) =N—O-alkyl or =N—O—H group
(viii) branched alkenyl
(ix) alkyl-alcohol group
(x) amide or alkylamide wherein (a) the alkyl of the alkylamide is —CH₂— or —CH₂CH₂—, (b) the amide is di-substituted and/or (c) the amide is substituted with at least one of alkylheterocycle group, alkenylheterocycle group, alkylheteroaryl group, alkenylheteroaryl group, heteroaryl group, alkylamine group, alkyloxyalkyl group, alkylaryl group, straight or branched alkyl group,
(xi) —CHO so that R₁ together with R₃ provide the enol tautomer

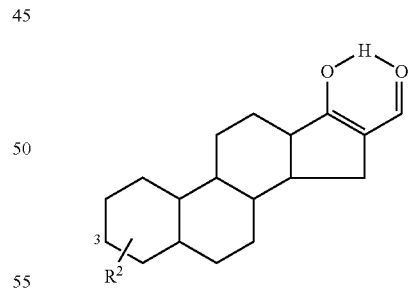

OR R₁ together with R³ form
(xii) a pyrazole wherein (a) R⁴ is =N—O-alkyl or =N—O—H group, (b) the pyrazole is substituted with one of alkyl-OH group, alkyl ester group, alkyloxyalkyl group, branched alkyl group, and an amide and/or (c) the 2 position is substituted with a group selected from —OH and —O-hydrocarbyl
(xiii) a heteroaryl ring to provide a compound of the formula

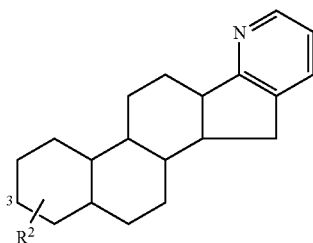

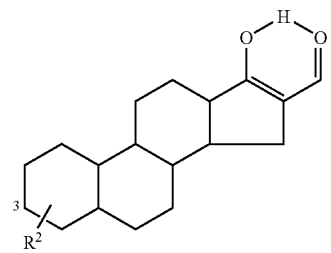

(II) R² is selected from
  groups capable of forming a hydrogen bond, a sulphamate group, a phosphonate group, a thiophosphonate group, a sulphonate group and a sulphonamide group; and
(III) R³ is selected from
  —OH, =O, or a —C(=O)— mimetic According to one aspect of the present invention, there is provided a pharmaceutical composition comprising a compound having Formula I

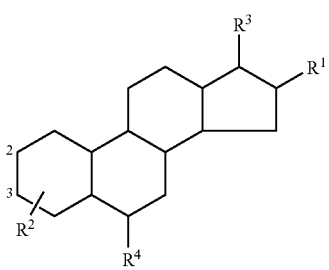

Formula I wherein
(I) R¹ is a selected from
  (i) an alkyloxyalkyl group
  (ii) a nitrile group, and wherein R² is capable of forming a hydrogen bond
  (iii) alkylaryl group, wherein the aryl group is substituted by other than a C1-10 group
  (iv) alkenylaryl group wherein the aryl group is substituted
  (v) alkylheteroaryl group, wherein when heteroaryl group comprises only C and N in the ring, the aryl group is substituted by other than a methyl group
  (vi) alkenylheteroaryl group
  (vii) =N—O-alkyl or =N—O—H group
  (viii) branched alkenyl
  (ix) alkyl-alcohol group
  (x) amide or alkylamide wherein (a) the alkyl of the alkylamide is —CH₂— or —CH₂CH₂—, (b) the amide is di-substituted and/or (c) the amide is substituted with at least one of alkylheterocycle group, alkenylheterocycle group, alkylheteroaryl group, alkenylheteroaryl group, heteroaryl group, alkylamine group, alkyloxyalkyl group, alkylaryl group, straight or branched alkyl group,
  (xi) —CHO so that R₁ together with R₃ provide the enol tautomer OR R₁ together with R³ form
  (xii) a pyrazole wherein (a) R⁴ is =N—O-alkyl or =N—O—H group, (b) the pyrazole is substituted with one of alkyl-OH group, alkyl ester group, alkyloxyalkyl group, branched alkyl group, and an amide and/or (c) the 2 position is substituted with a group selected from —OH and —O-hydrocarbyl
  (xiii) a heteroaryl ring to provide a compound of the formula

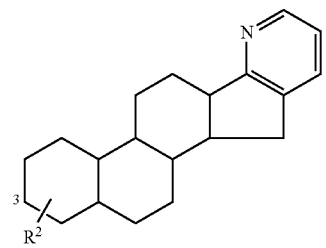

(II) R² is selected from
  groups capable of forming a hydrogen bond, a sulphamate group, a phosphonate group, a thiophosphonate group, a sulphonate group and a sulphonamide group; and
(III) R³ is selected from
  —OH, =O, or a —C(=O)— mimetic
optionally admixed with a pharmaceutically acceptable carrier, diluent, excipient or adjuvant.

According to one aspect of the present invention, there is provided a compound having Formula I

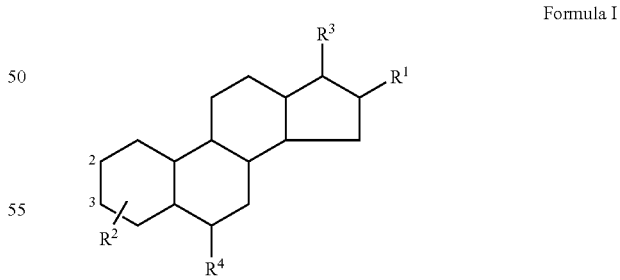

Formula I wherein
(I) R¹ is a selected from
  (i) an alkyloxyalkyl group
  (ii) a nitrile group, and wherein R² is capable of forming a hydrogen bond
  (iii) alkylaryl group, wherein the aryl group is substituted by other than a C1-10 group
  (iv) alkenylaryl group wherein the aryl group is substituted (v) alkylheteroaryl group, wherein when heteroaryl group comprises only C and N in the ring, the aryl group is substituted by other than a methyl group (vi) alkenylheteroaryl group (vii) =N—O-alkyl or =N—O—H group (viii) branched alkenyl (ix) alkyl-alcohol group (x) amide or alkylamide wherein (a) the alkyl of the alkylamide is —CH$_2$— or —CH$_2$CH$_2$—, (b) the amide is di-substituted and/or (c) the amide is substituted with at least one of alkylheterocycle group, alkenylheterocycle group, alkylheteroaryl group, alkenylheteroaryl group, heteroaryl group, alkylamine group, alkyloxyalkyl group, alkylaryl group, straight or branched alkyl group, (xi) —CHO so that R$_1$ together with R$_3$ provide the enol tautomer

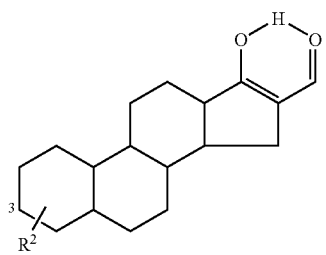

OR R$_1$ together with R$^3$ form (xii) a pyrazole wherein (a) R$^4$ is =N—O-alkyl or =N—O—H group, (b) the pyrazole is substituted with one of alkyl-OH group, alkyl ester group, alkyloxyalkyl group, branched alkyl group, and an amide and/or (c) the 2 position is substituted with a group selected from —OH and —O-hydrocarbyl (xiii) a heteroaryl ring to provide a compound of the formula

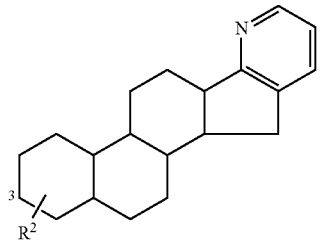

(II) R$^2$ is selected from groups capable of forming a hydrogen bond, a sulphamate group, a phosphonate group, a thiophosphonate group, a sulphonate group and a sulphonamide group; and (III) R$^3$ is selected from —OH, =O, or a —C(=O)— mimetic for use in medicine.

According to one aspect of the present invention, there is provided use of a compound in the manufacture of a medicament for use in the therapy of a condition or disease associated with adverse 17β-hydroxysteroid dehydrogenase (17β-HSD) levels, wherein the compound is of Formula I

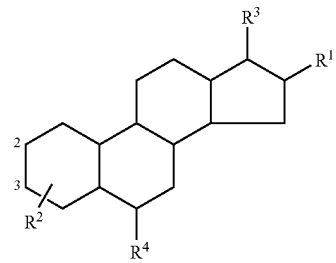

Formula I wherein (I) R$^1$ is a selected from (i) an alkyloxyalkyl group (ii) a nitrile group, and wherein R$^2$ is capable of forming a hydrogen bond (iii) alkylaryl group, wherein the aryl group is substituted by other than a C1-10 group (iv) alkenylaryl group wherein the aryl group is substituted (v) alkylheteroaryl group, wherein when heteroaryl group comprises only C and N in the ring, the aryl group is substituted by other than a methyl group (vi) alkenylheteroaryl group (vii) =N—O-alkyl or =N—O—H group (viii) branched alkenyl (ix) alkyl-alcohol group (x) amide or alkylamide wherein (a) the alkyl of the alkylamide is —CH$_2$— or —CH$_2$CH$_2$—, (b) the amide is di-substituted and/or (c) the amide is substituted with at least one of alkylheterocycle group, alkenylheterocycle group, alkylheteroaryl group, alkenylheteroaryl group, heteroaryl group, alkylamine group, alkyloxyalkyl group, alkylaryl group, straight or branched alkyl group, (xi) —CHO so that R$_1$ together with R$_3$ provide the enol tautomer

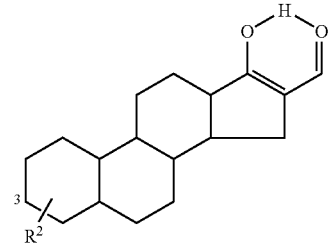

OR R$_1$ together with R$^3$ form (xii) a pyrazole wherein (a) R$^4$ is =N—O-alkyl or =N—O—H group, (b) the pyrazole is substituted with one of alkyl-OH group, alkyl ester group, alkyloxyalkyl group, branched alkyl group, and an amide and/or (c) the 2 position is substituted with a group selected from —OH and —O-hydrocarbyl (xiii) a heteroaryl ring to provide a compound of the formula

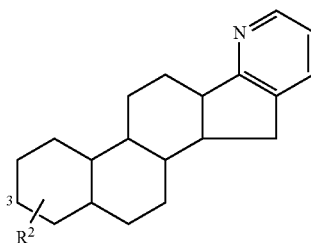

(II) $R^2$ is selected from
  groups capable of forming a hydrogen bond, a sulphamate group, a phosphonate group, a thiophosphonate group, a sulphonate group and a sulphonamide group; and
(III) $R^3$ is selected from
  —OH, =O, or a —C(=O)— mimetic According to one aspect of the present invention, there is provided use of a compound having Formula I

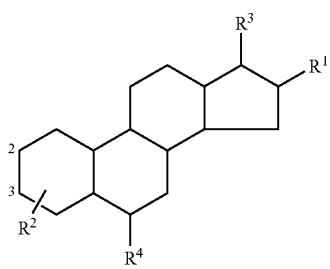

Formula I wherein
(I) $R^1$ is a selected from
  (i) an alkyloxyalkyl group
  (ii) a nitrile group, and wherein $R^2$ is capable of forming a hydrogen bond
  (iii) alkylaryl group, wherein the aryl group is substituted by other than a C1-10 group
  (iv) alkenylaryl group wherein the aryl group is substituted
  (v) alkylheteroaryl group, wherein when heteroaryl group comprises only C and N in the ring, the aryl group is substituted by other than a methyl group
  (vi) alkenylheteroaryl group
  (vii) =N—O-alkyl or =N—O—H group
  (viii) branched alkenyl
  (ix) alkyl-alcohol group
  (x) amide or alkylamide wherein (a) the alkyl of the alkylamide is —CH$_2$— or —CH$_2$CH$_2$—, (b) the amide is di-substituted and/or (c) the amide is substituted with at least one of alkylheterocycle group, alkenylheterocycle group, alkylheteroaryl group, alkenylheteroaryl group, heteroaryl group, alkylamine group, alkyloxyalkyl group, alkylaryl group, straight or branched alkyl group,
  (xi) —CHO so that $R_1$ together with $R_3$ provide the enol tautomer

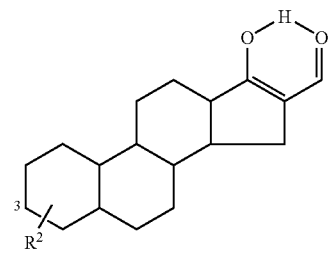

OR $R_1$ together with $R^3$ form
  (xii) a pyrazole wherein (a) $R^4$ is =N—O-alkyl or =N—O—H group, (b) the pyrazole is substituted with one of alkyl-OH group, alkyl ester group, alkyloxyalkyl group, branched alkyl group, and an amide and/or (c) the 2 position is substituted with a group selected from —OH and —O-hydrocarbyl
  (xiii) a heteroaryl ring to provide a compound of the formula

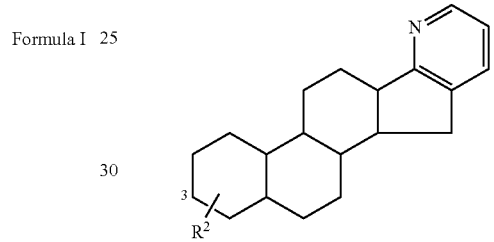

(II) $R^2$ is selected from
  groups capable of forming a hydrogen bond, a sulphamate group, a phosphonate group, a thiophosphonate group, a sulphonate group and a sulphonamide group; and
(III) $R^3$ is selected from
  —OH, =O, or a —C(=O)— mimetic
in the manufacture of a pharmaceutical for inhibiting 17β-hydroxysteroid dehydrogenase (17β-HSD) activity.

According to one aspect of the present invention, there is provided a method of inhibiting 17β-hydroxysteroid dehydrogenase (17β-HSD) activity in a subject in need of same, the method comprising administering a compound a compound having Formula I

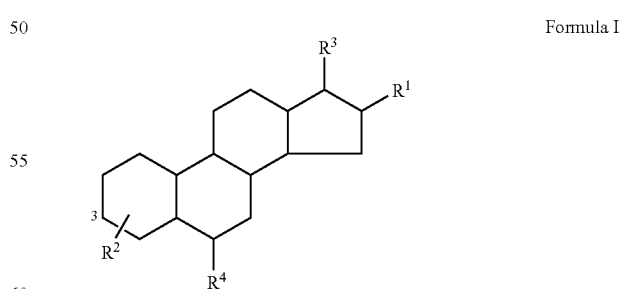

Formula I wherein
(I) $R^1$ is a selected from
  (i) an alkyloxyalkyl group
  (ii) a nitrile group
  (iii) alkylaryl group, wherein the aryl group is substituted by other than a methyl group (iv) alkenylaryl group
(v) alkylheteroaryl group, wherein when heteroaryl group comprises only C and N in the ring, the aryl group is substituted by other than a methyl group
(vi) alkenylheteroaryl group
(vii) =N—O-alkyl or =N—O—H group
(viii) carboxylic acid esters wherein (a) $R^3$ is =O and/or (b) the ester is selected from —$CO_2X$, —$CH_2CO_2X$, and —$CH_2CH_2CO_2X$, wherein X is a hydrocarbyl group
(ix) $CO_2H$ or alkyl-$CO_2H$ group, wherein alkyl is $CH_2$ or $CH_2CH_2$ group
(x) branched alkenyl
(xi) alkyl-alcohol group or alkenyl-alcohol group
(xii) amide or alkylamide wherein (a) the alkyl of the alkylamide is —$CH_2$— or —$CH_2CH_2$—, (b) the amide is di-substituted and/or (c) the amide is substituted with at least one of alkylheterocycle group, alkenylheterocycle group, alkylheteroaryl group, alkenylheteroaryl group, heteroaryl group, alkylamine group, alkyloxyalkyl group, alkylaryl group, straight or branched alkyl group,
(xiv) —CHO so that $R_1$ together with $R_3$ provide the enol tautomer

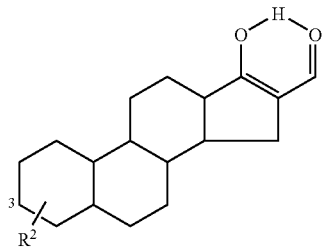

OR $R_1$ together with $R^3$ form
(xii) a pyrazole wherein (a) $R^4$ is =N—O-alkyl or =N—O—H group, (b) the pyrazole is substituted and/or (c) the 2 position is substituted with a group selected from —OH and —O-hydrocarbyl
(xiii) a heteroaryl ring to provide a compound of the formula

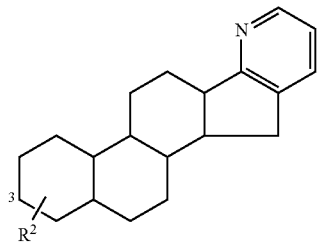

(II) $R^2$ is selected from
groups capable of forming a hydrogen bond, a sulphamate group, a phosphonate group, a thiophosphonate group, a sulphonate group and a sulphonamide group; and
(III) $R^3$ is selected from
—OH, =O, or a —C(=O)— mimetic Some Advantages One key advantage of the present invention is that the compounds of the present invention can act as 17β-HSD inhibitors.

Another advantage of the compounds of the present invention is that they may be potent in vivo.

Some of the compounds of the present invention may be non-oestrogenic compounds. Here, the term "non-oestrogenic" means exhibiting no or substantially no oestrogenic activity.

Another advantage is that some of the compounds may not be capable of being metabolised to compounds which display or induce hormonal activity.

Some of the compounds of the present invention are also advantageous in that they may be orally active.

Some of the compounds of the present invention may useful for the treatment of cancer, such as breast cancer, as well as (or in the alternative) non-malignant conditions, such as the prevention of auto-immune diseases, particularly when pharmaceuticals may need to be administered from an early age.

Thus, some of the compounds of the present invention are also believed to have therapeutic uses other than for the treatment of endocrine-dependent cancers, such as the treatment of autoimmune diseases.

For ease of reference, these and further aspects of the present invention are now discussed under appropriate section headings. However, the teachings under each section are not necessarily limited to each particular section.

Further/Preferable Aspects

The term "capable of forming a hydrogen bond" as used herein means a group having a region of negative charge capable of forming one part of a hydrogen bond.

The term "hydrocarbyl group" as used herein means a group comprising at least C and H and may optionally comprise one or more other suitable substituents. Examples of such substituents may include halo, alkoxy, nitro, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

A typical hydrocarbyl group is a hydrocarbon group. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

In some aspects of the present invention, the hydrocarbyl group is selected from optionally substituted alkyl group, optionally substituted haloalkyl group, aryl group, alkylaryl group, alkylarylakyl group, and an alkene group.

In some aspects of the present invention, the hydrocarbyl group is an optionally substituted alkyl group.

In some aspects of the present invention, the hydrocarbyl group is selected from $C_1$-$C_{10}$ alkyl group, such as $C_1$-$C_6$ alkyl group, and $C_1$-$C_3$ alkyl group. Typical alkyl groups include $C_1$ alkyl, $C_2$ alkyl, $C_3$ alkyl, $C_4$ alkyl, $C_5$ alkyl, $C_7$ alkyl, and $C_8$ alkyl.

In some aspects of the present invention, the hydrocarbyl group is selected from $C_1$-$C_{10}$ haloalkyl group, $C_1$-$C_6$ haloalkyl group, $C_1$-$C_3$ haloalkyl group, $C_1$-$C_{10}$ bromoalkyl group, $C_1$-$C_6$ bromoalkyl group, and $C_1$-$C_3$ bromoalkyl group. Typical haloalkyl groups include $C_1$ haloalkyl, $C_2$ haloalkyl, $C_3$ haloalkyl, $C_4$ haloalkyl, $C_5$ haloalkyl, $C_7$ haloalkyl, $C_8$ haloalkyl, $C_1$ bromoalkyl, $C_2$ bromoalkyl, $C_3$ bromoalkyl, $C_4$ bromoalkyl; $C_5$ bromoalkyl, $C_7$ bromoalkyl, and $C_8$ bromoalkyl.

In some aspects of the present invention, the hydrocarbyl group is selected from aryl groups, alkylaryl groups, alkylarylakyl groups, —$(CH_2)_{1-10}$-aryl, —$(CH_2)_{1-10}$-Ph, $(CH_2)_{1-10}$-Ph-$C_{1-10}$ alkyl, —$(CH_2)_{1-5}$-Ph, $(CH_2)_{1-5}$-Ph-$C_{1-5}$ alkyl, —$(CH_2)_{1-3}$-Ph, $(CH_2)_{1-3}$-Ph-$C_{1-3}$ alkyl, —$CH_2$-Ph, and —$CH_2$-Ph-$C(CH_3)_3$.

When the hydrocarbyl group is or contains an aryl group, the aryl group or one or more of the aryl groups may contain a hetero atom. Thus the aryl group or one or more of the aryl groups may be carbocyclic or more may heterocyclic. Typical hetero atoms include O, N and S, in particular N.

In some aspects of the present invention, the hydrocarbyl group is selected from —$(CH_2)_{1-10}$-cycloalkyl, —$(CH_2)_{1-10}$—$C_{3-10}$cycloalkyl, —$(CH_2)_{1-7}$—$C_{3-7}$cycloalkyl, —$(CH_2)_{1-5}$—$C_{3-5}$cycloalkyl, —$(CH_2)_{1-3}$—$C_{3-5}$cycloalkyl, and —$CH_2$—$C_3$cycloalkyl.

In some aspects of the present invention, the hydrocarbyl group is an alkene group. Typical alkene groups include $C_1$-$C_{10}$ alkene group, $C_1$-$C_6$ alkene group, $C_1$-$C_3$ alkene group, such as $C_1$, $C_2$, $C_3$, $C_4$, $C_5$, $C_6$, or $C_7$ alkene group. In a preferred aspect the alkene group contains 1, 2 or 3 C=C bonds. In a preferred aspect the alkene group contains 1 C=C bond. In some preferred aspect at least one C=C bond or the only C=C bond is to the terminal C of the alkene chain, that is the bond is at the distal end of the chain to the ring system.

Ring System

It will be evident to one skilled in the art that the present compounds contain a steroidal ring structure or are based thereon/derived therefrom. As it is well known in the art, a classical steroidal ring structure has the generic formula of:

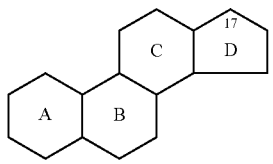

In the above formula, the rings have been labelled in the conventional manner.

An example of a bio-isostere is when any one or more of rings A, B, C and D is a heterocyclic ring and/or when any one or more of rings A, B, C and D has been substituted and/or when any one or more of rings A, B, C and D has been modified; but wherein the bio-isostere has steroidal properties.

In this regard, the ring system of the present invention is analogous to a steroidal ring structure and may be a bio-isostere of a steroidal ring structure.

The structure of a present polycyclic structure can be presented as:

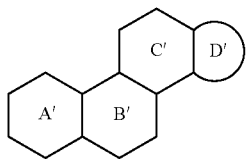

wherein each ring A', B', and C' independently represents a heterocyclic ring or a non-heterocyclic ring, and wherein each ring may be independently substituted or unsubstituted, saturated or unsaturated.

By way of example, any one or more of rings A', B', C' and D' may be independently substituted with suitable groups—such as an alkyl group, an aryl group, a hydroxy group, a halo group, a hydrocarbyl group, an oxyhydrocarbyl group etc.

At least one of A', B', and C' may be a heterocyclic group (a heterocycle) or a non-heterocyclic group.

At least one of A', B', C' and D' may be a saturated ring structure or an unsaturated ring structure (such as an aryl group).

Preferably, at least one of A', B', C' and D' is an aryl ring.

Preferably the compound will contain, inclusive of all substituents, no more than 50 about carbon atoms, more usually no more than about 30 to 40 carbon atoms.

An example of D' is a five or six membered ring.

Preferred steroidal nuclei rings A'-D' on which the compounds of the present invention may be based include rings A-D of:

Oestrones and Substituted Oestrones, viz:

| | |
|---|---|
| oestrone | 16β-OH-oestrone |
| 4-OH-oestrone | 17-deoxyoestrone |
| 6α-OH-oestrone | 2-OH-oestrone |
| 7α-OH-oestrone | 2-MeO-oestrone |
| 16α-OH-oestrone | oestrone |

Oestradiols and Substituted Oestradiols, viz:

| | |
|---|---|
| 4-OH-17β-oestradiol | 16β-OH-17β-oestradiol |
| 6α-OH-17β-oestradiol | 17α-oestradiol |
| 7α-OH-17β-oestradiol | 17β-oestradiol |
| 4-OH-17α-oestradiol | 17α-ethinyl-17β-oestradiol |
| 6α-OH-17α-oestradiol | 17β-ethinyl-17α-oestradiol |
| 7α-OH-17α-oestradiol | 17-deoxyoestradiol |
| 16α-OH-17α-oestradiol | 2-OH-17α-oestradiol |
| 16α-OH-17β-oestradiol | 2-OH-17β-oestradiol |
| 16β-OH-17α-oestradiol | 2-MeO-17α-oestradiol |
| | 2-MeO-17β-oestradiol |

Oestriols and Substituted Oestriols. viz:

oestriol 17-deoxyoestriol

4-OH-oestriol

2-OH-oestriol

6α-OH-oestriol

2-MeO-oestriol

7α-OH-oestriol

Dehydroepiandrosterones and Substituted Dehydroepiandrosterones. viz:

Dehydroepiandrosterones

16α-OH-dehydroepiandrosterone

6α-OH-dehydroepiandrosterone

16β-OH-dehydroepiandrosterone

7α-OH-dehydroepiandrosterone 5-androstenediol

In one preferred aspect of the present invention the compound is of Formula II

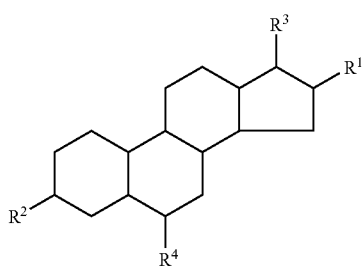

Formula II

In one preferred aspect of the present invention the compound is of Formula III

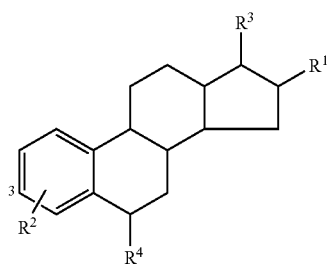

Formula III

In one preferred aspect of the present invention the compound is of Formula IV

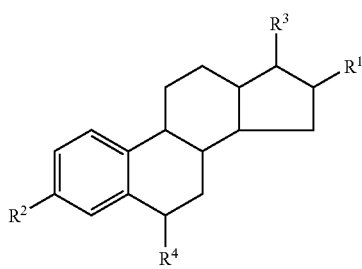

Formula IV $R^1$
Alkyloxyalkyl Group

In one preferred aspect of the present invention R1 of formula I is an alkyloxyalkyl group.

The alkyloxyalkyl group is a -alkyl-O-alkyl group.

Each alkyl of the group is preferably independently has from 1 to 20 carbons, preferably from 1 to 10 carbons, preferably from 1 to 5 carbons, preferably 1, 2 or 3 carbons.

Each alkyl of the group may be independently branched or straight chain. Preferably one or each alkyl is straight chain Particularly preferred alkyloxyalkyl groups are -EtOEt, -EtOMe, -MeOEt, and -MeOMe.

Nitrile Group

In one preferred aspect of the present invention $R^1$ may be a nitrile group or comprise a nitrile group. Nitrile group is understood to mean a —C≡N group.

In one preferred aspect of the present invention $R^1$ of formula I is a nitrile group.

In one preferred aspect when $R^1$ is a nitrile group, $R^2$ is —OH.

In one preferred aspect $R^1$ of formula I is a nitrile group and $R^2$ is —H.

Alkylaryl Group

In one preferred aspect of the present invention R1 of formula I is an alkylaryl group.

It will be understood that by alkylaryl group it is meant a group denoted by -alkyl-aryl.

The alkyl group preferably has from 1 to 20 carbons, preferably from 1 to 10 carbons, preferably from 1 to 5 carbons, preferably 1, 2 or 3 carbons.

The alkyl group may be branched or straight chain. Preferably the alkyl group is straight chained.

The aryl group typically has a six membered ring

The aryl group is substituted. In preferred aspects the aryl group of the alkylaryl group is substituted by a group selected from N,N-dialkyl, alkoxy, nitro (—$NO_2^-$), nitrile, and azaalkyl groups.

Preferably the N,N-dialkyl is —N(C1-10 alkyl)$_2$, —N(C1-5 alkyl)$_2$, or —N(C1-3 alkyl)$_2$. Particularly preferred is NMe$_2$.

Preferably the alkoxy group is C1-10 alkoxy, C1-5 alkoxy, and C1-3 alkoxy. Particularly preferred is methoxy.

In a highly preferred aspect the alkylaryl group is —CH$_2$-Ph.

Alkenylaryl Group

In one preferred aspect of the present invention R1 of formula I is an alkenylaryl group.

It will be understood that by alkylaryl group it is meant a group denoted by -alkenyl-aryl.

In one preferred aspect of the present invention, in the present use or method the aryl group of the alkenylaryl group is substituted.

The alkenyl group preferably has from 1 to 20 carbons, preferably from 1 to 10 carbons, preferably from 1 to 5 carbons, preferably 1, 2 or 3 carbons.

The alkenyl group may be branched or straight chain. Preferably the alkenyl group is straight chained.

The aryl group typically has a six membered ring

The aryl group is substituted. In preferred aspects the aryl group of the alkylaryl group is substituted by a group selected from N,N-dialkyl, alkoxy, nitro (—$NO_2^-$), nitrile, and azaalkyl groups.

Preferably the N,N-dialkyl is —N(C1-10 alkyl)$_2$, —N(C1-5 alkyl)$_2$, or —N(C1-3 alkyl)$_2$. Particularly preferred is NMe$_2$.

Preferably the alkoxy group is C1-10 alkoxy, C1-5 alkoxy, and C1-3 alkoxy. Particularly preferred is methoxy.

In a highly preferred aspect the alkenylaryl group is =CH-Ph.

Alkylheteroaryl Group

In one preferred aspect of the present invention R1 of formula I is an alkylheteroaryl group.

The alkyl group preferably has from 1 to 20 carbons, preferably from 1 to 10 carbons, preferably from 1 to 5 carbons, preferably 1, 2 or 3 carbons.

The alkyl group may be branched or straight chain. Preferably the alkyl group is straight chained.

The aryl group typically has a six membered ring

The heteroarylgroup contain carbon and hetero atoms. Typical hetero atoms include O, N and S, in particular N.

The aryl group may be substituted or unsubstituted. Preferably the aryl group is substituted. In preferred aspects the aryl group of the alkylaryl group is substituted by a group selected from N,N-dialkyl, alkoxy, nitro (—$NO_2^-$), nitrile, and azaalkyl groups.

Preferably the N,N-dialkyl is —N(C1-10 alkyl)$_2$, —N(C1-5 alkyl)$_2$, or —N(C1-3 alkyl)$_2$. Particularly preferred is NMe$_2$.

Preferably the alkoxy group is C1-10 alkoxy, C1-5 alkoxy, and C1-3 alkoxy. Particularly preferred is methoxy.

In a highly preferred aspect the alkylheteroaryl group is selected from

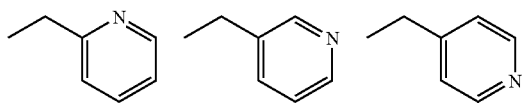

Alkenylheteroaryl Group

In one preferred aspect of the present invention R1 of formula I is an alkenylheteroaryl group. In one preferred aspect, R1 of formula I is an alkenylheteroaryl group, wherein the aryl group is substituted. Preferably R1 of formula I is an alkenylheteroaryl group wherein the aryl group is unsubstituted.

In one preferred aspect of the present invention R1 of formula I is an alkylheteroaryl group.

The alkenyl group preferably has from 1 to 20 carbons, preferably from 1 to 10 carbons, preferably from 1 to 5 carbons, preferably 1, 2 or 3 carbons.

The alkenyl group may be branched or straight chain. Preferably the alkenyl group is straight chained.

The aryl group typically has a six membered ring

The heteroaryl group contain carbon and hetero atoms. Typical hetero atoms include O, N and S, in particular N.

The aryl group may be substituted or unsubstituted. Preferably the aryl group is substituted. In preferred aspects the aryl group of the alkylaryl group is substituted by a group selected from N,N-dialkyl, alkoxy, nitro (—NO$_2$−), nitrile, and azaalkyl groups.

Preferably the N,N-dialkyl is —N(C1-10 alkyl)$_2$, —N(C1-5 alkyl)$_2$, or —N(C1-3 alkyl)$_2$. Particularly preferred is NMe$_2$.

Preferably the alkoxy group is C1-10 alkoxy, C1-5 alkoxy, and C1-3 alkoxy. Particularly preferred is methoxy.

In a highly preferred aspect the alkenylheteroaryl group is selected from

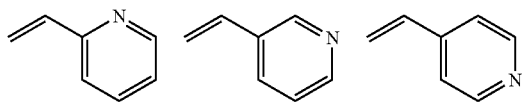

Oxime Group (=N—O-Alkyl or =N—O—H Group)

In one preferred aspect of the present invention R1 of formula I is an oxime group, namely =N—O-alkyl or =N—O—H group.

Preferably the oxime group is a =N—O-alkyl group

In one preferred aspect when R$^1$ is selected from =N—O-alkyl and =N—O—H groups and R$^3$ is a =N—O-alkyl group or =N—O—H group.

The alkyl group preferably has from 1 to 20 carbons, preferably from 1 to 10 carbons, preferably from 1 to 5 carbons, preferably 1, 2 or 3 carbons.

The alkyl group may be branched or straight chain. Preferably the alkyl group is straight chained.

We have also surprisingly found that when R$^3$ is a =N—O-alkyl group or =N—O—H group, it is not essential for R$^1$ to be a =N—O-alkyl or =N—O—H group if R$^4$ is a =N—O-alkyl or =N—O—H group. We have found that when R3 and R4 are independently selected from =N—O-alkyl and =N—O—H groups, a 17β-HSD inhibitor may be provided. Thus a further aspect the present invention provides a compound having Formula V

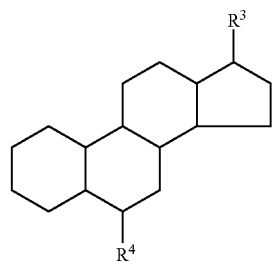

Formula V wherein R$^3$ and R4 are independently selected from =N—O-alkyl or =N—O—H group use of a compound in the manufacture of a medicament for use in the therapy of a condition or disease associated with 17β-hydroxysteroid dehydrogenase (17β-HSD), wherein the compound has Formula V

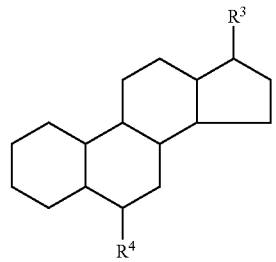

Formula V wherein R$^3$ and R4 are independently selected from =N—O-alkyl or =N—O—H group a pharmaceutical composition comprising a compound having Formula V

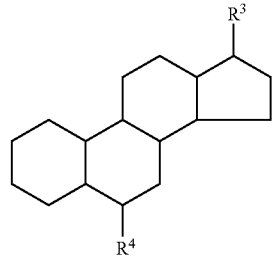

Formula V wherein R$^3$ and R4 are independently selected from =N—O-alkyl or =N—O—H group a compound having Formula V

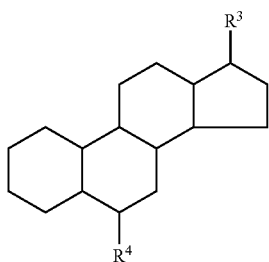

Formula V wherein $R^3$ and R4 are independently selected from =N—O-alkyl or =N—O—H group for use in medicine.

use of a compound in the manufacture of a medicament for use in the therapy of a condition or disease associated with adverse 17β-hydroxysteroid dehydrogenase (17β-HSD) levels, wherein the compound is of Formula V

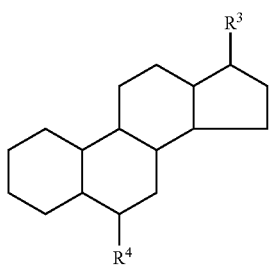

Formula V wherein $R^3$ and R4 are independently selected from =N—O-alkyl or =N—O—H group use of a compound having Formula V

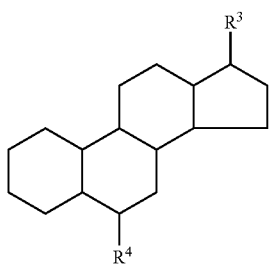

Formula V wherein $R^3$ and R4 are independently selected from =N—O-alkyl or =N—O—H group in the manufacture of a pharmaceutical for inhibiting 17β-hydroxysteroid dehydrogenase (17β-HSD) activity.

a method of inhibiting 17β-hydroxysteroid dehydrogenase (17β-HSD) activity in a subject in need of same, the method comprising administering a compound a compound having Formula V

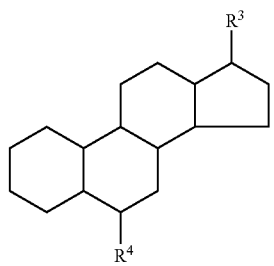

Formula V wherein $R^3$ and R4 are independently selected from =N—O-alkyl or =N—O—H group Carboxylic Acid Esters In one preferred aspect of the present invention $R^1$ of formula I is a carboxylic acid ester.

In some aspects, when $R^1$ of formula I is a carboxylic acid ester, $R^3$ is =O and/or the ester is selected from —$CO_2X$, —$CH_2CO_2X$, and —$CH_2CH_2CO_2X$, wherein X is a hydrocarbyl group.

In one preferred aspect of the present invention, in the present use or method the carboxylic acid ester is selected from —$CO_2X$, —$CH_2CO_2X$, and —$CH_2CH_2CO_2X$, wherein X is a hydrocarbyl group.

In some aspects, When $R^1$ of formula I is a carboxylic acid ester, $R^3$ is =O and the ester is selected from —$CO_2X$, —$CH_2CO_2X$, and —$CH_2CH_2CO_2X$, wherein X is a hydrocarbyl group.

Preferably X is a hydrocarbon group. More preferably X is an alkyl group such as an alkyl group preferably having from 1 to 20 carbons, preferably from 1 to 10 carbons, preferably from 1 to 5 carbons, preferably 1, 2 or 3 carbons.

The alkyl group may be branched or straight chain. Preferably the alkyl group is straight chained.

$CO_2H$ or Alkyl-$CO_2H$ Group

In one preferred aspect of the present invention R1 of formula I is —$CO_2H$ or alkyl-$CO_2H$ group The alkyl group may be branched or straight chain. Preferably the alkyl group is straight chained.

The alkyl group preferably has from 1 to 20 carbons, preferably from 1 to 10 carbons, preferably from 1 to 5 carbons, preferably 1, 2 or 3 carbons.

Branched Alkenyl

In one preferred aspect of the present invention R1 of formula I is a branched alkenyl group.

The branched alkenyl group preferably has from 1 to 20 carbons, preferably from 1 to 10 carbons, preferably from 1 to 5 carbons, preferably 1, 2, 3 or 4 carbons.

Alkyl-Alcohol Group or Alkenyl-Alcohol Group

In one preferred aspect of the present invention R1 of formula I is an alkyl-alcohol group or alkenyl-alcohol group.

The alkyl group may be branched or straight chain. Preferably the alkyl group is straight chained.

By alkyl-alcohol group or alkenyl-alcohol group it is meant a group of the formula $C_xH_{2x-2n-y}(OH)y$ wherein x is an integer, y is an integer and n is the degree of unsaturation.

Typically x is from 1 to 20, preferably from 1 to 10, preferably from 1 to 5, preferably 1, 2, 3 or 4. Typically y is 1, 2 or 3. Typically n is 0, 1, 2 or 3.

Preferably the alkenyl-alcohol has the following structural formula:

In one preferred aspect the alkenyl alcohol is substituted. In this aspect preferably a substituent replaces $H_a$ and/or $H_b$ in the following structural formula:

Suitable substituents include ester groups, haloalkyl groups, aryl groups such as heteroaryl groups, and alkyl groups.

Preferred substituted alkenyl-alcohol groups include

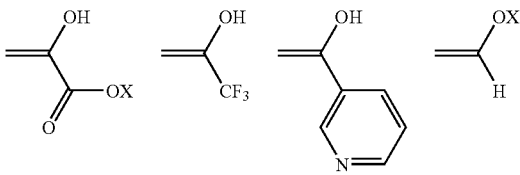

wherein X is a hydrocarbyl group, preferably a hydrocarbon, more preferably an alkyl group, preferably having from 1 to 20 carbons, preferably from 1 to 10 carbons, preferably from 1 to 5 carbons, preferably 1, 2, or 3 carbons. In a highly preferred aspect X is an ethyl group.

Amide or Alkylamide

In one preferred aspect of the present invention R1 of formula I is an amide or alkylamide group.

In one aspect, R1 of formula I is an amide or alkylamide. wherein (a) the alkyl of the alkylamide is —$CH_2$— or —$CH_2CH_2$—, (b) the amide is di-substituted and/or (c) the amide is substituted with at least one of alkylheterocycle group, alkenylheterocycle group, alkylheteroaryl group, alkenylheteroaryl group, alkylamine group, alkyloxyalkyl group, alkylaryl group, straight or branched alkyl group, Preferably, in one aspect, R1 of formula I is an amide or alkylamide wherein (a) the alkyl of the alkylamide is —$CH_2$— or —$CH_2CH_2$—, (b) the amide is di-substituted and/or (c) the amide is substituted with at least one of alkyl-heterocycle group, alkenylheterocycle group, alkylheteroaryl group, alkenylheteroaryl group, heteroaryl group, alkylamine group, alkyloxyalkyl group, alkylaryl group, straight or branched alkyl group, In one preferred aspect the amide is of the formula —C(=O)$NR^5R^6$ or —N(CO—$R^7$)$R^8$, wherein $R^5$, $R^6$, $R^7$ and $R^8$ are independently selected from H and hydrocarbyl groups.

Preferred amide groups include NHCO—$C_{1-10}$alkyl, CONH $C_{1-10}$alkyl, NHCO$(CH_2)_{1-10}CH_3$, CONH$(CH_2)_{1-10}$ $CH_3$, NHCO$(CH_2)_{3-7}CH_3$, CONH$(CH_2)_{3-7}CH_3$, NHCO $(CH_2)_6CH_3$, CONH$(CH_2)_6CH_3$.

In one preferred aspect the amide or alkylamide is an alkylamide.

Preferred alkylamide groups include $C_{1-10}$alkyl-NHCO— $C_{1-10}$alkyl, $C_{1-10}$alkyl-CONH—$C_{1-10}$alkyl, $C_{1-10}$alkyl-NHCO$(CH_2)_{1-10}CH_3$, $C_{1-10}$alkyl-CONH$(CH_2)_{1-10}CH_3$, $C_{1-10}$alkyl-NHCO$(CH_2)_{3-7}CH_3$, $C_{1-10}$alkyl-CONH$(CH_2)_{3-7}$ $CH_3$, $C_{1-10}$alkyl-NHCO$(CH_2)_6CH_3$, $C_{1-10}$alkyl-CONH $(CH_2)_6CH_3$.

In one preferred aspect the substituents of the di-substituted amide together form a cyclic structure.

In one preferred aspect the substituents of the di-substituted amide together form an aryl ring.

In one preferred aspect the substituents of the di-substituted amide together form a heterocyclic ring.

—CHO (Enol Tautomer)

In one preferred aspect of the present invention R1 of formula I is together with $R_3$ provide the enol tautomer

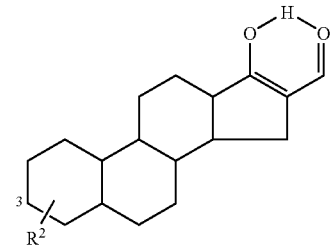

$R_1$ Together with $R^{3-}$ Pyrazole

In one preferred aspect of the present invention $R^1$ of formula I together with $R^3$ form a pyrazole.

In one preferred aspect of the present invention, in the present use or method the pyrazole is substituted. Preferably the pyrazole is substituted with one of alkyl-OH group, alkyl ester group, alkyloxyalkyl group, branched alkyl group, and an amide.

In one preferred aspect of the present invention $R^1$ of formula I together with $R^3$ form a pyrazole, wherein the pyrazole is substituted with one or more (i) an alkyloxyalkyl group, (ii) a nitrile group, (iii) alkylaryl group, (iv) alkenylaryl group, (v) alkylheteroaryl group, (vi) alkenylheteroaryl group, (viii) carboxylic acid ester, (ix) $CO_2H$ or alkyl-$CO_2H$ group, (x) branched alkenyl, (xi) alkyl-alcohol group or alkenyl-alcohol group, (xii) amide or alkylamide, as described herein.

In one preferred aspect of the present invention, when $R^1$ and $R^3$ form a pyrazole, the 2 position of the ring system is substituted with a group selected from —OH and —O-hydrocarbyl, preferably selected from —OH and —O-alkyl. The alkyl group preferably has from 1 to 20 carbons, preferably from 1 to 10 carbons, preferably from 1 to 5 carbons, preferably 1, 2, 3 or 4 carbons.

By the term "the 2 position of the ring system" it is meant the position on the steriodal ring system which is labelled '2' on the formula below:

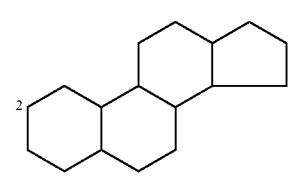

In one preferred aspect of the present invention, when $R^1$ and $R^3$ form a pyrazole the pyrazole is substituted. In this aspect, the addition of substituents to the pyrazole ring may remove unsaturation.

Examples of substituted pyrazole rings include:

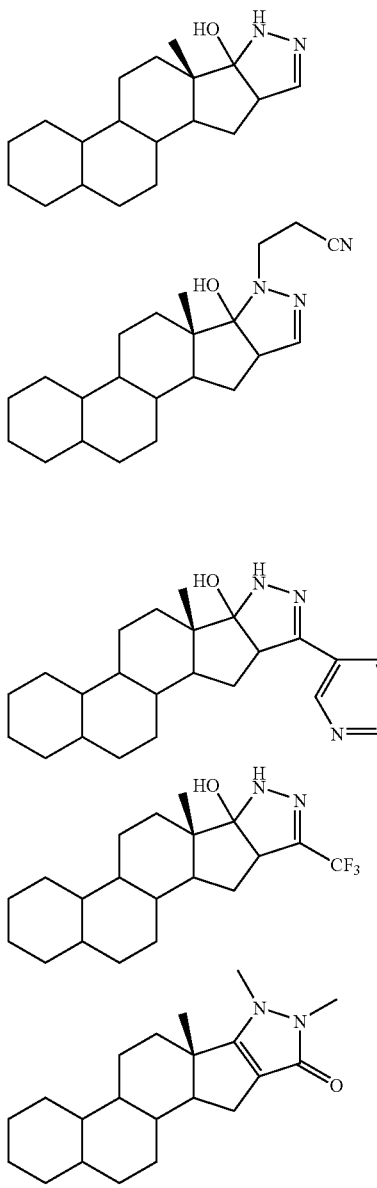

R₁ Together with R³⁻ Heteroaryl Ring

In one preferred aspect of the present invention $R^1$ of formula I together with $R^3$ forms a heteroaryl ring The aryl group typically has a six membered ring The heteroarylgroup contains carbon and hetero atoms. Typical hetero atoms include O, N and S, in particular N.

The aryl group may be substituted or unsubstituted. Preferably the aryl group is unsubstituted.

R²

$R^2$ is selected from groups capable of forming a hydrogen bond, a sulphamate group, a phosphonate group, a thiophosphonate group, a sulphonate group and a sulphonamide group.

Preferably $R^2$ is selected from groups capable of forming a hydrogen bond and a sulphamate group.

Preferably the sulphamate group is of the formula

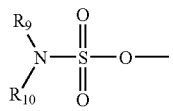

wherein $R^9$ and $R^{10}$ are independently selected from H, alkyl, cycloalkyl, alkenyl and aryl, or combinations thereof, or together represent alkylene, wherein the or each alkyl or cycloalkyl or alkenyl or optionally contain one or more hetero atoms or groups.

In one preferable aspect at least one of $R^9$ and $R^{10}$ is H.
In one preferable aspect $R^9$ and $R^{10}$ are both H
Preferably the group capable of forming a hydrogen bond are selected from —OH
R³

$R^2$ is selected from —OH, =O, or a —C(=O) mimetic.
The term "—C(=O) mimetic" would be understood to one skilled in the art Preferably the —C(=O) mimetic is selected from —CN, =N—O-alkyl group, =N—O—H group, pyridine, pyrimidine, and groups of the formula

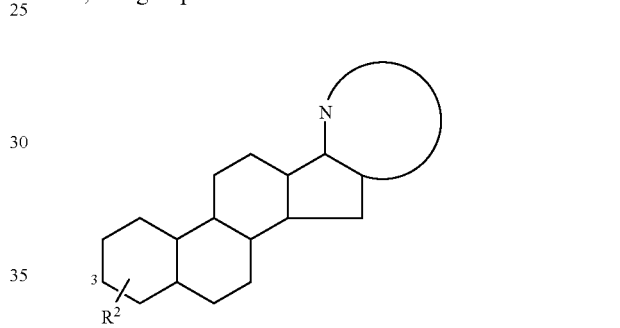

In one preferred aspect $R^3$ is selected from —OH, and =O.
In one preferred aspect $R^3$ is =O.

Substituents

The compound of the present invention may have substituents other than those of the ring systems show herein. Furthermore the ring systems herein are given as general formulae and should be interpreted as such. The absence of any specifically shown substituents on a given ring member indicates that the ring member may substituted with any moiety of which H is only one example. The ring system may contain one or more degrees of unsaturation, for example is some aspects one or more rings of the ring system is aromatic. The ring system may be carbocyclic or may contain one or more hetero atoms.

The compound of the invention, in particular the ring system compound of the invention of the present invention may contain substituents other than those show herein. By way of example, these other substituents may be one or more of: one or more sulphamate group(s), one or more phosphonate group(s), one or more thiophosphonate group(s), one or more sulphonate group(s), one or more sulphonamide group(s), one or more halo groups, one or more O groups, one or more hydroxy groups, one or more amino groups, one or more sulphur containing group(s), one or more hydrocarbyl group(s)—such as an oxyhydrocarbyl group.

In general terms the ring system A'B'C'D' of the present compounds may contain a variety of non-interfering substituents. In particular, the ring system A'B'C'D' may contain one or more hydroxy, alkyl especially lower ($C_1$-$C_6$) alkyl, e.g.

methyl, ethyl, n-propyl, isopropyl, n-butyl, sec-butyl, tert-butyl, n-pentyl and other pentyl isomers, and n-hexyl and other hexyl isomers, alkoxy especially lower ($C_1$-$C_6$, e.g. methoxy, ethoxy, propoxy etc., alkinyl, e.g. ethinyl, or halogen, e.g. fluoro substituents.

For some compounds of the present invention, it is preferred that the ring system is substituted with a oxyhydrocarbyl group. More preferably the A' ring of the ring system is substituted with a oxyhydrocarbyl group.

For some compounds of the present invention, it is highly preferred that at least the 2 position of the A' ring of the ring system is substituted with a oxyhydrocarbyl group.

The term "oxyhydrocarbyl" group as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

In one embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Typically, the oxyhydrocarbyl group is of the formula $C_{1-6}O$ (such as a $C_{1-3}O$).

For some compounds of the present invention, it is highly preferred that the A' ring of the ring system is substituted with an alkoxy group.

For some compounds of the present invention, it is highly preferred that at least the 2 position of the A' ring of the ring system is substituted with an alkoxy group.

Preferably the alkoxy group is methoxy.

For some compounds of the present invention, it is preferred that the ring system is substituted with a hydrocarbylsulphanyl group. More preferably the A' ring of the ring system is substituted with a hydrocarbylsulphanyl group. The term "hydrocarbylsulphanyl" means a group that comprises at least hydrocarbyl group (as herein defined) and sulphur, preferably —S-hydrocarbyl, more preferably —S-hydrocarbon. That sulphur group may be optionally oxidised.

For some compounds of the present invention, it is highly preferred that at least the 2 position of the A' ring of the ring system is substituted with a hydrocarbylsulphanyl group.

Preferably the hydrocarbylsulphanyl group is —S—$C_{1-10}$ alkyl, more preferably —S—$C_{1-5}$ alkyl, more preferably —S—$C_{1-3}$ alkyl, more preferably —S—$CH_2CH_2CH_3$, —$CH_2CH_3$ or —$SCH_3$ For some compounds of the present invention, it is highly preferred that at least the A' ring of the ring system is substituted with an hydrocarbyl group.

For some compounds of the present invention, it is highly preferred that at least the 2 position of the A' ring of the ring system is substituted with an alkyl group.

Preferably the alkyl group is ethyl.

For some compounds of the present invention, it is highly preferred that the compound comprises at least two or more of sulphamate group, a phosphonate group, a thiophosphonate group, a sulphonate group or a sulphonamide group.

For some compounds of the present invention, it is highly preferred that the compound comprises at least two sulphamate groups.

For some compounds of the present invention, it is highly preferred that the compound comprises at least two sulphamate groups, wherein said sulphamate groups are not on the same ring.

For some compounds of the present invention, it is highly preferred that the A' ring of the ring system comprises at least one sulphamate group and wherein the D' ring of the ring system comprises at least one sulphamate group.

In some aspects of the present invention, preferably the A' ring contain one or more of an alkoxy substituent and an alkyl substituent. Thus according to further aspects of the present invention, the compound has one of the following formulae

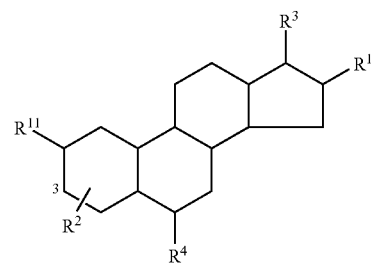

Formula VI

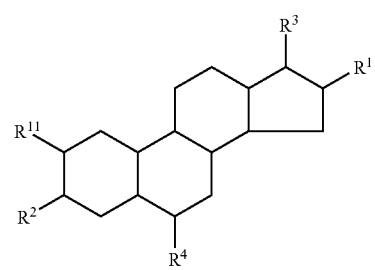

Formula VII

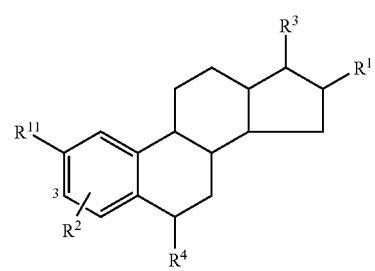

Formula VIII

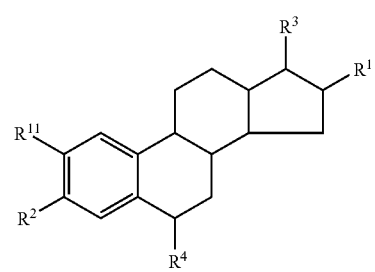

Formula IX wherein $R^{11}$ is an alkoxy group or an alkyl group

Preferably $R^{11}$ is an alkyl group. Preferably $R^{11}$ is a $C_1$-$C_{10}$ alkyl group, preferably a $C_1$-$C_6$ alkyl group, preferably a $C_1$-$C_3$ alkyl group. Preferably $R^{11}$ is —$CH_3$ or —$CH_2CH_3$.

In another preferred aspect, $R^{11}$ is an alkoxy group. Preferably $R^{11}$ is methoxy.

Further Aspects

According to a further aspect of the present invention there is provided a method comprising (a) performing a steroid dehydrogenase assay with one or more candidate compounds having the formula as defined herein; (b) determining whether one or more of said candidate compounds is/are capable of modulating steroid dehydrogenase activity; and (c) selecting one or more of said candidate compounds that is/are capable of modulating steroid dehydrogenase activity.

According to a further aspect of the present invention there is provided a method comprising (a) performing a steroid dehydrogenase assay with one or more candidate compounds having the formula as defined herein; (b) determining whether one or more of said candidate compounds is/are capable of inhibiting steroid dehydrogenase activity; and (c) selecting one or more of said candidate compounds that is/are capable of inhibiting steroid dehydrogenase activity.

In any one of the methods of the present invention, one or more additional steps may be present. For example, the method may also include the step of modifying the identified candidate compound (such as by chemical and/or enzymatic techniques) and the optional additional step of testing that modified compound for steroid dehydrogenase inhibition effects (which may be to see if the effect is greater or different). By way of further example, the method may also include the step of determining the structure (such as by use of crystallographic techniques) of the identified candidate compound and then performing computer modelling studies—such as to further increase its steroid dehydrogenase inhibitory action. Thus, the present invention also encompasses a computer having a dataset (such as the crystallographic co-ordinates) for said identified candidate compound. The present invention also encompasses that identified candidate compound when presented on a computer screen for the analysis thereof—such as protein binding studies.

According to one aspect of the present invention, there is provided a compound identified by the method of the present invention.

According to one aspect of the present invention, there is provided a compound according to the present invention for use in medicine.

According to one aspect of the present invention, there is provided a pharmaceutical composition comprising the compound according to the present invention optionally admixed with a pharmaceutically acceptable carrier, diluent, excipient or adjuvant.

According to one aspect of the present invention, there is provided the use of a compound according to the present invention in the manufacture of a medicament for use in the therapy of a condition or disease associated with steroid dehydrogenase.

According to one aspect of the present invention, there is provided the use of a compound according to the present invention in the manufacture of a medicament for use in the therapy of a condition or disease associated with adverse steroid dehydrogenase levels.

For some applications, preferably the compounds have no, or a minimal, oestrogenic effect.

For some applications, preferably the compounds have an oestrogenic effect.

For some applications, preferably the compounds have a reversible action.

For some applications, preferably the compounds have an irreversible action.

In one embodiment, the compounds of the present invention are useful for the treatment of breast cancer.

The compounds of the present invention may be in the form of a salt.

The present invention also covers novel intermediates that are useful to prepare the compounds of the present invention. For example, the present invention covers novel alcohol precursors for the compounds. By way of further example, the present invention covers bis protected precursors for the compounds. Examples of each of these precursors are presented herein. The present invention also encompasses a process comprising each or both of those precursors for the synthesis of the compounds of the present invention.

We have also identified that in some aspects of the present invention the present compounds may also inhibit the activity of steroid dehydrogenase (HSD).

By steroid dehydrogenase or HSD it is meant 17β hydroxy steroid dehydrogenase. In one aspect the 17β hydroxy steroid dehydrogenase is EC 1.1.1.62

Preferably the HSD is of Type 1, 3, 5 and/or 7. Preferably the HSD converts oestrone (ketone) to oestradiol (hydroxy).

Preferably the HSD is of Type 2 and/or 8. Preferably the HSD converts oestradiol (hydroxy) to oestrone (ketone).

In some aspects of the present invention, it is preferred that the steroid dehydrogenase is steroid dehydrogenase Type I.

In some aspects of the present invention, it is preferred that the steroid dehydrogenase is steroid dehydrogenase Type II Preferably the HSD is of Type 1, 3, 5 and/or 7. Preferably the HSD converts oestrone (ketone) to oestradiol (hydroxy).

Preferably the HSD is of Type 2 and/or 8. Preferably the HSD converts oestradiol (hydroxy) to oestrone (ketone).

Steroid Dehydrogenase

Steroid dehydrogenase or "DH" for short may be classified as consisting of two types—Type I and Type II. The two types of enzyme, such as oestradiol 17β-hydroxysteroid dehydrogenases (E2HSD), have pivotal roles in regulating the availability of ligands to interact with the oestrogen receptor. Type I reduces oestrone (E1) to the biologically active oestrogen, oestradiol (E2) while E2HSD Type II inactivates E2 by catalysing its oxidation to E1.

DH Inhibitor

It is believed that some disease conditions associated with DH activity are due to conversion of a nonactive, oestrone to an active, oestradiol. In disease conditions associated with DH activity, it would be desirable to inhibit DH activity.

Here, the term "inhibit" includes reduce and/or eliminate and/or mask and/or prevent the detrimental action of DH.

DH Inhibitor

In accordance with the present invention, the compound of the present invention is capable of acting as an DH inhibitor.

Here, the term "inhibitor" as used herein with respect to the compound of the present invention means a compound that can inhibit DH activity—such as reduce and/or eliminate and/or mask and/or prevent the detrimental action of DH. The DH inhibitor may act as an antagonist.

The ability of compounds to inhibit steroid dehydrogenase activity can be assessed using either T47D breast cancer cells in which E2HSD Type I activity is abundant or MDA-MB-231 cells for Type II inhibitor studies. In both cell lines formation of products is linear with respect to time and cell numbers. Details on a suitable Assay Protocol are presented in the Examples section.

It is to be noted that the compound of the present invention may have other beneficial properties in addition to or in the alternative to its ability to inhibit DH activity.

Steroid Sulphatase

In some aspects the compounds defined herein may also inhibit steroid sulphatase.

Steroid sulphatase—which is sometimes referred to as steroid sulphatase or steryl sulphatase or "STS" for short—hydrolyses several sulphated steroids, such as oestrone sulphate, dehydroepiandrosterone sulphate and cholesterol sulphate. STS has been allocated the enzyme number EC 3.1.6.2.

STS has been cloned and expressed. For example see Stein et al (J. Biol. Chem. 264:13865-13872 (1989)) and Yen et al (Cell 49:443-454(1987)).

STS is an enzyme that has been implicated in a number of disease conditions.

By way of example, workers have found that a total deficiency in STS produces ichthyosis. According to some workers, STS deficiency is fairly prevalent in Japan. The same workers (Sakura et al, J Inherit Metab Dis 1997 November; 20(6):807-10) have also reported that allergic diseases—such as bronchial asthma, allergic rhinitis, or atopic dermatitis—may be associated with a steroid sulphatase deficiency.

In addition to disease states being brought on through a total lack of STS activity, an increased level of STS activity may also bring about disease conditions. By way of example, and as indicated above, there is strong evidence to support a role of STS in breast cancer growth and metastasis.

STS has also been implicated in other disease conditions. By way of example, Le Roy et al (Behav Genet 1999 March; 29(2):131-6) have determined that there may be a genetic correlation between steroid sulphatase concentration and initiation of attack behaviour in mice. The authors conclude that sulphatation of steroids may be the prime mover of a complex network, including genes shown to be implicated in aggression by mutagenesis.

STS Inhibition

It is believed that some disease conditions associated with STS activity are due to conversion of a nonactive, sulphated oestrone to an active, nonsulphated oestrone. In disease conditions associated with STS activity, it would be desirable to inhibit STS activity.

Here, the term "inhibit" includes reduce and/or eliminate and/or mask and/or prevent the detrimental action of STS.

STS Inhibitor

In accordance with the present invention, the compound of the present invention is capable of acting as an STS inhibitor.

Here, the term "inhibitor" as used herein with respect to the compound of the present invention means a compound that can inhibit STS activity—such as reduce and/or eliminate and/or mask and/or prevent the detrimental action of STS. The STS inhibitor may act as an antagonist.

The ability of compounds to inhibit oestrone sulphatase activity can be assessed using either intact MCF-7 breast cancer cells or placental microsomes. In addition, an animal model may be used. Details on suitable Assay Protocols are presented in following sections. It is to be noted that other assays could be used to determine STS activity and thus STS inhibition. For example, reference may also be made to the teachings of WO-A-99/50453.

Preferably, for some applications, the compound is further characterised by the feature that if the sulphamate group were to be substituted by a sulphate group to form a sulphate derivative, then the sulphate derivative would be hydrolysable by an enzyme having steroid sulphatase (E.C. 3.1.6.2) activity—i.e. when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a Km value of less than 200 mmolar, preferably less than 150 mmolar, preferably less than 100 mmolar, preferably less than 75 mmolar, preferably less than 50 mmolar, when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a Km value of less than 200 µmolar, preferably less than 150 µmolar, preferably less than 100 µmolar, preferably less than 75 µmolar, preferably less than 50 µmolar, when incubated with steroid sulphatase EC 3.1.6.2 at pH 7.4 and 37° C.

In a preferred embodiment, the compound of the present invention is not hydrolysable by an enzyme having steroid sulphatase (E.C. 3.1.6.2) activity.

For some applications, preferably the compound of the present invention has at least about a 100 fold selectivity to a desired target (e.g. STS), preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

It is to be noted that the compound of the present invention may have other beneficial properties in addition to or in the alternative to its ability to inhibit HSD activity.

Sulphamate Group

In one embodiment, the ring X has a sulphamate group as a substituent. The term "sulphamate" as used herein includes an ester of sulphamic acid, or an ester of an N-substituted derivative of sulphamic acid, or a salt thereof.

If $R^1$ is a sulphamate group then the compound of the present invention is referred to as a sulphamate compound.

Typically, the sulphamate group has the formula:

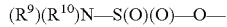

wherein preferably $R^9$ and $R^{10}$ are independently selected from H, alkyl, cycloalkyl, alkenyl and aryl, or combinations thereof, or together represent alkylene, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^9$ and/or $R^{10}$ is alkyl, the preferred values are those where $R^9$ and $R^{10}$ are each independently selected from lower alkyl groups containing from 1 to 6 carbon atoms, that is to say methyl, ethyl, propyl etc. $R^4$ and $R^5$ may both be methyl. When $R^9$ and/or $R^{10}$ is aryl, typical values are phenyl and tolyl ($PhCH_3$; o). Where $R^9$ and $R^{10}$ represent cycloalkyl, typical values are cyclopropyl, cyclopentyl, cyclohexyl etc. When joined together $R^9$ and $R^{10}$ typically represent an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the HSD inhibitory activity of the compound in question. Exemplary non-interfering substituents include hydroxy, amino, halo, alkoxy, alkyl and aryl.

In some embodiments, the sulphamate group may form a ring structure by being fused to (or associated with) one or more atoms in or on group X.

In some embodiments, there may be more than one sulphamate group. By way of example, there may be two sulphamates (i.e. bis-sulphamate compounds). If these compounds are based on a steroidal nucleus, preferably the second (or at least one of the additional) sulphamate group is located at position 17 of the steroidal nucleus. These groups need not be the same.

In some preferred embodiments, at least one of $R^9$ and $R^{10}$ is H.

In some further preferred embodiments, each of $R^9$ and $R^{10}$ is H.

Phosphonate Group

If $R^1$ is a phosphonate group then the compound of the present invention is referred to as a phosphonate compound.

Typically, the phosphonate group has the formula:

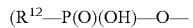

$(R^{12}\text{—}P(O)(OH)\text{—}O\text{—}$ wherein preferably $R^{12}$ is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^{12}$ is alkyl, $R^{12}$ may be a lower alkyl groups containing from 1 to 6 carbon atoms, that is to say methyl, ethyl, propyl etc. By way of example, $R^{12}$ may be methyl. When $R^6$ is aryl, typical values are phenyl and tolyl ($PhCH_3;o$). Where $R^6$ represents cycloalkyl, typical values are cyclopropyl, cyclopentyl, cyclohexyl etc. $R^{12}$ may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the HSD inhibitory activity of the compound in question. Exemplary non-interfering substituents include hydroxy, amino, halo, alkoxy, alkyl and aryl.

In some embodiments, the phosphonate group may form a ring structure by being fused to (or associated with) one or more atoms in or on group X.

In some embodiments, there may be more than one phosphonate group. By way of example, there may be two phosphonates (i.e. bis-phosphonate compounds). If these compounds are based on a steroidal nucleus, preferably the second (or at least one of the additional) phosphonate group is located at position 17 of the steroidal nucleus. These groups need not be the same.

Thiophosphonate Group

If $R^2$ is a thiophosphonate group then the compound of the present invention is referred to as a thiophosphonate compound.

Typically, the thiophosphonate group has the formula:

$(R^{13})\text{—}P(S)(OH)\text{—}O\text{—}$ wherein preferably $R^{13}$ is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^7$ is alkyl, $R^7$ may be a lower alkyl groups containing from 1 to 6 carbon atoms, that is to say methyl, ethyl, propyl etc. By way of example, $R^7$ may be methyl. When $R^{13}$ is aryl, typical values are phenyl and tolyl ($PhCH_3;o$). Where $R^{13}$ represents cycloalkyl, typical values are cyclopropyl, cyclopentyl, cyclohexyl etc. $R^{13}$ may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the HSD inhibitory activity of the compound in question. Exemplary non-interfering substituents include hydroxy, amino, halo, alkoxy, alkyl and aryl.

In some embodiments, the thiophosphonate group may form a ring structure by being fused to (or associated with) one or more atoms in or on group X.

In some embodiments, there may be more than one thiophosphonate group. By way of example, there may be two thiophosphonates (i.e. bis-thiophosphonate compounds). If these compounds are based on a steroidal nucleus, preferably the second (or at least one of the additional) thiophosphonate group is located at position 17 of the steroidal nucleus. These groups need not be the same.

Sulphonate Group

If $R^2$ is a sulphonate group then the compound of the present invention is referred to as a sulphonate compound.

Typically, the sulphonate group has the formula:

$(R^{14})\text{—}S(O)(O)\text{—}O\text{—}$ wherein preferably $R^{14}$ is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention may contain one or two N-alkyl, N-alkenyl, N-cycloalkyl or N-aryl substituents, preferably containing or each containing a maximum of 10 carbon atoms. When $R^{14}$ is alkyl, $R^{14}$ may be a lower alkyl groups containing from 1 to 6 carbon atoms, that is to say methyl, ethyl, propyl etc. By way of example, $R^{14}$ may be methyl. When $R^{14}$ is aryl, typical values are phenyl and tolyl ($PhCH_3;o$). Where $R^{14}$ represents cycloalkyl, typical values are cyclopropyl, cyclopentyl, cyclohexyl etc. $R^{14}$ may even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the HSD inhibitory activity of the compound in question. Exemplary non-interfering substituents include hydroxy, amino, halo, alkoxy, alkyl and aryl.

In some embodiments, the sulphonate group may form a ring structure by being fused to (or associated with) one or more atoms in or on group X.

In some embodiments, there may be more than one sulphonate group. By way of example, there may be two sulphonates (i.e. bis-sulphonate compounds). If these compounds are based on a steroidal nucleus, preferably the second (or at least

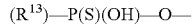

one of the additional) sulphonate group is located at position 17 of the steroidal nucleus. These groups need not be the same.

Combination of Sulphonate/Phosphonate/Thiophosphonate/Sulphamate

For some compounds of the present invention there may be present one of a sulphonate as herein defined or a phosphonate as herein defined or a thiophosphonate as herein defined or a sulphamate as herein defined; and another of a sulphonate as herein defined or a phosphonate as herein defined or a thiophosphonate as herein defined or a sulphamate as herein defined. By way of example, the compound of the present invention may comprise one sulphamate group and one phosphonate group.

If these compounds of the present invention are based on a steroidal nucleus, preferably the other of said groups is located at position 17 of the steroidal nucleus.

Assay for Determining STS Activity Using Cancer Cells (Protocol 1)

Inhibition of Steroid Sulphatase Activity in MCF-7 Cells

Steroid sulphatase activity is measured in vitro using intact MCF-7 human breast cancer cells. This hormone dependent cell line is widely used to study the control of human breast cancer cell growth. It possesses significant steroid sulphatase activity (Macindoe et al. Endocrinology, 123, 1281-1287 (1988); Purohit & Reed, Int. J. Cancer, 50, 901-905 (1992)) and is available in the U.S.A. from the American Type Culture Collection (ATCC) and in the U.K. (e.g. from The Imperial Cancer Research Fund).

Cells are maintained in Minimal Essential Medium (MEM) (Flow Laboratories, Irvine, Scotland) containing 20 mM HEPES, 5% foetal bovine serum, 2 mM glutamine, non-essential amino acids and 0.075% sodium bicarbonate. Up to 30 replicate 25 cm2 tissue culture flasks are seeded with approximately $1 \times 10^5$ cells/flask using the above medium. Cells are grown to 80% confluency and the medium is changed every third day.

Intact monolayers of MCF-7 cells in triplicate 25 cm$^2$ tissue culture flasks are washed with Earle's Balanced Salt Solution (EBSS from ICN Flow, High Wycombe, U.K.) and incubated for 3-4 hours at 37° C. with 5 pmol ($7 \times 10^5$ dpm) [6,7-3H]oestrone-3-sulphate (specific activity 60 Ci/mmol from New England Nuclear, Boston, Mass., U.S.A.) in serum-free MEM (2.5 ml) together with oestrone-3-sulphamate (11 concentrations: 0; 1 fm; 0.01 pM; 0.1 pM; 1 pM; 0.01 nM; 0.1 nM; 1 nM; 0.01 mM; 0.01 mM; 1 mM). After incubation each flask is cooled and the medium (1 ml) is pipetted into separate tubes containing [14C]oestrone ($7 \times 103$ dpm) (specific activity 97 Ci/mmol from Amersham International Radiochemical Centre, Amersham, U.K.). The mixture is shaken thoroughly for 30 seconds with toluene (5 ml). Experiments have shown that>90% [14C] oestrone and<0.1% [3H]oestrone-3-sulphate is removed from the aqueous phase by this treatment. A portion (2 ml) of the organic phase is removed, evaporated and the 3H and 14C content of the residue determined by scintillation spectrometry. The mass of oestrone-3-sulphate hydrolysed was calculated from the 3H counts obtained (corrected for the volumes of the medium and organic phase used, and for recovery of [14C] oestrone added) and the specific activity of the substrate. Each batch of experiments includes incubations of microsomes prepared from a sulphatase-positive human placenta (positive control) and flasks without cells (to assess apparent non-enzymatic hydrolysis of the substrate). The number of cell nuclei per flask is determined using a Coulter Counter after treating the cell monolayers with Zaponin. One flask in each batch is used to assess cell membrane status and viability using the Trypan Blue exclusion method (Phillips, H. J. (1973) In: Tissue culture and applications, [eds: Kruse, D. F. & Patterson, M. K.]; pp. 406-408; Academic Press, New York).

Results for steroid sulphatase activity are expressed as the mean±1 S.D. of the total product (oestrone+oestradiol) formed during the incubation period (20 hours) calculated for 106 cells and, for values showing statistical significance, as a percentage reduction (inhibition) over incubations containing no oestrone-3-sulphamate. Unpaired Student's t-test was used to test the statistical significance of results.

Assay for Determining STS Activity Using Placental Microsomes (Protocol 2)

Inhibition of Steroid Sulphatase Activity in Placental Microsomes

Sulphatase-positive human placenta from normal term pregnancies are thoroughly minced with scissors and washed once with cold phosphate buffer (pH 7.4, 50 mM) then re-suspended in cold phosphate buffer (5 ml/g tissue). Homogenisation is accomplished with an Ultra-Turrax homogeniser, using three 10 second bursts separated by 2 minute cooling periods in ice. Nuclei and cell debris are removed by centrifuging (4° C.) at 2000 g for 30 minutes and portions (2 ml) of the supernatant are stored at 20° C. The protein concentration of the supernatants is determined by the method of Bradford (Anal. Biochem., 72, 248-254 (1976)).

Incubations (1 ml) are carried out using a protein concentration of 100 mg/ml, substrate concentration of 20 mM [6,7-3H]oestrone-3-sulphate (specific activity 60 Ci/mmol from New England Nuclear, Boston, Mass., U.S.A.) and an incubation time of 20 minutes at 37° C. If necessary eight concentrations of compounds are employed: 0 (i.e. control); 0.05 mM; 0.1 mM; 0.2 mM; 0.4 mM; 0.6 mM; 0.8 mM; 1.0 mM. After incubation each sample is cooled and the medium (1 ml) was pipetted into separate tubes containing [14C]oestrone ($7 \times 103$ dpm) (specific activity 97 Ci/mmol from Amersham International Radiochemical Centre, Amersham, U.K.). The mixture is shaken thoroughly for 30 seconds with toluene (5 ml). Experiments have shown that>90% [14C]oestrone and<0.1% [3H]oestrone-3-sulphate is removed from the aqueous phase by this treatment. A portion (2 ml) of the organic phase was removed, evaporated and the 3H and 14C content of the residue determined by scintillation spectrometry. The mass of oestrone-3-sulphate hydrolysed is calculated from the 3H counts obtained (corrected for the volumes of the medium and organic phase used, and for recovery of [14C]oestrone added) and the specific activity of the substrate.

Animal Assay Model for Determining STS Activity (Protocol 3)

Inhibition of Oestrone Sulphatase Activity in Vivo

The compounds of the present invention may be studied using an animal model, in particular in ovariectomised rats. In this model compounds which are oestrogenic stimulate uterine growth.

The compound (10 mg/Kg/day for five days) was administered orally to rats with another group of animals receiving vehicle only (propylene glycol). A further group received the compound EMATE subcutaneously in an amount of 10 μg/day for five days. At the end of the study samples of liver tissue were obtained and oestrone sulphatase activity assayed using 3H oestrone sulphate as the substrate as previously described (see PCT/GB95/02638).

Animal Assay Model for Determining Oestrogenic Activity (Protocol 4)

Lack of in Vivo Oestrogenicity

The compounds of the present invention may be studied using an animal model, in particular in ovariectomised rats. In this model, compounds which are oestrogenic stimulate uterine growth.

The compound (10 mg/Kg/day for five days) was administered orally to rats with another group of animals receiving vehicle only (propylene glycol). A further group received the estrogenic compound EMATE subcutaneously in an amount of 10 μg/day for five days. At the end of the study uteri were obtained and weighed with the results being expressed as uterine weight/whole body weight×100.

Compounds having no significant effect on uterine growth are not oestrogenic.

Biotechnological Assays for Determining STS Activity (Protocol 5)

The ability of compounds to inhibit oestrone sulphatase activity can also be assessed using amino acid sequences or nucleotide sequences encoding STS, or active fragments, derivatives, homologues or variants thereof in, for example, high-through put screens.

Any one or more of appropriate targets—such as an amino acid sequence and/or nucleotide sequence—may be used for identifying an agent capable of modulating STS in any of a variety of drug screening techniques. The target employed in such a test may be free in solution, affixed to a solid support, borne on a cell surface, or located intracellularly. The abolition of target activity or the formation of binding complexes between the target and the agent being tested may be measured.

The assay of the present invention may be a screen, whereby a number of agents are tested. In one aspect, the assay method of the present invention is a high through put screen.

Techniques for drug screening may be based on the method described in Geysen, European Patent Application 84/03564, published on Sep. 13, 1984. In summary, large numbers of different small peptide test compounds are synthesised on a solid substrate, such as plastic pins or some other surface. The peptide test compounds are reacted with a suitable target or fragment thereof and washed. Bound entities are then detected—such as by appropriately adapting methods well known in the art. A purified target can also be coated directly onto plates for use in a drug screening techniques. Alternatively, non-neutralising antibodies can be used to capture the peptide and immobilise it on a solid support.

This invention also contemplates the use of competitive drug screening assays in which neutralising antibodies capable of binding a target specifically compete with a test compound for binding to a target.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

In one preferred aspect, the present invention relates to a method of identifying agents that selectively modulate STS, which compounds have the formula (Ia).

Reporters

A wide variety of reporters may be used in the assay methods (as well as screens) of the present invention with preferred reporters providing conveniently detectable signals (e.g. by spectroscopy). By way of example, a reporter gene may encode an enzyme which catalyses a reaction which alters light absorption properties.

Other protocols include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes may even be used. These and other assays are described, among other places, in Hampton R et al (1990, Serological Methods, A Laboratory Manual, APS Press, St Paul Minn.) and Maddox D E et al (1983, J Exp Med 15 8:121 1).

Examples of reporter molecules include but are not limited to (β-galactosidase, invertase, green fluorescent protein, luciferase, chloramphenicol, acetyltransferase, (-glucuronidase, exo-glucanase and glucoamylase. Alternatively, radiolabelled or fluorescent tag-labelled nucleotides can be incorporated into nascent transcripts which are then identified when bound to oligonucleotide probes.

By way of further examples, a number of companies such as Pharmacia Biotech (Piscataway, N.J.), Promega (Madison, Wis.), and US Biochemical Corp (Cleveland, Ohio) supply commercial kits and protocols for assay procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752 ; 3,939,350; 3,996,345; 4,277,437; 4,275,149 and U.S. Pat. No. 4,366,241.

Host Cells

The term "host cell"—in relation to the present invention includes any cell that could comprise the target for the agent of the present invention.

Thus, a further embodiment of the present invention provides host cells transformed or transfected with a polynucleotide that is or expresses the target of the present invention. Preferably said polynucleotide is carried in a vector for the replication and expression of polynucleotides that are to be the target or are to express the target. The cells will be chosen to be compatible with the said vector and may for example be prokaryotic (for example bacterial), fungal, yeast or plant cells.

The gram negative bacterium *E. coli* is widely used as a host for heterologous gene expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus *Bacillus* are very suitable as heterologous hosts because of their capability to secrete proteins into the culture medium. Other bacteria suitable as hosts are those from the genera *Streptomyces* and *Pseudomonas*.

Depending on the nature of the polynucleotide encoding the polypeptide of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

Examples of suitable expression hosts within the scope of the present invention are fungi such as *Aspergillus* species (such as those described in EP-A-0184438 and EP-A-0284603) and *Trichoderma* species; bacteria such as *Bacillus* species (such as those described in EP-A-0134048 and EP-A-0253455), *Streptomyces* species and *Pseudomonas* species; and yeasts such as *Kluyveromyces* species (such as those described in EP-A-0096430 and EP-A-0301670) and *Saccharomyces* species. By way of example, typical expression hosts may be selected from *Aspergillus niger, Aspergillus niger* var. *tubigenis, Aspergillus niger* var. *awamori, Aspergillus aculeatis, Aspergillus nidulans, Aspergillus orvzae, Trichoderma reesei, Bacillus subtilis, Bacillus licheniformis, Bacillus amyloliquefaciens, Kluyveromyces lactis* and *Saccharomyces cerevisiae*.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.
Organism The term "organism" in relation to the present invention includes any organism that could comprise the target according to the present invention and/or products obtained therefrom. Examples of organisms may include a fungus, yeast or a plant.

The term "transgenic organism" in relation to the present invention includes any organism that comprises the target according to the present invention and/or products obtained.
Transformation of Host Cells/Host Organisms As indicated earlier, the host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the nucleotide sequence may need to be suitably modified before transformation—such as by removal of introns.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401-429, Allen and Unwin, London) and by King et al (1989, Molecular and Cell Biology of Yeasts, E F Walton and G T Yarronton, eds, pp 107-133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

A review of the principles of heterologous gene expression in *Saccharomyces cerevisiae* and secretion of gene-products is given by E Hinchcliffe E Kenny (1993, "Yeast as a vehicle for the expression of heterologous genes", Yeasts, Vol 5, Anthony H Rose and J Stuart Harrison, ads, 2nd edition, Academic Press Ltd.).

Several types of yeast vectors are available, including integrative vectors, which require recombination with the host genome for their maintenance, and autonomously replicating plasmid vectors.

In order to prepare the transgenic *Saccharomyces*, expression constructs are prepared by inserting the nucleotide sequence into a construct designed for expression in yeast. Several types of constructs used for heterologous expression have been developed. The constructs contain a promoter active in yeast fused to the nucleotide sequence, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic *Saccharomyces* according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163-168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, e.g. G418.

Another host organism is a plant. The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205-225) and Christou (Agro-Food-Industry Hi-Tech March/April 1994 17-27). Further teachings on plant transformation may be found in EP-A-0449375.

Thus, the present invention also provides a method of transforming a host cell with a nucleotide sequence that is to be the target or is to express the target. Host cells transformed with the nucleotide sequence may be cultured under conditions suitable for the expression of the encoded protein. The protein produced by a recombinant cell may be displayed on the surface of the cell. If desired, and as will be understood by those of skill in the art, expression vectors containing coding sequences can be designed with signal sequences which direct secretion of the coding sequences through a particular prokaryotic or eukaryotic cell membrane. Other recombinant constructions may join the coding sequence to nucleotide sequence encoding a polypeptide domain which will facilitate purification of soluble proteins (Kroll D J et al (1993) DNA Cell Biol 12:441-53).
Variants/Homologues/Derivatives In addition to the specific amino acid sequences and nucleotide sequences mentioned herein, the present invention also encompasses the use of variants, homologue and derivatives thereof. Here, the term "homology" can be equated with "identity".

In the present context, an homologous sequence is taken to include an amino acid sequence which may be at least 75, 85 or 90% identical, preferably at least 95 or 98% identical. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is -12 for a gap and -4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

A further useful reference is that found in FEMS Microbiol Lett 1999 May 15;174(2):247-50 (and a published erratum appears in FEMS Microbiol Lett 1999 Aug. 1;177(1):187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below.

Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Expression Vectors

The nucleotide sequence for use as the target or for expressing the target can be incorporated into a recombinant replicable vector. The vector may be used to replicate and express the nucleotide sequence in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The protein produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Fusion Proteins

The target amino acid sequence may be produced as a fusion protein, for example to aid in extraction and purification. Examples of fusion protein partners include glutathione-S-transferase (GST), 6xHis, GAL4 (DNA binding and/or transcriptional activation domains) and (-galactosidase. It may also be convenient to include a proteolytic cleavage site between the fusion protein partner and the protein sequence of interest to allow removal of fusion protein sequences. Preferably the fusion protein will not hinder the activity of the target.

The fusion protein may comprise an antigen or an antigenic determinant fused to the substance of the present invention. In this embodiment, the fusion protein may be a non-naturally occurring fusion protein comprising a substance which may act as an adjuvant in the sense of providing a generalised stimulation of the immune system. The antigen or antigenic determinant may be attached to either the amino or carboxy terminus of the substance.

In another embodiment of the invention, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

Therapy

The compounds of the present invention may be used as therapeutic agents—i.e. in therapy applications.

The term "therapy" includes curative effects, alleviation effects, and prophylactic effects.

The therapy may be on humans or animals, preferably female animals.

Pharmaceutical Compositions

In one aspect, the present invention provides a pharmaceutical composition, which comprises a compound according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Combination Pharmaceutical

The compound of the present invention may be used in combination with one or more other active agents, such as one or more other pharmaceutically active agents.

By way of example, the compounds of the present invention may be used in combination with other STS inhibitors and/or other inhibitors such as an aromatase inhibitor (such as for example, 4hydroxyandrostenedione (4-OHA)) and/or steroids—such as the naturally occurring stemeurosteroids dehydroepiandrosterone sulfate (DHEAS) and pregnenolone sulfate (PS) and/or other structurally similar organic compounds. Examples of other STS inhibitors may be found in the above references. By way of example, STS inhibitors for use in the present invention include EMATE, and either or both of the 2-ethyl and 2-methoxy 17-deoxy compounds that are analogous. to compound 5 presented herein.

In addition, or in the alternative, the compound of the present invention may be used in combination with a biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc. For some applications, preferably, the biological response modifier is a cytokine. Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)—such as TNF-$\alpha$; Interferon alpha, beta and gamma; TGF-$\beta$. For some applications, preferably the cytokine is tumour necrosis factor (TNF). For some applications, the TNF may be any type of TNF—such as TNF-$\alpha$, TNF-$\beta$, including derivatives or mixtures thereof. More preferably the cytokine is TNF-$\alpha$. Teachings on TNF may be found in the art—such as WO-A-98/08870 and WO-A-98/13348.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous; subcutaneous, intraocular or transdermal administration. Depending upon the need, the agent may be administered at a dose of from 0.01 to 30 mg/kg body weight, such as from 0.1 to 10 mg/kg, more preferably from 0.1 to 1 mg/kg body weight.

By way of further example, the agents of the present invention may be administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing, therapy.

Aside from the typical modes of delivery—indicated above—the term "administered" also includes delivery by techniques such as lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Thus, for pharmaceutical administration, the STS inhibitors of the present invention can be formulated in any suitable manner utilising conventional pharmaceutical formulating techniques and pharmaceutical carriers, adjuvants, excipients, diluents etc. and usually for parenteral administration. Approximate effective dose rates may be in the range from 1 to 1000 mg/day, such as from 10 to 900 mg/day or even from 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

Cell Cycling

The compounds of the present invention may be useful in the method of treatment of a cell cycling disorder.

As discussed in "Molecular Cell Biology" 3rd Ed. Lodish et al. pages 177-181 different eukaryotic cells can grow and divide at quite different rates. Yeast cells, for example, can divide every 120 min., and the first divisions of fertilised eggs in the embryonic cells of sea urchins and insects take only 1530 min. because one large pre-existing cell is subdivided. However, most growing plant and animal cells take 10-20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been thoroughly analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_0$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA; during S (DNA replication), it has between x and 2x, and when in $G_2$ (or M), it has 2x of DNA.

The stages of mitosis and cytokinesis in an animal cell are as follows (a) Interphase.

The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope. In a diploid cell before DNA replication there are two morphologic chromosomes of. each type, and the cell is said to be 2n. In $G_2$, after DNA replication, the cell is 4n. There are four copies of each chromosomal DNA. Since the sister chromosomes have not yet separated from each other, they are called sister chromatids.

b) Early Prophase.

Centrioles, each with a newly formed daughter centriole, begin moving toward opposite poles of the cell; the chromosomes can be seen as long threads. The nuclear membrane begins to disaggregate into small vesicles.

(c) Middle and Late Prophase.

Chromosome condensation is completed; each visible chromosome structure is composed of two chromatids held together at their centromeres. Each chromatid contains one of the two newly replicated daughter DNA molecules. The microtubular spindle begins to radiate from the regions just adjacent to the centrioles, which are moving closer to their poles. Some spindle fibres reach from pole to pole; most go to chromatids and attach at kinetochores.

(d) Metaphase.

The chromosomes move toward the equator of the cells where they become aligned in the equatorial plane. The sister chromatids have not yet separated.

(e) Anaphase.

The two sister chromatids separate into independent chromosomes. Each contains a centromere that is linked by a spindle fibre to one pole, to which it moves. Thus one copy of each chromosome is donated to each daughter call. Simultaneously, the cell elongates, as do the pole-to-pole spindles. Cytokinesis begins as the cleavage furrow starts to form.

(f) Telophase.

New membranes form around the daughter nuclei; the chromosomes uncoil and become less distinct, the nucleolus becomes visible again, and the nuclear membrane forms around each daughter nucleus. Cytokinesis is nearly complete, and the Spindle disappears as the microtubules and other fibres depolymerise. Throughout mitosis the "daughter" centriole at each pole grows until it is full-length. At telophase. the duplication of each of the original centrioles is completed, and new daughter centrioles will be generated during the next interphase.

(g) Interphase.

Upon the completion of cytokinesis, the cell enters the $G_1$ phase of the cell cycle and proceeds again around the cycle.

It will be appreciated that cell cycling is an extremely important cell process. Deviations from normal cell cycling can result in a number of medical disorders. Increased and/or unrestricted cell cycling may result in cancer. Reduced cell cycling may result in degenerative conditions. Use of the compound of the present invention may provide a means to treat such disorders and conditions.

Thus, the compound of the present invention may be suitable for use in the treatment of cell cycling disorders such as cancers, including hormone dependent and hormone independent cancers.

In addition, the compound of the present invention may be suitable for the treatment of cancers such as breast cancer, ovarian cancer, endometrial cancer, sarcomas, melanomas, prostate cancer, pancreatic cancer etc. and other solid tumours.

For some applications, cell cycling is inhibited and/or prevented and/or arrested, preferably wherein cell cycling is prevented and/or arrested. In one aspect cell cycling may be inhibited and/or prevented and/or arrested in the $G_2/M$ phase. In one aspect cell cycling may be irreversibly prevented and/ or inhibited and/or arrested, preferably wherein cell cycling is irreversibly prevented and/or arrested.

By the term "irreversibly prevented and/or inhibited and/or arrested" it is meant after application of a compound of the present invention, on removal of the compound the effects of the compound, namely prevention and/or inhibition and/or arrest of cell cycling, are still observable. More particularly by the term "irreversibly prevented and/or inhibited and/or arrested" it is meant that when assayed in accordance with the cell cycling assay protocol presented herein, cells treated with a compound of interest show less growth after Stage 2 of the protocol I than control cells. Details on this protocol are presented below.

Thus, the present invention provides compounds which: cause inhibition of growth of oestrogen receptor positive (ER+) and ER negative (ER−) breast cancer cells in vitro by preventing and/or inhibiting and/or arresting cell cycling; and/or cause regression of nitroso-methyl urea (NMU) induced mammary tumours in intact animals (i.e. not ovariectomised), and/or prevent and/or inhibit and/or arrest cell cycling in cancer cells; and/or act in vivo by preventing and/or inhibiting and/or arresting cell cycling and/or act as a cell cycling agonist.

Cell Cycling Assay (Protocol 6)

Procedure
Stage 1

MCF-7 breast cancer cells are seeded into multi-well culture plates at a density of 105 cells/well. Cells were allowed to attach and grown until about 30% confluent when they are treated as follows:

Control—no treatment
Compound of Interest (COI) 20 μM

Cells are grown for 6 days in growth medium containing the COI with changes of medium/COI every 3 days. At the end of this period cell numbers were counted using a Coulter cell counter.

Stage 2

After treatment of cells for a 6-day period with the COI cells are re-seeded at a density of $10^4$ cells/well. No further treatments are added. Cells are allowed to continue to grow for a further 6 days in the presence of growth medium. At the end of this period cell numbers are again counted.

Assay for Determining DH Activity Using Cancer Cells (Protocol 7)

Conversion of oestrone to oestradiol (E1→E2, E2DH Type I) and oestradiol to oestrone (E2→E1, E2DH Type II) was measured in intact cell monolayers of T47D and MDA-MB-231 breast cancer cells respectively. Cells were cultured in flasks until they were 80-90% confluent. $^3$H-E1 or $^3$H-E2 (6 pmol, ~90 Ci/mmol) were added to each flask in the absence (control) or presence of various test compounds (10 μM) in 2.5 ml of medium. Substrate was also added to flasks without cells and incubated in parallel (blanks).

After incubation with T47D cells for 30 min or MDA cells for 3 h at 37° C., 2 ml of the medium was added to test tubes containing $^{14}$C-E2 or $^{14}$C-E1 (~5000 cpm) and 50 μg E2 or E1 respectively. Steroids were extracted from the aqueous medium with diethyl ether (4 ml). The ether phase was decanted into separate tubes after freezing the aqueous phase in solid carbon dioxide-methanol mixture. The ether was evaporated to dryness under a stream of air at 40° C. The residue was dissolved in a small volume of diethyl ether and applied to TLC plates containing a fluorescent indicator. E1 and E2 were separated by TLC using DCM-Ethyl acetate (4:1 v/v). The position of the product from each incubation flask was marked on the TLC plate after visualisation under UV light. The marked regions were cut out and placed in scintillation vials containing methanol (0.5 ml) to elute the product. The amount of $^3$H-product formed and $^{14}$C-E1 or $^{14}$C-E2 recovered were calculated after scintillation spectrometry. The amount of product formed was corrected for procedural losses and for the number of cells in each flask.

Cancer

As indicated, the compounds of the present invention may be useful in the treatment of a cell cycling disorder. A particular cell cycling disorder is cancer.

Cancer remains a major cause of mortality in most Western countries. Cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

It is known that oestrogens undergo a number of hydroxylation and conjugation reactions after their synthesis. Until recently it was thought that such reactions were part of a metabolic process that ultimately rendered oestrogens water soluble and enhanced their elimination from the body. It is now evident that some hydroxy metabolites (e.g. 2-hydroxy and 16alpha-hydroxy) and conjugates (e.g. oestrone sulphate, E1S) are important in determining some of the complex actions that oestrogens have in the body.

Workers have investigated the formation of 2- and 16-hydroxylated oestrogens in relation to conditions that alter the risk of breast cancer. There is now evidence that factors which increase 2-hydroxylase activity are associated with a reduced cancer risk, while those increasing 16alpha-hydroxylation may enhance the risk of breast cancer. Further interest in the biological role of oestrogen metabolites has been stimulated by the growing body of evidence that 2-methoxyoestradiol is an endogenous metabolite with anti-mitotic properties. 2-MeOE2 is formed from 2-hydroxy oestradiol (2-OHE2) by catechol oestrogen methyl transferase, an enzyme that is widely distributed throughout the body.

Workers have shown that in vivo 2-MeOE2 inhibits the growth of tumours arising from the subcutaneous injection of Meth A sarcoma, B16 melanoma or MDA-MB-435 oestrogen receptor negative (ER−) breast cancer cells. It also inhibits endothelial cell proliferation and migration, and in vitro angiogenesis. It was suggested that the ability of 2-MeOE2 to inhibit tumour growth in vivo may be due to its ability to inhibit tumour-induced angiogenesis rather than direct inhibition of the proliferation of tumour cells.

The mechanism by which 2-MeOE2 exerts its potent anti-mitogenic and anti-angiogenic effects is still being elucidated. There is evidence that at high concentrations it can inhibit microtubule polymerisation and act as a weak inhibitor of colchicine binding to tubulin. Recently, however, at concentrations that block mitosis, tubulin filaments in cells were not found to be depolymerised but to have an identical morphology to that seen after taxol treatment. It is possible, therefore, that like taxol, a drug that is used for breast and ovarian breast cancer therapy, 2-MeOE2 acts by stabilising microtubule dynamics.

While the identification of 2-MeOE2 as a new therapy for cancer represents an important advance, the bioavailability of orally administered oestrogens is poor. Furthermore, they can undergo extensive metabolism during their first pass through the liver. As part of a research programme to develop a steroid sulphatase inhibitor for breast cancer therapy, oestrone-3-O-sulphamate (EMATE) was identified as a potent active site-directed inhibitor. Unexpectedly, EMATE proved to possess potent oestrogenic properties with its oral uterotrophic activity in rats being a 100-times higher than that of oestradiol. Its enhanced oestrogenicity is thought to result from its absorption by red blood cells (rbcs) which protects it from inactivation during its passage through the liver and which act as a reservoir for its slow release for a prolonged period of time. A number of A-ring modified analogues were synthesised and tested, including 2-methoxyoestrone-3-O-sulphamate. While this compound was equipotent with EMATE as a steroid sulphatase inhibitor, it was devoid of oestrogenicity.

We believe that the compound of the present invention provides a means for the treatment of cancers and, especially, breast cancer.

In addition or in the alternative the compound of the present invention may be useful in the blocking the growth of cancers including leukaemias and solid tumours such as breast, endometrium, prostate, ovary and pancreatic tumours.

Therapy Concerning Oestrogen

We believe that some of the compounds of the present invention may be useful in the control of oestrogen levels in the body—in particular in females. Thus, some of the compounds may be useful as providing a means of fertility control—such as an oral contraceptive tablet, pill, solution or lozenge. Alternatively, the compound could be in the form of an implant or as a patch.

Thus, the compounds of the present invention may be useful in treating hormonal conditions associated with oestrogen.

In addition or in the alternative the compound of the present invention may be useful in treating hormonal conditions in addition to those associated with oestrogen. Hence, the compound of the present invention may also be capable of affecting hormonal activity and may also be capable of affecting an immune response.

Neurodegenerative Diseases

We believe that some of the compounds of the present invention may be useful in the treatment of neurodegenerative diseases, and similar conditions.

By way of example, it is believed that STS inhibitors may be useful in the enhancing the memory function of patients suffering from illnesses such as amnesia, head injuries, Alzheimer's disease, epileptic dementia, presenile dementia, post traumatic dementia, senile dementia, vascular dementia and post-stroke dementia or individuals otherwise seeking memory enhancement.

TH1

We believe that some of the compounds of the present invention may be useful in TH1 implications.

By way of example, it is believed that the presence of STS inhibitors within the macrophage or other antigen presenting cells may lead to a decreased ability of sensitised T cells to mount a TH1 (high IL-2, IFNγ low IL-4) response. The normal regulatory influence of other steroids such as glucocorticoids would therefore predominate.

Inflammatory Conditions

We believe that some of the compounds of the present invention may be useful in treating inflammatory conditions—such as conditions associated with any one or more of: autoimmunity, including for example, rheumatoid arthritis, type I and II diabetes, systemic lupus erythematosus, multiple sclerosis, myasthenia gravis, thyroiditis, vasculitis, ulcerative colitis and Crohn's disease, skin disorders e.g. psoriasis and contact dermatitis; graft versus host disease; eczema; asthma and organ rejection following transplantation.

By way of example, it is believed that STS inhibitors may prevent the normal physiological effect of DHEA or related steroids on immune and/or inflammatory responses.

The compounds of the present invention may be useful in the manufacture of a medicament for revealing an endogenous glucocorticoid-like effect Other Therapies It is also to be understood that the compound/composition of the present invention may have other important medical implications.

For example, the compound or composition of the present invention may be useful in the treatment of the disorders listed in WO-A-99/52890—viz:

In addition, or in the alternative, the compound or composition of the present invention may be useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the compound or composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g.; treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as unregulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Sulphamate Compound Preparation

The sulphamate compounds of the present invention may be prepared by reacting an appropriate alcohol with a suitable chloride. By way of example, the sulphamate compounds of the present invention may be prepared by reacting an appropriate alcohol with a suitable sulfamoyl chloride, of the formula $R^9R^{10}NSO_2Cl$.

Typical conditions for carrying out the reaction are as follows.

Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporated with toluene affords a crude residue which is further purified by flash chromatography.

Preferably, the alcohol is derivatised, as appropriate, prior to reaction with the sulfamoyl chloride. Where necessary, functional groups in the alcohol may be protected in known manner and the protecting group or groups removed at the end of the reaction.

Preferably, the sulphamate compounds are prepared according to the teachings of Page et al (1990 Tetrahedron 46; 2059-2068).

The phosphonate compounds may be prepared by suitably combining the teachings of Page et al (1990 Tetrahedron 46; 2059-2068) and PCT/GB92/01586.

The sulphonate compounds may be prepared by suitably adapting the teachings of Page et al (1990 Tetrahedron 46; 2059-2068) and PCT/GB92/01586.

The thiophosphonate compounds may be prepared by suitably adapting the teachings of Page et al (1990 Tetrahedron 46; 2059-2068) and PCT/GB91/00270.

Preferred preparations are also presented in the following text.

SUMMARY

In summation, the present invention provides compounds for use as steroid dehydrogenase inhibitors, and pharmaceutical compositions for the same.

EXAMPLES

The present invention will now be described only by way of example.

Example

Section 1

16-(4-Dimethylamino-benzylidene)-3-hydroxy-13-methyl-6,7,8,9,11,12,13,14,15,16-decahydro-cyclopenta[a]phenanthron-17-one

STX477 (CAB02143, GMA01044)

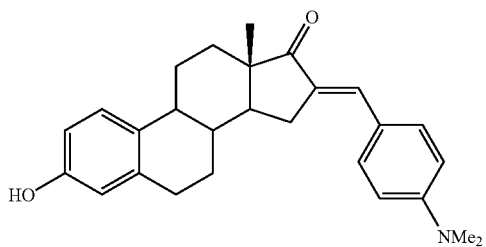

To a stirred suspension of estrone (4.05 g, 15 mmol) and 4-dimethylaminobenzaldehyde (2.24 g, 15 mmol) in ethanol (120 cm³) was added sodium hydroxide (3.0 g, 75 mmol) and the resulting yellow solution was stirred at room temperature for 72 h. To this solution was added glacial acetic acid (20 cm³) and the resulting yellow precipitate was collected by filtration and washed with water (100 cm³), ethanol (50 cm³), diethyl ether (50 cm³) and hexane (100 cm³) before being dried under reduced pressure. Yield 66%. $^1$H NMR (400 MHz, DMSO-$d_6$) δ 0.86 (s, 3H), 1.34-1.61 (m, 6H), 1.82-1.86 (m, 1H), 1.98-2.02 (m, 1H), 2.15-2.19 (m, 1H), 2.32-2.34 (m, 1H), 2.73-2.86 (m, 3H), 2.97 (s, 6H), 6.45 (d, J=2.7 Hz, 1H), 6.51 (appdd, J=8.4, 2.5 Hz, 1H), 6.74 (d, J=8.6 Hz, 2H), 7.04 (d, J=8.6 Hz, 1H), 7.20 (s, 1H), 7.48 (d, J=8.6 Hz, 2H), 9.02 (s, 1H); MS (FAB+) calcd. 401.2, obsd. 402.2 (M+H$^+$)

16-(4-Dimethylamino-benzylidene)-13-methyl-7,8,9,11,12,13,14,15,16,17-decahydro-6H-cyclopenta[a]phenanthrene-3,17-diol

STX511 (CAB02158, GMA01006)

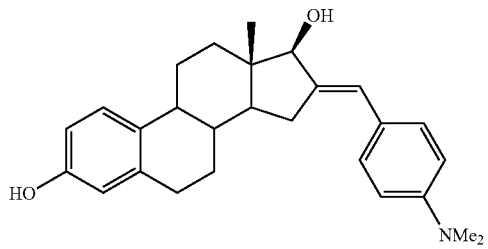

To a cooled (ice bath) solution of 16-(4-dimethylaminobenzylidene estrone (0.402 g, 1 mmol) in THF (20 cm³) and ethanol (20 cm³) was added NaBH$_4$ (0.100 g, 2.6 mmol) and the reaction was allowed to warm to room temperature and stirred overnight. The mixture was concentrated in vacuo until precipitate began to appear before water (50 cm³) was added to precipitate the product as a white powder. This powder was collected by filtration and washed with water (50 cm³), methanol (20 cm³) and diethyl ether (50 cm³). before being dried under reduced pressure. Yield 86%. $^1$H NMR (400 MHz, DMSO-$d_6$) δ 0.59 (s, 3H), 1.24-1.43 (m, 6H), 1.84-1.95 (m, 1H), 2.08-2.20 (m, 2H), 2.26-2.34 (m, 1H), 2.55-2.65 (m, 1H), 2.70-2.80 (m, 2H), 2.89 (s, 6H), 3.95 (s, 1H), 4.99 (d, J=6.2 Hz, 1H), 6.27 (d, J=2.0 Hz, 1H), 6.45 (d, J=2.7 Hz, 1H), 6.51 (appdd, J=8.4, 2.5 Hz, 1H), 6.70 (d, J=9.0 Hz, 2H), 7.05 (d, J=8.6 Hz, 1H), 7.22 (d, J=9.0 Hz, 2H), 9.01 (s, 1H); HPLC (98%, Rt=3.52, 10:90 H$_2$O:MeOH); MS (FAB+) calcd. 403.3, obsd. 403.2 (M$^+$)

General Procedure for Hydrogenation Reactions:

The starting 16-methylene estradiol was dissolved in a volume of THF and the same volume of ethanol added to the solution. The solution was then degassed by bubbling nitrogen through for 40 min before Pd/C (5% wt., catalytic) was added and hydrogen gas (balloon) was passed over the reaction. The reaction was stirred under hydrogen at room temperature overnight before being filtered through celite.

16-(4-Dimethylamino-benzyl)-13-methyl-7,8,9,11,12,13,14,15,16,17-decahydro-6H-cyclopenta[a]phenanthrene-3,17-diol

STX594 (GMA01008)

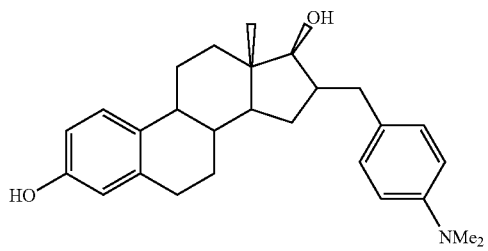

Purification by column chromatography using hexane followed by 20% ethyl acetate in hexane as eluent gave the product, R$_f$ 0.33 (20% EtOAc in hexane), in 45% yield. $^1$H NMR (400 MHz, DMSO-$d_6$) δ 0.75 (S, 3H), 0.92-1.08 (M, 2H), 1.10-1.36 (M, 4H), 1.49-1.55 (m, 1H), 1.66-1.71 (m, 1H), 1.87 (d, J=12.1 Hz, 1H), 2.13 (d, J=13.3 Hz, 1H), 2.19-2.29 (m, 2H), 2.58-2.73 (m, 2H), 2.83 (s, 6H), 2.88-2.93 (m, 1H), 3.63-3.66 (m, 1H), 4.60 (d, J=4.7 Hz, 1H), 6.41 (d, J=2.3 Hz, 1H), 6.49 (dd, J=8.2, 2.7 Hz), 6.64 (d, J=9.0 Hz, 2H), 6.99 (d, J=8.6 Hz, 2H), 7.03 (d, J=8.2 Hz, 1H), 8.98 (s, 1H, OH); HPLC (92%, Rt=3.28, 10:90 H$_2$O:MeOH); MS (FAB+) calcd 405.2, obsd 405.2 (M$^+$), Acc. Mass (FAB+) calcd 405.2668, obsd 405.2668 (M$^+$)

13-Methyl-16-pyridin-2-ylmethyl-7,8,9,11,12,13,14,15,16,17-decahydro-6H-cyclopenta[□]phenanthrene-3-17-diol

STX567 (GMA01018)

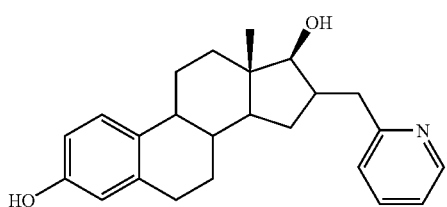

Purification by column chromatography using 100% hexane to 100% ethyl acetate as eluent gave the product, R$_f$ 0.1 (25% EtOAc 75% hexane), in 57% yield. $^1$H NMR (400 MHz, DMSO-d$_6$) δ □0.76 (s, 3H), 1.04-1.07 (m, 2H), 1.15-1.36 (m, 6H), 1.55-1.60 (m, 1H), 1.64-1.71 (m, 1H), 1.87 (d, J=2.1 Hz, 1H), 2.20-2.25 (m, 1H), 2.60-2.72 (m, 3H), 3.12 (d, J=8.6 Hz, 1H), 3.68-3.71 (m, 1H), 4.97 (d, J=4.7 Hz, 1H), 6.41 (d, J=2.7 Hz, 1H), 6.49 (dd, J=8.4, 2.5 Hz, 1H), 7.04 (d, J=8.2 Hz, 1H), 7.15-7.19 (m, 1H), 7.25 (d, J=7.8 Hz, 1H), 7.67 (dt, J=7.6, 2.0 Hz, 1H), 8.44-8.465 (m, 1H), 8.99 (s, 1H); HPLC (98%, Rt=2.62, 10:90 H$_2$O:MeOH); MS (FAB+) calcd 363.2, obsd 364.1 (M+H$^+$), Acc. Mass (FAB+) calcd 364.2276, obsd 364.2297 (M+H$^+$)

13-Methyl-16-pyridin-3-ylmethyl-7,8,9,11,12,13,14,15,16,17-decahydro-6H-cyclopenta[a]phenanthrene-3,17-diol

STA 542 (GMA01022)

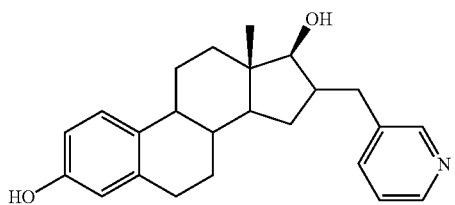

Purification by column chromatography using 100% hexane to 100% ethyl acetate as eluent gave the product, (R$_f$ 0.1 (25% EtOac in hexane) in 88% yield. $^1$H NMR (270 MHz, DMSO-d$_6$) δ □0.76 (s, 3H), 1.00-1.04 (m, 2H), 1.20-1.35 (m, 5H), 1.54-1.56 (m, 1H), 1.73-1.90 (m, 2H), 2.13-2.32 (m, 3H), 2.64 (m, 2H), 3.01 (d, J=9.4 Hz, 1H), 4.77 (d, J=4.5 Hz, 1H), 6.41 (d, J=2.5 Hz, 1H), 6.49 (dd, J=8.4, 2.5 Hz, 1H), 7.03 (d, J=8.4 Hz, 1H), 7.25-7.31 (m, 1H), 7.60-7.64 (m, 1H), 8.34-8.39 (m, 1H), 8.41 (d, J=1.7 Hz, 1H), 9.02 (s, 1H); HPLC (97%, Rt=2.50, 10:90 H$_2$O:MeOH); MS (FAB+) calcd 363.2, obsd 364.1 (M+H$^+$), Acc. Mass (FAB+) calcd. 364.2276, obsd 364.2287 (M+H$^+$)

13-Methyl-16-pyridin-4-ylmethyl-7,8,9,11,12,13,14,15,16,17-decahydro-6H-cyclopenta[a]phenanthrene-3,17-diol

STX543 (GMA01020)

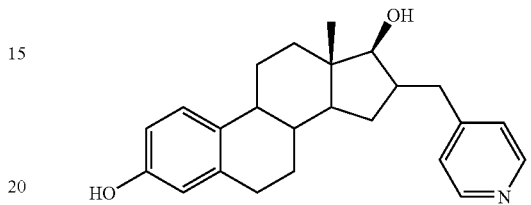

Purification by column chromatography using 100% hexane to 100% ethyl acetate as eluent. Gave the product, (R$_f$ 0.1 (25% EtOAc 75% hexane) in 96% yield; $^1$H NMR (400 MHz, DMSO-d$_6$) δ □0.76 (s, 3H), 0.94-1.10 (m, 2H), 1.12-1.36 (m, 5H), 1.54-1.60 (m, 1H), 1.65-1.71 (m, 1H), 1.85-1.89 (m, 1H), 2.20-2.42 (m, 3H), 2.64-2.68 (m, 2H), 2.98-3.02 (m, 1H), 3.66-3.70 (m, 1H), 4.75 (d, J=4.7 Hz, 1H), 6.40 (d, J=2.3 Hz, 1H), 6.49 (dd, J=8.4, 2.5 Hz, 1H), 7.03 (d, J=8.2 Hz, 1H), 7.23 (d, J=6.2 Hz, 2H), 8.41 (d, J=5.9 Hz, 2H), 8.99 (s, 1H); HPLC (92%, Rt=2.44, 10:90 H$_2$O:MeOH); MS (FAB+) calcd 363.2, obsd 364.1 (M+H$^+$), Acc. Mass (FAB+) calcd 364.2276, obsd 364.2294 (M+H$^+$)

Acetic acid 8-acetyl-6a-methyl-4b,5,6,6a,8,10,10a,10b,11,12-decahydro-7,8-diaza-pentaleno[2,1-a]phenanthene-2-yl ester (GMA01110)

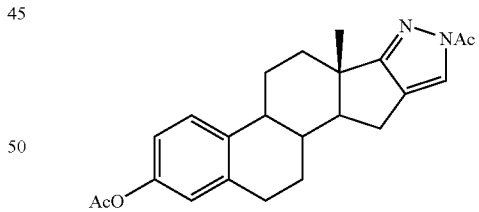

To a solution of the starting pyrazole (0.598 g, 2 mmol) in dry pyridine (8 cm$^3$) was added acetic anhydride (2 cm$^3$) and the mixture was refluxed under nitrogen for 16 h. The mixture was then cooled and poured onto ice and the resulting cream coloured precipitate was collected by filtration and purified by column chromatography using ethyl acetate/hexane (1/1), R$_f$ 0.48. Yield: 40%. $^1$H NMR (270 MHz, CDCl$_3$) δ □1.07 (s, 3H), 1.40-1.60 (m, H), 1.62-2.10 (m, 5H), 2.28 (s, 3H, OAc), 2.28-2.48 (m, 4H), 2.64 (s, 3H, OAc), 2.64-2.72 (m, 1H), 2.87-2.96 (m, 2H), 6.82 (d, J=2.2 Hz, H), 6.86 (appdd, J=8.4, 2.5 Hz, 1H), 7.30 (d=8.4 Hz, 1H), 7.86 (s, 1H); LCMS (ES+) 380.23 (M+2H$^+$)

Acetic acid 8-acetyl-6a-methyl-12-oxo-4b,5,6,6a,8,10,10a,10b,11,12-decahydro-7,8-diaza-pentaleno-[2,1-a]phenanthren-2-yl ester (GMA01120)

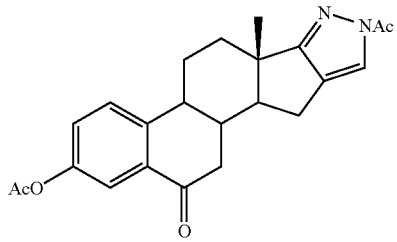

To a solution of the bis-acetate protected pyrazole starting material (0.121 g, 0.32 mmol) in acetonitrile (2.5 cm$^3$) was added t-butylhydroperoxide (0.14 cm$^3$ of a 70% wt. solution in water, 1 mmol) and chromium hexacarbonyl (0.021 g, 0.09 mmol). The solution was heated to reflux for 24 h before being cooled to room temperature. Water (10 cm$^3$) was added and the products extracted with diethyl ether (3×10 cm$^3$). The ether extracts were combined, washed with water, aqueous saturated bicarbonate and brine before being dried (MgSO$_4$) and concentrated in vacuo. The desired product was isolated by flash column chromatography using ethyl acetate/hexane (1/1) as eluent (R$_f$ 0.4). Yield 23%, $^1$H NMR (400 MHz, CDCl$_3$) δ □1.09 (s, 3H), 1.8-2.0 (m, 2H), 2.2-2.5 (m, 4H), 2.33 (s, 3H), 2.5-2.9 (m, 5H), 2.65 (s, 3H), 7.34 (dd, J=2.5, 8.4 Hz, 1H), 7.65 (d, J=8.6 Hz, 1H), 7.79 (d, J=2.3 Hz, 1H), 7.88 (s, 1H)

2-Hydroxy-6a-methyl-5,6,6a,8,10,10a,10b,11-octahydro-4bH-7,8-diazo-pentaleno[2,1-a]phenanthren-12-one

STX737 (GMA01138)

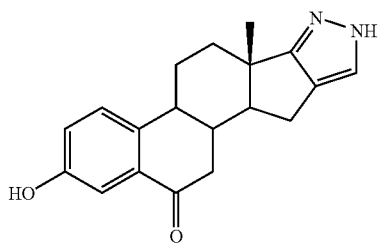

The bis-acetate protected starting material (0.0137 g) was dissolved in ethanol (1 cm$^3$). To this was added a solution of KOH (0.004 g) in ethanol/water (2 cm$^3$ of 1/1) and the mixture was shaken then left at room temperature for 30 min. TLC at this stage showed no starting material remaining therefore the mixture was acidified with glacial acetic acid, concentrated in vacuo and water added. The solution was left standing overnight during which time a pale orange precipitate formed. This powder was collected by filtration. Yield 46%. $^1$H NMR (400 MHz, DMSO-D$_6$) δ □0.91 (s, 3H), 1.60-1.82 (m, 2H), 2.1-2.35 (m, 4H), 2.4-2.7 (m, 5H), 7.02 (dd, J=8.6, 2.7 Hz, 1H), 7.29 (d, J=2.7 Hz, 1H), 7.34 (d, J=8.6 Hz, 1H), 9.65 (s, 1H), 12.04 (bs, 1H); LCMS: (ES+) 309.99 (M+2H$^+$); Acc. Mass (FAB$^+$) calcd 309.16030, obsd. 309.16132 (M+H$^+$)

6a-Methyl-4b,5,6,6a,8,10,10a,10b,11,12-decahydro-7,8-diaza-pentaleno[2,1-a]phenanthrene-2,9-diol

STX820 (GMA02024)

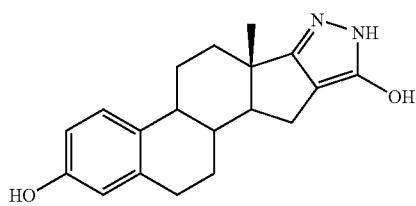

To a suspension of the starting ester (0.657 g, 2 mmol) in toluene (10 cm$^3$) was added hydrazine monohydrate (0.11 cm$^3$, 2.2 mmol) and the mixture was heated at 150° C. in a sealed tube for 4 h. During this time the starting material dissolved then another white precipitate formed. The reaction was then cooled to room temperature, acidified with glacial acetic acid and water was added to ensure that all product precipitated. The white powder was collected by filtration and washed with water, a small amount of ethanol, diethyl ether and hexane. LCMS showed two compounds with masses corresponding to the desired product (312) and the hydrazone derivative of estrone (285). Flash chromatography using 10% methanol in DCM to 100% methanol failed to separate these. Recrystallisation was attempted by suspending the solid in ethanol then slowly adding aqueous NaOH until the solid dissolved, followed by acidification to pH3 with glacial acetic acid. No precipitate formed initially therefore a small amount of water was added until a fine white powder precipitated. This was shown by LCMS and HPLC to be the desired product. Yield of pure product, 18%; total product recovered, 50%. $^1$H NMR (400 MHz, DMSO-d$_6$) δ □0.89 (s, 3H), 1.30-1.70 (m, 4H), 1.80-1.87 (m, 1H), 1.93-2.11 (m, 3H), 2.17-2.40 (m, 3H), 2.71-2.78.(m, 2H), 6.43 (d, J=2.2 Hz, 1H), 6.50 (dd, J=8.1, 2.6 Hz, 1H), 7.03 (d, J=8.4 Hz, 1H), 9.01 (s, 1H), 10.3 (bs, 1H); HPLC (100%, Rt=2.33, 20:80 H$_2$O:MeOH); LCMS (APCI) 311.29 (M+H$^+$), Acc. Mass (FAB+) calcd. 311.1759, obsd. 311.1761 (M+H$^+$)

General Procedure for Amide Coupling Using a Radleys GreenHouse Synthesiser.

To a solution of the acid starting material (0.107 g, 0.25 mmol) in dry DCM (2 cm$^3$) and triethylamine (0.02 cm$^3$, 0.18 mmol) was added a solution of EDC (0.058 g, 0.3 mmol) triethylamine (0.017 cm$^3$, 0.16 mmol) and DMAP (catalytic) in dry DCM (1 cm$^3$) under nitrogen and the reaction was stirred at room temperature for 30 min. To this solution was then added amine (1.1 eq) and stirring under nitrogen was continued for 12 h, followed by standing under nitrogen for 14 h. The solution was then washed with saturated aqueous NaHCO$_3$ before separation and concentration of the organic layer and purification by flash chromatography.

2-Benzyloxy-6a-methyl-4b,5,6,6a,8,10,10a,10b,11,12-decahydro-7,8-diaza-pentaleno[2,1-a]phenanthrene-9-carboxylic acid isopropylamide (GMA02038-6)

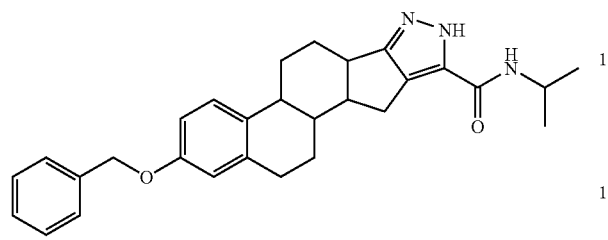

Yield 16%. $R_f$ 0.72 (EtOAc); $^1$H NMR (270 MHz, CDCl$_3$) δ 0.97 (s, 3H), 1.18 (s, 3H), 1.20 (s, 3H), 1.37-1.92 (m, 5H), 2.08-2.46 (m, 5H), 2.71 (dd, J=13.9, 6.2 Hz, 1H), 2.83-2.90 (m, 2H), 4.13-4.26 (m, 1H), 4.98 (S, 2H), 5.83 (bs, 1H), 6.68 (d, J=2.9 Hz, 1H), 6.73 (dd, J=8.4, 2.9 Hz, 1H), 7.15 (d, J=8.4 Hz, 1H), 7.22-7.38 (m, 5H); LCMS (ES+) 470.37 (M+H$^+$)

2-Hydroxy-6a-methyl-4b,5,6,6a,8,10,10a,10b,11,12-decahydro-7,8-diaza-pentaleno[2,1-a]phenanthrene-9-carboxylic acid isopropyl amide

STX857 (GMA02046)

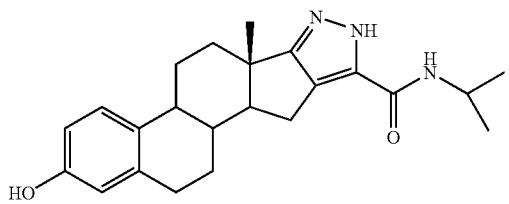

A solution of the benzyl protected starting material (0.020 g, 0.04 mmol) in THF (5 cm$^3$) and ethanol (5 cm$^3$) was degassed by bubbling nitrogen through for 30 min before Pd/C (5% wt., catalytic) was added and hydrogen gas (balloon) was passed over the reaction. Stirring at room temperature under a hydrogen blanket was continued overnight before the mixture was filtered through celite and the celite washed with ethyl acetate and methanol. The filtrate was concentrated in vacuo to give a white solid, $R_f$ 0.60 (EtOAc). Yield 0.096 g, 63%. $^1$H NMR (270 MHz, CDCl$_3$) δ 0.97 (s, 3H), 1.25 (s, 3H), 1.27 (s, 3H), 1.47-1.95 (m, 4H), 2.13-2.53 (m, 6H), 2.77 (dd, J=13.9, 6.2 Hz, 1H), 2.87-2.94 (m, 2H), 4.19-4.30 (m, 1H), 5.88 (d, J=8.1 Hz, 1H), 6.60 (d, J=2.93 Hz, 1H), 6.65 (dd, J=8.3, 2.93 Hz, 1H), 7.16 (d, J=8.4 Hz, 1H); HPLC (95%, Rt=1.72, 4:96 H$_2$O:MeOH); LCMS (AP−) 378.35 (M−H$^+$)

2-Hydroxy-6a-methyl-4b,5,6,6a,8,10,10a,10b,11,12-decahydro-7,8-diaza-pentaleno[2,1-a]phenanthrene-9-carboxylic acid (pyridin-3-ylmethyl)-amide

STX860 (GMA02056/3)

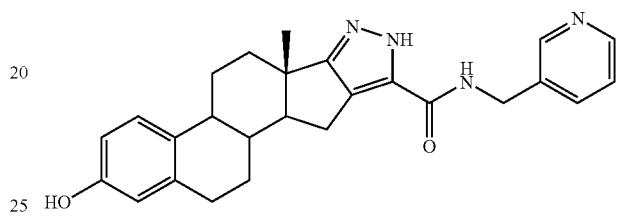

To a suspension of acid starting material (0.170 g, 0.5 mmol) in dry DCM (10 cm$^3$) under nitrogen was added DMAP (catalytic), EDC (0.116 g, 0.6 mmol) and triethylamine (0.06 cm$^3$, 0.55 mol) and the solution was stirred at room temperature for 20 min. To this mixture was added 3-(aminomethyl) pyridine (0.06 cm$^3$, 0.55 mmol), followed by dry DMF (10 cm$^3$) to ensure complete dissolution of starting materials, and the reaction was stirred at room temperature under nitrogen for 24 h. The solution was washed with saturated aqueous bicarbonate and the organic layer separated and concentrated in vacuo. To the resulting concentrated solution (in DMF) was added hexane followed by a small amount of DCM. The resulting cream-coloured precipitate was collected by filtration and purified by flash chromatography using DCM followed by 10% MeOH in DCM as eluent, giving a white crystalline solid. $R_f$ 0.40 (10% MeOH in DCM), Yield 0.034 g, 16%. $^1$H NMR (400 MHz, DMSO-d$_6$) δ ☐0.92 (s, 3H), 1.37-2.36 (m, 10H), 2.63-2.89 (m, 3H), 4.41 (appd, J=22.3 Hz, 2H), 6.44 (d, J=2.3 Hz, 1H), 6.51 (dd, J=8.2, 2.3 Hz, 1H), 7.04 (d, J=8.2 Hz, 1H), 7.33 (apps, 1H), 7.69 (apps, 1H), 7.69-8.63 (m, 3H), 9.02 (s, 1H), 12.65 & 12.92 (s, 0.5H, tautomers NH on pyrazole ring); HPLC (98%, Rt=2.04, 10:90 H$_2$O:MeOH); LCMS (ES+) 429.19 (M+H$^+$)

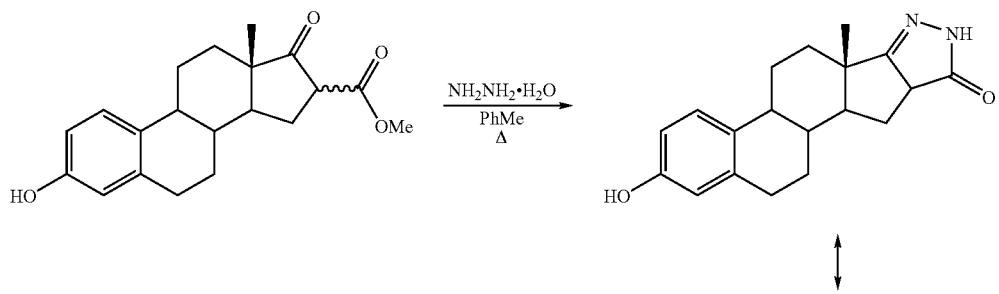

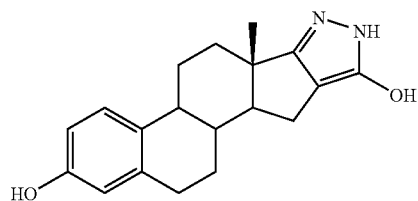
Route to STX820
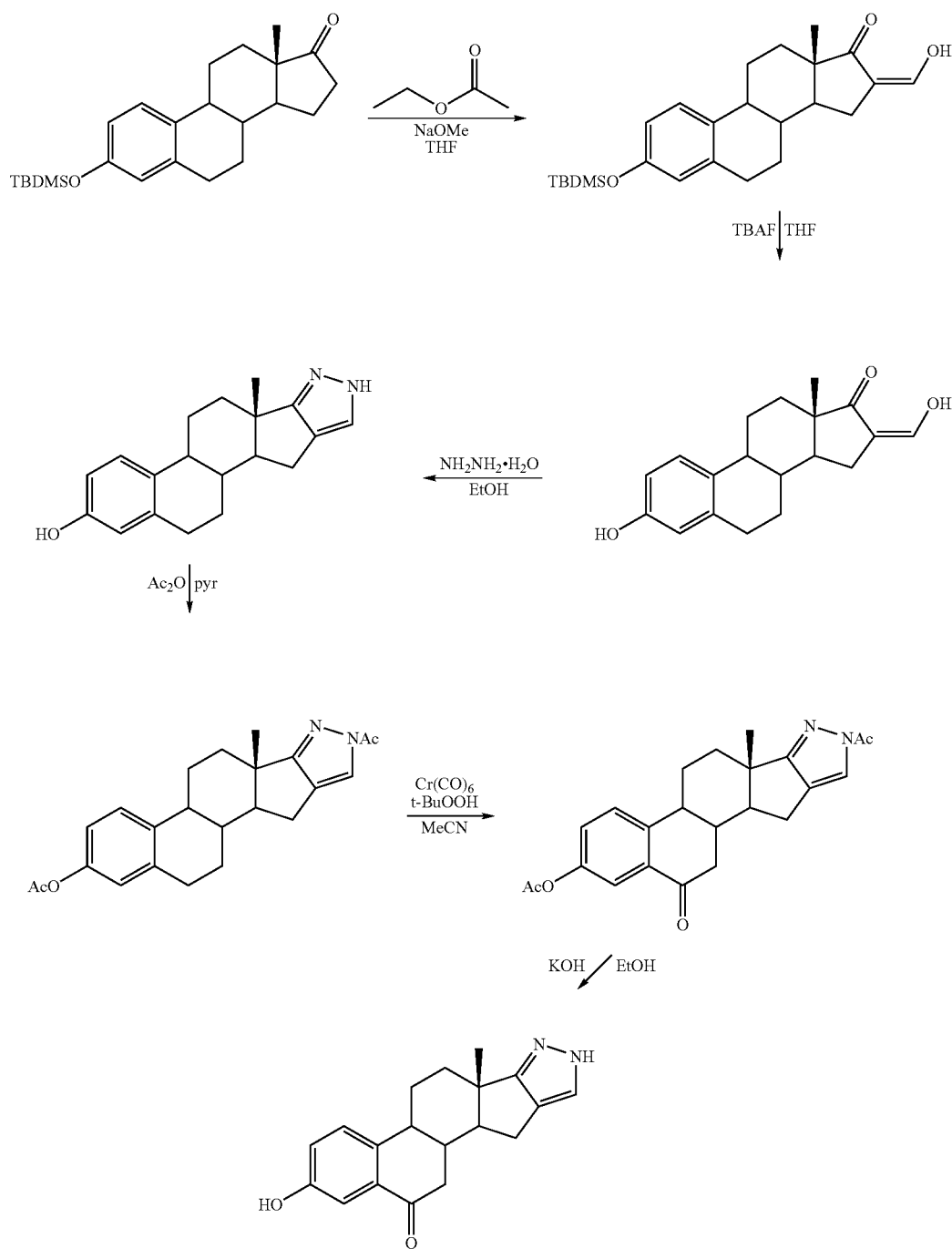

Route to STX737

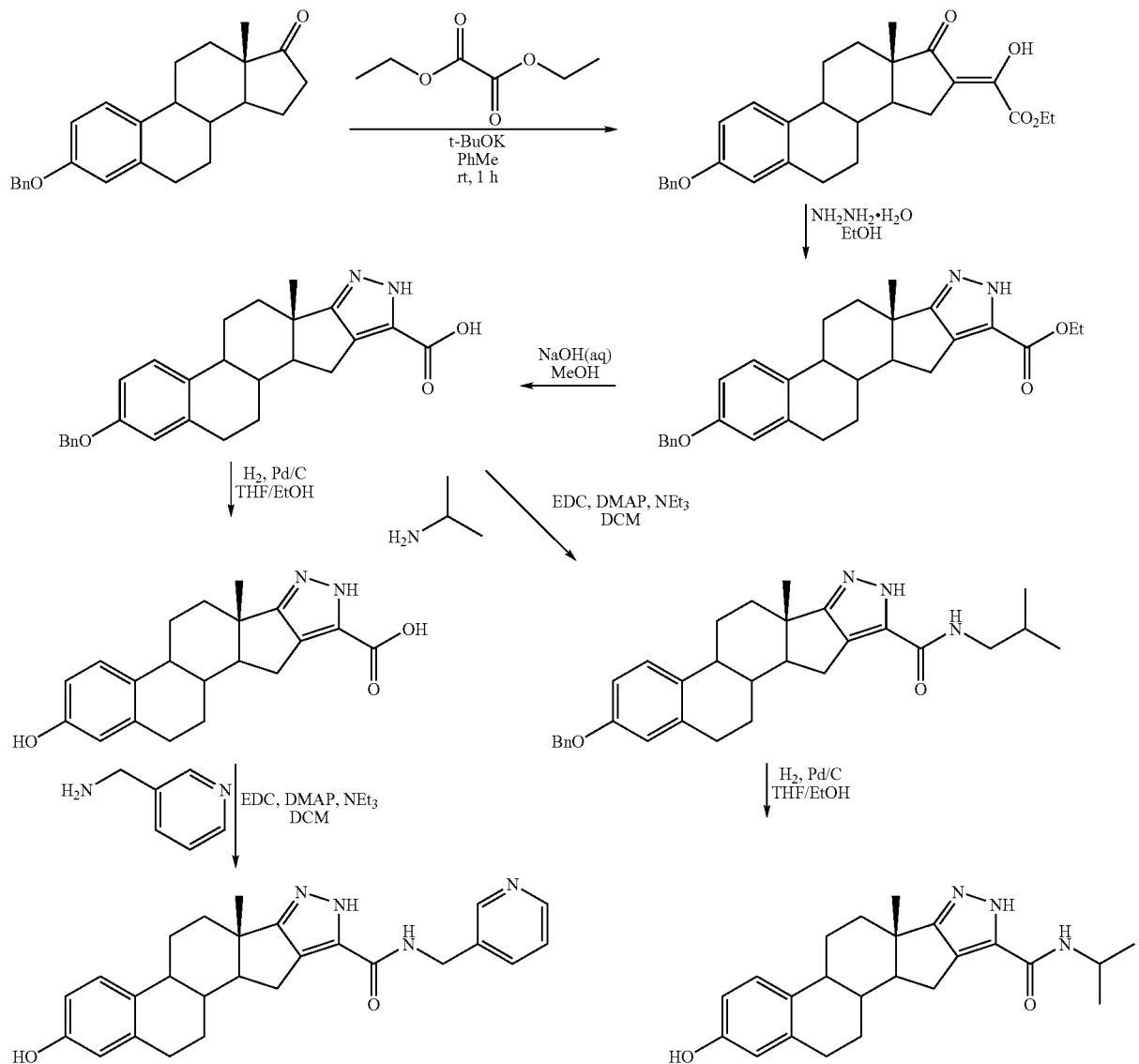

Routes to STX857 and STX860

GMA03034 [3-(tert-Butyl-dimethyl-silanyloxy)-2-ethyl-13-methyl-17-oxo-6,7,8,9,11,12,13,14,15,17-decahydro-cyclopenta[a]phenanthren-16-ylidene]-hydroxy-acetic acid ethyl ester

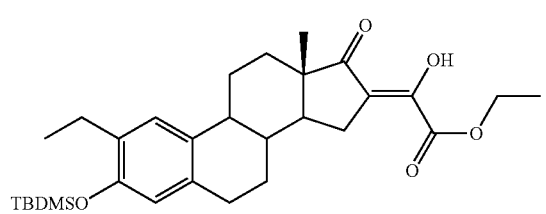

To a stirred solution of TBDMS protected estrone (1.275 g, 3.1 mmol) in toluene (30 cm$^3$) was added diethyl oxalate (0.84 cm$^3$, 6.2 mmol) and potassium t-butoxide (0.45 g, 4 mmol) and the reaction was stirred at rt overnight. The reaction was acidified with glacial acetic acid and concentrated in vacuo before ethyl acetate (30 cm$^3$) was added. The solution was washed with water (30 cm$^3$) and brine (30 cm$^3$) before being concentrated in vacuo to give a white powder. This powder was washed with ethanol/water and collected by filtration. Yield quantitative.

$^1$H NMR δ (270 MHz, CDCl$_3$) 0.21 (s, 6H, (CH$_3$)$_2$Si), 0.98 (s, 3H, 18-CH$_3$), 0.99 (s, 9H, (CH$_3$)$_3$C), 1.15 (t, J=7.5 Hz, 3H, ArCH$_2$CH$_3$), 1.38 (t, J=7.2 Hz, 3H, OCH$_2$CH$_3$), 1.54-1.69 (m, 6H), 2.00-2.05 (m, 2H), 2.27-2.47 (m, 3H), 2.55 (q, J=7.5 Hz, 2H, ArCH$_2$CH$_3$), 2.80-2.86 (m, 2H), 3.03-3.11 (m, 1H), 4.35 (q, J=7.2 Hz, 2H, OCH$_2$CH$_3$), 6.48 (s, 1H, 4-H), 7.03 (s, 1H, 1-H); FAB-LRMS (MH$^+$) 513.3 m/z; FAB-HRMS calcd for C$_{30}$H$_{44}$O$_2$Si 512.2958 found (M$^+$) 512.2965 m/z

GMA03035 2-(tert-Butyl-dimethyl-silanyloxy)-3-ethyl-6a-methyl-4b,5,6,6a,8,10,10a,10b,11,12-decahydro-7,8-diaza-pentaleno[2,1-a]phenanthrene-9-carboxylic acid ethyl ester.

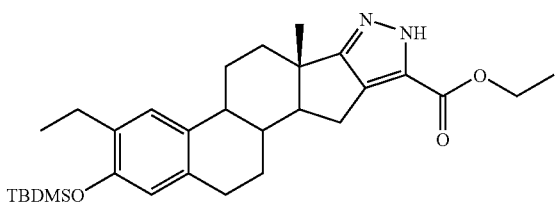

To a stirred suspension of sm (1.53 g, 3 mmol) in ethanol (25 cm$^3$) was added hydrazine monohydrate (9.17 cm$^3$, 3.4 mmol) at which time the sm dissolved. Stirring at room temperature was continued overnight during which time the solution became cloudy. To this was added p-toluene sulphonic acid (~0.1 g) and the mixture was heated for 5 min to aromatise the pyrazole ring. The solution was concentrated in vacuo until precipitate began to form before water was added and the white powder was collected by filtration, washed with water and air-dried. Yield ~quantitative. $^1$H NMR δ (270 MHz, CDCl$_3$) 0.22 (s, 6H, (CH$_3$)$_2$Si), 0.98 (s, 3H, 18-CH$_3$), 0.99 (s, 9H, (CH$_3$)$_3$C), 1.16 (t, J=7.5 Hz, 3H, ArCH$_2$CH$_3$), 1.37 (t, J=7.1 Hz, 3H, OCH$_2$CH$_3$), 1.40-2.18 (6H), 2.30-2.50 (4H), 2.56 (q, J=7.5 Hz, 2H, ArCH$_2$CH$_3$), 2.81-2.96 (m, 3H), 4.35 (q, J=7.1 Hz, 2H, OCH$_2$CH$_3$), 6.49 (s, 1H, 4-H), 7.06 (s, 1H, 1-H); HPLC>96% (R$_t$=6.69, 100% MeCN); FAB-LRMS (MH$^+$) 509.2 m/z; FAB-HRMS calcd for C$_{34}$H$_{41}$N$_2$O$_3$ 509.3168 found (MH$^+$) 509.3178 m/z
STX1066, GMA02187

3-Ethyl-2-hydroxy-6a-methyl-4b,5,6,6a,8,10,10a,10b,11,12-decahydro-7,8-diaza-pentaleno[2,1-a]phenanthrene-9-carboxylic acid

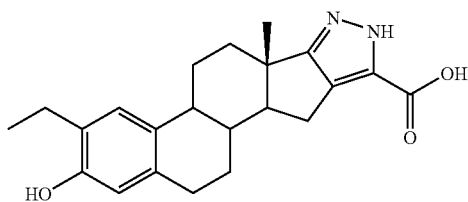

To a stirred suspension of sm (1.27 g, 2.64 mmol) in MeOH (30 cm$^3$) was added aqueous NaOH (0.211 g in 16 cm$^3$) and the mixture was refluxed overnight (the sm dissolved on heating). The reaction was cooled, acidified with glacial acetic acid and concentrated in vacuo until precipitate began to form (~half volume). Water (20 cm$^3$) was added and the resulting precipitate was collected by filtration. This was dissolved in methanol, concentrated and dried in vacuo. Yield 57%.

(400 MHz, CD$_3$OD) 1.02 (s, 3H, 18-CH$_3$), 1.16 (t, J=7.4 Hz, 3H, ArCH$_2$CH$_3$), 1.36-1.47 (m, 1H), 1.56-1.83 (3H), 1.93-1.99 (m, 1H), 2.02-2.15 (m, 1H), 2.22-2.28 (m, 2H), 2.36-2.43 (m, 2H), 2.55 (q, J=7.4 Hz, 2H, ArCH$_2$CH$_3$), 2.72-2.90 (m, 3H), 6.44 (s, 1H, 4-H), 6.95 (s, 1H, 1-H); HPLC>92% (R$_t$=1.49, 70% MeCN in H$_2$O); ES-ve-MS (M-H$^+$) 365.16 m/z; FAB-HRMS calcd for C$_{22}$H$_{27}$N$_2$O$_3$ 367.2022 found (MH$^+$) 367.2010 m/z General Procedure for Amide Coupling:

To a stirred suspension of acid sm (0.045 g, 0.123 mmol) in dry DCM (8 cm$^3$) under N$_2$ was added DMAP (catalytic), EDC (0.071 g, 0.37 mmol) and NEt$_3$ (0.02 cm$^3$) and the solution was stirred at rt for 30 min. To this was then added amine (0.02 cm$^3$) and stirring was continued for 4 d. The solution was washed with saturated bicarbonate, the organic layer separated and the aqueous layer washed with DCM. The organic layers were combined and concentrated in vacuo and the product purified by flash chromatography (Flashmaster II) using an elution gradient of DCM to 10%, MeOH in DCM.
STX1013, GMA02188

3-Ethyl-2-hydroxy-6a-methyl-4b,5,6,6a,8,10,10a,10b,11,12-decahydro-7,8-diaza-pentaleno[2,1-a]phenanthrene-9-carboxylic acid (pyridin-3-ylmethyl)-amide

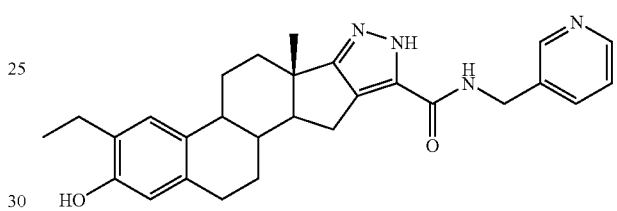

Yield 39%; $^1$H NMR δ (270 MHz, CD$_3$OD) 1.03 (s, 3H, 18-CH$_3$), 1.15 (t, J=7.4 Hz, 3H, ArCH$_2$CH$_3$), 1.39-1.52 (m, 1H), 1.59-1.87 (m, 3H), 1.94-2.00 (m, 1H), 2.14-2.50 (5H), 2.55 (q, J=7.4 Hz, 2H, ArCH$_2$CH$_3$), 2.78-2.90 (3H), 4.58 (s, 2H), 6.45 (s, 1H, 4-H), 6.97 (s, 1H, 1-H), 7.38-7.43 (m, 1H), 7.85 (d, J=7.7 Hz, 1H), 8.43 (d, J=3.7 Hz, 1H), 8.56 (s, 1H); HPLC>97% (R$_t$2.11, 70% MeCN in H$_2$O); ES+ve-MS (MH$^+$) 457.38 m/z; FAB-HRMS calcd for C$_{28}$H$_{33}$N$_4$O$_2$ 457.2603 found (MH$^+$) 457.2589 m/z
STX1144, GMA03074-1

3-Ethyl-2-hydroxy-6a-methyl-4b,5,6,6a,8,10,10a,10b,11,12-decahydro-7,8-diaza-pentalano[2,1-a]phenanthrene-9-carboxylic acid (pyridin-2-ylmethyl)-amide

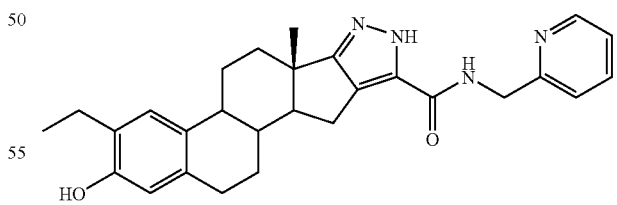

Yield 41%; $^1$H NMR δ (270 MHz, CD$_3$OD) 1.01 (s, 3H, 18-CH$_3$), 1.14 (t, J=7.4 Hz, 3H, ArCH$_2$CH$_3$), 1.31-1.47 (m, 1H), 1.57-1.83 (m, 3H), 1.93-2.00 (m, 1H), 2.14-2.50 (5H), 2.54 (q, J=7.4 Hz, 2H, ArCH$_2$CH$_3$), 2.71-2.86 (3H), 4.64 (s, 2H), 6.44 (s, 1H, 4-H), 6.95 (s, 1H, 1-H), 7.27-7.31 (m, 1H), 7.45 (d, J=8.0 Hz, 1H), 7.78 (dt, J=7.7, 1.6 Hz, 1H), 8.48 (d, J=4.7 Hz, 1H); HPLC>92% (R$_t$2.15, 80% MeCN in H$_2$O); ES-ve-MS (M-H$^+$) 455.36 m/z; FAB-HRMS calcd for C$_{28}$H$_{33}$N$_4$O$_2$ 457.2603 found (MH$^+$) 457.2607 m/z

STX1084, GMA03056-2

3-Ethyl-2-hydroxy-6a-methyl-4b,5,6,6a,8,10,10a,10b,11,12-decahydro-7,8-diaza-pentaleno[2,1-a]phenanthrene-9-carboxylic acid (2-pyridin-2-yl-ethyl)-amide

STX1145, GMA03074.2

3-Ethyl-2-hydroxy-6a-methyl-4b,5,6,6a,8,10,10a,10b,11,12-decahydro-7,8-diaza-pentaleno[2,1-a]phenanthrene-9-carboxylic acid (2-methoxy-ethyl)-amide

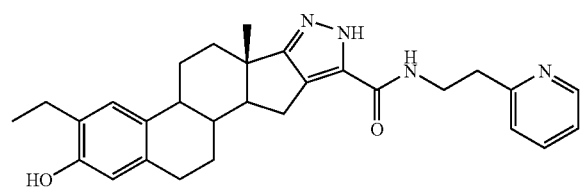

Yield 46%; $^1$H NMR δ (270 MHz, CD$_3$OD) 1.00 (s, 3H, 18-CH$_3$), 1.14 (t, J=7.5 Hz, 3H, ArCH$_2$CH$_3$), 1.33-1.49 (m, 1H), 1.54-1.83 (3H), 1.93-2.02 (m, 1H), 2.04-2.43 (5H), 2.54 (q, J=7.5 Hz, 2H, CH$_2$CH$_3$), 2.71-2.90 (3H), 3.07 (t, J=7.1 Hz, 2H, —CH$_2$CH$_2$—), 3.70 (dt, J=6.9, 1.7 Hz, 2H, —CH$_2$CH$_2$), 6.45 (s, 1H, 4-H), 6.96 (s, 1H, 1-H), 7.26-7.31 (m, 1H), 7.36 (d, J=7.7 Hz, 1H), 7.77 (dt, J=7.7, 1.7 Hz, 1H), 8.47-8.50 (m, 1H); HPLC>97% (R$_t$ 3.41, 70% MeCN in H$_2$O); ES–ve–MS (M–H$^+$) 469.55 m/z; FAB-HRMS calcd for C$_{29}$H$_{35}$N$_4$O$_2$ 471.2760 found (MH$^+$) 471.2747 m/z

STX1085, GMA03056-1

3-Ethyl-2-hydroxy-6a-methyl-4b,5,6,6a,8,10,10a,10b,11,12-decahydro-7,8-diaza-pentaleno[2,1-a]phenanthrene-9-carboxylic acid (2-pyridin-3-yl-ethyl)-amide Yield 36%; $^1$H NMR δ (270 MHz, CD$_3$OD) 1.02 (s, 3H, 18-CH$_3$), 1.15 (t, J=7.4 Hz, 3H, ArCH$_2$CH$_3$), 1.34-1.50 (m, 1H), 1.53-1.85 (m, 3H), 1.93-2.00 (m, 1H), 2.17-2.47 (5H), 2.54 (q, J=7.4 Hz, 2H, —CH$_2$CH$_3$), 2.73-2.87 (3H), 3.3-3.4 (4H, —CH$_2$CH$_2$—), 3.53 (s, 3H, O—CH$_3$), 6.45 (s, 1H, 4-H), 6.96 (s, 1H, 1-H), HPLC>96%; (R$_t$ 2.11, 80% MeCN in H$_2$O); ES–ve–MS (M–H$^+$) 422.35 m/z; FAB-HRMS calcd for C$_{25}$H$_{34}$N$_3$O$_3$ 424.2600 found (MH$^+$) 424.2606 m/z

STX1146, GMA03074-4

3-Ethyl-2-hydroxy-6a-methyl-4b,5,6,6a,8,10,10a,10b,11,12-decahydro-7,8-diaza-pentaleno[2,1-a]phenanthrene-9-carboxylic acid (5-methyl-pyrazin-2-ylmethyl)-amide

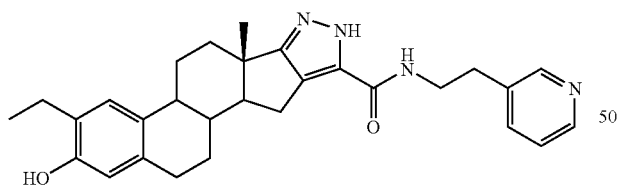

Yield 51%; $^1$H NMR δ (270 MHz, CD$_3$OD) 1.02 (s, 3H, 18-CH$_3$), 1.15 (t, J=7.4 Hz, 3H, ArCH$_2$CH$_3$), 1.30-1.49 (m, 1H), 1.59-1.86 (m, 3H), 1.93-2.01 (m, 1H), 2.10-2.45 (5H), 2.55 (q, J=7.4 Hz, 2H, -CH$_2$CH$_3$), 2.72-2.85 (3H), 2.95 (t, J=7.1 Hz, 2H, —CH$_2$CH$_2$—), 3.61 (t, J=7.3 Hz, 2H, —CH$_2$CH$_2$—), 6.46 (s, 1H, 4-H), 6.97 (s, 1H, 1-H), 7.37-7.42 (m, 1H), 7.79 (d, J=7.7 Hz, 1H), 8.40 (d, J=4.2 Hz, 1H), 8.45 (s, 1H); HPLC>98%; (R$_t$3.09, 70% MeCN in H$_2$O); ES–ve–MS (M–H$^+$) 469.49 m/z; FAB-HRMS calcd for C$_{29}$H$_{35}$N$_4$O$_2$ 471.2760 found (MH$^+$) 471.2756 m/z Yield 42%; $^1$H NMR δ (270 MHz, CD$_3$OD) 1.01 (s, 3H, 18-CH$_3$), 1.14 (t, J=7.4 Hz, 3H, ArCH$_2$CH$_3$), 1.31-1.47 (m, 1H), 1.52-1.83 (m, 3H), 1.92-2.00 (m, 1H), 2.15-2.58 (7H), 2.52 (s, 3H, ArCH$_3$), 2.69-2.86 (3H), 4.64 (s, 2H), 6.44 (s, 1H, 4-H), 6.95 (s, 1H, 1-H), 7.27-7.31 (m, 1H), 8.46 (d, J=1.1 Hz, 1H), 8.49 (s, 1H); HPLC>94% (R$_t$ 2.08, 80% MeCN in H$_2$O); ES–ve–MS (M–H$^+$) 470.35 m/z; FAB-HRMS calcd for C$_{28}$H$_{34}$N$_5$O$_2$ 472.2713 found (MH$^+$) 472.2718 m/z.

STX1166, GMA03092

3-Ethyl-2-hydroxy-6a-methyl-4b,5,6,6a,8,10,10a,
10b,11,12-decahydro-7,8-diaza-pentaleno[2,1-a]
phenanthrone-9-carboxylic acid (benzo[1,3]dioxol-
5ylmethyl)-amide

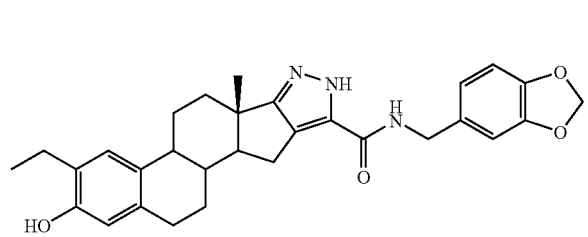

Yield 56%; $^1$H NMR δ (400 MHz, CD$_3$OD) 1.08 (s, 3H, 18-CH$_3$), 1.19 (t, J=7.4 Hz, 3H, ArCH$_2$CH$_3$), 1.48-2.52 (10H), 2.59 (q, J=7.8 Hz, 2H), 2.80-2.95 (m, 3H), 4.48 (s, 2H), 5.95 (s, 2H), 6.49 (s, 1H), 6.79-6.89 (m, 3H), 7.01 (s, 1H); HPLC>98% (R$_t$ 7.29, 90% MeCN in H$_2$O); APCI (M–H$^+$) 498.32 m/z; FAB-HRMS calcd for C$_{28}$H$_{34}$N$_5$O$_2$ found (MH$^+$) m/z.

GMA03028

(3-Benzyloxy-2-ethyl-13-methyl-17-oxo-6,7,8,9,11,
12,13,14,15,17-decahydro-cyclopenta[a]phenan-
thren-16-ylidene)-hydroxy-acetic acid ethyl ester

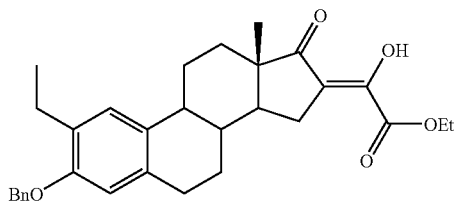

To a stirred solution of benzyl protected 2-ethyl estrone (2.00 g, 5.15 mmol) in toluene (20 cm$^3$) was added diethyl oxalate (1.40 cm$^3$, 10.20 mmol) followed by potassium t-butoxide (0.693 g, 6.18 mmol) and the reaction was stirred at rt for 16 h. The solution was acidified with glacial acetic acid before being concentrated in vacuo. To the residue was added ethyl acetate (30 cm$^3$) and the solution washed with water (30 cm$^3$) and brine (30 cm$^3$). The organic layer was concentrated in vacuo to give a white powder, which was washed with ethanol/water and collected by filtration. Yield 97%; $^1$H NMR δ (270 MHz, CDCl$_3$) 0.99 (s, 3H, 18-CH$_3$), 1.20 (t, J=7.5 Hz, 3H, ArCH$_2$CH$_3$), 1.38 (t, J=7.2 Hz, 3H, OCH$_2$CH$_3$), 1.41-1.69 (6H), 2.00-2.05 (m, 2H), 2.30-2.50 (m, 3H), 2.66 (q, J=7.5 Hz, 2H, ArCH$_2$CH$_3$), 2.88-2.91 (m, 2H), 3.04-3.10 (m, 1H), 4.35 (q, J=7.2 Hz, 2H, OCH$_2$CH$_3$), 5.04 (s, 2H, ArCH$_2$O), 6.64 (s, 1H, 4-H), 7.09 (s, 1H, 1-H), 7.26-7.45 (m, 5H); HPLC>97% (R$_f$=2.86, 98% MeCN in H$_2$O); ES–ve-MS (M–H$^+$) 487 m/z; FAB-HRMS calcd for C$_{31}$H$_{36}$O$_5$ 488.2563 found (M$^+$) 488.2569 m/z.

GMA03029

2-Benzyloxy-3ethyl-6a-methyl-4b,5,6,6a,8,10,10a,
10b,11,12-decahydro-7,8-diaza-pentaleno[2,1-a]
phenanthrene-9-carboxylic acid ethyl ester

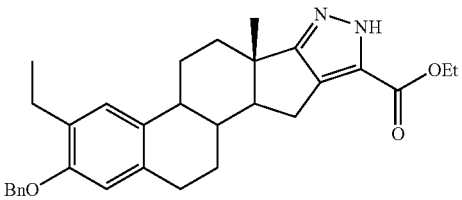

To a stirred suspension of sm (2.44 g, 5 mmol) in ethanol (50 cm$^3$) was added hydrazine monohydrate (0.3 cm$^3$, 6 mmol) at which time the sm dissolved. Stirring at room temperature was continued overnight before the white precipitate was collected by filtration and washed with water. The filtrate was acidified with glacial acetic acid and more precipitate formed and was collected. The precipitates were combined, and suspended in ethanol before p-toluene sulphonic acid (~0.1 g) was added. The mixture was heated for 5 min to aromatise the pyrazole ring then stirred at rt for 1 h. The pale yellow solution was concentrated in vacuo until precipitate began to form before water was added and the white powder was collected by filtration, washed with water and air-dried. Yield 96%; $^1$H NMR δ (270 MHz, CDCl$_3$) 1.03 (s, 3H, 18-CH$_3$), 1.21 (t, J=7.5 Hz, 3H, ArCH$_2$CH$_3$), 1.37 (t, J=7.2 Hz, 3H, OCH$_2$CH$_3$), 1.45-2.20 (6H), 2.32-2.50 (m, 4H), 2.67 (q, J=7.5 Hz, 2H, ArCH$_2$CH$_3$), 2.82-2.96 (m, 3H), 4.35 (q, J=7.2 Hz, 2H, OCH$_2$CH$_3$), 5.05 (s, 2H, ArCH$_2$O), 6.65 (s, 1H, 4-H), 7.12 (s, 1H, 1-H), 7.28-7.46 (m, 5H); HPLC>92% (R$_t$=5.17, 94% MeCN in H$_2$O); ES–ve-MS (M–H$^+$) 483 m/z; FAB-HRMS calcd for C$_{31}$H$_{36}$N$_2$O$_3$ 484.2726 found (M$^+$) 484.2730 m/z.

STX1057, GMA03032/2, GMA03062

3-Ethyl-2-hydroxy-6a-methyl-4b,5,6,6a,8,10,10a,
10b,11,12-decahydro-7,8-diaza-pentaleno[2,1-a]
phenanthrene-9-carboxylic acid ethyl ester

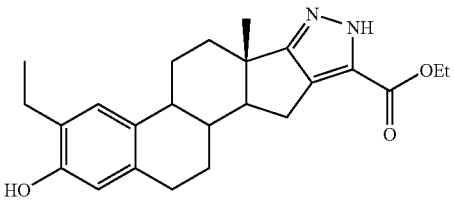

A suspension of sm (3.40 g, 7 mmol) in MeOH (70 cm$^3$) was degassed by bubbling. nitrogen through for 30 min. To this was added Pd/C (5% wt., catalytic) and degassing was continued for a further 10 min before hydrogen gas was passed over the reaction and stirring under hydrogen was continued for a further 3 d. The mixture was filtered through celite, the celite washed with ethyl acetate and methanol and the filtrate concentrated in vacuo. The product was purified by flash chromatography (Flashmaster II) using a gradient elution of hexane to 1:1 ethyl acetate:hexane. R$_f$ (1/1 ethyl acetate/hexane) 0.24. Yield 89%; $^1$H NMR δ (270 MHz, CD$_3$OD) 1.03 (s, 3H, 18-CH$_3$), 1.15 (t, J=7.5 Hz, 3H, ArCH$_2$CH$_3$), 1.36 (t, J=7.2 Hz, 3H, OCH$_2$CH$_3$), 1.39-2.20 (6H), 2.26-2.44 (m, 4H), 2.53 (q, J=7.3 Hz, 2H, ArCH$_2$CH$_3$), 2.79-2.86 (m, 3H), 4.34 (q, J=7.1 Hz, 2H, OCH$_2$CH$_3$), 6.46 (s, 1H, 4-H), 6.97 (s, 1H, 1-H); FAB-HRMS calcd for for C$_{24}$H$_{30}$N$_2$O$_3$ 395.2335 found (M$^+$) 395.2312 m/z.

STX1024, GMA03008, GMA03044/3, GMA03063

3-Ethyl-6a-methyl-2-sulfamoyloxy-4b,5,6,6a,8,10,10a,10b,11,12-decahydro-7,8-diaza-pentaleno[2,1-a]phenenthrene-9-carboxylic acid ethyl ester

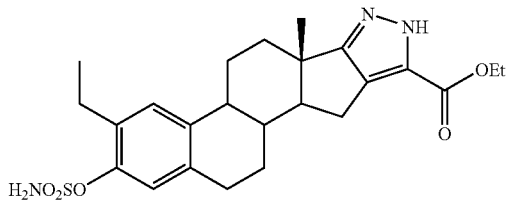

A solution of sulfamoyl chloride (30 cm$^3$ of a 0.68 M solution in toluene, 20.4 mmol) was concentrated in vacuo without heating then cooled on ice under nitrogen. To this was added DMA (15 cm$^3$) and this mixture added to a cooled (ice/acetone bath) solution of sm (2.42 g, 6.13 mmol) in DMA (10 cm$^3$). The stirred solution was allowed to warm to rt overnight before being diluted with water (60 cm$^3$) and the product extracted with ethyl acetate (100 cm$^3$), giving an oily solution in DMA. This was redissolved in ethyl acetate and washed again with water before concentration to give a cream coloured crystalline solid. Recrystallisation from DCM/hexane gave 2 g, 69% yield of product. $^1$H NMR δ (270 MHz, CD$_3$OD) 1.04 (s, 3H, 18-CH$_3$), 1.20 (t, J=7.5 Hz, 3H, ArCH$_2$CH$_3$), 1.36 (t, J=7.1 Hz, 3H, OCH$_2$CH$_3$), 1.39-2.20 (6H), 2.29-2.50 (m, 4H), 2.71 (q, J=7.5 Hz, 2H, ArCH$_2$CH$_3$), 2.81-2.92 (m, 3H), 4.33 (q, J=7.1 Hz, 2H, OCH$_2$CH$_3$), 7.09 (s, 1H, 4-H), 7.22 (s, 1H, 1-H); HPLC>97% (R$_t$=2.40, 80% MeCN in H$_2$O); FAB-LRMS (MH$^+$) 474 m/z; FAB-HRMS calcd for for C$_{24}$H$_{32}$N$_3$O$_5$S 474.2063 found (MH$^+$) 474.2067 m/z.

GMA03064

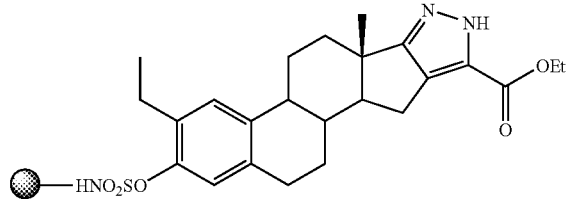

To a suspension of 2-chlorotrityl chloride resin (2.27 g, 1.1 mmol/g theoretical loading) swollen in anhydrous DCM (12 cm$^3$) and DIPEA (5.34 cm$^3$, 29.5 mmol) under nitrogen was added sm (2.00 g, 4.22 mmol) as a solid in portions followed by a further volume of DCM (5 cm$^3$). The reaction was shaken at rt for 96 h before the resin was collected by filtration and washed three times with DCM, methanol and again with DCM.

GMA03068

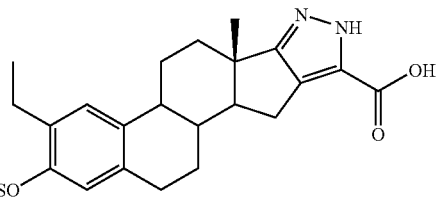

To the loaded resin (3.74 g) swollen in THF (25 cm$^3$) was added slowly aqueous sodium hydroxide (30 cm$^3$ of 1N) and the mixture was shaken at rt for 24 h. The resin was collected by filtration, washed with THF/water (1/1) and washed with MeOH and DCM before being dried in vacuo.

STX1080, GMA03052-1

3Ethyl-6a-methyl-2-sulfamoyloxy-4b,5,6,6a,8,10,10a,10b,11,12-decahydro-7,8-diaza-pentaleno[2,1-a]phenanthrene-9-carboxylic acid

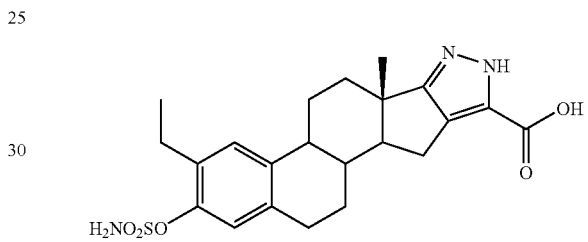

The loaded resin (0.03 g) was placed in a fritted syringe and washed with TFA/DCM (20 cm$^3$ of 1/1, added portion-wise with 5 min between washings) followed by DCM. The washings were combined and concentrated in vacuo. The resin loading from the weight of the crude was calculated to be 0.8 mmol/g.

Purification by flash chromatography (Flashmaster II) using a gradient elution of DCM to 10% MeOH in DCM gave the product R$_f$ 0.6 (10% MeOH in DCM).

$^1$H NMR δ (270 MHz, CD$_3$OD) 1.04 (s, 3H, 18-CH$_3$), 1.20 (t, J=7.5 Hz, 3H, ArCH$_2$CH$_3$), 1.46-1.90 (5H), 1.99-2.07 (m, 1H), 2.12-2.23 (m, 1H), 2.31-2.51 (4H), 2.71 (q, J=7.5 Hz, 2H, ArCH$_2$CH$_3$), 2.82-2.92 (3H), 7.09 (s, 1H, 4-H), 7.22 (s, 1H, 1-H); HPLC>93% (R$_t$ 1.45, 70% MeCN in H$_2$O); ES+ve–MS (MH$^+$) 468 m/z; FAB-HRMS calcd for for C$_{22}$H$_{28}$N$_3$O$_5$S 446.1750 found (MH$^+$) 446.1713 m/z.

General Procedure for Amide Coupling on Resin-Bound Starting Material;

To the loaded resin (0.200 g) swollen in dry DCM (3 cm$^3$) under N$_2$ was added bromo-tris-pyrrolidinophosphonium hexafluorophosphate (PyBOP, 0.260 g, 0.5 mmol) and N-hydroxybenzotriazole (HOBt, 0.070 g, 0.5 mmol) followed by DIPEA (0.18 cm$^3$, 1.0 mmol). The mixture was shaken for 10 min before addition of amine (0.06 cm$^3$) and shaking under N$_2$ at rt was continued for 72 h. The resin was collected in a fritted syringe and washed with DMF, DCM and MeOH (×3) and again with DCM (×3) before cleavage of the product using TFA/DCM (1/1). Purification by flash chromatography (Flashmaster II) using a gradient elution of DCM to 10% MeOH in DCM yielded the sulfamates in yields of 1-53% and HPLC purities of 88-98%.

STX1083, GMA03052-2/3

Sulfamic acid 3-ethyl-6a-methyl-9-[(pyridin-2-ylmethyl)-carbamoyl]-4b,5,6,6a,8,10,10a,10b,11,12-decahydro-7,8-diaza-pentaleno[2,1-a]phenanthren-2-yl ester

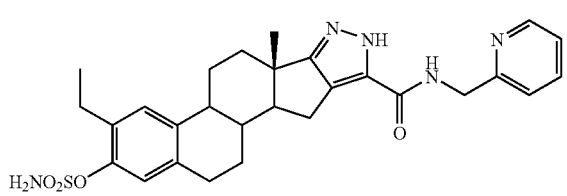

Yield 53%; $^1$H NMR δ (270 MHz, CD$_3$OD) 1.04 (s, 3H, 18-CH$_3$), 1.19 (t, J=7.5 Hz, 3H, ArCH$_2$CH$_3$), 1.39-1.55 (m, 1H), 1.59-1.88 (m, 3H), 1.98-2.04 (m, 1H), 2.14-2.58 (5H), 2.70 (q, J=7.5 Hz, 2H, ArCH$_2$CH$_3$), 2.78-2.98 (3H), 4.64 (s, 2H), 7.08 (s, 1H, 4-H), 7.20 (s, 1H, 1-H), 7.28-7.33 (m, 1H), 7.42 (d, J=7.9 Hz, 1H), 7.80 (dt, J=7.8, 1.7 Hz, 1H), 8.49 (d, J=4.5 Hz, 1H); HPLC>97% (R$_t$ 2.11, 70% MeCN in H$_2$O); ES–ve–MS (M–H$^+$) 534 m/z; FAB-HRMS calcd for for C$_{26}$H$_{34}$N$_5$O$_4$S 536.2332 found (MH$^+$) 536.2330 m/z.

STX1082 GMA03052-3/3

Sulfamic acid 3-ethyl-6a-methyl-9-(2-pyridin-3-yl-ethylcarbamoyl)-4b,5,6,6a,8,10,10a,10b,11,12-decahydro-7,8-diaza-pentaleno[2,1-a]phenanthren-2-yl ester

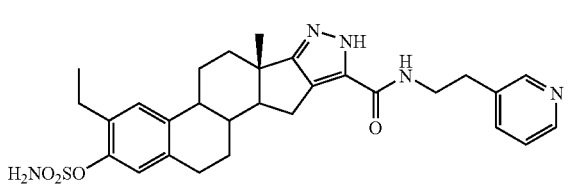

Yield 7%; $^1$H NMR δ (270 MHz, CD$_3$OD) 1.02 (s, 3H, 18-CH$_3$), 1.20 (t, J=7.5 Hz, 3H, ArCH$_2$CH$_3$), 1.46-1.89 (4H), 1.98-2.04 (m, 1H), 2.15-2.52 (5H), 2.65-2.98 (7H), 3.60 (t, J=6.7 Hz, 2H, —CH$_2$CH$_2$), 7.04 (s, 1H, 4-H), 7.21 (s, 1H, 1-H), 7.36-7.41 (m, 1H), 7.78 (dt, J=6.2, 1.7 Hz, 1H), 8.39 (dd, J=4.8, 1.7 Hz, 1H), 8.44 (d, J=1.7 Hz, 1H); LC purity>95%; ES–ve–MS (M–H$^+$) 548 m/z; FAB-HRMS calcd for for C$_{29}$H$_{38}$N$_5$O$_4$S 550.2488 found (MH$^+$) 550.2499 m/z.

STX1081, GMA03052-4/3

Sulfamic acid 3-ethyl-6a-methyl-9-(2-pyridin-2-yl-ethylcarbamoyl)-4b,5,6,6a,8,10,10a,10b,11,12-decahydro-7,8-diaza-pentaleno[2,1-a]phenanthren-2-yl ester

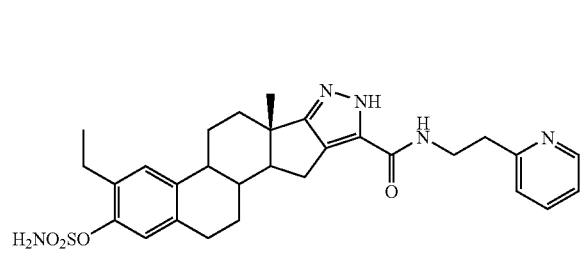

Yield 25%; $^1$H NMR 3 (270 MHz, CD$_3$OD) 1.02 (s, 3H, 18-CH$_3$), 1.20 (t, J=7.5 Hz, 3H, ArCH$_2$CH$_3$), 1.46-1.88 (4H), 1.98-2.05 (m, 1H), 2.12-2.52 (5H), 2.71 (q, J=7.5 Hz, 2H, CH$_2$CH$_3$), 2.77-2.92 (3H), 3.07 (t, J=6.9 Hz, 2H, —CH$_2$CH$_2$), 3.71 (dt, J=7.2, 1.8 Hz, 2H, —CH$_2$CH$_2$), 7.09 (s, 1H, 4-H), 7.20 (s, 1H, 1-H), 7.26-7.29 (m, 1H), 7.36 (d, J=7.9 Hz, 1H), 7.77 (dt, J=7.7, 1.9 Hz, 1H), 8.47-8.50 (m, 1H); HPLC>98% (R$_t$ 1.96, 90% MeCN in H$_2$O); ES–ve–MS (M–H$^+$) 548 m/z; FAB-HRMS calcd for for C$_{29}$H$_{38}$N$_5$O$_4$S 550.2488 found (MH$^+$) 550.2483 m/z.

STX1123 GMA03072-1/2

Sulfamic acid 3-ethyl-6a-methyl-9-[(pyridin-3-ylmethyl)-carbamoyl]-4b,5,6,6a,8,10,10a,10b,11,12-decahydro-7,8-diaza-pentaleno[2,1-a]phenanthren-2-yl ester

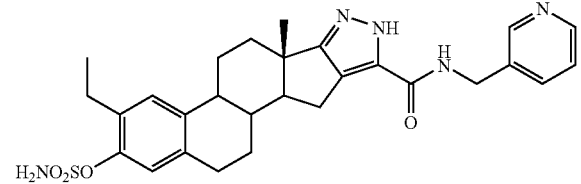

Yield 8%; $^1$H NMR δ (400 MHz, CD$_3$OD) 1.06 (s, 3H, 18-CH$_3$), 1.21 (t, J=7.4 Hz, 3H, ArCH$_2$CH$_3$), 1.47-1.57 (m, 1H), 1.65-1.90 (3H), 2.04-2.07 (m, 1H), 2.14-2.33 (2H), 2.39-2.53 (3H), 2.72 (q, J=7.4 Hz, 2H, ArCH$_2$CH$_3$), 2.90-2.94 (3H), 4.58 (s, 2H), 7.09 (s, 1H, 4-H), 7.21 (s, 1H, 1-H), 7.40-7.43 (m, 1H), 7.85 (d, J=7.8 Hz, 1H), 8.42 (d, J=4.7 Hz, 1H), 8.54 (d, J=2.0 Hz, 1H); HPLC>99% (R$_t$ 1.91, 80% MeCN in H$_2$O); ES+ve–MS (MH$^+$) 536.31 m/z; FAB-HRMS calcd for for C$_{28}$H$_{34}$N$_5$O$_4$S 536.2332 found (MH$^+$) 536.2330 m/z.

STX1124, GMA03072-2/2

Sulfamic acid 3-ethyl-6a-methyl-9-[(5-methyl-pyrazin-2-ylmethyl)-carbamoyl]-4b,5,6,6a,8,10,10a,10b,11,12-decahydro-7,8-diaza-pentaleno[2,1-a]phenanthren-2-yl ester

STX1126, GMA03072-5/2

Sulfamic acid 3-ethyl-9-(ethyl-methyl-carbamoyl)-6a-methyl-4b,5,6,6a,8,10,10a,10b,11,12-decahydro-7,8-diaza-pentaleno[2,1-a]phenanthren-2-yl ester

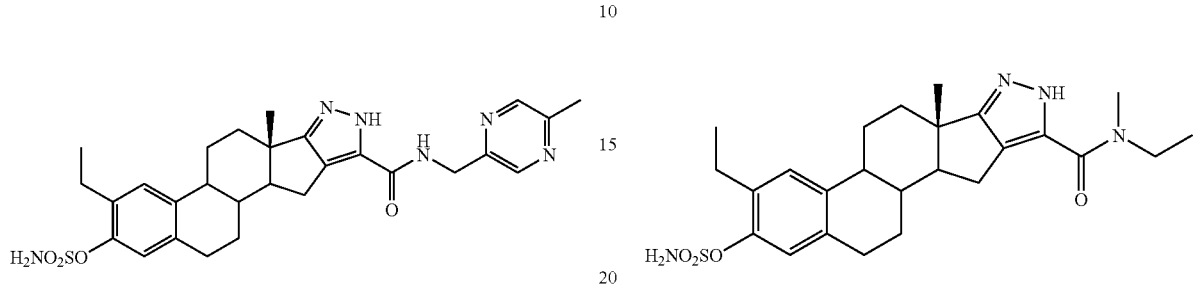

Yield 8%; $^1$H NMR δ (400 MHz, CD$_3$OD) 1.06 (s, 3H, 18-CH$_3$), 1.22 (t, J=7.4 Hz, 3H, ArCH$_2$CH$_3$), 1.47-1.57 (m, 1H), 1.65-1.90 (3H), 2.03-2.07 (m, 1H), 2.14-2.55 (5H), 2.72 (q, J=7.4 Hz, 2H, ArCH$_2$CH$_3$), 2.90-2.94 (3H), 4.66 (s, 2H), 7.09 (s, 1H, 4-H), 7.21 (s, 1H, 1-H), 8.48 (s, 1H), 8.49 (s, 1H); HPLC>99% (R$_t$ 1.93, 80% MeCN in H$_2$O); ES+ve–MS (MH$^+$) 551.18 m/z; FAB-HRMS calcd for for C$_{28}$H$_{35}$N$_6$O$_4$S 551.2441 found (MH$^+$) 551.2447 m/z Yield 5%; $^1$H NMR δ (400 MHz, CD$_3$OD) 1.08 (s, 3H, 18-CH$_3$), 1.20-1.25 (6H), 1.30-1.6 (1H), 1.65-1.90 (3H), 2.01-2.09 (m, 1H), 2.16-2.50 (5H), 2.72 (q, J=7.4 Hz, 2H, ArCH$_2$CH$_3$), 2.84-2.93 (3H), 3.06-3.26 (3H), 3.46-3.64 (m, 2H), 7.09 (s, 1H, 4-H), 7.22 (s, 1H, 1-H); HPLC>98% (R$_t$ 2.43, 5 to 95% MeCN in H$_2$O over 10 min); ES+ve–MS (MH$^+$) 487.24 m/z; FAB-HRMS calcd for for C$_{25}$H$_{35}$N$_4$O$_4$S 487.2379 found (MH$^+$) 487.2396 m/z.

STX1125, GMA03072-4a

Sulfamic acid 3-ethyl-9-(2-methoxy-ethylcarbamoyl)-6a-methyl-4b,5,6,6a,8,10,10a,10b,11,12-decahydro-7,8diaza-pentaleno[2,1-a]phenanthren-2-yl ester

STX1152, GMA03076-1

Sulfamic acid 3-ethyl-9-[(furan-2-ylmethyl)-carbamoyl]-6a-methyl-4b,5,6,6a,8,10,10a,10b,11,12-decahydro-7,8-diaza-pentaleno[2,1-a]phenanthren-2-yl ester

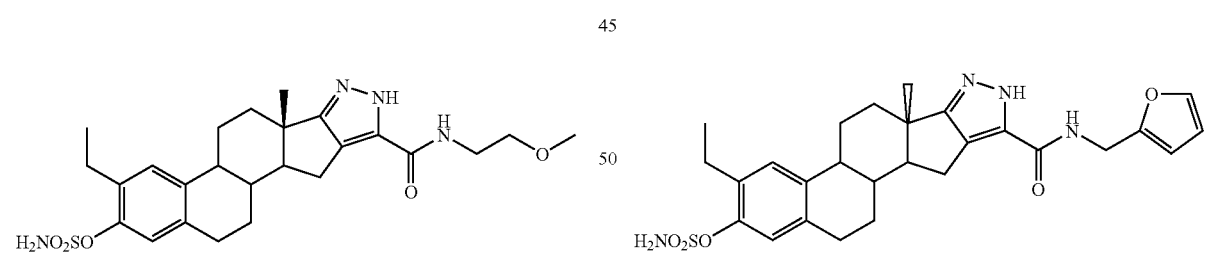

Yield 10%; $^1$H NMR δ (400 MHz, CD$_3$OD) 1.06 (s, 3H, 18-CH$_3$), 1.22 (t, J=7.4 Hz, 3H, ArCH$_2$CH$_3$), 1.47-1.57 (m, 1H), 1.65-1.90 (3H), 2.03-2.09 (m, 1H), 2.18-2.55 (5H), 2.72 (q, J=7.4 Hz, 2H, ArCH$_2$CH$_3$), 2.84-2.95 (3H), 3.3-3.55 (7H), 7.09 (s, 1H, 4-H), 7.22 (s, 1H, 1-H); HPLC>88% (R$_t$ 3.28, 5 to 95% MeCN in H$_2$O over 10 min); ES+ve–MS (MH$^+$) 503.24 m/z; FAB-HRMS calcd for for C$_{25}$H$_{35}$N$_4$O$_5$S 503.2328 found (MH$^+$) 503.2325 m/z.

Yield 6%; $^1$H NMR δ (270 MHz, CD$_3$OD) 1.02 (s, 3H, 18-CH$_3$), 1.20 (t, J=7.5 Hz, 3H, ArCH$_2$CH$_3$), 1.46-1.89 (4H), 1.95-2.06 (m, 1H), 2.12-2.52 (5H), 2.71 (q, J=7.5 Hz, 2H, CH$_2$CH$_3$), 2.81-2.91 (3H), 4.52 (s, 2H), 6.28-6.36 (m, 2H), 7.09 (s, 1H, 4-H), 7.21 (s, 1H, 1-H), 7.43 (s, 1H); HPLC>91% (R$_t$ 2.17, 70% MeCN in H$_2$O); ES−ve–MS (M−H$^+$) 523.27 m/z; FAB-HRMS calcd for for C$_{27}$H$_{33}$N$_4$O$_5$S 525.2172 found (MH$^+$) 525.2176 m/z

STX1153, GMA03076-3

Sulfamic acid 9-[(benzo[1,3]dioxol-5-ylmethyl)-carbamoyl]-3-ethyl-6a-methyl-4b,5,6,6a,8,10,10a,10b,11,12-decahydro-7,8-diaza-pentaleno[2,1-a]phenanthren-2-yl ester

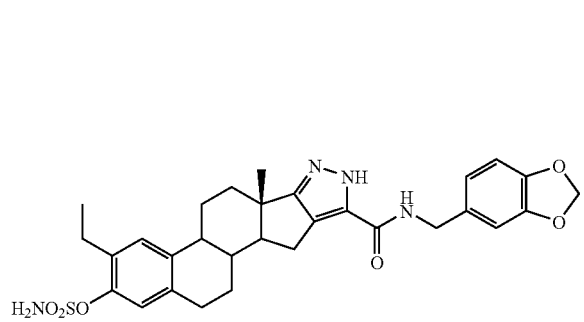

Yield 1%; $^1$H NMR δ (270 MHz, CD$_3$OD) 1.06 (s, 3H, 18-CH$_3$), 1.20 (t, J=7.5 Hz, 3H, ArCH$_2$CH$_3$), 1.46-2.54 (10H), 2.71 (q, J=7.5 Hz, 2H, CH$_2$CH$_3$), 2.81-3 (3H), 4.45 (s, 2H), 5.91 (s, 2H), 6.74-6.85 (2H), 7.09 (s, 1H, 4-H), 7.21 (s, 1H, 1-H); HPLC>93% (R$_t$ 5.39, 5 to 95% MeCN in H$_2$O over 10 min); ES−ve−MS (M−H$^+$) 577.26 m/z; FAB-HRMS calcd for for C$_{30}$H$_{35}$N$_4$O$_6$S 579.2277 found (MH$^+$) 579.2257 m/z

STX1154, GMA03076-4

Sulfamic acid 3-ethyl-9-[2-(1H-indol-3-yl)-ethylcarbamoyl]-6a-methyl-4b,5,6,6a,8,10,10a,10b,11,12-decahydro-7,8-diaza-pentaleno[2,1-a]phenanthren-2-yl ester

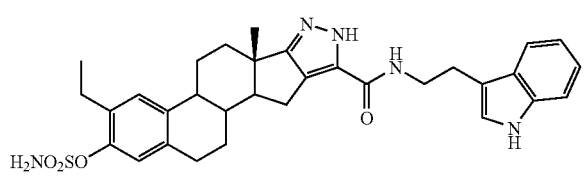

Yield 3%; $^1$H NMR δ (270 MHz, CD$_3$OD) 1.00 (s, 3H, 18-CH$_3$), 1.20 (t, J=7.5 Hz, 3H, ArCH$_2$CH$_3$), 1.46-2.52 (11H), 2.71 (q, J=7.5 Hz, 2H, CH$_2$CH$_3$), 2.90-2.92 (2H), 3.03-3.08 (2H, —CH$_2$CH$_2$), 3.63-3.67 (2H, —CH$_2$CH$_2$), 6.95-7.12 (4H), 7.21 (s, 1H, 1-H), 7.34 (d, J=8.0 Hz, 1H), 7.56-7.59 (1H); HPLC>98% (R$_t$ 2.22, 70% MeCN in H$_2$O); ES−ve−MS (M−H$^+$) 586.33 m/z; FAB-HRMS calcd for for C$_{32}$H$_{38}$N$_5$O$_4$S 588.2645 found (MH$^+$) 588.2659 m/z

STX1155, GMA03076-6

Sulfamic acid 3-ethyl-6a-methyl-9-phenethylcarbamoyl-4b,5,6,6a,8,10,10a,10b,11,12-decahydro-7,8-diaza-pentaleno[2,1-a]phenanthren-2-yl ester Yield 9%; $^1$H NMR δ (270 MHz, CD$_3$OD) 1.03 (s, 3H, 18-CH$_3$), 1.20 (t, J=7.5 Hz, 3H, ArCH$_2$CH$_3$), 1.46-1.90 (4H), 1.98-2.05 (m, 1H), 2.12-2.52 (5H), 2.71 (q, J=7.5 Hz, 2H, CH$_2$CH$_3$), 2.77-2.99 (5H), 3.55-3.61 (2H, —CH$_2$CH$_2$), 7.10 (s, 1H, 4-H), 7.20-7.30 (6H); HPLC>93% (R$_t$ 2.83, 70% MeCN in H$_2$O); ES−ve−MS (M−H$^+$) 547.27 m/z; FAB-HRMS calcd for for C$_{30}$H$_{37}$N$_4$O$_4$S 549.2536 found (MH$^+$) 549.2532 m/z.

GMA03036

2-Benzyloxy-7-(2-cyano-ethyl)-3-ethyl-4b,5,6,6a,7,10,10a,10b,11,12-decahydro-7,8-diazapentaleno[2,1-a]phenanthrene-9-carboxylic acid ethyl ester To a stirred suspension of sm (0.17 g, 0.35 mmol) in ethanol (10 cm$^3$) was added 2-cyanoethylhydrazine (0.05 cm$^3$) and the dark orange solution was stirred at rt overnight. The resulting dark brown solution was acidified with glacial acetic acid and water (10 cm$^3$) was added. The solution was concentrated in vacuo to ~1 cm$^3$ before more water was added until the product precipitated as a yellowish powder. This was collected by filtration and washed with water. $^1$H NMR at this stage showed that the pyrazole ring was still hydrated therefore the product was redissolved in ethanol, p-toluene sulphonic acid monohydrate was added and the solution heated for a few min. The solution was then concentrated in vacuo until precipitate began to form, water (20 cm$^3$) was added and the resulting orange powder was collected by filtration. The product was purified by flash chromatography using a gradient elution of hexane to 1:1 ethyl acetate:hexane. Yield 0.032 g, 17%

$^1$H NMR δ (270 MHz, CDCl$_3$) 1.08 (s, 3H, 18-CH$_3$), 1.21 (t, J=7.5 Hz, 3H, ArCH$_2$CH$_3$), 1.38 (t, J=7.1 Hz, 3H, OCH$_2$CH$_3$), 1.35-2.08 (6H), 2.30-2.58 (4H), 2.67 (q, J=7.6 Hz, 2H, ArCH$_2$CH$_3$), 2.80-2.91 (3H), 3.05-3.08 (m, 2H), 4.27-4.41 (4H), 5.04 (s, 2H, ArCH$_2$O), 6.65 (s, 1H, 4-H), 7.08 (s, 1H, 1-H), 7.27-7.45 (m, 5H); ES+ve−MS (M+H$^+$) 560 m/z.

GMA03043, STX1079

7-(2-cyano-ethyl)-3-ethyl-4b,5,6,6a,7,10,10a,10b,11,12-decahydro-7,8-diazapentaleno[2,1-a]phenanthrene-9-carboxylic acid ethyl ester

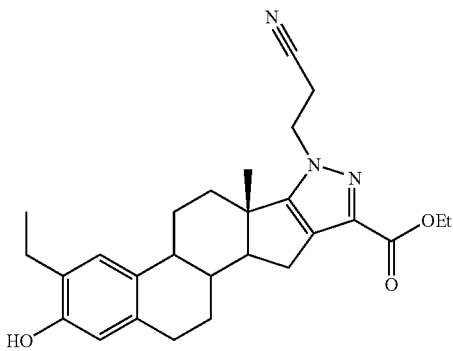

A stirred solution of sm (0.03 g, 0.06 mmol) in THF (2 cm$^3$) and ethanol (3 cm$^3$) was degassed by bubbling N$_2$ through for 20 min before Pd/C (5% wt., catalytic) was added. Degassing was continued for a further 10 min before H$_2$ gas was passed over the reaction and the reaction was stirred under a hydrogen blanket overnight. The mixture was filtered through celite and the product purified by flash chromatography using a gradient elution of DCM to 10% MeOH in DCM. Yield 0.025 g, 93%; $^1$H NMR δ (270 MHz, CDCl$_3$) 1.07 (s, 3H, 18-CH$_3$), 1.21 (t, J=7.4 Hz, 3H, ArCH$_2$CH$_3$), 1.37 (t, J=7.0 Hz, 3H, OCH$_2$CH$_3$), 1.31-1.52 (m, 1H), 1.57-2.08 (5H), 2.23-2.47 (4H), 2.60 (q, J=7.4 Hz, 2H, ArCH$_2$CH$_3$), 2.78-2.87 (3H), 2.97-3.14 (m, 2H), 4.23-4.41 (4H), 6.51 (s, 1H, 4-H), 7.00 (s, 1H, 1-H); HPLC>94% (R$_t$ 2.67, 80% MeCN in H$_2$O); ES+ve-MS (MH$^+$) 448 m/z

GMA02180

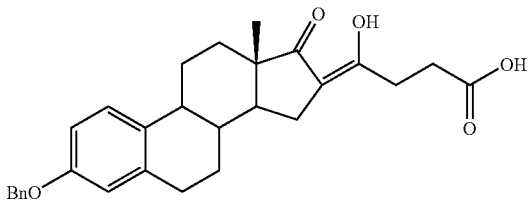

To a solution of benzyl protected estrone (1.08 g, 3.0 mmol) in dry THF (20 cm$^3$) under N$_2$, cooled to −78° C. (dry ice/acetone bath) was added slowly drop-wise LDA (6.0 cm$^3$ of a 1.8 M soln, 3.3 mmol) and the reaction was stirred at −78° C. for 30 min. To this was then added a solution of succinic anhydride (0.30 g, 3.0 mmol) in dry THF (15 cm$^3$) and the reaction was allowed to warm slowly to rt overnight. The mixture was poured into 5% HCl (120 cm$^3$) and the products extracted with diethyl ether (2×60 cm$^3$). The ether extracts were combined and concentrated in vacuo. Flash chromatography using a gradient elution of DCM to 10% MeOH in DCM resulted in separation of starting material (2.7 mmol) from a mixture which was used without further purification for the following reaction.

GMA02181

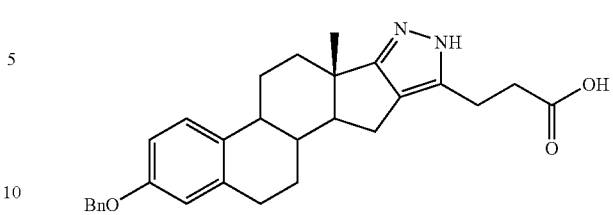

To a solution of crude sm (0.29 g, assume 0.3 mmol) in EtOH (5 cm$^3$) was added hydrazine monohydrate (0.07 cm$^3$, 1.4 mmol) and the reaction was stirred at rt for 3 h then heated to reflux for 30 min to ensure complete reaction and aromatisation of the pyrazole ring. The reaction was cooled, acidified with glacial acetic acid and water was added until the product precipitated as a pale orange powder. Yield 0.098 g; $^1$H NMR δ (270 MHz, DMSO-d$_6$) 0.89 (s, 3H, 18-CH$_3$), 1.24-1.69 (5H), 2.09-2.57 (5H), 2.73-2.84 (m, 4H), 5.06 (s, 2H), 6.73-6.79 (2H), 7.19 (d, J=8.9 Hz, 1H), 7.32-7.45 (5H); HPLC>80% (R$_t$=1.89, 80% MeCN in H$_2$O); FAB-LRMS (MH$^+$) 457 m/z; FAB-HRMS calcd for for C$_{29}$H$_{33}$N$_2$O$_3$ 457.2491 found (MH$^+$) 457.2479 m/z.

GMA02190

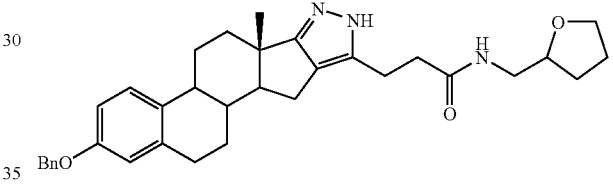

To a stirred solution of sm (0.090 g, assume 0.2 mmol) in dry DCM (5 cm$^3$) was added DMAP (catalytic), EDC (0.046 g, 0.24 mmol) and NEt$_3$ (0.02 cm$^3$) and the solution was stirred for 15 min before addition of tetrahydrofurfuryl amine (0.023 cm$^3$, 0.22 mmol). The reaction was stirred for 40 h before being diluted with DCM (15 cm$^3$) and the solution washed with sat. aq. bicarb. Flash chromatography using a gradient elution of DCM to 10% MeOH in DCM yielded 0.035 g, 0.064 mmol of product.

NMR δ (270 MHz, CD$_3$OD) 0.96 (s, 3H, 18-CH$_3$), 1.33-2.66 (16H), 2.82-2.91 (4H), 3.16-3.29 (3H), 3.56-3.93 (3H), 4.98 (s, 2H), 6.67 (d, J=2.5 Hz, 1H), 6.73 (dd, J=8.5, 2.5 Hz, 1H), 7.16 (d, J=8.7 Hz, 1H), 7.27-7.41 (5H); FAB-LRMS (MH$^+$) 540 m/z

GMA03014, STX1035

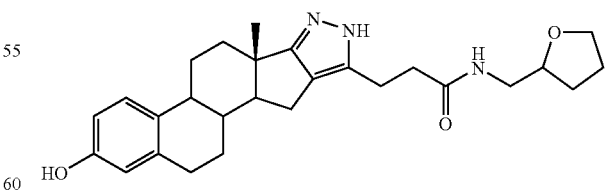

A stirred solution of sm (0.034 g, 0.06 mmol) in THF (2 cm$^3$) and ethanol (3 cm$^3$) was degassed by bubbling N$_2$ through for 20 min before Pd/C (5% wt., catalytic) was added. Degassing was continued for a further 10 min before H$_2$ gas was passed over the reaction and the reaction was stirred under a hydrogen blanket overnight. Tlc showed the presence of sm therefore stirring under $H_2$ was continued for a further 72 h. The mixture was filtered through celite and the product purified by flash chromatography using a gradient elution of DCM to 10% MeOH in DCM. Yield 0.012 g, 44%; $^1$H NMR δ (270 MHz, $CD_3OD$) 0.99 (s, 3H, 18-$CH_3$), 1.28-2.12 (9H), 2.21-2.46 (4H), 2.53 (t, J=7.4 Hz, 2H ) 2.62 (dd, J=13.4, 6.2 Hz, 1H), 2.82-2.84 (m, 2H), 2.90 (t, J=7.4 Hz, 2H), 3.22-3.3 (m, 3H), 3.67-3.96 (3H), 6.50 (d, J=2.5 Hz, 1H), 6.55 (dd, J=8.4, 2.7 Hz, 1H), 7.09 (s, 1H); HPLC>97% ($R_t$ 2.03, 70% MeCN in $H_2O$); ES+ve–MS ($MH^+$) 450 m/z; FAB-HRMS calcd for for $C_{27}H_{36}N_3O_3$ 450.2757 found ($MH^+$) 450.2745 m/z.

Section 2

3-Benzyloxy-13-methyl-6,7,8,9,11,12,13,14,15,16-decahydro-cyclopenta[a]phenanthren-17-one (JAC01002)

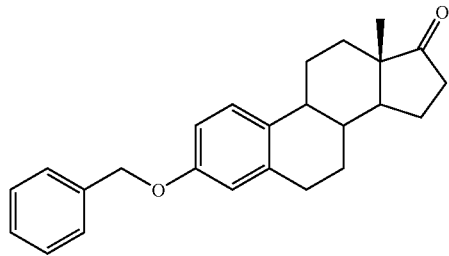

A solution of 15 g (55 mmol) of estrone in DMF (110 mL) was cooled to 0° C. and 2.44 g (61 mmol) of NaH (60% in oil) were added slowly. The mixture was stirred at 0° C. under $N_2$ for 1 h before addition of 13.2 mL (111 mmol) of benzyl bromine dropwise at 0° C. The reaction was then heated to 80° C. for 4 h. After cooling, the mixture was poured into water. The suspension was extracted by diethyl ether (5 times). The mixed organic layer were washed with 2N HCl (3 times) and brine, dried over $Na_2SO_4$ and concentrated in vacuo. Recrystallisation of the solid residue in ethanol gave 12.33 g (62%) of JAC01002 as beige solid. $^1$H NMR (400 MHz, $CDCl_3$) δ 0.92 (s, 3H, $CH_3$); 1.49-1.63 (m, 6H); 1.99-2.05 (m, 3H); 2.17 (dAB, J=18.9, 8.9 Hz, 1H); 2.23 (m, 1H); 2.40 (m, 1H); 2.51 (dAB, J=18.9, 8.9, 1H); 2.85 (m, 2H, $CH_2^6$); 5.05 (s, 2H, $OH_2Ph$); 6.74 (d, J=2.8 Hz, 1H, $H_4$); 6.80 (dd, J=8.5, 2.8 Hz, 1H, $H_2$); 7.21 (d, J=8.5 Hz, 1H, $H_1$); 7.30-7.45 (m, 5H); Acq. Mass ($FAB^+$) calcd 360.2089, obsd 360.21675 ($M^+$).

3-Benzyloxy-13-methyl-17-oxo-7,8,9,11,12,13,14,15,16,17-decahydro-6H-cyclopenta[a]phenanthrene-16-carboxylic acid methyl ester (JAC01011). [*J. Org. Chem.* 1991, 65, 6199-6205]

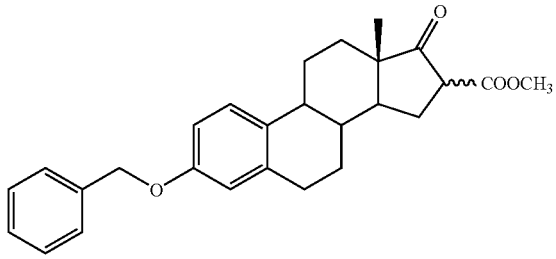

3.48 g (87 mmol) of NaH (60% in oil) were covered with anhydrous THF (50 mL), treated with 6.11 mL (72 mmol) of dimethylcarbonate, and heated to reflux while being magnetically stirred under $N_2$. A solution of benzylestrone (10.45 g, 29 mmol) in THF (50 mL) was added dropwise, and the reaction mixture was refluxed for 8 h, cooled to 0° C., and treated with 3M acetic acid (50 mL) in advance of being poured into brine. The product was extracted into $CHCl_3$ (3 times), dried over $Na_2SO_4$ and evaporated.

Recrystallisation of the solid residue in methanol gave 9.8 g (81%) of JAC01011 as beige solid. $^1$H NMR (400 MHz, $CDCl_3$) δ □0.97 (s, 1.05H, $CH_3$); 0.99 (s, 1.95H, $CH_3$); 1.34-1.74 (m, 6H); 1.90-2.50 (m, 6H); 2.92 (m, 2H, $CH_2^6$); 3.22 (dd, J=10.1, 8.6 Hz, 0.65H, CHCO); 3.58 (dd, J=9.4, 1.7 Hz, 0.35H, CHCO); 3.77 (s, 3H, $OCH_3$); 5.03 (s, 2H, $CH_2Ph$); 6.73 (d, J=2.5 Hz, 1H, $H_4$); 6.80 (dd, J=8.6, 2.5 Hz, 1H, $H_2$); 7.20 (d, 1H, J=8.6 Hz, 1H, $H_1$); 7.30-7.50 (m, 5H); MS ($FAB^+$) calcd 418.21, obsd 418.20 ($M^+$).

3-Benzyloxy-17α,β-hydroxy-13-methyl-7,8,9,11,12,13,14,15,16,17-decahydro-6H-cyclopenta[a]phenanthrene-16-carboxylic acid methyl ester (JAC01013, STX 569) and (JAC01013B, STX570)

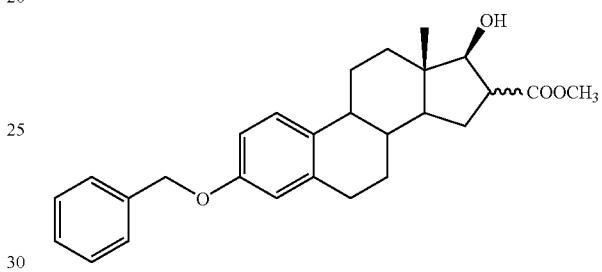

Solid $NaBH_4$ (456 mg, 12 mmol) was added to a cold (0° C.), magnetically stirred solution of JAC01011 (5 g, 12 mmol) in THF/MeOH (90:10), and the reaction mixture was stirred for 4 h at 0° C., treated with 2N HCl until acidic pH and extracted with ether (twice). The combine organic layers were washed with brine, dried over $Na_2SO_4$ and evaporated in vacuo. The solid was purified by column chromatography using $CHCl_3$/EtOAc (90:10) as eluant to give 2.48 g of STX569 (48%) and 0.91 g of STX570 (18%) as white solids.

3-Benzyloxy-17β-hydroxy-13-methyl-7,8,9,11,12,13,14,15,16,17-decahydro-6H-cyclopenta[a]phenanthrene-16-carboxylic acid methyl ester (JAC01013, STX569)

$^1$H NMR (400 MHz, $CDCl_3$): δ 0.85 (s, 3H, $CH_3$); 1.19 (ddd, J=12.9, 10.9, 6.2 Hz, 1H); 1.29-1.43 (m, 2H); 1.46-1.56 (m, 2H); 1.76 (dt, J=12.9, 8.6 Hz, 1H); 1.90 (m, 1H); 2.00-2.13 (m, 2H); 2.23 (m, 1H); 2.33 (m, 1H); 2.86 (m, 2H, $CH_2^6$); 3.15 (q, J=9.8 Hz, 1H, CHCOO); 3.34 (d, J=8.2 Hz, 1H, OH); 3.72 (s, 3H, $OCH_3$); 3.89 (dd, J=9.8, 8.2 Hz, 1H, CHO); 5.04 (s, 2H, $CH_2Ph$); 6.72 (d, J=2.7 Hz, 1H, $H_4$); 6.79 (dd, J=8.4, 2.7 Hz, 1H, $H_2$); 7.21 (d, J=8.6 Hz, 1H, $H_1$); 7.30-7.46 (m, 5H, Ph); Acq. Mass ($FAB^+$) calcd 420.2301, obsd 420.2298; Anal. Calcd for $C_{27}H_{32}O_4$: C, 77.11%; H. 7.67%; obsd C, 76.70%; H, 7.62%; purity: 99%.

3-Benzyloxy-17α-hydroxy-13-methyl-7,8,9,11,12,13,14,15,16,17-decahydro-6H-cyclopent[a]phenanthrene-16-carboxylic acid methyl ester (JAC01013B, STX 570)

$^1$H NMR (400 MHz, $CDCl_3$): δ 0.84 (s, 3H, $CH_3$); 1.20-1.60 (m, 5H); 1.72 (app. q, J=12.4 Hz, 1H); 1.85-1.88 (m, 1H); 1.97 (dt, J=12.1, 3.3 Hz, 1H); 2.02-2.10 (m, 2H); 2.22 (m, 1H); 2.32 (m, 1H); 2.77 (ddd, J=12.1, 8.4, 4.0 Hz, 1H, CHCOO); 2.86 (m, 2H, CH$_2^6$); 3.75 (s, 3H, OCH$_3$); 3.89 (dd, J=8.1, 4.4 Hz, 1H, CHO); 5.04 (s, 2H, CH$_2$Ph); 6.73 (d, J=2.9 Hz, 1H, H$_4$); 6.79 (dd, J=8.4, 2.6 Hz, 1H, H$_2$); 7.21 (d, J=8.1 Hz, 1H, H$_1$); 7.30-7.46 (m, 5H, Ph); Acq. Mass (FAB$^+$) calcd 420.2301, obsd 420.2301; Anal. Calcd for C$_{27}$H$_{32}$O$_4$: C, 77.11%; H, 7.67%; obsd C, 76.60%; H, 7.71%; purity: 99%.

3-Benzyloxy-16-hydroxymethyl-13-methyl-7,8,9,11, 12,13,14,15,16,17-decahydro-6H-cyclopenta[a] phenanthren-17-ol (JAC01023C)

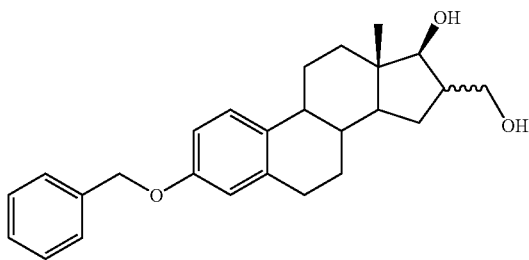

Solid NaBH$_4$ (452 mg, 12 mmol) was added to a cold (0° C.), magnetically stirred solution of JAC01011 (5 g, 12 mmol) in THF/MeOH (90:10), and the reaction mixture was stirred for 18 h at 0-20° C., treated with 2N HCl until acidic pH and extracted with ether (twice). The combine organic layers were washed with brine, dried over Na$_2$SO$_4$ and evaporated in vacuo. The solid was purified by column chromatography using CHCl$_3$/EtOAc (90:10) as eluant to give 1.95 g of STX569 (39%), 0.55 g of STX570 (18%) and 0.63 g of JAC01023C (13%) as white solids. $^1$H NMR (270 MHz, DMSO-d$_6$): δ 0.68 (s, 3H, CH$_3$); 0.95-1.45 (m, 4H); 1.70-1.90 (m, 4H); 2.00-2.35 (m, 4H); 2.75 (m, 2H, CH$_2^6$); 3.29 (m, 8H); 3.67 (m, 2H); 4.13 (dd, J=5.9, 4.4 Hz, 1H, CHO); 4.60 (d, J=4.4 Hz, 1H, OH); 5.03 (s, 2H, CH$_2$Ph); 6.69 (d, J=2.7 Hz, 1H, H$_4$); 6.74 (dd, J=8.4, 2.7 Hz, 1H, H$_2$); 7.14 (d, J=8.6 Hz, 1H, H$_1$); 7.25-7.46 (m, 5H, Ph); Acq. Mass (FAB$^+$) calcd 392.2351, obsd 392.2342.

3-Benzyloxy-16-(1,3-dioxo-1,3-dihydro-isoindol-2-ylmethyl)-13-methyl-17-oxo-7,8,9,11,12,13,14,15, 16,17-decahydro-6H-cyclopenta[a]phenanthrene-16-carboxylic acid methyl eater (JAC01159)

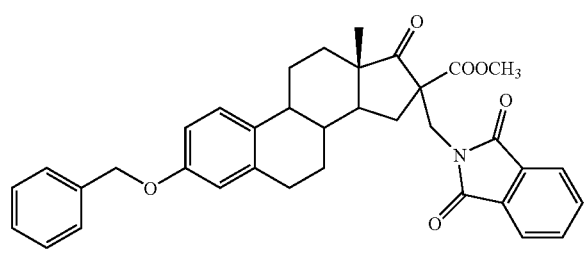

57 mg NaH (60% in oil, 1.43 mmol) was suspended in 2 mL dry THF. The suspension was cooled to 0° C. in an ice bath and 500 mg of JAC01011 (1.19 mmol) solubilized in 5 mL dry THF were added dropwise. The mixture was stirred for 30 min and the N-(Bromomethyl)phtalimide (344 mg, 1.43 mmol) in 3 mL dry THF was added dropwise. The reaction was stirred at 0° C. for 1 h and allowed to react at room temperature for a further 12 h. 1N HCl was added to the mixture and the acidic layer was extracted with diethylether (3 times). The combined organic layers were washed with sat. NaHCO$_3$ (3 times), brine, dried over Na$_2$SO$_4$ and evaporated in vacuo to give JAC01159 as a white solid. This compound was used without further purification. $^1$H NMR (270 MHz, CDCl$_3$): δ 0.85 (s, 3H, CH$_3$); 1.30-1.70 (m, 5H); 1.85-1.95 (m, 2H); 2.10-2.40 (m, 4H); 2.79 (m, 2H, CH$_2^6$); 3.75 (s, 3H, OCH$_3$); 3.96 (d, J=14.1 Hz, 1H, NCH$_2$); 4.17 (d, J=14.1 Hz, 1H, NCH$_2$); 4.96 (s, 2H, CH$_2$Ph); 6.66 (d, J=2.6 Hz, 1H, H$_4$); 6.73 (dd, J=8.4, 2.6 Hz, 1H, H$_2$); 7.12 (d, J=8.4 Hz, 1H, H$_1$); 7.24-7.37 (m, 5H); 7.67 (dd, J=5.1, 2.7 Hz, 2H); 7.77 (dd, J=5.1, 2.7 Hz, 2H).

Representative Procedure for Debenzylation:

3-Hydroxy-13-methyl-17-oxo-7,8,9,11,12,13,14,15, 16,17-decahydro-6H-cyclopenta[a] phenanthrene-16-carboxylic acid methyl ester (JAC01012, STX568)

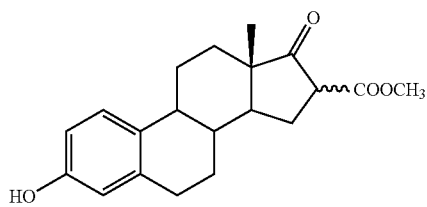

2.5 g (5.97 mmol) of JAC01011 were solubilized in THF (30 mL). A catalytic amount of 10% Pd/C was added and the reaction mixture was stirred at room temperature under H$_2$ for 8 h. Pd/C was filtered over celite and the filtrate was evaporated in vacuo. Recrystallisation of the solid residue in methanol gave 1.82 g (93%) of STX568 as a white solid. $^1$H NMR (400 MHz, DMSO-d$_6$): δ 0.87 (s, 1.95H, CH$_3$); 0.91 (s, 1.05H, CH$_3$); 1.20-2.40 (m, 11H); 2.75 (m, 2H, CH$_2^6$); 3.39 (dd, J=9.8, 8.6 Hz, 0.65H, CHCOO); 3.65 (s, 1.05H, OCH$_3$); 3.65 (s, 1.95H, OCH$_3$); 3.80 (dd, J=9.8, 8.6 Hz, 0.35H, CHCOO); 6.45 (d, J=2.3 Hz, 1H, H$_4$); 6.05 (dd, J=8.6, 2.7, 1H, H$_2$); 7.04 (d, J=8.2 Hz, 1H, H$_1$); 9.04 (s, 1H, OH); mp: 215-217° C.; Acq. Mass (FAB$^+$) calcd 328.1675, obsd 328.1684; Anal. Calcd for C$_{20}$H$_{32}$O$_4$: C, 73.15%; H, 7.37%; obsd C, 72.9%; H, 7.34%; purity: 97%.

This Same Procedure Afforded the Following Phenols in the Indicated Yields:

3,17-Dihydroxy-13-methyl-7,8,9,11,12,13,14,15,16, 17-decahydro-6H-cyclopenta [a]phenanthrene-16-carboxylic acid methyl ester (JAC01027, STX572)

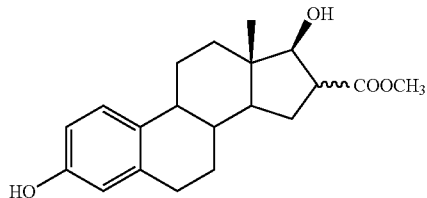

Recrystallisation of the solid residue in methanol/water. Yield=92%, white solid. $^1$H NMR (400 MHz, DMSO-d$_6$): δ 0.75 (s, 3H; CH$_3$); 1.04-1.46 (m, 5H); 1.64-1.86 (m, 4H); 2.08

(td, J=10.5, 3.3 Hz, 1H); 2.22 (m, 1H); 2.70 (m, 2H, $CH_2^6$); 3.05 (q, J=9.0 Hz, 1H, CHCO); 3.56 (s, 3H, $OCH_3$); 3.83 (dd, J=10.5, 5.5 Hz, 1H, CHO); 5.02 (d, J=5.0 Hz, 1H, OH); 6.42 (d, J=2.7 Hz, 1H, $H_4$); 6.48 (dd, J=8.2, 2.7 Hz, 1H, $H_2$); 7.03 (d, J=8.6 Hz, 1H, $H_1$); 8.99 (s, 1H, phenol); Acq. Mass ($FAB^+$) calcd 330.1831, obsd 330.1831; mp: 222-224° C.; Anal. Calcd for $C_{20}H_{28}O_4$: C, 72.70%; H, 7.93%; obsd C, 72.90%; H, 7.90%; purity: 95%.

16-Hydroxymethyl-13-methyl-7,8,9,11,12,13,14,15, 16,17-decahydro-6H-cyclopenta[a]phenanthrene-3, 17-diol (JAC01049, STX612)

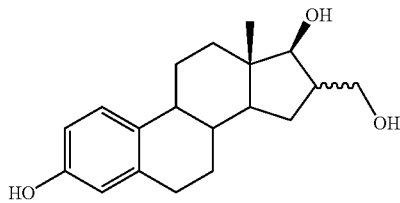

Yield=78%, white solid. $^1$H NMR (400 MHz, DMSO-$d_6$): δ 0.72 (s, 3H, $CH_3$); 1.06 (m, 2H); 1.16-1.42 (m, 4H); 1.84 (m, 3H); 2.10 (td, J=10.0, 3.3 Hz, 1H); 2.24 (m, 2H); 2.72 (m, 2H, $CH_2^6$); 3.34 (m, 1H); 3.70 (m, 2H); 4.18 (dd, J=6.2, 4.8 Hz, 1H, CHO); 4.64 (d, J=4.8 Hz, OH); 6.45 (d, J=2.6 Hz, 1H, $H_4$); 6.52 (dd, J=8.4, 2.6 Hz, 1H, $H_2$); 7.06 (d, J=8.4 Hz, 1H, $H_1$); 9.02 (s, 1H, phenol); mp: decomposition; MS ($FAB^+$) calcd 302.19, obsd 302.1 ($M^+$); Anal. Calcd for $C_{19}H_{26}O_3$: C, 75.46%; H, 8.67%; obsd C, 75.2%; H, 8.7%; purity: 100%.

16-(1,3-Dioxo-1,3-dihydro-isoindol-2-ylmethyl)-3-hydroxy-13-methyl-17-oxa-7,8,9,11,12,13,14,15,16, 17-decahydro-6H-cyclopenta[a]phenanthrene-16-carboxylic acid methyl ester (JACO1171-4, STX780)

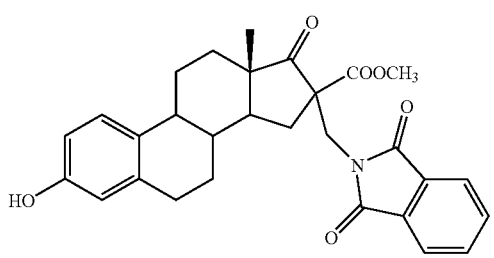

Purification by column chromatography using flash column ISOLUTE SI 1 g and an elution gradient Hexane/Ethyl Acetate. The white solid was precipitated in Ethyl acetate/Hexane. Yield=6.9%, white solid. $^1$H-NMR (270 MHz, MeOH-$d_3$): δ 0.89 (s, 3H, $CH_3$); 1.20-1.75 (m, 5H); 1.85-2.05 (m, 2H); 2.10-2.50 (m, 4H); 2.80 (m, 2H, $CH_2^6$); 3.72 (s, 3H, $OCH_3$); 4.08 (d, J=5.5 Hz, 1H, $NCH_2$); 6.66 (d, J=2.6 Hz, 1H, $H_4$); 6.73 (dd, J=8.4, 2.6 Hz, 1H, $H_2$); 7.12 (d, J=8.4 Hz, 1H, $H_1$); 7.75-7.90 (m, 4H); MS ($APCI^+$) calcd 487.20, obsd 489.36 (M+2); purity: 88%.

3-Benzyloxy-17-hydroxy-13-methyl-7,8,9,11,12,13, 14,15,16,17-decahydro-6H-cyclopenta[a]phenanthrene-16-carboxylic acid (JAC01083)

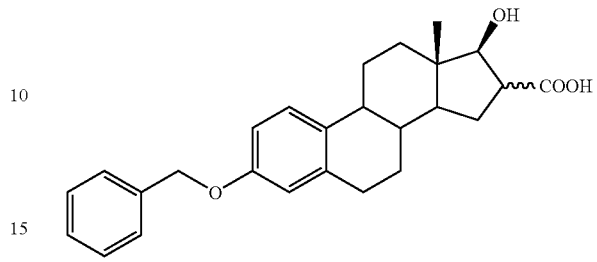

2 g (4.75 mmol) of STX569 were solubilized in 20 mL THF and 285 mg (7.13 mmol) NaOH solubilized in 5 mL water were added to the solution which was stirred at room temperature for 24 h. The solvents were evaporated and 6N HCl was added to the residue. The acidic layer was extracted by diethyl ether (5 times). The combined organic layers were extracted with 10% $K_2CO_3$ (5 times). This basic solution was made acidic adding 6N HCl and extracted by ethyl acetate (5 times). The combine organic layers were washed with brine, dried over $Na_2SO_4$ and evaporated in vacuo. The white solid was suspended in hexane and filtered to give 720 mg (37%) of JAC01083. $^1$H NMR (270 MHz, DMSO-$d_6$): δ 0.68 (s, 1.05H, $CH_3$); 0.72 (s, 1.95H, $CH_3$); 1.00-1.50 (m, 6H); 1.60-1.90 (m, 3H); 2.11 (m, 1H); 2.26 (m, 1H); 2.74 (m, 2H, $CH_2^6$); 2.92 (q, J=8.9 Hz, 0.65H, CHCO); 3.68 (dd, J=7.2, 5.3 Hz, 0.35H, CHCO); 3.80 (d, J=10.5 Hz, 0.65H, CHO); 4.91 (d, J=5.3, 0.35H, CHO); 5.03 (s, 2H, $CH_2Ph$); 6.68 (s, 1H, $H_4$); 6.74 (dd, J=8.6, 2.6 Hz, 1H, $H_2$); 7.14 (d, J=8.6 Hz, 1H, $H_1$); 7.25-7.50 (m, 5H, Ph).

3-Hydroxy-13-methyl-17-oxo-7,8,9,11,12,13,14,15, 16,17-decahydro-6H-cyclopenta[a]phenanthrene-16-carboxylic acid (JAC01043, STX610)

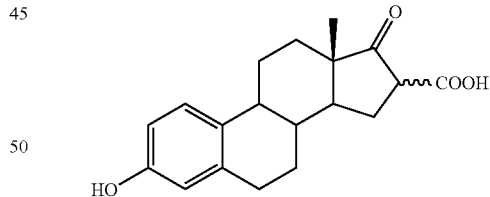

2.14 g (6.51 mmol) of STX568 were suspended in 46 mL of 5N NaOH and stirred at room temperature for 72 h until complete solubilization. After cooling to 0° C., 6N HCl was added dropwise to the solution until pH 1. The acidic layer was extracted by diethyl ether (3 times). The combined organic layers were washed with brine, dried over $Na_2SO_4$ and evaporated in vacuum at room temperature. The solid was suspended in hexane, filtered, washed with hexane and dried in vacuo to give 1.56 g (76%) of STX610 as beige solid, which was used without further purification. $^1$H NMR (270 MHz, DMSO-$d_6$): δ 0.84 (s, 1.95H, $CH_3$); 0.88 (s, 1.05H, $CH_3$); 1.20-1.55 (m, 4H); 1.70-2.00 (m, 3H); 2.10-2.35 (m, 4H); 2.74 (m, 2H, $CH_2^8$); 3.22 (t, J=8.6 Hz, 0.65H, CHCOO); 3.60 (t, J=8.6 Hz, 0.35H, CHCOO); 6.43 (d, J=2.4 Hz, 1H, $H_4$); 6.50 (dd, J=8.4, 2.4 Hz, 1H, $H_2$); 7.03 (d, J=8.4 Hz, 1H, $H_1$); 9.02 (s, 1H, phenol); Acq. Mass (FAB$^+$) calcd 314.1518, obsd 314.1524; purity: 95%.

NB: decomposed with time to give estrons at room temperature.

3,17-Dihydrox-13-methyl-7,8,9,11,12,13,14,15,16, 17-decahydro-6H-cyclopenta[a]phenanthrene-16-carboxylic acid (JACO1041, STX611)

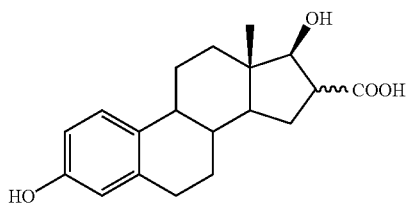

1.1 g (3.20 mmol) of STX572 were suspended in 10 mL MeOH and 0.58 g (14 mmol) NaOH solubilized in 3 mL water were added to the suspension. The solution was stirred at room temperature for 5 h. The solvents were evaporated and 6N HCl was added to the residue. The acidic layer was extracted by ethyl acetate (5 times) and the combined organic layers were washed with brine, dried over $Na_2SO_4$ and evaporated in vacuo. Recrystallisation of the solid residue in acetonitrile gave 470 mg (46%) of STX611 as a white solid. $^1$H NMR (400 MHz, DMSO-$d_6$): δ 0.69 (s, 1.86H, $CH_3$); 0.73 (s, 1.14H, $CH_3$); 1.20-1.40 (m, 5H); 1.45-1.85 (m, 4H); 2.10 (m, 1H); 2.20 (m, 1H); 2.45 (m, 0.62H, CHCOO); 275 (m, 2H, $CH_2{}^6$); 2.95 (q, J=9.0 Hz, 0.38H, CHCOO); 3.69 (d, J=8.00 Hz, 0.62H, CHO); 3.60 (d, J=10.8 Hz, 0.38H, CHO); 4.92 (bs, 1H, OH); 6.42 (d, J=2.7 Hz, 1H, $H_4$); 6.48 (dd, J=8.2, 2.7 Hz, 1H, $H_2$); 7.03 (d, J=8.2 Hz, 1H, $H_1$); 8.99 (s, 1H, phenol); mp: decomp.; Acq. Mass (FAB$^+$) calcd 316.1675, obsd 316.1677; purity: 95%.

Solid Phase Chemistry

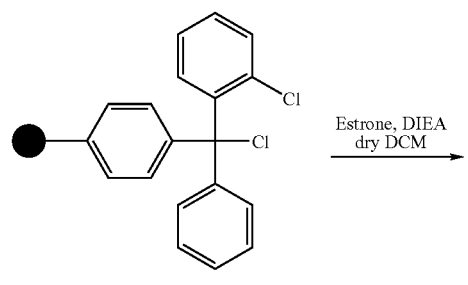

Loading = 1.1 mmol/g resin

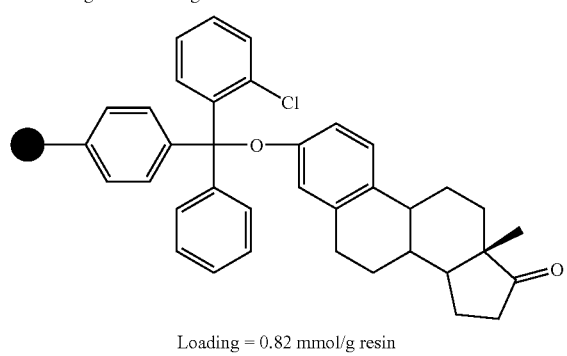

Loading = 0.82 mmol/g resin

Loading of Estrone on 2-chloro Triytl Resin.

500 mg of 2-chloro-trityl resin (loading of 1.1 mmol/g resin) were swollen in 7 mL dry DCM and 3 mL DIEA for 15 min. before addition of estrone. The mixture was shacked for 72 h at room temperature under $N_2$. The resin was filtered, washed with DCM, DMF, MeOH (3 cycles) and MeOH (5 times) and dried in vacuo. IR (cm$^{-1}$) 1736 (C=O, ketone). Determination of estrone's loading. 51.4 mg of loaded resin were swollen in 1 ml DCM in a filter funnel, 10 mL DCM/MeOH/TFA (7:1:2) were added (5 fractions of 2 mL) and the filtrate was evaporated in vacuo to give 11.5 mg of a white solid corresponding to estrone when structure checked by $^1$H NMR. The loading was then determined: 0.82 mmol/g resin.

NB: When addition DCM/MeOH/TFA, the resin became purple.

Combinatorial Library Construction:

Method A:

Step 1: Loading of JAC01041 on Oxime Resin.

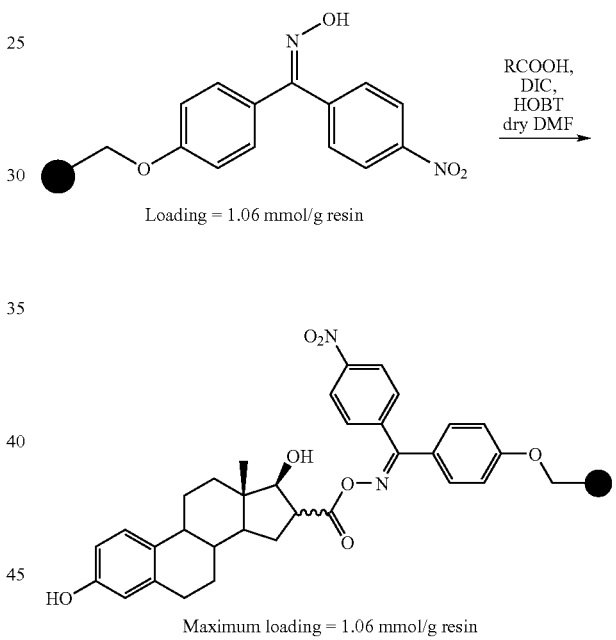

Maximum loading = 1.06 mmol/g resin 500 mg of oxime resin (loading of 1.06 mmol/g resin) were swollen in 7 mL dry DMF for 15 min after which 251 mg of JAC01041 were added followed by the addition of 41 μL DIC and 358 mg HOBT. The mixture was shaken for 48 h at room temperature under inert atmosphere and the resin was filtered, washed with DCM, DMF, MeOH (3 cycles) and MeOH (5 times) and dried in vacuo. IR (cm$^{-1}$) 1750 (C=O, ester); 1600 (C=N, oxime).

Step 2: Amidification.

200 mg of oxime resin loaded with JAC01041 (maximum loading of 1.06 mmol/g resin) were swollen in 4 mL dry DCM and 47 μL (0.53 mmol) furfurylamine were added to the suspension. The mixture was shacked at 40° C. under nitrogen atmosphere for 24 h. After filtration, the resin was washed with DCM (5 times) and the filtrated was evaporated in vacuo.

Method B:
Step 1: Active Ester Formation.

3-Benzyloxy-17-hydroxy-13-methyl-7,8,9,11,12,13,14,15,16,17-decahydro-6H-cyclopento[a]phenanthrene-16-carboxylic acid 4-nitro-phenyl ester (JAC0177)

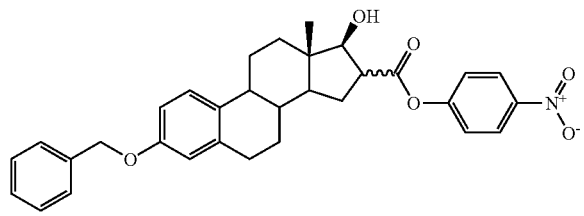

[*Helv. Chim. Act.* 1963, 795-804]. 400 mg of JAC01083 were solubilized in 4 mL dry DMF and 0.14 mL triethylamine (0.98 mmol) and 299 mg bis-(4nitrophenyl) carbonate (0.98 mmol) were successively added. The solution was stirred at room temperature for 2 h under $N_2$ atmosphere. The solution was cooled to 0° C. and 2N HCl was added. The mixture was extracted with DCM (3 times). The combined organic layers were washed with sat. $NaHCO_3$ (5 times) and brine, dried over $Na_2SO_4$ and evaporated in vacuo. The residue was purified by column chromatography ISOLUTE SI 20 g using an elution gradient Hexane/Ethyl Acetate to give 270 mg of JAC01177 as a yellow solid (52%). $^1$H NMR (270 MHz CDCl$_3$): δ 0.87 (s, 3H, CH$_3$); 1.27-1.50 (m, 4H); 1.80-2.05 (m, 4H); 2.10-2.40 (m, 3H); 2.84 (m, 2H, CH$_2^6$); 3.05 (ddd, J=11.7, 7.7, 3.7 Hz, 1H, CHCO); 4.06 (dd, J=8.1, 5.1 Hz, 1H, CHO); 5.01 (s, 2H, CH$_2$Ph); 6.70 (d, J=2.6 Hz, 1H, H$_4$); 6.76. (dd, J=8.8, 2.6 Hz, 1H, H$_2$); 7.19 (d, J=8.8 Hz, 1H, H$_1$); 7.25-7.45 (m, 7H); 8.27 (d, J=12.1 Hz, 2H); MS (FAB$^+$) calcd 527.23, obsd 527.4 (M$^+$); 389.4 (M–pNO$_2$PhO); 91.1 (PhCH$_2^+$).

Step 2: General Procedure for Amidification.
The active ester JAC01177 (0.17 mmol) was solubilized in 2 mL dry acetonitrile and the amine (2 eq) was added to the mixture. The solution was stirred overnight at room temperature and the solvents were evaporated in vacuo. The residue was purified by column chromatography using flash column ISOLUTE SI 5 g and an elution gradient Hexane/Ethyl Acetate.

Step 3: General Procedure for Debenzylation:
The benzylated amide was solubilized in THF (3 mL). A catalytic amount of 5% Pd/C was added and the reaction mixture was stirred at room temperature under H$_2$ for 24 h. Pd/C was filtered over paper and the filtrate was evaporated in vacuo. The final product was precipitated in a mixture Ethyl Acetate/Hexane.

| Reference | Method |
|---|---|
| STX 679 | A |
| STX 779 | B |
| STX 798 | B |
| STX 799 | B |
| STX 800 | B |
| STX 801 | B |
| STX 802 | B |
| STX 803 | B |
| STX 844 | B |
| STX 845 | B |

3-Benzyloxy-17-hydroxy-13-methyl-7,8,9,11,12,13,14,15,16,17-decahydro-6H-cyclopenta[a]phenanthrene-16-carboxylic acid (tetrahydro-furan-2-ylmethyl)-amide (JAC01163-3)

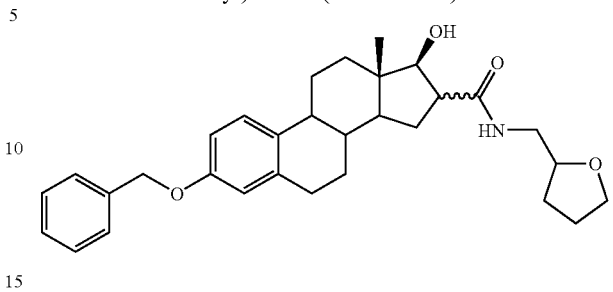

Method B, step 2. Yield=96%. $^1$H NMR (270 MHz, CDCl$_3$): δ 0.74 (s, 3H, CH$_3$); 1.10-1.60 (m, 7H); 1.70-2.00 (m, 5H); 2.05-2.30 (m, 3H); 2.50 (m, 1H); 2.74 (m, 2H, CH$_2^6$); 3.09 (m, 1H); 3.50 (m, 1H); 3.60-3.85 (m, 3H); 3.90 (m, 1H), 4.94 (s, 2H, CH$_2$Ph); 6.42 (t, J=5.5 Hz, 1H, NH); 6.63 (s, 1H, H$_4$); 6.68 (dd, J=8.4, 2.2 Hz, 1H, H$_2$); 7.10 (d, J=8.4 Hz, 1H, H$_1$); 7.20-7.40 (m, 5H).

3-Benzyloxy-17-hydroxy-13-methyl-7,8,9,11,12,13,14,15,16,17-decahydro-6H-cyclopenta[a]phenanthrene-16-carboxylic acid (pyridin-2-ylmethyl)-amide (JAC01179-1, STX789)

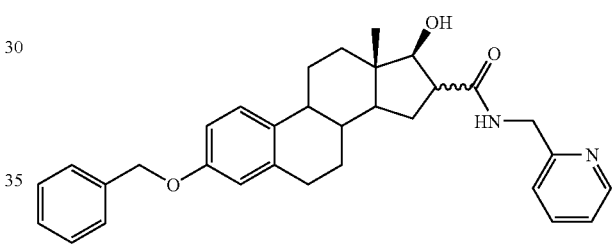

Method B, step 2. Yield=94%. $^1$H NMR (270 MHz, CDCl$_3$): δ 0.78 (s, 3H, CH$_3$); 1.20-1.60 (m, 8H); 1.70-1.90 (m, 2H); 2.05-2.30 (m, 3H); 2.63 (ddd, J=11.0, 8.0, 3.7 Hz, 1H, CHCO); 2.75 (m, 2H, CH$_2^6$); 3.73 (d, J=8.0 Hz, 1H, CHO); 4.30-4.43 (dAB, J=16.5, 4.8 Hz, 1H, NCH$_2$); 4.60-4.75 (dAB, J=16.5, 6.6 Hz, 1H, NCH$_2$); 4.95 (s, 2H, CH$_2$Ph); 6.64 (d, J=2.9 Hz, 1H, H$_4$); 6.70 (dd, J=8.4, 2.9 Hz, 1H, H$_2$); 6.90 (t, J=5.1 Hz, 1H, NH); 7.10 (d, J=8.4 Hz, 1H, H$_1$); 7.13-7.40 (m, 6H); 7.59 (td, J=7.7, 1.8 Hz, 1H, H$_{5'}$); 8.43 (d, J=5.1 Hz, 1H, H$_{3'}$); MS (FAB$^+$) calcd 496.27, obsd 497.3 (M+1).

3-Benzyloxy-17-hydroxy-13-methyl-7,8,9,11,12,13,14,15,16,17-decahydro-6H-cyclopenta[a]phenanthrene-16-carboxylic acid (pyridin-3-ylmethyl)-amide (JAC01179-2, STX790)

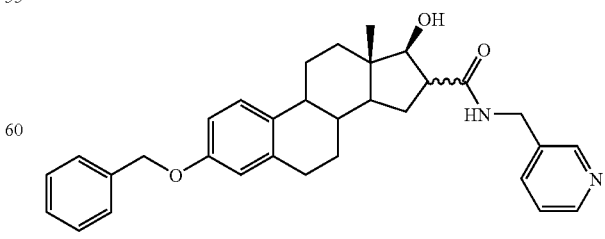

Method B, step 2. Yield=82%. $^1$H NMR (270 MHz, CDCl$_3$): δ 0.81 (s, 3H, CH$_3$); 1.10-1.60 (m, 8H); 1.79 (m, 2H); 2.05-2.30 (m, 3H); 2.57 (ddd, J=11.3, 8.4, 3.3 Hz, 1H, CHCO); 2.75 (m, 2H, CH$_2^6$); 3.72 (d, J=8.4 Hz, 1H, CHO); 4.25-4.55 (dAB, J=15.0, 6.2, 5.5 Hz, 2H, NCH$_2$); 4.95 (s, 2H, CH$_2$Ph); 6.63 (d, J=2.6 Hz, 1H, H$_4$); 6.70 (dd, J=8.4, 2.6 Hz, 1H, H$_2$); 7.10 (d, J=8.4 Hz, 1H, H$_1$); 7.14-7.40 (m, 6H); 7.58 (d, J=7.7 Hz, 1H, H$_{4'}$); 8.40 (dd, J=4.8, 1.4 Hz, 1H, H$_{6'}$); 8.42 (d, J=1.8 Hz, 1H, H$_{2'}$); MS (FAB$^+$) calcd 496.3, obsd 497.3 (M+1).

3-Benzyloxy-17-hydroxy-13-methyl-7,8,9,11,12,13, 14,15,16,17-decahydro-6H-cyclopenta[a]phenan-threne-16-yl)-(4-methyl-piperazin-1-yl)-methanone (JAC01179-3, STX791)

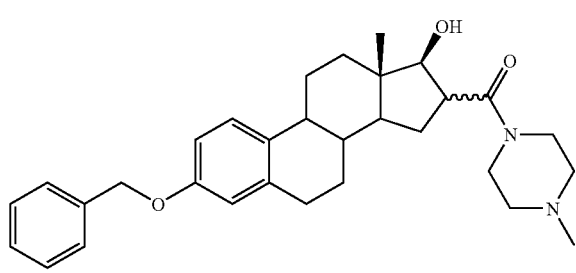

Method B, step 2. Yield=86%. $^1$H NMR (270 MHz, CDCl$_3$): δ 0.83 (s, 3H, CH$_3$); 1.30-1.60 (m, 7H); 1.70-1.85 (m, 2H); 2.15-2.45 (m, 10H); 2.75-2.95 (m, 3H); 3.40-3.80 (m, 4H); 4.20 (d, J=7.0 Hz, 1H); 5.00 (s, 2H, CH$_2$Ph); 6.68 (d, J=2.6 Hz, 1H, H$_4$); 6.75 (dd, J=8.8, 2.6 Hz, 1H, H$_2$); 7.15 (d, J=8.8 Hz, 1H, H$_1$); 7.29-7.42 (m, 5H); MS (FAB$^+$) calcd 488.3, obsd 489.3 (M+1).

3-Benzyloxy-17-hydroxy-13-methyl-7,8,9,11,12,13, 14,15,16,17-decahydro-6H-cyclopenta[a]phenan-threne-16-carboxylic acid ethyl-methyl-amide (JAC01179-4, STX794)

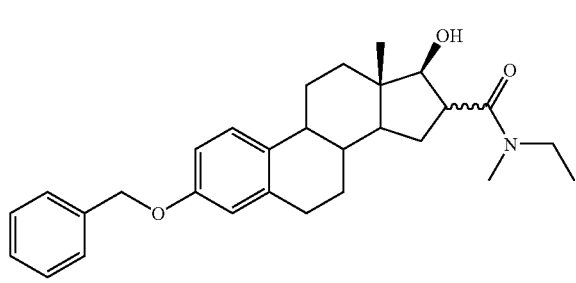

Method B, step 2. Yield=35%. $^1$H NMR (400 MHz, CDCl$_3$): δ 0.88 (s, 3H, CH$_3$); 1.13 (t, J=7.0 Hz, 1.5H, CH$_2$CH$_3$); 1.21 (t, J=7.0 Hz, 1.5H, CH$_2$CH$_3$); 1.32-1.60 (m, 8H); 1.68-1.88 (m, 4H); 1.98 (m, 1H); 2.24 (m, 1H); 2.33 (m, 1H, CHCO); 2.70 (m, 1H); 2.84 (m, 2H, CH$_2^6$); 2.96 (s, 1.5H, NCH$_3$); 3.03 (s, 1.5H, NCH$_3$); 3.30-3.48 (m, 2H, CH$_2$CH$_3$); 4.24 (app.t, J=7.4 Hz, 1H, CHO); 5.04 (s, 2H, CH$_2$Ph); 6.72 (d, J=2.4 Hz, 1H, H$_4$); 6.79 (dd, J=8.6, 2.4 Hz, 1H, H$_2$); 7.22 (d, J=8.6 Hz, 1H, H$_1$); 7.36-7.48 (m, 5H); MS (FAB$^+$) calcd 447.3, obsd 448.3 (M+1).

3-Benzyloxy-17-hydroxy-13-methyl-7,8,9,11,12,13, 14,15,16,17-decahydro-6H-cyclopante[a]phenan-threne-16-carboxylic acid isopropylamide (JAC01179-5, STX 795)

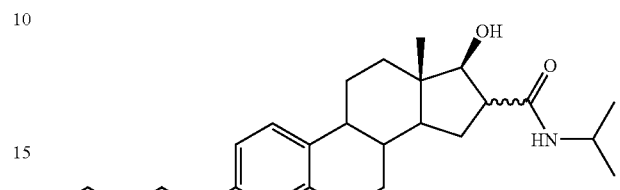

Method B, step 2. Yield=92%. $^1$H NMR (270 MHz, CDCl$_3$): δ 0.80 (s, 3H, CH$_3$); 1.14 (d, J=7.0 Hz, 6H, 2×CH$_3$); 1.28-1.60 (m, 6H); 1.80-1.92 (m, 3H); 2.10-2.36 (m, 3H); 2.48 (ddd, J=11.7, 8.4, 4.0 Hz, 1H, CHCO); 2.81 (m, 2H, CH$_2^6$); 3.76 (dd, J=8.0, 5.1 Hz, 1H, CHO); 4.09 (septuplet, J=7.0 Hz, 1H, CH(CH$_3$)$_2$); 5.01 (s, 2H, CH$_2$Ph); 5.72 (d, J=8.1 Hz, 1H, NH); 6.70 (d, J=2.7 Hz, 1H, H$_4$); 6.75 (dd, J=8.4, 2.7 Hz, 1H, H$_2$); 7.17 (d, J=8.4 Hz, 1H, H$_1$); 7.29-7.43 (m, 5H); MS (FAB$^+$) calcd 447.3, obsd 448.3 (M+1).

3-Benzyloxy-17-hydroxy-13-methyl-7,8,9,11,12,13, 14,15,16,17-decahydro-6H-cyclopenta[a]phenan-threne-16-carboxylic acid (1-methyl-1H-pyrrol-2-ylmethyl)-amide (JAC01179-6, STX793)

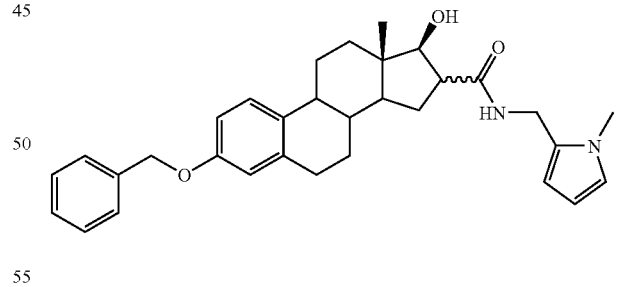

Method B, step 2. Yield=86%. $^1$H NMR (270 MHz, CDCl$_3$): δ 0.79 (s, 3H, CH$_3$); 1.27-1.65 (m, 6H); 1.80-1.92 (m, 3H); 2.10-2.36 (m, 3H); 2.54 (ddd, J=11.7, 8.4, 4.0 Hz, 1H, CHCO); 2.82 (m, 2H, CH$_2^6$); 4.44 (t, J=5.1 Hz, 1H, CH$_2$N); 5.01 (s, 2H, CH$_2$Ph); 5.98 (t, J=5.1 Hz, 1H, NH); 6.04 (m, 2H, H$_{3'}$, H$_{5'}$); 6.59 (t, J=2.2 Hz, H$_{4'}$); 6.70 (d, J=2.6 Hz, 1H, H$_4$); 6.76 (dd, J=8.8, 2.6 Hz, 1H, H$_2$); 7.17 (d, J=8.8 Hz, 1H, H$_1$); 7.29-7.43 (m, 5H); MS (FAB$^+$) calcd 498.3, obsd 499.3 (M+1).

3-Benzyloxy-17-hydroxy-13-methyl-7,8,9,11,12,13, 14,15,16,17-decahydro-6H-cyclopenta[a]phenanthrene-16-carboxylic acid (5-methyl-pyrazin-2-ylmethyl)-amide (JAC01179-7, TX 792)

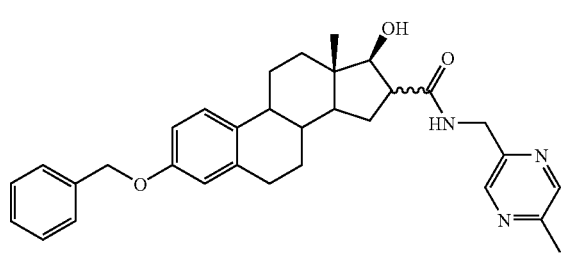

Method B, step 2. Yield=85%. ¹H NMR (270 MHz, CDCl₃): δ 0.83 (s, 3H, CH₃); 1.20-1.60 (m, 9H); 1.87 (m, 1H); 2.10-2.35 (m, 1H); 2.50 (d, J=5.1 Hz, 1H, OH); 2.54 (s, 3H, HarCH₃); 2.65 (m, 1H, CHCO); 2.81 (m, 2H, CH₂⁶); 3.75 (dd, J=8.4, 5.1 Hz, CHO); 4.40-4.80 (dAB, J=16.0, 6.6, 4.8 Hz, NCH₂); 5.01 (s, 2H, CH₂Ph); 6.70 (m, 2H, H₄+NH); 6.74 (dd, J=8.4, 2.6 Hz, 1H, H₂); 7.17 (d, J=8.4 Hz, 1H, H₁); 7.28-7.43 (m, 5H); 8.36 (s, 1H); 8.47 (s, 1H); MS (FAB⁺) calcd 511.3, obsd 512.3 (M+1).

3-Benzyloxy-17-hydroxy-13-methyl-7,8,9,11,12,13, 14,15,16,17-decahydro-6H-cyclopenta[a]phenanthrene-16-carboxylic acid (pyridin-3-ylethyl)-amide (JAC01185, STX814)

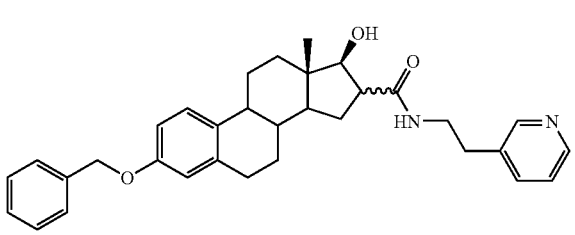

Method B, step 2. Yield=58%. ¹H NMR (270 MHz, CDCl₃): δ 0.73 (s, 3H, CH₃); 1.10-1.60 (m, 7H); 1.81 (m, 2H); 2.05-2.30 (m, 3H); 2.45 (ddd, J=11.7, 8.4, 3.7 Hz, 1H, CHCO); 2.77 (m, 2H, CH₂⁶); 3.30-3.65 (m, 3H); 4.94 (s, 2H, CH₂Ph); 6.19 (t, J=5.5 Hz, 1H, NH); 6.64 (d, J=2.6 Hz, 1H, H₄); 6.68 (dd, J=8.4, 2.6 Hz, 1H, H₂); 7.10 (d, J=8.4 Hz, 1H, H₁); 7.15-7.38 (m, 6H); 7.49 (m, 1H); 8.36 (m, 2H); MS (FAB⁺) calcd 510.3, obsd 511.3 (M+1).

3-Benzyloxy-17-hydroxy-13-methyl-7,8,9,11,12,13, 14,15,16,17-decahydro-6H-cyclopenta[a]phenanthrene-16-carboxylic acid (1-phenyl-ethyl)-amide (JAC01185-4A, STX815)

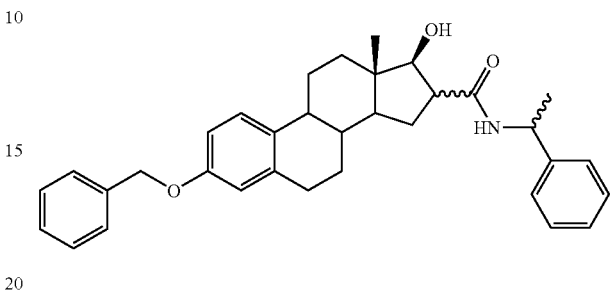

Method B, step 2. Yield=46%. ¹H NMR (270 MHz, CDCl₃): δ 0.80 (s, 3H, CH₃); 1.20-1.60 (m, 10H); 1.84 (m, 2H); 2.10-2.35 (m, 3H); 2.57 (ddd, J=11.7, 8.4, 3.7 Hz, 1H, CHCO); 2.81 (m, 2H, CH₂⁶); 3.71 (dd, J=8.8, 5.5 Hz, 0.71H, CHO); 3.80 (m, 0.28H, CHO); 5.00 (s, 2H, CH₂Ph); 5.12 (m, ¹H, CHPh); 6.22 (m, 1H, NH); 6.69 (d, J=2.9 Hz, 1H, H₄); 6.76 (dd, J=8.5, 2.9 Hz, 1H, H₂); 7.12 (d, J=8.5 Hz, 1H, H₁); 7.15-7.45 (m, 10H); MS (FAB⁺) calcd 509.3, obsd 510.3 (M+1).

3-Benzyloxy-17-hydroxy-13-methyl-7,8,9,11,12,13, 14,15,16,17-decahydro-6H-cyclopenta[a]phenanthrene-16-carboxylic acid (1-phenyl-ethyl)-amide (JAC01185-4B, STX816)

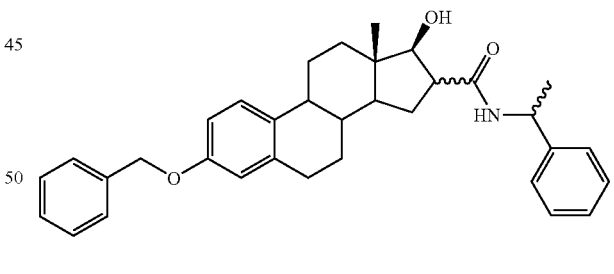

Method B, step 2. Yield=24%. ¹H NMR (270 MHz, CDCl₃): δ 0.79 (s, 3H, CH₃); 1.20-1.60 (m, 10H); 1:87 (m, 3H); 2.10-2.38 (m, 3H); 2.53 (ddd, J=11.0, 8.1, 3.3 Hz, 1H, CHCO); 2.80 (m, 2H, CH₂⁶); 3.81 (dd, J=8.1, 5.1 Hz, 1H, CHO); 5.00 (s, 2H, CH₂Ph); 5.12 (m, 1H, CHPh); 6.20 (m, 1H, NH); 6.69 (d, J=2.6 Hz, 1H, H₄); 6.75 (dd, J=8.6, 2.6 Hz, 1H, H₂); 7.12 (d, J=8.6 Hz, 1H, H₁); 7.20-7.50 (m, 10H); MS (FAB⁺) calcd 509.3, obsd 510.3 (M+1).

This second isomer has been isolated from the same reaction as STX815.

101

3-Benzyloxy-17-hydroxy-13-methyl-7,8,9,11,12,13,14,15,16,17-decahydro-6H-cyclopenta[a]phenanthrene-16-carboxylic acid (2-piperazin-1-yl-ethyl)-amide (JAC01185-2, STX817)

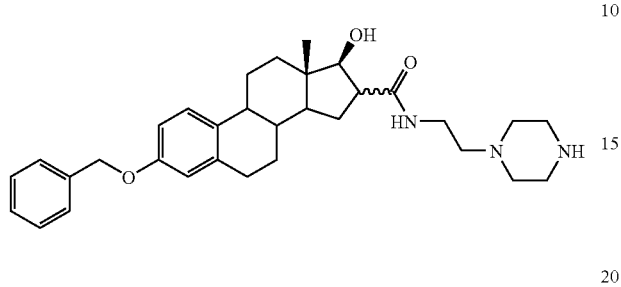

Method B, step 2. Yield=73%. $^1$H NMR (270 MHz, CDCl$_3$): δ 0.81 (s, 3H, CH$_3$); 1.20-1.60 (m, 6H); 1.80-2.05 (m, 2H); 2.10-2.60 (m, 11H); 2.75-2.95 (m, 6H); 3.10-3.40 (m, 1H); 3.55-3.70 (m, 2H); 5.00 (s, 2H, CH$_2$Ph); 6.01 (b s, 1H, NH); 6.69 (d, J=2.6 Hz, 1H, H$_4$); 6.75 (dd, J=8.4, 2.6 Hz, 1H, H$_2$); 7.17 (d, J=8.4 Hz, 1H, H$_1$); 7.30-7.35 (m, 10H); MS (FAB$^+$) calcd 517.3, obsd 518.4 (M+1).

3-Benzyloxy-17-hydroxy-13-methyl-7,8,9,11,12,13,14,15,16,17-decahydro-6H-cyclopenta[a]phenanthrene-16-carboxylic acid (pyridin-4-ylmethyl)-amide (JAC01191-1, STX818)

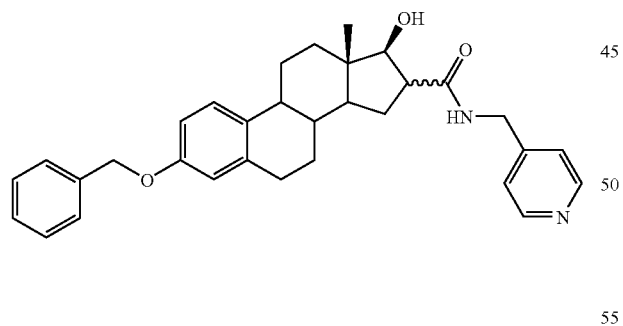

Method B, step 2. Yield=92%. $^1$H NMR (270 MHz, CDCl$_3$): δ 0.83 (s, 3H, CH$_3$); 1.20-1.65 (m, 7H); 1.80-1.95 (m, 2H); 2.15-2.40 (m, 3H); 2.64 (ddd, J=12.4, 8.4, 3.6 Hz, 1H, CHCO); 2.82 (m, 2H, CH$_2^6$); 3.79 (d, J=8.4 Hz, 1H, CHO); 4.35-4.60 (dAB, J=16.1, 8.4, 6.2 Hz, 2H, NCH$_2$); 5.01 (s, 2H, CH$_2$Ph); 6.44 (m, 1H, NH); 6.70 (d, J=2.2 Hz, 1H, H$_4$); 6.75 (dd, J=8.4, 2.2 Hz, 1H, H$_2$); 7.15-7.45 (m, 8H); 8.51 (d, J=5.8 Hz, 2H, H$_{2'}$, H$_{5'}$); MS (FAB$^+$) calcd 496.3, obsd 497.3 (M+1).

102

3,17-Dihydroxy-13-methyl-7,8,9,11,12,13,14,15,16,17-decahydro-6H-cyclopente[a]phenenthrene-16-carboxylic acid (furan-2-ylmethyl)-amide (JAC01081B, STX679)

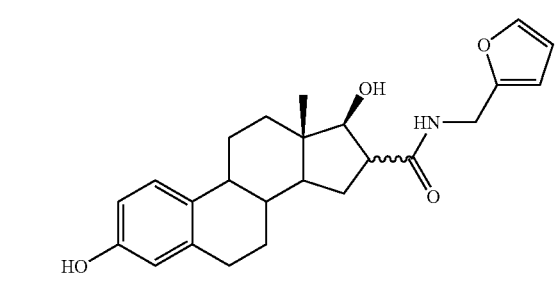

Method A, step 2. The brown oil was purified by column chromatography using EtOAc/Hexane (50:50) as eluant gave 3 mg (3.6% over 2 steps) of STX679 as a yellow solid. $^1$H NMR (400 MHz, CDCl$_3$): δ 0.82 (s, 2.49H, CH$_3$); 0.84 (s, 0.51H, CH$_3$); 1.08-1.60 (m, 6H); 1.80 (m, 2H); 2.20 (m, 2H); 2.30 (m, 1H); 2.58 (m, 1H, CHCO); 2.80 (m, 2H, CH$_2^6$); 3.74 (d, J=8.4 Hz, 0.83H, CHO); 3.80 (d, J=8.9 Hz, 0.17H, CHO); 4.41 (d, J=5.7 Hz, 2H, CH$_2$N); 6.15 (dd, J=3.2, 1.7 Hz, 1H, furane H$_3$); 6.25 (m, 1H, furane H$_4$); 6.50 (d, J=2.7 Hz, 1H, H$_4$); 6.55 (dd, J=8.4, 2.7 Hz, 1H, H$_2$); 7.04 (d, J=8.1 Hz, 1H, H$_1$); 7.28 (dd, J=2.0; 1.0 Hz, 1H, furane H$_5$); MS (FAB$^+$) calcd 395.21, obsd 396.18 (M+1); purity: 98%.

3,17-Dihydroxy-13-methyl-7,8,9,11,12,13,14,15,16,17-decahydro-6H-cyclopenta[a]phenanthrene-16-carboxylic acid (tetrahydro-furan-2-ylmethyl)-amide (JAC01171-3, STX779)

Method B, step 3. Yield=12%, white solid. $^1$H NMR (MeOH-d$_3$, 270 MHz): δ 0.81 (s, 3H, CH$_3$); 1.26-1.45 (m, 6H); 1.50-1.70 (m, 3H); 1.80-2.00 (m, 6H); 2.15 (m, 1H); 2.30 (m, 1H); 2.60 (ddd, J=11.4, 8.1, 3.7 Hz, 1H, CHCO); 2.78 (m, 2H, CH$_2^6$); 3.70-3.95 (m, 3H); 3.98 (m, 1H); 6.45 (d, J=2.6 Hz, 1H, H$_4$); 6.52 (dd, J=8.4, 2.6 Hz, 1H, H$_2$); 7.06 (d, J=8.4 Hz, 1H, H$_1$); MS (APCI$^+$) calcd 399.53, obsd 401.34 (M+2); Purity: 99%

3,17-Dihydroxy-13-methyl-7,8,9,11,12,13,14,15,16,17-decahydro-6H-cyclopenta[a]phenanthrene-16-carboxylic acid (pyridin-3-ylmethyl)-amide (JAC01181-2, STX798)

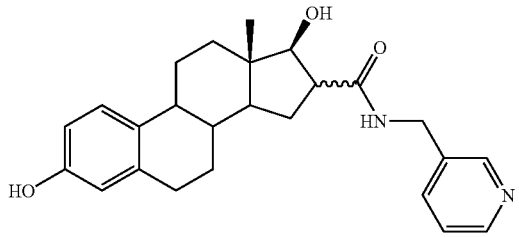

Method B, step 3. Yield=36%. ¹H NMR (270 MHz, DMSO-$d_6$): δ 0.69 (s, 3H, $CH_3$); 1.10-1.40 (m, 7H); 1.45-1.60 (m, 2H); 1.60-1.85 (m, 4H); 2.20 (m, 2H); 2.67 (m, 2H, $CH_2^6$); 2.86 (m, 2H); 3.65 (m, 1H); 4.29 (d, J=5.5 Hz, 1H); 4.80-5.05 (m, 1H); 6.41 (s, 1H, $H_4$); 6.48 (dd, J=8.4, 2.2 Hz, 1H, $H_2$); 7.02 (d, J=8.4 Hz, 1H, $H_1$); 7.33 (m, 0.5H); 7.62 (m, 1H); 8.26 (m, 0.5H); 8.42 (dd, J=4.8, 1.8 Hz, 1H); 8.47 (m, 1H); 9.00 (bs, 1H, phenol). MS (APCI⁺) calcd 406.5, obsd 408.3 (M+2); Purity: 100%

3,17-Dihydroxy-13-methyl-7,8,9,11,12,13,14,15,16,17-decahydro-6H-cyclopenta[a]phenanthrene-16-yl)-(4-methyl-piperazin-1-yl)-methanone (JAC01181-3, STX799)

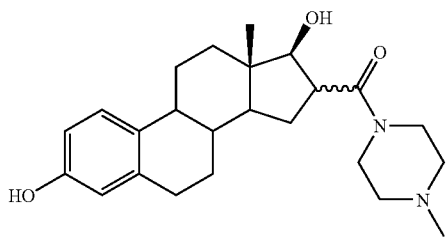

Method B, step 3. Yield=58%. ¹H NMR (270 MHz, $CDCl_3$): δ 0.83 (s, 3H, $CH_3$); 1.26-1.55 (m, 6H); 1.65-1.85 (m, 3H); 1.89 (m, 1H); 2.25 (m, 1H); 2.30 (s, 3H, $NCH_3$); 2.40 (m, 4H); 2.78 (m, 2H, $CH_2^6$); 2.88 (m, 1H, CHCO); 3.40-3.80 (m, 4H); 4.17 (d, J=7.7 Hz, CHO); 6.53 (d, J=2.7 Hz, 1H, $H_4$); 6.61 (dd, J=8.4, 2.7 Hz, 1H, $H_2$); 7.12 (d, J=8.4 Hz, 1H, $H_1$). MS (APCI⁺) calcd 398.5, obsd 400.3 (M+2); Purity: 100%.

3,17-Dihydroxy-13-methyl-7,8,9,11,12,13,14,15,16,17-decahydro-6H-cyclopenta[a]phenanthrene-16-carboxylic acid ethyl-methyl-amide (JAC01181-4, STX800)

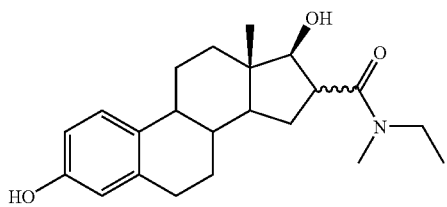

Method B, step 3. Yield=75%. ¹H NMR (400 MHz, DMSO-$d_6$): δ 0.70 (s, 3H, $CH_3$); 0.98 (t, J=6.8 Hz, 1.5H, $CH_2CH_3$); 1.07 (t, J=7.0 Hz, 1.5H, $CH_2CH_3$); 1.10-1.30 (m, 6H); 1.45-1.85 (m, 4H); 2.05 (m, 1H); 2.20 (m, 1H); 2.67 (m, 2H, $CH_2^6$); 2.79 (s, 1.5H, $NCH_3$); 2.88 (m, 1H, CHCO); 2.96 (s, 1.5H, $NCH_3$); 3.30-3.48 (m, 2H, $CH_2CH_3$); 3.78 (dd, J=12.8, 7.0 Hz, 1H); 4.76 (t, J=5.3 Hz, NH); 6.41 (d, J=2.6 Hz, 1H, $H_4$); 6.47 (dd, J=8.2, 2.6 Hz, 1H, $H_2$); 7.02 (d, J=8.2 Hz, 1H, $H_1$); 8.99 (s, 1H, phenol). MS (APCI⁺) calcd 357.5, obsd 359.3 (M+2); Purity: 100%.

3-17-Dihydroxy-13-methyl-7,8,9,11,12,13,14,15,16,17-decahydro-6H-cyclopenta[a]phenanthrene-16-carboxylic acid isopropylamide (JAC01181-5, STX 801)

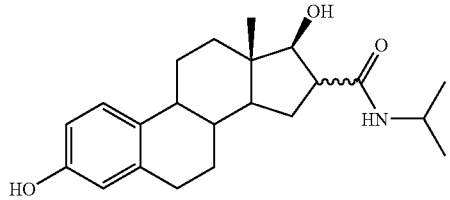

Method B, step 3. Yield=50%. ¹H NMR (270 MHz, $CDCl_3$): δ 0.79 (s, 3H, $CH_3$); 1.14 (d, J=6.6 Hz, 6H, 2×$CH_3$); 1.20-1.60 (m, 6H); 1.84 (m, 2H); 2.09-2.20 (m, 2H); 2.22-2.34 (m, 1H); 2.48 (ddd, J=12.1, 8.4, 4.0 Hz, 1H, CHCO); 2.77 (m, 2H, $CH_2^6$); 3.76 (d, J=8.4 Hz, 1H); 4.09 (m, 1H, C$H(CH_3)_2$); 5.73 (app. d, J=7.3 Hz, 1H, NH); 6.54 (d, J=2.7 Hz, 1H, $H_4$); 6.61 (dd, J=8.4, 2.7 Hz, 1H, $H_2$); 7.11 (d, J=8.4 Hz, 1H, $H_1$). MS (APCI⁺) calcd 357.5, obsd 359.2 (M+2); Purity: 100%.

3,17-Dihydroxy-13-methyl-7,8,9,11,12,13,14,15,16,17-decahydro-6H-cyclopenta[a]phenenthrene-16-carboxylic acid (1-methyl-1H-pyrrol-2-ylmethyl)-amide (JAC01181-6, STX802)

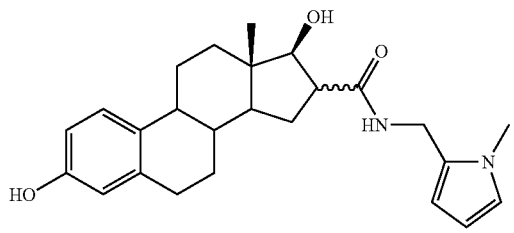

Method B, step 3. Yield=45%. ¹H NMR (270 MHz, $CDCl_3$): δ 0.78 (s, 3H, $CH_3$); 1.20-1.65 (m, 8H); 1.80-1.92 (m, 3H); 2.10-2.20 (m, 2H); 2.25 (m, 1H); 2.50 (ddd, J=11.7, 8.4, 4.0 Hz, 1H, CHCO); 2.84 (m, 2H, $CH_2^6$); 3.57 (s, 3H); 3.78 (d, J=8.1 Hz, 1H, CHO); 4.44 (t, J=5.8 Hz, 1H, $CH_2N$); 5.99 (t, J=5.1 Hz, 1H, NH); 6.05 (m, 2H); 6.54 (d, J=2.9 Hz, 1H, $H_4$); 6.57-6.64 (m, 2H); 7.10 (d, J=8.4 Hz, 1H, $H_1$). MS (APCI⁺) calcd 408.5, obsd 408.3 (M⁺), 410.3 (M+2); Purity: 100%.

3,17-Dihydroxy-13-methyl-7,8,9,11,12,13,14,15,16,17-decahydro-6H-cyclopenta[a]phenanthrene-16-carboxylic acid (5-methyl-pyrazin-2-ylmethyl)-amide (JAC01181-7, STX803)

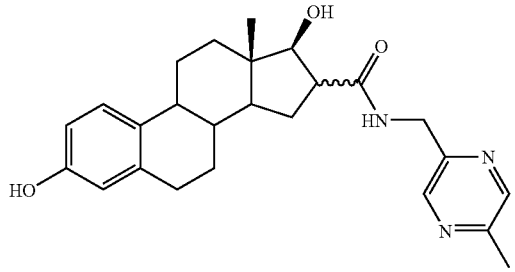

Method B, step 3. Yield=26%. $^1$H NMR (270 MHz, CDCl$_3$): δ 0.82 (s, 3H, CH$_3$); 1.20-1.65 (m, 8H); 1.75-1.95 (m, 2H); 2.05-2.40 (m, 3H); 2.54 (s, 3H, HarCH$_3$); 2.64 (m, 1H, CHCO); 2.81 (m, 2H, CH$_2^6$); 3.77 (d, J=8.4 Hz, CHO); 4.40-4.80 (ddAB, J=16.5, 7.0, 5.1 Hz, NCH$_2$); 6.54 (app. s, 1H, H$_4$); 6.60 (dd, J=8.4, 2.6 Hz, 1H, H$_2$); 6.72 (t, J=5.1 Hz, 1H, NH); 7.10 (d, J=8.4 Hz, 1H, H$_1$); 8.36 (s, 1H); 8.48 (s, 1H). MS (APCI$^+$) calcd 421.54, obsd 423.3 (M+2); Purity: 100%.

3,17-Dihydroxy-13-methyl-7,8,9,11,12,13,14,15,16,17-decahydro-6H-cyclopenta[a]phenanthrene-16-carboxylic acid (1-phenyl-ethyl)-amide (JAC01193-3, STX844)

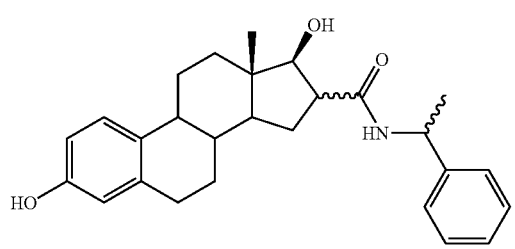

[Starting material was STX815]. Method B, step 3. Yield=7.3%. $^1$H NMR (270 MHz, DMSO-d$_6$): δ 0.70 (s, 3H, CH$_3$); 1.10-1.38 (m, 9H); 1.65-1.85 (m, 3H); 2.05 (m, 1H); 2.20 (m, 1H); 2.68 (m, 2H, CH$_2^6$); 3.60 (m, 1H, CHCO); 4.80-5.00 (m, 2H); 6.41 (app. s, 1H, H$_4$); 6.48 (dd, J=8.1, 2.9 Hz, 1H, H$_2$); 7.02 (d, J=8.1 Hz, 1H, H$_1$); 7.20 (m, 1H); 7.25-7.40 (m, 5H); 8.03 (d, J=8.4 Hz, 1H, NH); 8.97 (s, 1H, OH); MS (APCI$^+$) calcd 419.25, obsd 420.42, Purity: 98%.

3,17-Dihydroxy-13-methyl-7,8,9,11,12,13,14,15,16,17-decahydro-6H-cyclopenta[a]phenanthrene-16-carboxylic acid (pyridin-4ylmethyl)-amide JAC001193-5, STX845)

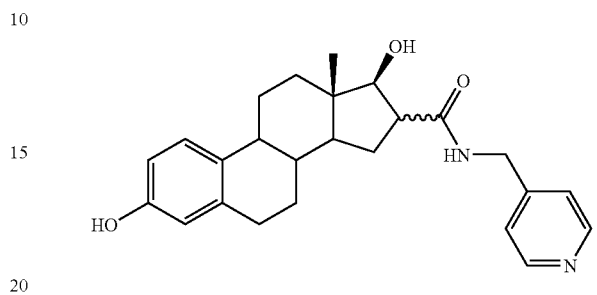

Method B, step 3. Yield=17%. $^1$H NMR (270 MHz, DMSO-d$_6$): δ 0.60 (s, 0.86H, CH$_3$); 0.63 (s, 2.14H, CH$_3$); 1.10-1.25 (m, 5H); 1.35-1.80 (m, 4H); 2.02 (m, 1H); 2.13 (m, 1H); 2.60 (m, 2H, CH$_2^6$); 2.81 (m, 1H); 3.60 (dd, J=8.1, 4.4 Hz, 1H, CHO); 4.10-4.30 (dAB, J=16.1, 6.2 Hz, 2H, NCH$_2$); 4.76 (d, J=5.9 Hz, 0.29H, CHO); 4.92 (d, J=4.4 Hz, 0.71 H, CHO); 6.33 (app. s, 1H, H$_4$); 6.40 (app. d, J=8.4 Hz, 1H, H$_2$); 6.94 (d, J=8.4 Hz, 1H, H$_1$); 7.16 (app. d, J=5.5 Hz, 2H); 8.22 (t, J=5.8 Hz, 1H, NH); 8.39 (dd, J=4.7, 1.4 Hz, 2H); 8.92 (s, 1H, OH); MS (APCI$^+$) calcd 406.2, obsd 407.3 (M+1); Purity: 96%

Section 3

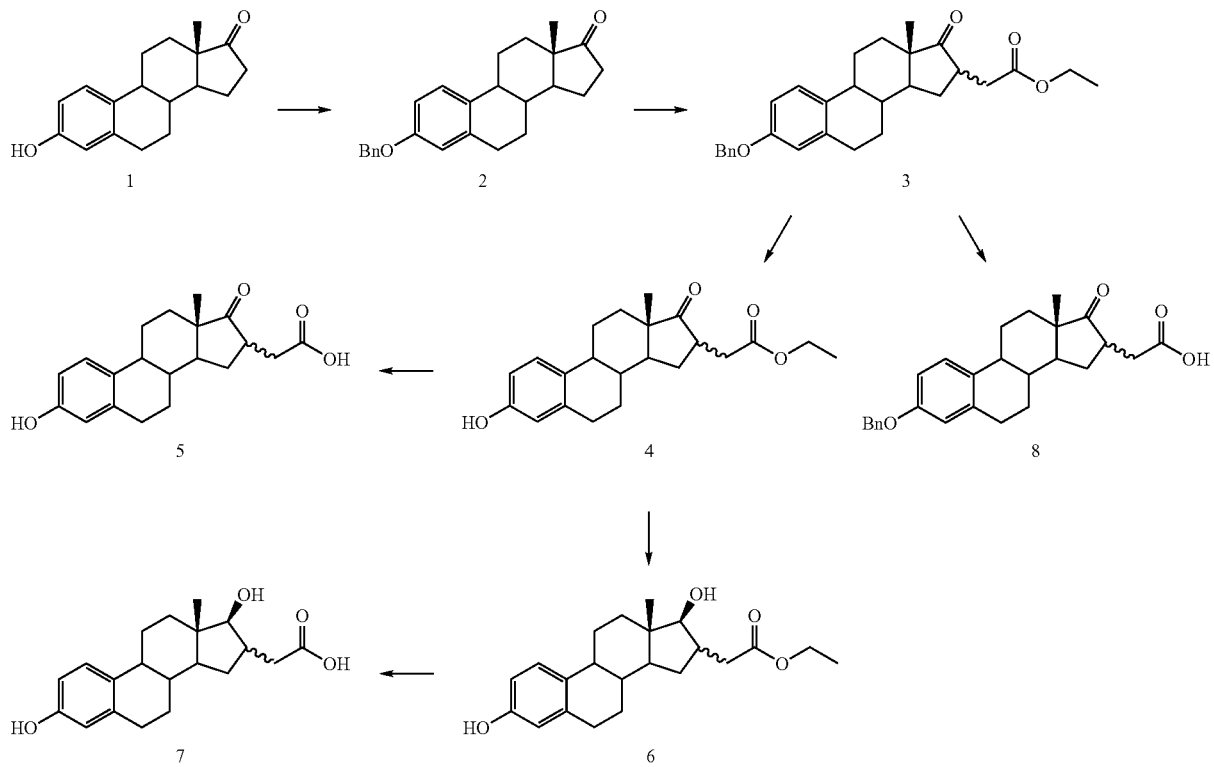

Scheme 1: Synthesis of common intermediate acids (5 and 7) from Estrone

EXPERIMENTAL

General Methods. Unless otherwise noted, all reactions were conducted in oven-dried glassware using HPLC grade solvents. Purification of compounds was carried out using Argonaut pre-packed columns (Flash Column Chromatography) using flash vacuum system. Thin-layer chromatography (TLC) was performed on plates Kieselgel 60 $F_{254}$ (Merck). $^1$H NMR was measured with a Jeol 270 MHz NMR spectrometer or 400 MHz Bruker NMR spectrometer in deuterated-solvents as the internal reference. Low resolution mass spectral data were obtained either on a Micromass platform LCZ (ES+, APCI+) or FAB. High resolution mass was obtained using FAB technique Waters Alliance-HT-2790 system with a column Symmetry$^R$ C18 was used to determine the purity using HPLC spectra with 10% water in Methanol as eluent, $R_T$ values are quoted for these conditions.

2-Benzyl estrone 2 (HDS01-082)

To a solution of 3-hydroxy estrone (10.00 g, 0.036 mol) in THF (180 ml) under nitrogen, was added sodium hydride (1.056 g, 0.044 mol) portion wise and stirred at room temperature for 30 minutes. Benzyl bromide (7.52 g, 0.044 mol) was added at r.t. and the reaction mixture was refluxed overnight. The completion of the reaction was monitored by tlc (ethyl acetate:hexane, 3:7). The crude mixture was cooled to r.t., quenched by addition of water (drop wise). The organic phase was extracted with DCM (2×100 ml), followed by ethyl acetate (2×100 ml) and the combined organic extracts were dried and concentrated in vacuo to obtain a colourless solid. The crude solid was dissolved in EtOH containing 5% EtOAc, left in a refrigerator to obtain the required product 2 (10.711 g, 82%) as a crystalline colourless solid. Analytical data see JAC01-002

3-Benzyloxy-16-methylene Estrone Carboxylic Acid Ethyl Ester 3 (HDS01-086 and HDS01-126)

To a solution of Lithium Diisopropylamide (5.66 ml, 1.8M solution in heptanes, THF, and ethyl benzene) in THF (20 ml) was added a solution of estrone benzyl ether 2 (3.90 g, 10.8 mmol) in THF (30 ml) at 0° C. The reaction mixture was stirred at 0° C. for approximately 15 minutes and cooled to −45° C. A solution of ethyl bromoacetate (5.344 g, 32 mmol) in THF (10.0 ml) was added drop wise over 10 minutes and stirred at −45° C. for a period of 8 h and room temperature overnight. The reaction was monitored by tic., The crude reaction mixture was quenched with saturated $NH_4Cl$, extracted the product into DCM (2×100 ml), dried and concentrated in vacuo to obtain a yellow oily product. The crude product was purified by Flash Chromatography ($SiO_2$, ethyl acetate hexane gradient elution) to obtain the required product 3 (4.91 g, 70%, a mixture of diastereoisomers) as a pale yellow solid: $^1$H NMR (CDCl$_3$) δ 0.928 and 1.002 (2×s, 3H each, Me), 1.295 (t, 3H, CH$_3$), 1.41-1.61 (m, 6H), 1.77-1.82 (m, 1H), 1.93-2.03 (m, 3H), 2.26-2.30 (broad m, 1H), 2.38-2.41 (dd, J=8.2, 5.4 Hz, 1H), 2.42-2.55 (m, 1H), 2.76-2.81 (dAB, J=16.0, 3.90 Hz, 1H), 2.88-2.92 (broad m, 2H), 2.98-3.53 (m, 1H), 4.17-4.19 (q, 2H, CH$_2$), 5.04 (s, 1H, benzylic), 6.74-6.75 (app d, 1H, aromatic), 6.79-6.82 (2×d, J=2.7 Hz each, 1H, aromatic) 7.332-7.456 (m, 6H); LCMS [(M+2)$^+$= 448], (M+H$_2$O)=465; HPLC (99%, R$_t$=6.11)

3-Hydroxy-16-methylene Estrone Carboxylic Acid Ethyl Ester 4 (STX573, HDS01-090)

A solution of 3-Benzyloxy-16-methylene carboxylic acid ethyl ester 3 (1.50 g, 3.36 mmol) was dissolved in EtOH (15 ml) and the mixture was degassed approximately 20 minutes and debenzylation was carried out under a hydrogen balloon at r.t. for 48 hours. The completion of the reaction was monitored using tlc (EtOAc:hexane, 3:7). The crude reaction mixture was filtered through a pad of celite, the filtrate was concentrated to obtain a sticky white solid which was then purified by column chromatography (5-20% ethyl acetate in hexane) to obtain the debenzylated product 4 (0.828 g, 70%, mixture of 2 diastersomers 3:1) as a white solid: 1H NMR (CDCl$_3$) [chemical shifts of major to minor isomer ratio approximately 3:1 was determined using Me signals at 13-position], δ 0.916 and 0.988 (major isomer) [2×s, 3H, 2×Me], 1.27-1.29 (t, integrating to more than 3H, J=7.0 Hz, CH$_3$), 1.40-1.60 (m, 6H), 1.75-1.80 (m, 1H), 1.92-2.23 (m, 6H), 2.28-2.35 (dAB, J=16.4 and 10.1 Hz, 1H), 2.36-2.39 (m; 1H), 2.47-2.54 (dAB, J=18.7, 8.5 Hz, 1H, minor isomer), 2.74-2.79 (dd, J=3.9, 4.2 Hz, 1H), 2.85-2.88 (m, 2H), 2.99-3.02 (m, 1H), 4.15-4.17 (q, 2H, CH$_2$), 4.63 (1H, OH), 6.57-6.58 (appd, 1H, aromatic), 6.62-6.65 (dd, J=8.5, 2.7 Hz, 1H), 7.13-7.16 (dd, J=8.5, 3.9 Hz, 1H); Mass (FAB) (M+1)$^+$=357; Acc. Mass (FAB$^+$) calcd 357.2065, obsd 357.2054; HPLC (99%, R$_t$=2.01).

3-Hydroxy-17-hydroxy-16-methylene Estrone Carboxylic Acid Ethyl Ester 6 (STX 574, HDS01-094)

A solution of 3-Hydroxy-16-methylene carboxylic acid ethyl ester 4 (1.20 g, 3.3 mmol) in MeOH (15 ml) was cooled to 0° C. and added NaBH$_4$ (0.191 g, 5.0 mmol) over 15 minutes. The reaction mixture was warmed to r.t., stirred overnight. The reaction was monitored by tlc (EtOAC:Hexane, 1:1). The crude mixture was quenched with water and extracted the aqueous layer with Ethyl Acetate and DCM. The combined organics were washed with saturated NaCl, dried and concentrated to obtain a white solid and then recrystalised with DCM and Hexane to obtain pure compound 6 (0.791 g, 71%) as a white solid: $^1$H NMR (CDCl$_3$) [chemical shifts of major to minor isomer ratio approximately 3:1 was determined using Me signals at 13-position]δ 0.784 and 0.852 (major isomer) [2×s, 3H each, 2×Me], 1.280 (t, J=7.4 Hz, integrating to more than 3H, CH$_3$), 1.30-1.48 (m, 6H), 1.71-1.88 (m, 3H), 1.96-2.05 (1H, m), 2.24-2.56 (m, 4H), 2.54-2.56 (dd, J=7.4, 2.3 Hz, approximately 1.5H), 2.79-2.83 (m, 3H), 3.01-3.02 (d, J=3.9 Hz, 1H), 3.37-3.40 (dd, J=7.4, 3.5 Hz, 1H), 4.13-4.18 (q, J=7.0 Hz, 2H), 4.65-4.70 (broad 2×s, 1H), 6.55-6.56 (appd, 1H, aromatic), 6.61-6.64 (dd, J=8.5, 2.7 Hz, 1H, aromatic) 7.14-7.16 (d, J=8.2 Hz, 1H, aromatic); (FAB) (M+1)$^+$=359; Acc. Mass (FAB$^+$) calcd 359.2222, obsd 357.2220; HPLC (99%, R$_t$=1.89).

3-Hydroxy-17-hydroxy-16-methylene Estrons Carboxylic Acid 7 (STX603, HDS01-096)

The Ethyl Ester 6 (0.780 g, 2.1 mmol) was dissolved in a mixture of THF:MeOH:H$_2$O (1:1:0.5, 10 ml) in a seal tube and added NaOH (0.43 g, 10.5 mmol). The mixture was heated to 80° C. overnight. The reaction was monitored by tlc (EtOAc:Hexane, 1:1). The crude mixture was acidified to pH=3-4, extracted with EtOAc and DCM. The combined organics were dried (MgSO$_4$) and concentrated to obtain a white solid. The solid was recrystalised with MeOH and hexane to obtain pure acid 7 (0.700 g, 101%) as a white solid: $^1$H NMR (CD$_3$)$_2$—SO) [chemical shifts of major to minor isomer ratio approximately 3:1 was determined using Me signals at 13-position]δ 0.649 and 0.688 (2×s, 3H, 2×CH$_3$) 1.148-1.308 (m, 8H), 1.47-1.56 (q, J=12.4, 1H), 1.90-2.19

(m, 6H), 2.65-2.68 (m, approximately 3H), 3.15-3.16 (broad m, 1H), 4.673-4.682 (broad d, 1H) 6.40-6.41 (appd, 1H, aromatic), 6.47-6.49 (dd, J=8.2, 2.3 Hz, 1H, aromatic), 7.01-7.03 (d, J=8.5 Hz, aromatic), 8.98 (s, 1H), 11.9 (broad s, 1H); matic), 7.17-7.19 (d, J=8.5 Hz, 1H, aromatic), 7.31-7.44 (5H, aromatic); LCMS [(M)$^+$=417]; (FAB) (M+1)$^+$=418; Acc. Mass (FAB$^+$) calcd 418.2099, obsd 418.2148; HPLC (99%, R$_t$=1.89).

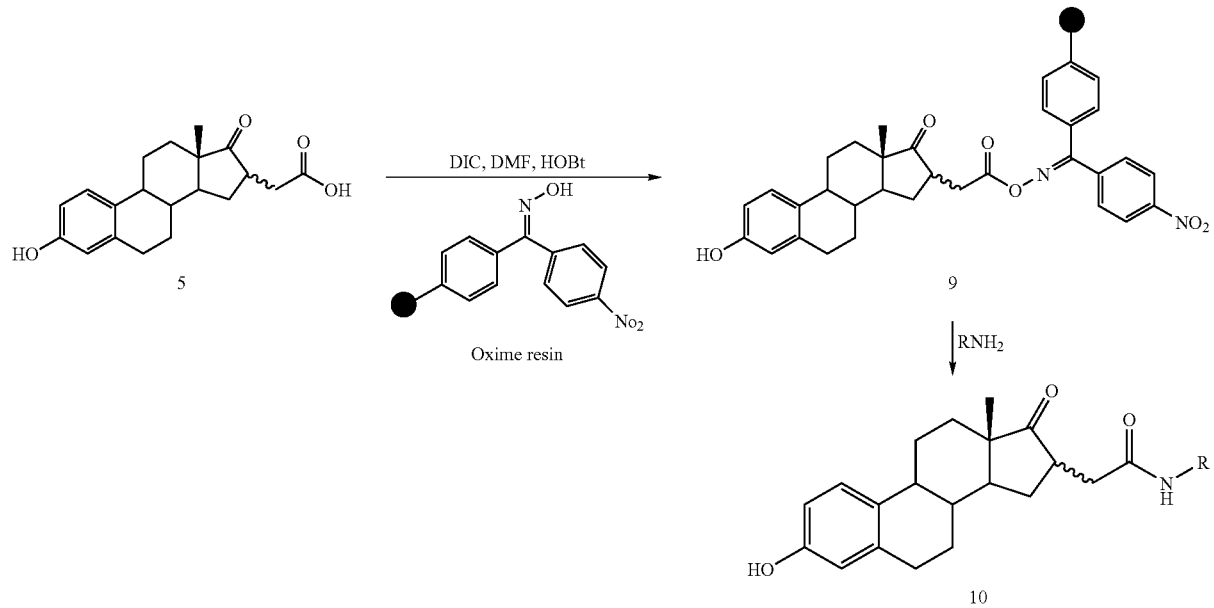

Scheme 2: Synthesis of amides on a solid support Method-A (FAB) (M)$^+$=330; Acc. Mass (FAB$^+$) calcd 330.1831, obsd 330.1832; HPLC (>95%, R$_t$=2.21).

3-Hydroxy-17-oxo-16-methylene Estrone Carboxylic Acid 5 (STX604, HDS01-098)

The reaction was carried out using the procedure outlined for compound 7 with 3-Hydroxy-16-methylene carboxylic acid ethyl ester 4 (1.00 g, 2.8 mmol), NaOH (0.56 g, 1.4 mmol) and THF:MeOH:H$_2$O (1:1:0.5, 10 ml). The product 5 (0.940 g, 102%) was isolated as a white solid after recrystalisaton: $^1$H NMR (CD$_3$)$_2$—SO) [chemical shifts of major to minor isomer ratio approximately 3:1 was determined using Me signals at 13-position]δ 0.786 [major isomer] and 0.896 (2×s, 3H each, 2×Me), 1.31-1.52 (broad m, 8H), 1.74-1.77 (m, 1H), 1.88-1.91 (m, 1.5H), 2.16-2.22 (m, 3H), 2.27-2.33 (m, 3H), 2.48-2.49 (2×d, J=195 Hz, 1H), 2.72-2.74 (m, 2.5H), 6.43 6.44 (appd, 1H, aromatic), 6.48-6.51 (d, J=8.5, 2.4 Hz, aromatic), 7.02-7.04 (d, J=8.5 Hz, aromatic), 9.0 (broad s, 1H); (FAB) (M+1)$^+$=329; Acc. Mass (FAB$^+$) calcd 329.1752, obsd 330.1751; HPLC (>95%, R$_t$=2.60).

3-Hydroxy-17-oxo-16-methylene Estrone Carboxylic Acid 8 (STX666, HDS01-109)

The reaction was carried out using the procedure outlined for compound 7 with 3-benzyloxy-16-methylene carboxylic acid ethyl ester 3 (1.714 g, 3.8 mmol), NaOH (1.537 g, 38.4 mmol) and THF:MeOH:H$_2$O (1:1:0.5, 10 ml). The product 8 (1.114 g, 90%) was isolated as a white solid after recrystalisation: Diagnostic signals $^1$H NMR (CD$_3$)$_2$—SO) δ 0.81, 0.84 (2×s, CH$_3$), 1.36-1.91 (m, 6H), 2.19-2.25 (m, 2H), 2.33-2.37 (dd, J=9.3 Hz, 2H), 2.59-2.63 (2×d, J=0.2 Hz each, 0.5H), 2.81-2.83 (m, 2H), 5.06 (s, 2H, benzylic), 6.72 (appd, 1H, aromatic), 6.73-6.77 (dd, J=8.5 and 5.8 Hz, 1H, aro- Scheme 3: Parallel synthesis of amides in solution phase Method-B

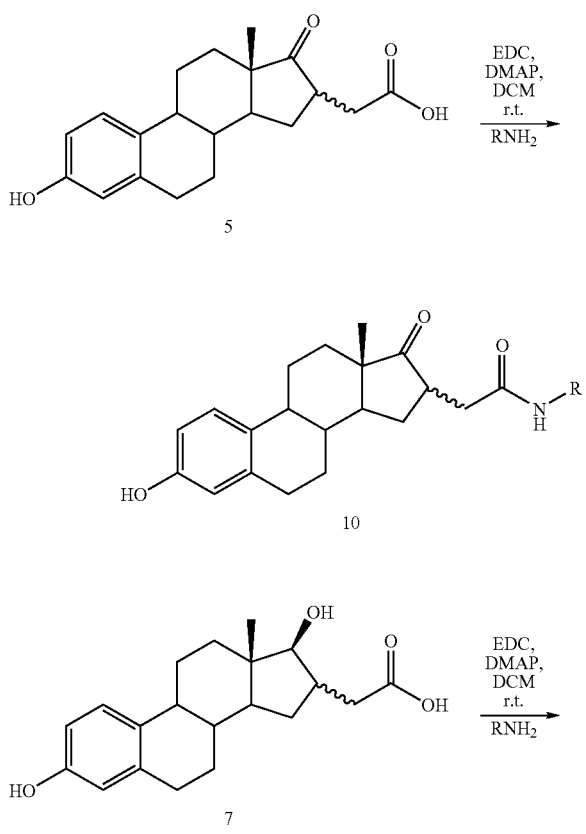

111

-continued

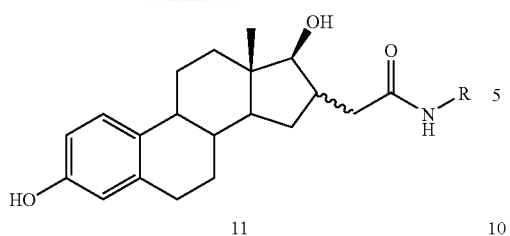

11

Synthesis of Resin Bound Intermediate 9 (HDS01-104):

The Oxime resin (0.500 g, loading 1.06 mmol/g) was swollen in a minimum amount of DMF (7 ml), added the estrone carboxylic acid 5 (STX604) [0.521 g, 5.3 mmol] followed by Di-isopropyl carbodiimide [DIC] (0.667 g, 5.3 mmol) and Hydroxy benztriazole [HOBt] (0.715 g, 5.3 mmol). The reaction mixture was shaken using a flask shaker for approximately 72 hours under $N_2$. The yellow reaction mixture obtained after 72 hours was filtered, and washed with DCM, DMF, MeOH (3 cycles with each solvent), finally MeOH (5 times) and dried in vacuo to obtain resin bound intermediate 8 as yellow beads: IR $(cm^{-1})$ 1662 (C=O), 1739 (CO—O—N=), 3502 (OH).

Parallel Synthesis of Estrone-Amides; Method A:

The resin bound estrone intermediate 9 (0.100 g, 0.106 mmol) was suspended in anhydrous DCM (3.0 ml) under $N_2$ in a glass tube in Radleys GreenHouse Synthesiser, added the corresponding amines (5 molar equivalents) and heated at 40° C. under $N_2$ for 72 h. The reaction mixtures were filtered and the filtrates were evaporated using Genevac to obtain a pale yellow solid. The crude compounds were purified using the Flash vacuum system and pre-packed columns (5 or 10 g) with DCM: MeOH (gradient elution, starting with 2% MeOH in DCM) to obtain pure compounds (average recovery 14 mg/100 mg of resin bound intermediate).

Parallel Synthesis of 16-methylene Estrone-Amides; Method B:

The carboxylic acid 5 (0.050 g, 0.15 mmol) or 7 (0.50 g, 0.15 mmol) was suspended in DCM (1.0 ml) in a glass tube in Radleys GreenHouse Parallel Synthesiser, added a solution of EDC (0.043 g, 0.227 mmol), DMAP (catalytic amount, 5 mg, and $Et_3N$ (0.100 ml) in DCM (1.0 ml). The reaction mixture was stirred approximately for 30 minutes and the corresponding amines (5 molar equivalents) in DCM (1.0 ml) were added and stirred overnight. [The total volume of DCM used in each reaction was 3.0 ml]. The completion of the reactions were monitored by tlc (EtOAc:Hexane, 2:7). The crude mixtures were evaporated in the Genevac and purified using the Flash vacuum system and pre-packed columns (5 or 10 g) with DCM:MeOH (gradient elution, starting with 2% MeOH in DCM) to obtain pure compounds.

112

Synthesis of 3-Hydroxy-17-oxo-16-methylene Estrone Carboxy-furfuryl Amide (STX 672, HDS01-112-3)

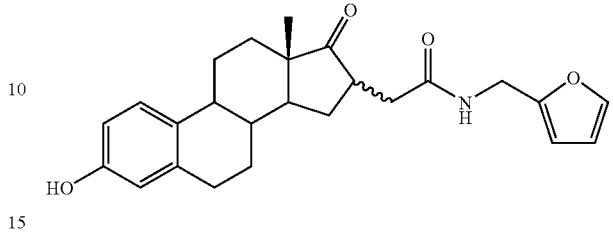

Method B, Yield=33%. $^1H$ NMR $(CDCl_3)$ δ 0.908, 0.964, 1.021 (3×s, 3×Me), 1.39-1.59 (broad m, 6H), 1.94-1.97 (m, 2H), 2.23-2.37 (m, 2H), 2.82-2.87 (m, 1.5H), 4.28-4.44 (d, J=5.4 Hz, $CH_2$), 6.23-6.24 (m, 2H, aromatic), 6.57-6.65 (m, 2H, aromatic), 7.10-7.12 (m, 1H, aromatic), 6.34-6.35 (appd, 1H, aromatic), LCMS $[(M+1)^+=407]$; Acc. Mass $(FAB^+M+1)$ calcd 408.3172, obsd 408.2174; HPLC (90%, $R_t$=1.47).

Synthesis of 3-Hydroxy-17-oxo-16-methylene Estrone Carboxy-tetrahydro-2-furyl Amide (STX671, HDS01-112-6)

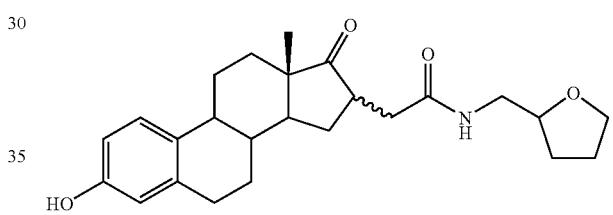

Method B, Yield=40%. $^1H$ NMR $(CDCl_3)$ δ 0.69, 0.73, 0.83, 0.87 and 0.87 (4×s, approximately 3H each, Methyl signals), 1.2-1.55 (broad m, 7H), 1.74-1.94 (broad m, 4H), 2.08-2.29 (broad m, 2H), 2.29-2.78 (m, 3H), 3.01-3.07 (m, 1H), 3.50-3.92 (m, 2.5H), 6.15-6.57 (m, 3.5H, aromatic), 6.79-7.08 (m, 1.5H, aromatic); LCMS $[(M+1)^+=411]$; Acc. Mass $(FAB^+M+1)$ calcd 412.2487, obsd 408.2491; HPLC (90%, $R_t$=1.49).

Synthesis of 3-Hydroxy-17-oxo-16-methylene Estrone Carboxy-3-pyridylamide (STX670, HDS01-112-2 and HDS01-168)

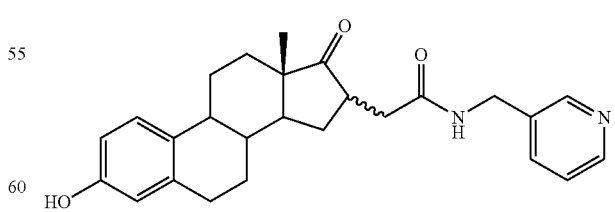

Method B, Yield=50%, $^1H$ NMR δ $(CD_3)_2$—SO), 0.778-0.883 (4×s, 3H), 1.26-1.55 (m, 6.5H), 1.61-1.84 (m, 6H), 2.04-2.41 (m, 6H), 2.29-2.89 (m, 6H), 4.13-4.17 (d, J=15.6 Hz, 1H), 4.27-4.29 (d, J=5.8 Hz, 2H), 4.35-4.37 (d, J=7.0 Hz, 0.5H), 4.48-4.52 (d, J=15.2, 1H), 5.76 (s, 1H), 6.39 (s, 1H), 6.04-6.50 (m, 3H, aromatic), 6.9 (2×d, J=8.2 Hz, 1H), 7.0 (d, J=8.5 Hz, 0.5H), 7.28-7.35 (m, 2H), 7.63-7.65 and 7.73-7.75 (2×d, J=8.2 Hz each), 8.35-8.54 (m, 2H), 8.9 9.0 (2×s, 2H); LCMS [(M+1)$^+$=419, (Rt=858)]; HPLC (100%, R$_t$=2.08).

A single diastereomer of STX670 shows the following analytical data.

MP=210-211° C., $^1$H NMR δ (CD$_3$OD), 0.86-0.88 (s, 3H, Me), 1.28-1.57 (broad m, 5H), 1.88-2.15 (broad m, 2H), 2.60-2.82 (broad m, 4H), 4.42 (s, 1H), 6.49-6.51 (appd, 1H, aromatic), 6.54-6.55 (d, J=2.47 Hz, aromatic), 7.05-7.08 (d, J=8.16 Hz, 1H, aromatic), 7.39-7.44 (dd, J=7.91 and 5.19 Hz, 1H, aromatic), 7.80-7.83 (d, J=7.91 Hz, 1H, aromatic), 8.43-8.45 (appd, 1H, aromatic), 8.51 (s, 1H, aromatic) LCMS [(M+1)$^+$=419, Rt=6.70]; HPLC (100%, R$_t$=2.26).

Synthesis of 3-Hydroxy-17-hydroxy-16-methylene Estrone Carboxy-3-pyridylamide (STX 669HDS01-112-1)

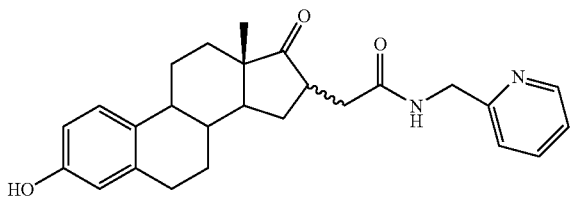

Method B, Yield=40%, $^1$H NMR δ (CDCl$_3$), 0.778-0.883 (4×s, 3H), 1.26-1.55 (m, 6.5H), 1.61-1.84 (m, 6H), 2.04-2.41 (m, 6H), 2.29-2.89 (m, 6H), 4.13-4.17 (d, J=15.6 Hz, 1H), 4.27-4.29 (d, J=5.8 Hz, 2H), 4.35-4.37 (d, J=7.0 Hz, 0.5H), 4.48-4.52 (d, J=15.2 Hz, 1H), 5.76 (s, 1H), 6.39 (s, 1H), 6.04-6.50 (m, 3H, aromatic), 6.9 (2×d, J=8.2 Hz, 1H), 7.0 (d, J=8.5 Hz, 0.5H), 7.28-7.35 (m, 2H), 7.63-7.65 and 7.73-7.75 (2×d, J=8.2 Hz each), 8.35-8.54 (m, 2H), 8.9 9.0.(2×s, 2H); LCMS [(M)$^+$=418]; Acc. Mass (FAB$^+$M+1) calcd 419.2334, obsd 419.2349; HPLC (100%, R$_t$=1.83).

Synthesis of 3-Hydroxy-17-hydroxy-16-methylene Estrone Carboxy-N,N-dimethylpropyl Amide (STX688, HDS01-116-1)

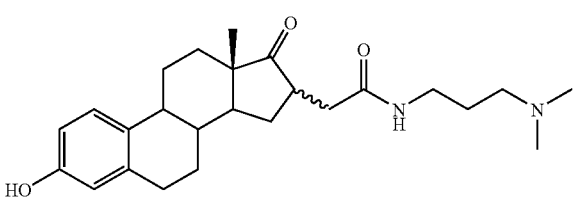

Method A. $^1$H NMR (CDCl$_3$), δ 0.768 (Major isomer) and 0.90 (2×s, 6H, 2×Me), 1.2-1.61 (broad m, 8H), 1.71-1.99 (broad m, 5H), 2.25 and 2.93 (2×s, 6H each, 2×Me), 2.30-2.36 (m, 2H), 2.30-2.56 (m, 2H), 2.56-2.78 (broad m, 2H), 2.89-2.90 (d, J=3.1 Hz, 1H) 2.93-2.94 (d, J=3.1 Hz, 1H), 3.40-3.67 (m, 4H), 6.52 (appd, 1H, aromatic), 6.54-6.56 (dd, J=8.5, 2.7 Hz), 7.04-7.06 (d, J=8.2 Hz, 1H, aromatic); LCMS [(M)$^+$=411 and (M+1)$^+$=412]; HPLC (98%, R$_t$=1.51).

Synthesis of 3-Hydroxy-17-hydroxy-16-methylene Estrone Carboxy-ethyl-methoxyamide (STX689, HDS01-116-3)

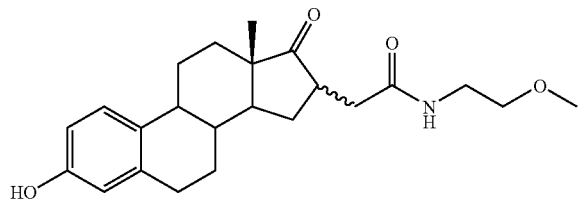

Method A. $^1$H NMR (CDCl$_3$), δ 0.766, 0.852, 0.898 and 1.182 (Me signals, approximately), 1.210-1.475 (broad m, 8H), 1.57-2.30 (m, 13H), 2.50-2.82 (m, 5H), 3.27-3.39 (4×s, OMe), 4.85-4.93 (broad s, 1H), 5.93-6.08 (2×s, 2H), 6.50-6.55 (m, 1H, aromatic), 6.55-6.57 (m, 1H, aromatic), 7.05-7.07 (m, 1H, aromatic); LCMS [(M+1)$^+$=386]; HPLC (99%, R$_t$=1.47).

Synthesis of 3-Hydroxy-17-hydroxy-16-methylene Estrone Carboxy-ethyl-methoxyamide (HDS01-100-2)

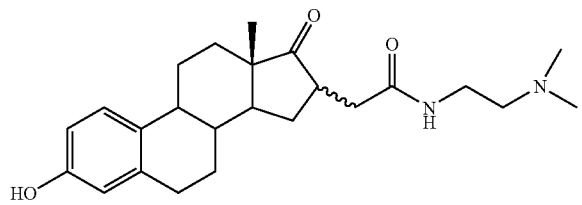

Method B. $^1$H NMR (CDCl$_3$), δ 0.768 (Major isomer) and 0.90 (2×s, 6H, 2×Me), 1.2-1.61 (broad m, 8H), 1.71-1.99 (broad m, 5H), 2.25 and 2.93 (2×s, 6H), 2.30-2.36 (m, 2H), 2.39-2.56 (m, 2H), 2.56-2.78 (broad m, 2H), 2.89-2.90 (d, J=3.1 Hz, 2.93-2.94 (d, J=3.1 Hz, 1H), 3.40-3.67 (m, 4H), 6.5 (appd, 1H, aromatic), 6.54-6.56 (dd, J=8.5, 2.7 Hz), 7.04-7.06 (d, J=8.2 Hz, 1H, aromatic); FAB [(M+1)$^+$=399]; Acc. Mass (FAB$^{+M+}$1) calcd 399.2647, obsd 399.2627; HPLC (99%, R$_t$=1.51).

Synthesis of 3-Hydroxy-17-oxo-16-methylene estrone carboxy-α-methyl benzyl amide (STX690, HDS01-116-64)

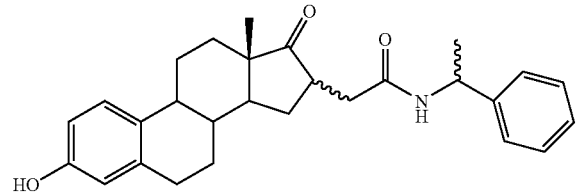

Method A. This compound exists as a mixture of 4 diastereomers. Diagnostic signals of ¹H NMR (CDCl₃), δ 0.69, 0.73, 0.88, 0.89 (4×s, Methyl signals), 1.41-1.44 (m, benzylic methyl), 2.76-2.78 (m, 2H), 5.01-5.06 (m, 1H, Benzyic), 6.50 (appd, 1H, aromatic), 6.55-6.57 (broad d, 2H, aromatic), 7.03-7.06 (m, 1H, aromatic), 7.17-7.29 (m, aromatic); LCMS [(M+1)$^+$=432]; HPLC (99%, $R_t$=1.51).

Synthesis of 3-Hydroxy-17-oxo-16-methylene estrone carboxy-2-ethyl pyridylamide (STX691, HDS01-116-5)

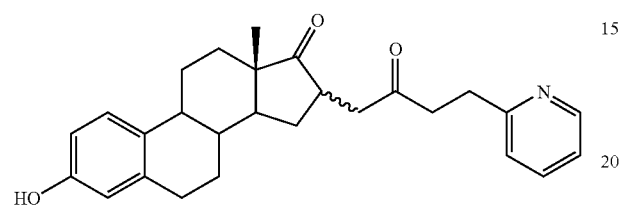

Method A. Diagnostic signals of ¹H NMR (CDCl₃), δ 0.75, 0.80 and 0.92 and 1.0 (3×Me signals), 1.20-2.84 (broad m, approximately 14 H), 3.0-3.03 (m, 2H), 3.36-3.62 (m, 0.5H), 3.64-3.69 (m, 2H), 6.57-6.59 (m, 1H, aromatic), 6.63-6.64 and 6.65-6.66 (d, J=2.7 Hz each, 1H, aromatic), 6.72-6.75 (m, 0.5H), 7.09-7.30 (m, 4.5H, aromatic), 7.64-7.68 (m, 2H, aromatic), 8.40-8.42 (m, 0.5H, aromatic), 8.52-8.53 (m, 1H, aromatic); LCMS [(M+1)$^+$=433 and (M–OH)$^+$=415]; FAB [(M+1)$^+$=433]; HPLC (99%, $R_t$=1.51).

Synthesis of 3-Hydroxy-17-hydroxy-16-methylene estrone carboxy-tetrahydro-2-furyl amide (STX668, HDS01-110-6)

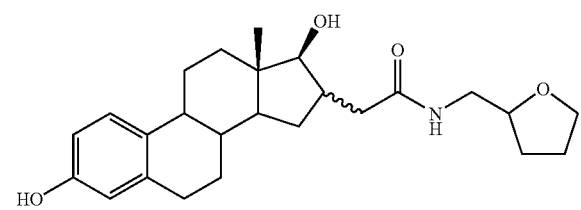

Method B, Yield=33%. ¹H NMR (CDCl₃) δ 0.78 (2×s, 3H, 2×Me), 0.86-0.89 (m, 1H), 1.19-1.55 (broad m, 7H), 1.69-1.96 (m, 2H), 2.10-2.32 (broad m, 3H), 2.74-2.84 (m, 2H), 3.73-3.74 (m, 1H), 3.73-3.74 (d, J=5.8 Hz, 1H), 4.46-4.48 (broad m, 1H), 6.57 (appd, 1H, aromatic), 6.62-6.65 (m, 1H, aromatic), 7.13-7.17 (m, 1H). LCMS [(M–C₅H₉NO)$^+$=313]; HPLC (95%, $R_t$=1.57).

Synthesis of 3-hydroxy-17-hydroxy-16-methylene estrone carboxy-furfuryl amide (STX667, HDS01-110-3)

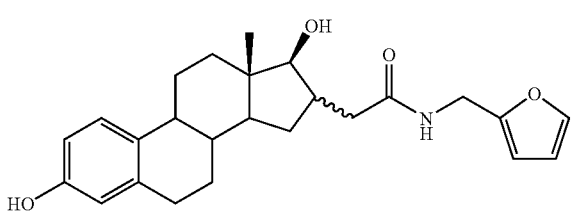

Method B, Yield=37%. ¹H NMR (CDCl₃) δ 0.076, 0.77, 0.79, (3×s, approximately 3H each, Methyl signals), 1.25-1.58 (broad m, 14H), 1.86-1.95 (m, 1H), 2.02-2.42 (m, 3.5H), 2.47-2.49 (m, 0.5H), 2.78-2.87 (3H, m), 3.41-3.43 (dd, J=2.3 and 1.9 Hz, 1H), 4.44-4.45 (d, J=5.4 Hz, 1H), 6.01, (broad s, 1H), 6.24-6.25 (d, J=2.3 Hz, 1H, aromatic), 6.33-6.64 (2 sets of multiplets, 4H, aromatic), 7.14-7.16 (d, J=8.5 Hz, 1.5H, aromatic), 7.28-7.35 (m, 1H, aromatic), 7.36-7.37 (m, 1H, aromatic); LCMS [(M–1)$^+$=408 ($R_t$=8.58)]; HPLC (100%, $R_t$=2.08); Acc. Mass (FAB$^+$M+1) calcd 410.2331, obsd 410.2317; HPLC (90%, $R_t$=1.82 and 1.90).

Scheme 4: Parallel synthesis of amides on solid support Method-C

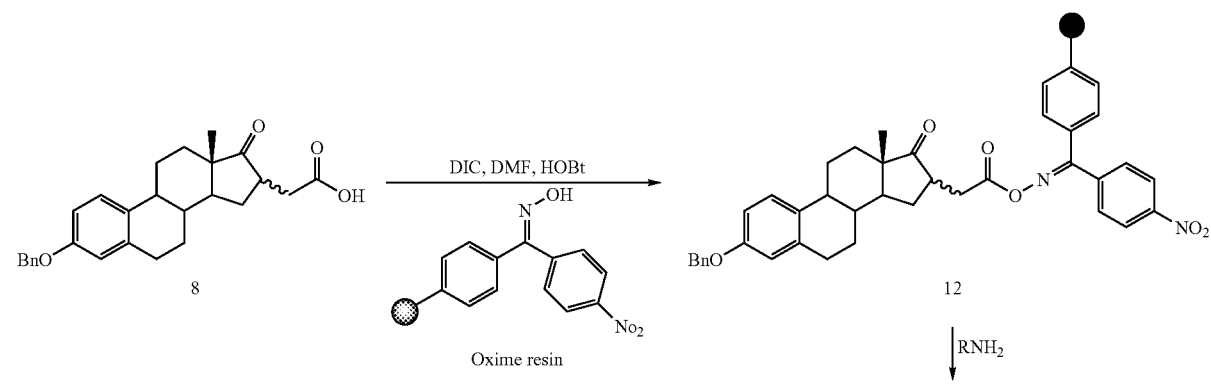

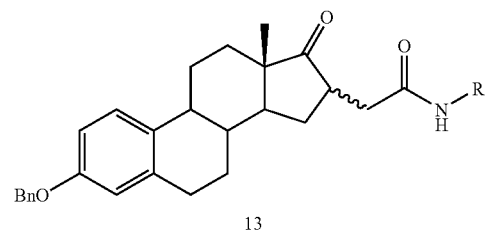

13

Synthesis of Resin Bound Intermediate 12 (HDS01-120):

The Oxime resin (2.0 g, loading 1.06 mmol/g) was swollen in a minimum amount of DMF (7 ml), added the estrone carboxylic acid 8 (1.428 g, 3.18 mmol) followed by Di-isopropyl carbodiimide [DIC] (1.33 g, 10.6 mmol) and Hydroxy benzotriazole [HOBt] (1.431 g, 10.6 mmol). The reaction mixture was shaken using a flask shaker for approximately 72 hours under $N_2$. The yellow reaction mixture obtained after 72 hours was filtered, and washed with DCM, DMF, MeOH (3 cycles with each solvent), finally MeOH (5 times) and dried in vacuo to obtain resin bound intermediate 8 (2.391 g) as yellow beads: IR (cm$^{-1}$) 1662 (C=O), 1739 (CO—O—N=), 3502 (OH).

Parallel Synthesis of Estrone-Amides; Method C:

The resin bound estrone intermediate 12 (Scheme 4) (0.100 g, 0.106 mmol) was suspended in anhydrous DCM (3.0 ml) under $N_2$ in a glass tube in Radleys GreenHouse Synthesiser, added the corresponding amines (5 molar equivalents) and heated at 40° C. under $N_2$ for 72 h. The reaction mixtures were filtered and the filtrates were evaporated using Genevac to obtain a pale yellow solid. The crude compounds were purified using the Flash vacuum system and pre-packed columns (5 or 10 g) with DCM: MeOH (gradient elution, starting with 2% MeOH in DCM) to obtain pure benzylated intermediates (average recovery 15 mg/100 mg of resin bound intermediate, analysed by $^1$H nmr). These intermediates were then debenzylated under a balloon of $H_2$ in the GreenHouse Synthesiser to obtain final compounds in average 90% purity.

Synthesis of 3-hydroxy-17-hydroxy-16-methylene estrone carboxy-N-methyl-N-ethyl amide (STX741, HDS01-128-1)

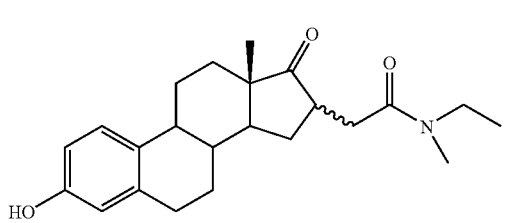

Method C, Yield=40%. $^1$H NMR (CDCl$_3$) δ 0.81 and 0.90 (2×s, 3H, 2×CH$_3$, 3:1), 1.01-1.24 (m, 5H), 1.66-2.60 (m, 6H), 2.75-80 (m, 2.5H), 2.86-2.90 (2×s, 4.5H, 2×CH$_3$), 3.25-3.28 (m, $_1$H), 4.79 (broad s, 1H), 6.50 (app d, 1H, aromatic), 6.51-6.56 (2×d, J=2.9 and 2.5 Hz, 1H, aromatic), 7.05-7.08 (d, J=8.4 Hz, 1H, aromatic); LCMS [(M+2)$^+$=371, (R$_t$=6.08)]; HPLC (85%, R$_t$=2.29).

Synthesis of 3-hydroxy-17-hydroxy-16-methylene estrone carboxy-N,N-diethyl amide (STX742, HDS01-128-2)

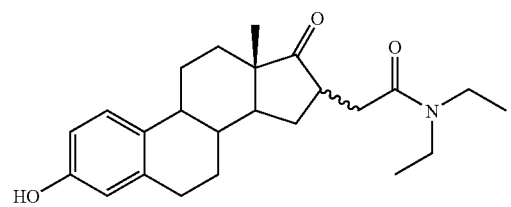

Method C, Yield=40%. $^1$H NMR (CDCl$_3$) δ 0.78 (major isomer) and 0.89 (2×s, 2×CH$_3$), 1.03-1.13 (m, approximately 6H), 1.39-1.59 (m, 5H), 1.89-1.94 (m, 1.5H), 2.13-2.91 (m, 5H), 3.20-3.36 (m, 4H), 5.05-5.27 (broad s, 1H), 6.51-6.52 (appd, 1H, aromatic), 6.55-6.59 (dd, J=2.9 and 2.5 Hz, 1H, aromatic), 7.05-7.08 (d, J=8.8 Hz, 1H, aromatic); LCMS [(M+2)$^+$=385, (R$_t$=6.55)]; HPLC (86%, R$_t$=2.37).

Synthesis of 3-hydroxy-17-hydroxy-16-methylene estrone carboxy-N-isopropyl amide (STX743, HDS01-128-4)

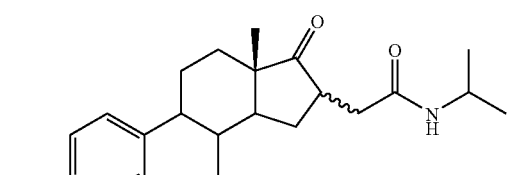

Method C, Yield=40%. $^1$H NMR (CDCl$_3$) δ 0.83 [Major isomer] and 0.95 (2×s, CH$_3$ signals, 3:1), 1.12 (d, J=1.4 Hz, CH$_3$), 1.14-1.15 (d, J=2.20 Hz, CH$_3$), 1.90-2.64 (m, 2H), 2.80-2.85 (m, 2H), 4.91 (broad s, 1H), 6.56 (app d, 1H, aromatic), 6.59-6.60 and 6.62-6.63 (dd, J=2.9 and 2.5 Hz, 1H, aromatic), 7.10-7.13 (d, J=8.0 Hz, 1H, aromatic); LCMS [(M+2)$^+$=371, (R$_t$=5.83)]; HPLC (93%, R$_t$=2.27).

119

Synthesis of 3-hydroxy-17-hydroxy-16-methylene estrone carboxy-N-ethyl amide (STX744, HDS01-128-5)

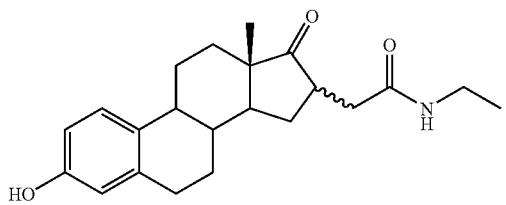

Method C, Yield=40%. $^1$H NMR (CDCl$_3$) δ 0.78 [Major isomer] and 0.81 (2×s, CH$_3$ signals, 3:1), 1.05-1.10 (t, J=6.9 Hz, CH$_3$), 1.35-0.45 (m, approximately 4H), 1.89-2.64 (m, 11H), 2.79-2.80 (m, 2H), 3.18-3.24 (m, 2H, CH$_2$), 4.83 (broad s, 1H), 6.51 (appd, 1H, aromatic), 6.54-6.55 and 6.57-6.59 (dd, J=2.5 and 2.9 Hz, 1H, aromatic), 7.05-7.08 (d, J=8.4 Hz, 1H, aromatic); LCMS [(M+2)$^+$=357, [(M+Na)$^+$=379]; HPLC (87%, R$_t$=2.17).

Synthesis of 3-hydroxy-17-hydroxy-16-methylene estrone carboxy-N-methyl amide (STX745, HDS01-128-6)

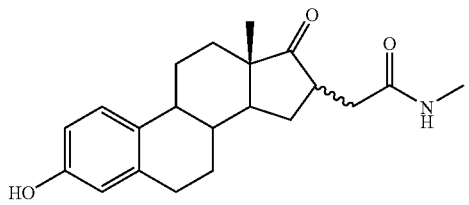

Method C, Yield=40%. $^1$H NMR (CDCl$_3$) δ 0.77 [major isomer], 0.85, 0.90 (3×s, CH$_3$ signals), 1.43-1.52 (m, 5H), 1.89-1.93 (m, 2H), 2.15-2.31 (m, 3H), 2.49-2.68 (m, 2H), 2.72 and 2.74 (2×s, 3H, Me), 2.75-2.80 (m, 2H), 4.94-4.95 (broad s, 1H), 5.91 (broad s, 1H), 6.52 (app d, 1H, aromatic), 6.55-6.56 and 6.58-6.59 (dd, J=2.9 Hz each, 1H, aromatic), 7.04-7.08 (d, J=8.4 Hz, 1H, aromatic), LCMS [(M−30)$^+$=311]; HPLC (97%, R$_t$=2.12).

Synthesis of 3-hydroxy-17-hydroxy-16-methylene estrone carboxy-N-methyl amide (STX746, HDS01-128-9)

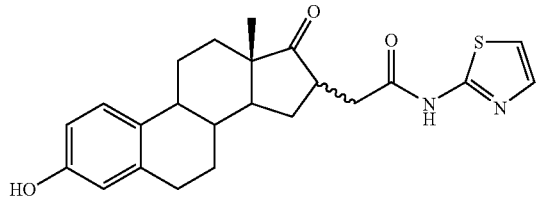

Method C, Yield=40%. $^1$H NMR (CDCl$_3$) δ 0.88 (Major isomer) and 0.93 (s, CH$_3$), 1.4-1.66 (m, 6H), 1.97-2.00 (m, 2H), 2.39-3.15 (m, 6H), 4.94 (broad s, 1H), 6.51-6.53 (d, J=3.6 Hz, 1H, aromatic) 6.70 (app d, 1H, aromatic), 6.71-6.74 and 6.77-6.78 (2×d, J=2.5 Hz each, 1H, aromatic), 7.04-7.08 (d, J=8.4 Hz, 1H, aromatic), LCMS [(M)$^+$=412]; HPLC (77%, R$_t$=2.16).

120

Synthesis of 3-hydroxy-17-hydroxy-16-methylene estrone carboxy-N-methyl-N-ethyl amide (STX771, HDS01-138-1)

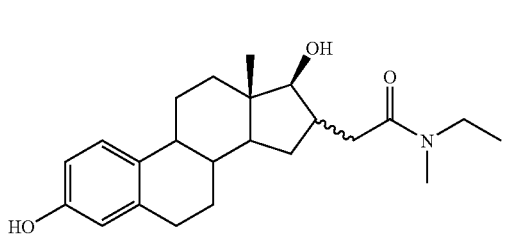

Method C, Yield=40%. $^1$H NMR (CDCl$_3$) δ 0.78 (Major isomer) 0.85 (s, 2×CH$_3$, 2:1), 1.08-1.19 (m, 5H), 1.79-2.66 (m, 9.5H), 2.77-2.80 (m, 4H), 2.90 and 2.96 (2×s, 4H approximately, CH$_3$), 3.27-3.41 (m, 4H), 3.81-3.94 (m, 1.5H), 4.46 (s, 1.5H), 6.54 (appd, 1H, aromatic), 6.58-6.62 (dd, J=8.4 and 2.5 Hz, 7.12-7.15 (d, J=8.4 Hz, aromatic); LCMS [(M−29)$^+$=341]; HPLC (92%, R$_t$=2.32).

Synthesis of 3-hydroxy-17-hydroxy-16-methylene estrone carboxy-N-N-diethyl amide (STX772, HDS01-138-2)

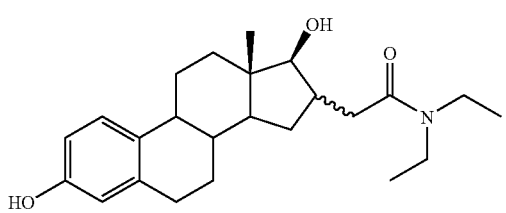

Method C, Yield=40%. $^1$H NMR (CDCl$_3$) δ 0.74 and 0.80 (2×s, 2×CH$_3$, 2:1), 1.02-1.15 (m, 6H), 1.70-2.65 (m, approximately 16H), 3.22-3.32 (m, 4H), 4.05 (appd, 1H), 4.69 and 4.99 (2×s, 1H), 6.48 (appd, 1H, aromatic), 6.49-6.56 (dd, J=8.4 and 5.8 Hz, 1H, aromatic), 7.07-7.10 (d, J=8.0 Hz, 1H, aromatic); LCMS [(M+2)$^+$=387]; HPLC (99%, R$_t$=2.48).

Synthesis of 3-hydroxy-17-hydroxy-16-methylene estrone carboxy-N-N-diethyl amide (STX773, HDS01-138-4)

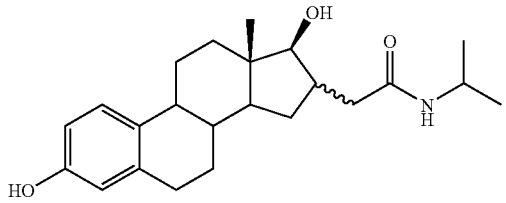

Method C, Yield=40%. $^1$H NMR (CDCl$_3$) δ 0.77 and 0.83 (2×s, 2×CH$_3$, 2:1), 1.16-1.15 (2×d, J=2.5 Hz each, isopropyl), 1.82-2.80 (m, approximately 14H), 3.82-3.85 (2× appd, 2H), 4.02-4.14 (m, 4H), 4.27-4.28 (appd, 1H), 4.59 (s, 2H), 5.3-5.4 (broad s, 2H), 6.53 (appd, 1H, aromatic), 6.54-6.62 (dd, J=11.0 and 2.9 Hz, 1H, aromatic), 7.12-7.15 (d, J=8.4 Hz, 1H, aromatic); LCMS [(M+2)$^+$=373]; HPLC (87%, R$_t$=2.31).

121

Synthesis of 3-hydroxy-17-hydroxy-16-methylene estrone carboxy-N-N-diethyl amide (STX774, HDS01-138-5)

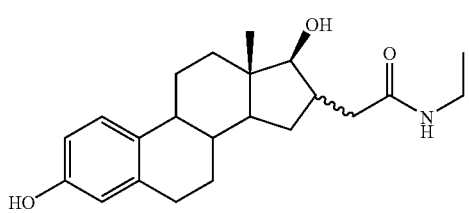

Method C, Yield=40%. $^1$H NMR (CDCl$_3$) δ 0.73 and 0.78 (2×s, 2×CH$_3$, 2:1), 1.05-1.10 (t, J=14.0, 6.9 Hz, CH$_3$), 1.78-2.77 (approximately 16H), 3.17-3.27 (m, 4H), 3.77-3.81 (d, J=9.5 Hz 1H), 5.55 (broad s, 1H), 6.48 (appd, 1H, aromatic), 6.49-6.56 (dd, J=8.4 and 5.5 Hz, 1H, aromatic), 7.10-7.07 (d, J=8.8 Hz; 1H, aromatic); LCMS [(M+2)$^+$=359]; HPLC (90%, R$_t$=2.10).

Synthesis of 3-hydroxy-17-hydroxy-16-methylene estrone carboxy-N-N-diethyl amide (STX775, HDS01-138-6)

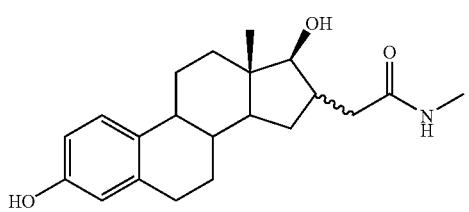

122

Method C, Yield=40%. $^1$H NMR (CDCl$_3$) δ 0.73 (s, 3H, CH$_3$), 1.78-2.77 (approximately 16H), 2.75-2.77 (2×s, 2×CH$_3$), 3.77-3.82 (d, J=9.5 Hz, 1H), 4.04-4.06 (broad s, 1); 5.56 (broad s, 1H), 6.48 (appd, 1H, aromatic), 6.49-6.56 (dd, J=8.0 and 5.5 Hz, 1H, aromatic), 7.07-7.10 (d, J=8.4 Hz, 1H, aromatic); LCMS [(M−CH$_3$)$^+$=327]; HPLC (90%, R$_t$=2.10).

Synthesis of 3-hydroxy-17-hydroxy-16-methylene estrone carboxy-N-propylamide (STX776, HDS01-138-8)

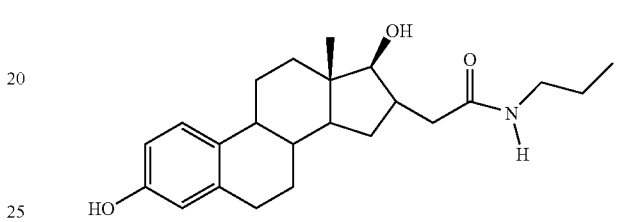

Method C, Yield=40%. $^1$H NMR (CDCl$_3$) δ 0.91 (s, 3H, CH$_3$), 0.84-0.96 (m, 3H), 1.23-1.26 (t, 2H), 1.48-1.51 (m, 8H), 2.13-2.33 (m, 4H), 2.85-2.88 (m, 2H), 3.16-3.23 (m, 2H), 4.98 (s, CH$_2$), 5.27-5.43 (broad s, 1H), 5.97 (broad s, 1H), 6.71 (appd, 1H, aromatic), 6.77-6.78 (dd, J=8.0 and 5.5 Hz, 1H, aromatic), 7.18-7.21 (d, J=8.4 Hz, 1H, aromatic) 7.29-7.41 (m, 5H, aromatic); HPLC (90%, R$_t$=2.10).

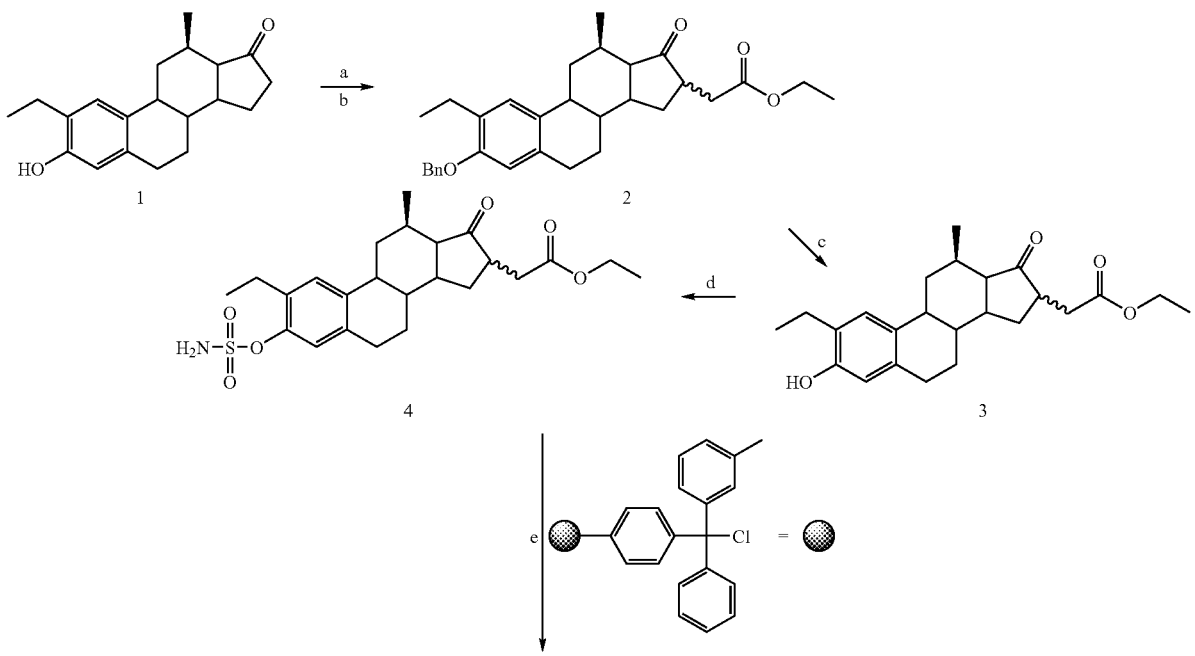

Scheme 1: Synthetic route to sulfamate and phenol libraries using a solid support -continued

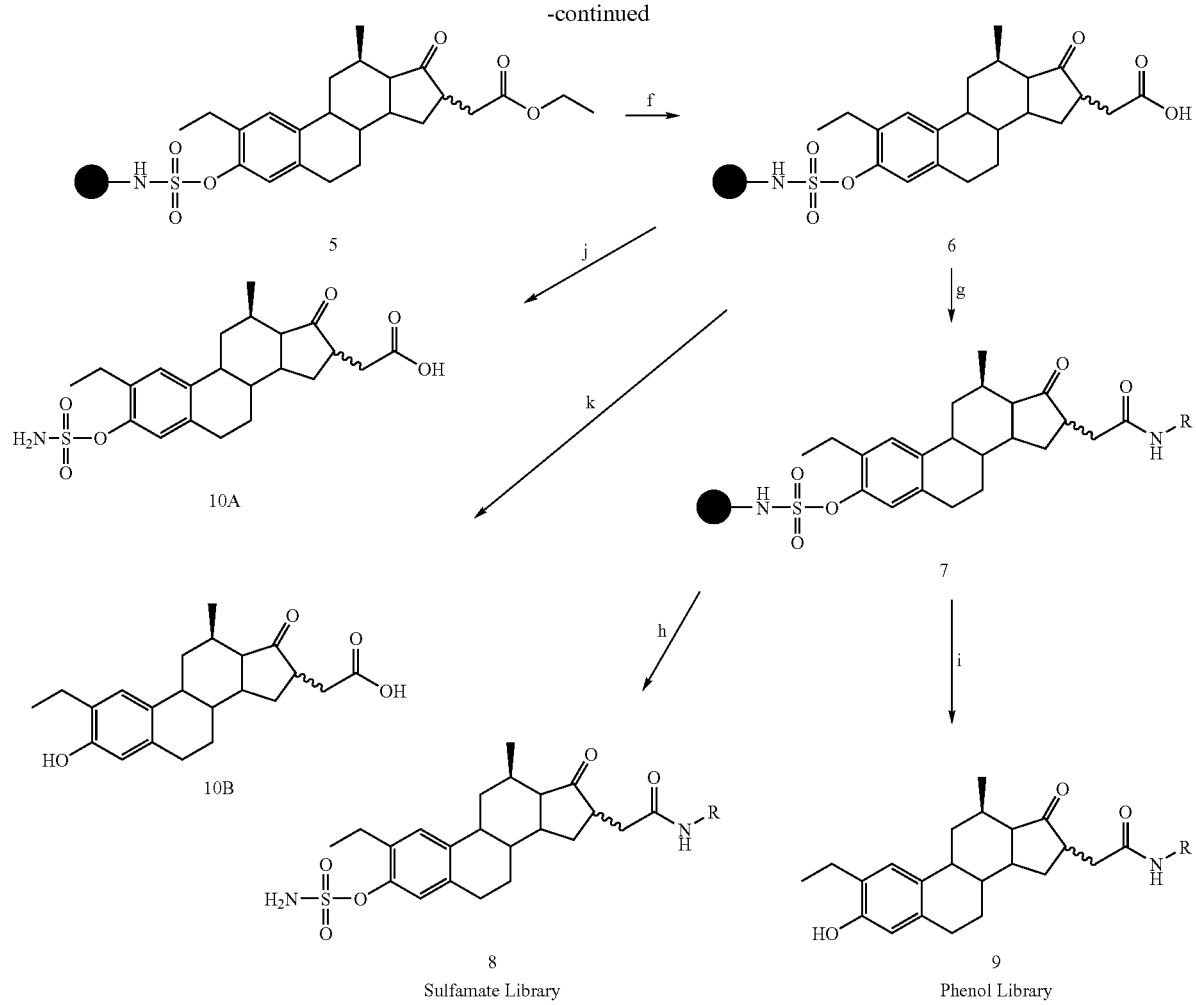

Sulfamate Library

Phenol Library

Reagents are: a) Benzyl bromide, K₂CO₃, DMF, r.t. b) LDA, THF, Ethyl bromoacetate, -78° C. - r.t. c) H₂, Pd/C, MeOH:THF (1:1) d) Sulfamoyl chloride, DMA, 0° C. to r.t. e) Trityl-Cl resin, DIPEA, DCM, 72 h. f) NaOH, THF:H₂O (1:1), r.t. g) EDCI, HOBt, PyBop, DIPEA, DCM, R—NH₂, r.t., O/N. h) TFA:DCM (50:50). i) Piperazine, THF. j) 50% TFA in DCM 20 min. k) Piperazine, THF, 70° C., 72 h.

Synthesis of 2-ethyl Benzyl Estrone (HDS02-054)

To a stirred solution of 2-ethyl estrone 1 (10.00 g, 33.5 mmol) in anhydrous DMF (100 ml) under inert atmosphere was added potassium carbonate (14.0 g, 100 mmol) followed by Benzyl bromide (4.78 ml, 40 mmol). The reaction was left to stir at r.t. over 2 days. The solid obtained was filtered using a Buchner funnel, dissolved in DCM, filtered to remove any inorganics and concentrated to obtain a white solid. The white solid obtained was re-crystallised with DCM:MeOH (90:10) to obtain the pure product the benzyl ether estrone derivative 2 (12.00 g, 92%) also as a white solid: ¹H NMR (270 MHz, CDCl₃) δ 0.90 (s, 3H, 18-CH₃), 1.17-1.23 (t, J=7.4 Hz, CH₂—CH₃), 1.51-2.29 (m, 14H), 2.45-2.55 (m, 4H, 16-CH₂), 2.62-2.70 (q, J=7.6 Hz, 2H, CH₃—CH₂), 2.84-2.90 (m, 2H, 6-CH₂), 5.04 (s, 2H, CH₂-phenyl) 6.64 (s, 4-H), 7.10 (s, 1-CH), 7.28-7.45 (m, 5H); FAB-HRMS calcd for C₂₇H₃₂O₂ 388.2357 found (M⁺) 388.2389.

Synthesis of Benzyl Ethyl Ester (HDS02-098, HDS02-108) 2

To a stirred solution of 2-Ethylbenzyl estrone (5.00 g, 12.8 mmol) in anhydrous THF under inert conditions was added a solution of LDA (4.07 ml, 1.8 M solution in heptane, THF, and Ethylbenzene) at −10° C. over a period of 20 min. The reaction mixture was cooled to −60° C., stirred 15 min, added ethyl bromoacetate drop wise over 10 min. and allowed to warm to rt overnight. Diluted the mixture with DCM, added saturated NH₄Cl and extracted with DCM. The organic phases were combined, dried, and concentrated to obtain a yellow solid which was then purified using Flash Master-11 (50 g column, DCM:MeOH, gradient elution) to obtain the pure product (6.101 g, 99% yield) as a pale yellow solid: ¹H NMR (270 MHz, CDCl₃) δ 0.869 and 0.978 (2×s, 3H, 18-CH₃), 1.17-1.23 (t, J=7.6 Hz, 3H, CH₂—CH₃), 1.24-1.29 (t, J=7.1 Hz, 3H, CH₂—CH₃), 1.32-2.59 (broad m, 12H), 2.62-2.70 (q, J=7.4 Hz, 2H, 2-CH₃—CH₂), 2.78-3.03 (broad m, 2H, 6-CH₂), 4.11-4.19 (q, J=7.17 Hz, 2H, CH₃—CH₂—O), 5.0 (s, 2H, CH₂-phenyl), 6.83 (s, 4-CH), 7.09 (s, 1-CH), 7.30-7.45 (m, 5H); FAB-MS (M⁺) 474 m/z.

Synthesis of 3-Hydroxy Estrone Derivative (HDS02-100, HDS02-110) 3

A solution of 2 (2.80 g, 5.9 mmol) in THF:MeOH (1:1, 40 ml) was degassed for 20 min. bubbling nitrogen gas. Added 5% Pd on C (10% Wt, 300 mg) and debenzylation was carried out using a balloon of H₂ for 24 h. The reaction was monitored using TLC (EtOAC:Hexane, 90:10). The crude mixture was filtered using a pad of celite, concentrated to obtain the debenzylated product 3 (2.210 g, 97%) as a colourless solid: ¹H NMR (270 MHz, CDCl$_3$) δ 0.85 and 0.96 (2×s, 3H, 18-CH$_3$), 1.17-1.28 (2×t overlapped, 6H, 2×CH$_2$—CH$_3$), 1.49-2.49 (m, 12H), 2.54-2.62 (q, J=7.4 Hz, 2H, 2-CH$_3$—CH$_2$), 2.72-3.02 (m, 4H), 4.11-4.16 (q, J=7.1 Hz, 2H, CH$_3$—CH$_2$—O), 4.54 (s, 1H, CH$_2$-Phenyl), 6.50 (s, 1H, 4-CH), 7.03 (s, 1H, 1-CH); HPLC>97% (R$_f$=6.53, 70% MeCN/water); ES–ve–MS (M–H$^+$) 383 m/z; (FAB-HRMS calcd for C$_{24}$H$_{32}$O$_4$ 384.2255 found (M$^+$) 384.2288 m/z.

Synthesis of Sulfamate Estrone Derivative (HDS02-102) 4

A solution of sulfamoyl chloride (57 ml, 0.68M solution in toluene) was evaporated bellow 30° C. using a rotary evaporator. The brown oil obtained was cooled to 0° C. under inert atmosphere, dissolved in anhydrous DMA (30 ml) and treated dropwise with 3 in anhydrous DMA (30 ml) using a cannula. The reaction mixture was left to stir at 0° C., warmed to r.t. overnight. TLC indicated the completion of the reaction (DCM:MeOH, 98:2). The crude mixture was diluted with EtOAC, washed with water (5×) and brine. The organic phase was dried and concentrated to obtain a pale yellow solid. The crude product was purified using Flash Master-11 (50 g column, DCM:MeOH, gradient elution) to obtain pure product 4 (5.901 g, 98%) as a colourless foamy solid: $^1$H NMR (270 MHz, DMSO-d$_6$) δ 0.81 and 0.92 (2×s, 3H each, 18-CH$_3$), 1.09-1.20 (2×t, J=4.9 and 7.4 Hz, 6H, 2×CH$_2$—CH$_3$), 1.33-2.47 (m, 12H), 2.58-2.66 (q, J=7.6 Hz, 2H, 2-CH$_2$—CH$_3$), 2.89-2.97 (m, 3H), 4.04-4.09 (q, J=6.9 Hz, 2H, 2-CH$_3$—CH$_2$) 7.02 (s, 1H, 4-CH), 7.21 (s, 1H, 1-CH), 7.95 (s, 2H, SO$_2$NH$_2$); HPLC>90% (R$_f$=6.53, 70% MeCN/water); ES–ve–MS (M–H$^+$) 462 m/z.

Synthesis of Resin Bound Estrone Sulfamate Derivative (HDS02-114) 5

The trityl chloride resin (2.60 g, Novabiochem, loading 1.1 mmol/g) was swollen in anhydrous DCM (25 ml) under inert atmosphere. Added estrone sulfamate (2.00 g, 4.31 mmol) followed by DIPEA (7.50 ml, 43.1 mmol). The mixture was shaken for approximately 75 h. The acidic minicleavage (50% TFA/DCM, 20 min.) of a sample from the reaction confirmed the completion of the reaction. The crude mixture was filtered, washed with DMF, DCM, MeOH (5 cycles each) and finally with MeOH (3 cycles). After drying under vacuum this resin bound intermediate 4 (3.78 g, loading 0.86 mmol/g, pale yellow) was stored in a refrigerator until taken to the next stage. The $^1$H NMR and other analysis of the cleaved compound was same as that is reported for 4.

Synthesis of Resin Bound Library Precursor Estrone Sulfamate (HDS02-112) 6

The resin 5 (6.00 g, loading 0.86 mmol/g) was swollen in THF (60 ml), and aqueous solution of NaOH (4M, 7 ml) was added slowly. The resin was shaken at r.t. for approximately 30 h, then filtered and washed with THF/H$_2$O (1:1, 3×50 ml), THF, DCM and MeOH (5 cycles each). Dried under vacuum to a constant weight to obtain resin bound acid 6 (5.25 g, 0.86 mmol/g loading) as pale yellow beads. Acidic minicleavage (50% TFA/DCM, 20 min.) of a sample of this resin confirmed the complete hydrolysis of the ester to the acid. This compound exist as a mixture of diastereomers $^1$H NMR of this compound is same as that reported for compound 10A.

Synthesis of Sulfamate Acid 10A (KRB01-137)

Resin 6 (200 mg, 0.154 mmol) was rinsed with a 50:50 solution of TFA/CH$_2$Cl$_2$ (10 mL, over a period of 20 min.) and the filtrate was evaporated under reduced pressure. The residue was recrystallized from hot methanol to yield 10A (50 mg, 74%) as a white solid: Mixture of Diastereomers $^1$H NMR (270 MHz, DMSO-d$_6$) δ 0.81 (3H, s, 18-CH$_3$), 1.13-1.15 (t, J=7.5 Hz, 2-CH$_2$CH$_3$), 1.45-2.50 (m, 13H), 2.57-2.64 (2H, q, J=7.5 Hz, 2-CH$_2$CH$_3$), 2.66-2.83 (m, 2H), 7.22 (s, 1H), 7.03 (s, 1H), 7.96 (s, 2H, NH$_2$); HPLC>94% (R$_f$=1.89, 10% water/acetonitrile); ES–ve–MS (M–H$^+$) 434 m/z.

Synthesis of Acid (KRB01-139)

Nucleophilic Cleavage to Form 10B: To resin 6 (300 mg, 0.231 mmol) was added piperazine (199 mg, 2.31 mmol) and anhydrous THF (5 mL) in a round bottom flask. The mixture was heated under N$_2$ to 65° C. for 48 h (without stirring), after which time the mixture was filtered and the resin was rinsed with MeOH and CH$_2$Cl$_2$ (5×). The combined washings were evaporated under reduced pressure and purified by flash chromatography on silica gel (eluted with 5%→15% methanol in CH$_2$Cl$_2$, piperazine sticks to baseline) to afford of 10B (60 mg, 73%) as a white solid: $^1$H NMR signals (270 MHz, CDCl$_3$) δ 0.98 and 0.87 (s, 18-CH$_3$, two diastereomers in approx. 1:3 ratio), 1.21 (3H, t, J=7.5 Hz, 2-CH$_2$CH$_3$), 1.20-1.38 (t, J=7.5 Hz, 3H, 2-CH$_2$CH$_3$), 1.45-2.50 (m, 13H), 2.54-2.64 (q, J=7.5 Hz, 2H, 2-CH$_2$CH$_3$), 2.79-2.82 (m, 2H), 2.96-2.98 (1H, dd, J=16.3, 4.2 Hz, 16-H), 6.51 (s, 1H), 7.03 (s, 1H); HPLC>99% (10% water/acetonitrile); ES–ve–MS (M–H$^+$) 356 m/z.

General Procedure for Synthesis of Sulfamate Amide Library

A stock solution of PyBOP (Benzotriazolyl-oxy-tris-pyrrolidino-phosphonium hexafluorophosphate) was prepared in 14 ml of DCM and 2.0 ml used for each reaction. A stock solution of HOBt ((N-hydroxy benzotriazole, 0.185 g/reaction) and DIPEA (0.297 ml/reaction) prepared in 9.0 ml of DCM and 1.0 ml used for each reaction.

The resin bound acid 6 (0.400 g, loading 0.86 mmol/g) was suspended in DCM (4.0 ml) under inert atmosphere in a 25 ml round bottom flask, added the activating agent PyBOP (0.715 g, 1.37 mmol,), followed by HOBt and DIPEA mixture (HOBt 0.185 g, 1.37 mmol, DIPEA 0.297 ml), and the amines (4 molar equivalents). The mixture was shaken for approximately 72 h using a flask shaker. The crude resins were then filtered, washed with DMF (5×), DCM (5×), MeOH (5×) using Argonaut Flash Vacuum Manifold and fritted syringes. The washed resins were dried under vacuum, one half of each resin was then transferred to Radleys Green House Synthesiser tubes to generate the phenol library. The remaining half was treated with 50% TFA in DCM over 20 min., TFA was evaporated using the Genevac and the products were purified using Flash Master-11 (DCM/MeOH, gradient elution, 5 or 10 g pre-packed columns) to generate the sulfamate library. The compounds generated exist as a mixture of diastereomers.

General Procedure for Synthesis of Phenol Library.

The resin bound sulfamate amides (0.200 g, 0.86 mmol/g) were suspended in anhydrous THF (4 ml) under inert atmosphere (Radleys Green House Parallel Synthesiser was used to carry out these reactions), treated with piperazine (0.75 g, 8.7 mmol) and refluxed at 70° C. for approximately 70 h. The resins were filtered, the filtrates were collected in to tubes, concentrated using the Genevac. These compounds were pre-absorbed onto silica gel, purified using the Flash Master-11 (Ethyl acetate/Hexane gradient elution) to give pure products as colourless solids. These compounds exist as a mixture of diastereomers.

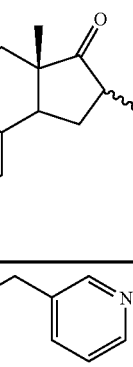

| Compound | R¹ | R² | HPLC Purity (%) |
|---|---|---|---|
| 11 (STX 1039) | SO₂NH₂ | 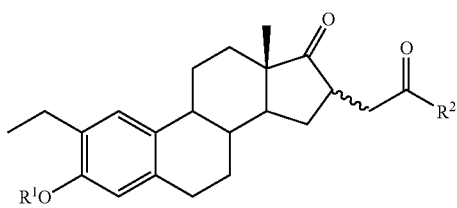 | >95 |
| 12 | SO₂NH₂ | 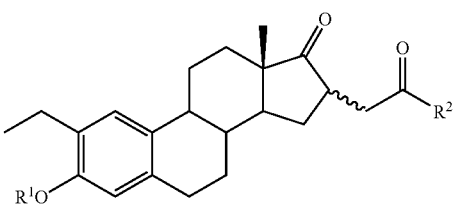 | >91 |
| 13 | SO₂NH₂ | 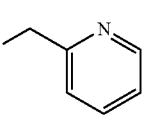 | >99 |
| 15 | SO₂NH₂ | 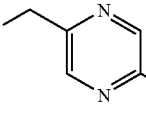 | >91 |
| 16 | SO₂NH₂ | 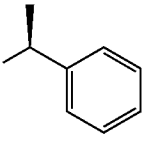 | >98 |
| 17 | SO₂NH₂ | 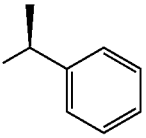 | 90 |
| 18 | SO₂NH₂ | 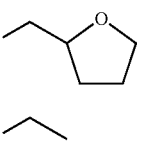 | >89 |
| 19 | SO₂NH₂ |  | >95 |
| 20 | SO₂NH₂ |  | >92 |
| 21 | SO₂NH₂ |  | >97 |
| 22 (STX 1040) | H | 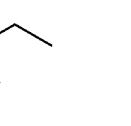 | >99 |
| 23 | H | 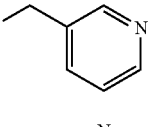 | >88 |

-continued

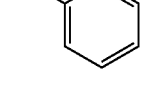

| Compound | R¹ | R² | HPLC Purity (%) |
|---|---|---|---|
| 24 | H | 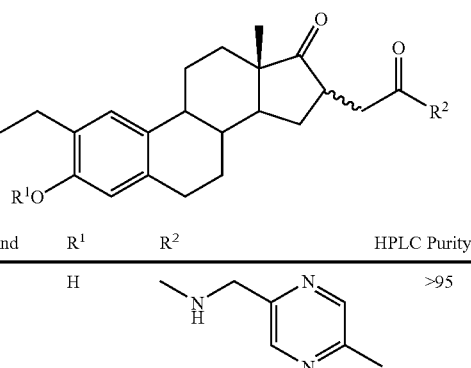 | >95 |
| 25 | H | 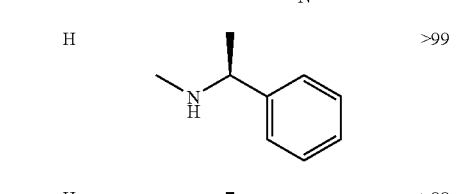 | >99 |
| 26 | H | 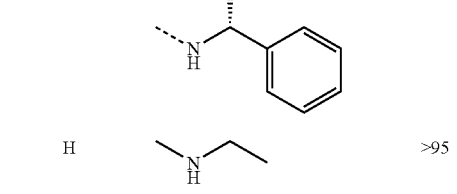 | >99 |
| 27 | H | 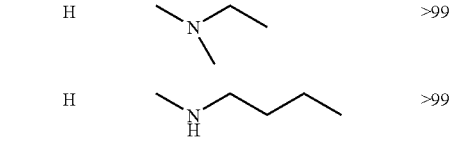 | >95 |
| 28 | H | 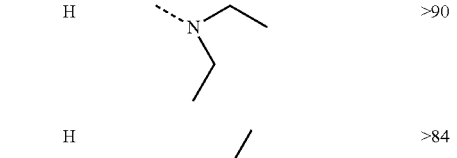 | >99 |
| 29 | H | 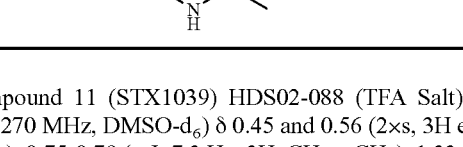 | >99 |
| 30 | H | 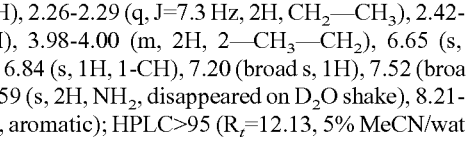 | >90 |
| 31 | H | 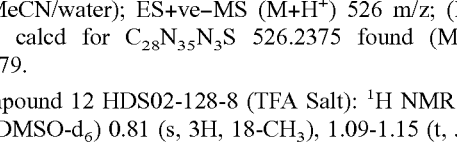 | >84 |

Compound 11 (STX1039) HDS02-088 (TFA Salt): $^1$H NMR (270 MHz, DMSO-$d_6$) δ 0.45 and 0.56 (2×s, 3H each, 18-CH₃), 0.75-0.79 (t, J=7.3 Hz, 3H, CH₂—CH₃), 1.33-2.47 (m, 12H), 2.26-2.29 (q, J=7.3 Hz, 2H, CH₂—CH₃), 2.42-2.59 (m, 3H), 3.98-4.00 (m, 2H, 2—CH₃—CH₂), 6.65 (s, 1H, 4-CH), 6.84 (s, 1H, 1-CH), 7.20 (broad s, 1H), 7.52 (broad m, 1H), 7.59 (s, 2H, NH₂, disappeared on D₂O shake), 8.21-8.17 (m, 3H, aromatic); HPLC>95 ($R_t$=12.13, 5% MeCN/water to 95% MeCN/water); ES+ve–MS (M+H⁺) 526 m/z; (FAB-HRMS calcd for C₂₈N₃₅N₃S 526.2375 found (M+H⁺) 526.2379.

Compound 12 HDS02-128-8 (TFA Salt): $^1$H NMR (270 MHz, DMSO-$d_6$) 0.81 (s, 3H, 18-CH₃), 1.09-1.15 (t, J=7.1 Hz, 3H, CH₂—CH₃), 1.33-2.47 (m, 12H), 2.61-2.64 (q, J=7.3 Hz, 2H, CH₂—CH₃), 2.82-2.90 (m, 3H), 4.36-4.38 (m, 2H, 2—CH₃—CH₂), 7.02 (s, 1H, 4-CH), 7.21 (s, 1H, 1-CH), 7.28-7.30 (m, 2H, aromatic) 7.52 (broad m, 1H), 7.96 (s, 2H, NH₂), 8.48-8.51 (m, 2H, aromatic); HPLC>91% ($R_t$=2.12, 70% MeCN/water); ES+ve–MS (M+H$^+$) 526 m/z; (FAB-HRMS calcd for C$_{28}$H$_{35}$N$_{35}$O$_5$S 526.2875 found (M+H$^+$) 526.2374

Compound 13 HDS02124-2 (TFA Salt): $^1$H NMR (400 MHz, DMSO-D$_6$) 0.805 (s, 3H, 18-CH$_3$), 1.10-1.13 (t, J=7.4 Hz, 3H, CH$_2$—CH$_3$), 1.37-2.45 (m, 12H), 2.58-2.62 (q, J=7.8 Hz, 2H, CH$_2$—CH$_3$), 2.80-2.87 (m, 3H), 4.34-4.36 (m, 2H, CH$_3$—CH$_2$), 6.99 (s, 1H, 4-CH), 7.18 (s, 1H, 1-CH), 1H), 7.92 (s, 2H, NH$_2$), 8.43 (2×s, 2H, aromatic) 8.51-8.84 (t, J=5.85 Hz, 1H, NH); ES+ve-MS (M+H$^+$) 541, (M+H−18$^+$) 523 m/z; HPLC>99% (R$_t$2.0, 80% MeCN/water); FAB-HRMS calcd for C$_{28}$H$_{36}$N$_4$O$_5$S 541.2484 found (M+H$^+$) 541.2478

Compound 15 HDS02128-2 (TFA Salt): 1H NMR (270 MHz, DMSO-d$_6$) 0.80 and 0.83 (s, 3H, 18-CH$_3$), 1.09-1.14 (t, J=7.4 Hz, 3H, CH$_2$—CH$_3$), 1.32-1.37 (d, J=6.8 Hz, 3H, CH—CH$_3$), 1.39-2.45 (m, 12H), 2.60-2.63 (q, J=7.6 Hz, 2H, CH$_2$—CH$_3$), 2.80-2.81 (m, 3H), 4.95-4.99 (m, 1H, CH$_3$—CH), 7.01 (s, 1H, CH), 7.20-7.22 (m, 2H, aromatic), 7.30-7.32 (m, 4H, aromatic), 7.95 (broad m, 2H, aromatic), 8.35-8.39 (broad t, 1H, NH); ES+ve-MS (M+H$^+$) 539 m/z; HPLC>91% (R$_t$=2.0, 70% MeCN/water); FAB-HRMS calcd for C$_{30}$H$_{38}$N$_2$O$_5$S 539.2579 found (M+H$^+$) 539.2579

Compound 16 HDS02123-3 (TFA Salt): $^1$H NMR (270 MHz, DMSO-d$_6$) 0.80 and 0.83 (2×s, 3H, 18-CH$_3$), 1.09-1.15 (t, J=7.1 Hz, 3H, CH$_2$—CH$_3$), 1.32-1.35 (d, J=6.8 Hz, 3H, CH—CH$_3$), 1.39-2.45 (m, 12H), 2.57-2.66 (q, J=7.9 Hz, 2H, CH$_2$—CH$_3$), 2.80-2.84 (m, 3H), 4.91-4.94 (m, 1H, CH$_3$—CH), 7.02 (s, 1H, CH), 7.21-7.23 (m, 2H, aromatic), 7.30-7.32 (m, 4H, aromatic), 7.94 (broad m, 2H, aromatic), 8.31-8.35 (broad t, J=3.57 Hz, 1H, NH); ES+ve-MS (M+H$^+$) 539 m/z; HPLC>98% (R$_t$=2.69, 70% MeCN/water); FAB-HRMS calcd for C$_{30}$H$_{38}$N$_2$O$_5$S 535.2579 found (M+H$^+$) 539.2574

Compound 17 HDS02120-2 (TFA Salt): $^1$H NMR (400 MHz, DMSO-d$_6$) 0.81 and 0.89 (2×s, 3H, 18-CH$_3$), 1.09-1.13 (t, J=7.1 Hz, 3H, CH$_2$—CH$_3$), 1.23-2.45 (m, 16H), 2.58-2.63 (q, J=7.4 Hz, 2H, CH$_2$—CH$_3$), 2.79-2.81 (m, 3H), 3.10-3.12 (m, 2H), 3.62-3.80 (m, 3H), 6.99 (s, 1H, CH), 7.18 (s, 1H, aromatic), 7.92 (broad m, 2H, aromatic); ES+ve-MS (M+H$^+$) 519 m/z; HPLC>90% (R$_t$=2.42, 70% MeCN/water).

Compound 18 HDS02128-1 (TFA Salt): $^1$H NMR (270 MHz, DMSO-d$_6$) 0.80 and 0.89 (2×s, 3H, 18-CH$_3$), 0.98-1.03 (t, J=7.1 Hz, 3H, CH$_2$—CH$_3$), 1.09-1.15 (t, J=7.4 Hz, 3H, CH$_2$—CH$_3$), 1.23-2.45 (m, 12H), 2.57-2.66 (q, J=7.4 Hz, 2H, CH$_2$—CH$_3$), 2.79-2.82 (m, 3H), 3.02-3.08 (q, J=7.4 Hz, CH$_2$—CH$_3$), 7.01 (s, 1H, CH), 7.21 (s, 1H, aromatic), 7.88 (broad t, 1H, NH), 7.95 (s, 2H, NH$_2$); ES+ve-MS (M+H$^+$) 463 m/z; HPLC>89% (R$_t$ 3.51, 5% MeCN/water to 95% MeCN/water); FAB-HRMS calcd for C$_{24}$H$_{34}$N$_2$O$_5$S 463.2266 found (M+H$^+$) 463.2282

Compound 19 HDS02128-4 (TFA Salt): $^1$H NMR (270 MHz, DMSO-d$_6$) 0.82 and 0.91 (2×s, 3H, 18-CH$_3$), 0.96-1.02 (t, J=7.1 Hz, 3H, CH$_2$—CH$_3$), 1.09-1.15 (t, J=7.4 Hz, 3H, CH$_2$—CH$_3$); 1.23-2.45 (m, 12H), 2.58-2.66 (q, J=7.4 Hz, 2H, CH$_2$—CH$_3$), 2.79-2.82 (m, 4H), 2.92 (s, N—CH$_3$), 7.01 (s, 1H, CH), 7.21 (s, 1H, aromatic), 7.95 (s, 2H, NH$_2$); ES+ve-MS (M+H$^+$) 477 m/z; HPLC>95% (R$_t$=2.44, 70% MeCN/water); FAB-HRMS calcd for C$_{25}$H$_{36}$N$_2$O$_5$S 477.2423 found (M+H$^+$) 477.2414

Compound 20 HDS02128-5 (TFA Salt): Diagnostic signals $^1$H NMR (270 MHz, DMSO-d$_6$) 0.81 (s, 3H, 18-CH$_3$), 0.83-0.90 (m, 6H), 1.09-1.15 (t, J=7.1 Hz, 3H, CH$_2$—CH$_3$), 1.23-2.45 (m, 12H), 2.59-2.66 (q, J=7.4 Hz, 2H, CH$_2$—CH$_3$), 2.79-2.82 (m, 3H), 3.00-3.06 (m, 2H), 7.02 (s, 1H, CH), 7.21 (s, 1H, aromatic), 7.82-7.87 (m, 1H, NH), 7.96 (s, 2H, NH$_2$); ES+ve-MS (M+H$^+$) 491 m/z; HPLC>92% (R$_t$=2.45, 70% MeCN/water); FAB-HRMS calcd for C$_2$H$_{38}$N$_2$O$_5$S 491.2579 found (M+H$^+$) 491.2581

Compound 21 HDS02128-6 (TFA Salt): $^1$H NMR (270 MHz, DMSO-d) 0.82 and 0.91 (2×s, 3H, 18-CH$_3$), 0.96-1.03 (t, J=6.8 Hz, 3H, CH$_2$—CH$_3$), 1.05-1.15 (m, 6H, 2×CH$_2$—CH$_3$), 1.23-2.45 (m, 12H), 2.58-2.63 (q, J=7.6 Hz, 2H, CH$_2$—CH$_3$), 2.79-2.82 (m, 3H), 3.25-3.10 (q, J=7.1 Hz, CH$_2$—CH$_3$), 7.01 (s, 1H, CH), 7.21 (s, 1H, aromatic), 7.94 (s, 2H, NH$_2$); ES+ve-MS (M+H$^+$) 491 m/z; HPLC>97% (R$_t$=2.65, 70% MeCN/water); FAB-HRMS calcd for C$_{26}$H$_{38}$N$_2$O$_5$S 491.2575 found (M+H$^+$) 491.2568

Compound 22 (STX1040) HDS02-080-1: $^1$H NMR (270 MHz, CDCl$_3$) 0.79 (s, 3H, 18-CH$_3$), 1.17-1.22 (t, J=7.6 Hz, 3H, CH$_2$—CH$_3$), 1.32-2.40 (m, 13H), 2.54-2.63 (q, J=7.6 Hz, 2H, CH$_2$—CH$_3$), 2.67-2.82 (m, 3H), 4.43-4.46 (m, 2H, NH—CH$_2$), 6.12 (broad s, 1H, OH), 6.41 (broad t, 1H, NH), 6.51 (s, 1H, aromatic), 6.39-6.41 (appt, J=5.9 Hz, 1H, NH), 6.70-6.72 (appt t, J=5.9 Hz, 1H, NH), 7.01 (s, 1H, CH), 7.28-7.30 (m, 1H, aromatic) 7.64-7.67 (appd, J=7.6 Hz, 1H, aromatic), 8.50-8.53 (m, 2H, aromatic); HPLC>99% (R$_t$=5.20, 5% MeCN/water to 95% MeCN/water); ES−ve-MS (M+H$^+$) 445 m/z.

Compound 23 HDS02-086-1: $^1$H NMR (270 MHz, CDCl$_3$) 0.46 (s, 3H, 18-CH$_3$), 0.81-0.88 (m, 2H), 1.14-1.24 (m, 4H), 1.32-2.85 (m, 15H), 4.39-4.90 (m, 2H, NH—CH$_2$), 6.48 (s, 1H, aromatic), 6.90-6.95 (broad t, 1H, NH), 6.97 (s, 1H, aromatic), 7.01-7.06 (s, 1H, aromatic), 7.27-7.39 (m, 1H, aromatic), 7.67-7.74 (m, 1H, aromatic), 8.52-8.54 (m, 1H, aromatic); HPLC>99% (R$_t$=2.25 and 2.76, 75% MeCN/water); ES−ve-MS (M+H$^+$) 445 m/z; FAB-HRMS calcd for C$_{28}$H$_{34}$N$_2$O$_3$ 447.2647 found (M+H$^+$) 447.2655

Compound 24 HDS02-086-4: $^1$H NMR (270 MHz, CDCl$_3$) 0.81 and 0.84 (2×s, 3H, 18-CH$_3$), 1.17-1.22 (m, 3H, 2×CH$_2$—CH$_3$), 1.32-2.40 (m, 13H), 2.54-2.63 (q, J=7.6 Hz, 2H, CH$_2$—CH$_3$), 2.67-2.82 (m, 3H), 4.55-4.57 and 4.80-4.82 (m, 2H, NH—CH$_2$), 6.19 (broad s, 1H, OH), 6.49 (s, 1H, CH), 7.02 (s, 1H, CH), 8.24, 8.37, 8.47, 8.60, 8.61 (4×s, 2H, CH); HPLC>95% (R$_t$=2.16 and 2.38, 80% MeCN/water); ES−ve-MS (M+H$^+$) 445 m/z; FAB-HRMS calcd for C$_{28}$H$_{35}$N$_3$O$_3$ 462.4756 found (M+H$^+$) 462.2744.

Compound 25 HDS02-134-2: $^1$H NMR (270 MHz, CDCl$_3$) 0.74 and 0.94 (2×s, 3H, 18-CH$_3$), 1.16-1.22 (t, J=7.6 Hz, 3H, CH$_2$—CH$_3$), 1.46-1.49 (d, J=6.8 Hz, 3H, CH—CH$_3$), 2.65-2.72 (dd, J=5.4 and 5.8 Hz, 1H), 1.32-2.40 (m, 12H), 2.53-2.61 (q, J=7.6 Hz, 2H, CH$_2$—CH$_3$), 2.67-2.82 (m, 3H), 4.9 and 5.0 (2×s, 1H, OH), 5.08-5.13 (m, CH—CH$_3$), 6.06-6.03 (d, J=8.2 Hz, 1H, NH), 6.30-6.33 (d, J=7.9 Hz, 1H, NH), 6.50 (s, 1H, CH), 7.02 (s, 1H, CH), 7.32-7.40 (m, 5H, aromatic); HPLC>99% (R$_t$=3.36, 80% MeCN/Water); ES+ve-MS (M+H$^+$) 460 m/z; FAB-HRMS calcd for C$_{30}$H$_{37}$NO$_3$ 460.2851 found (M+H$^+$) 460.2841

Compound 26 HDS02-134-3: $^1$H NMR (270 MHz, CDCl$_3$) 0.84 and 0.94 (2×s, 3H, 18-CH$_3$), 1.17-1.22 (t, J=7.4 Hz, 3H, CH$_2$—CH$_3$), 1.46-1.49 (d, J=6.8 Hz, 3H, CH—CH$_3$), 1.32-2.40 (m, 12H), 2.53-2.61 (q, J=7.6 Hz, 2H, CH$_2$—CH$_3$), 2.65-2.72 (dd, J=5.4 and 5.8 Hz, 1H), 2.79-2.82 (m, 3H), 4.71 and 4.75 (2×s, 1H, OH), 5.06-5.11 (m, CH—CH$_3$), 5.59-6.03 (d, J=8.2 Hz, 1H, NH), 6.30-6.33 (d, J=7.9 Hz, 1H, NH), 6.50 (s, 1H, CH), 7.02 (s, 1H, CH), 7.31-7.40 (m, 5H, aromatic); HPLC>99% (R$_t$=3.36, 70% MeCN/water); ES+ve-MS (M+H$^+$) 460 m/z; FAB-HRMS calcd for C$_{30}$H$_{37}$NO$_3$ 460.2851 found (M+H$^+$) 460.2842

Compound 27 HDS02-134-1: $^1$H NMR (270 MHz, CDCl$_3$) 0.81 and 0.95 (2×s, 3H, 18-CH$_3$), 1.10-1.16 (t, J=7.4

Hz, 3H, CH$_2$—CH$_3$), 1.16-1.12 (t, J=7.4 Hz, 3H, CH$_2$—CH$_3$), 1.42-2.43 (m, 13H), 2.55-2.62 (q, J=7.9 Hz, 2H, CH$_2$—CH$_3$), 2.65-2.82 (m, 3H), 3.22-3.32 (m, 2H, N—CH$_2$—CH$_3$), 4.94 and 5.03 (2×s, 1H, OH), 5.72 and 5.93 (2× broad t, 1H, NH), 6.51 (s, 1H, CH), 7.01 (s, 1H, CH); HPLC>95% (R$_f$=5.20, 70% MeCN/water); ES+ve–MS (M+H$^+$) 384 m/z; FAB-HRMS calcd for C$_{24}$H$_{33}$NO$_3$ 385.2538 found (M+H$^+$) 384.2532

Compound 28 HDS02-134-4: $^1$H NMR (270 MHz, CDCl$_3$) 0.82 and 0.94 (2×s, 3H, 18-CH$_3$), 1.06-1.12 (t, J=7.1 Hz, 3H, CH$_2$—CH$_3$), 1.16-1.22 (t, J=7.6 Hz, 3H, CH$_2$—CH$_3$), 1.92-2.43 (m, 13H), 2.53-2.61 (q, J=7.6 Hz, 2H, CH$_2$—CH$_3$), 2.78-2.82 (m, 3H), 2.91-2.95 (2×s, 3H, N—CH$_3$), 3.31-3.38 (m, 1H), 4.78-4.82 (broad s, 1H, OH), 6.51 (s, 1H, CH), 7.02 (s, 1H, CH); HPLC>99% (R$_f$=5.20, 70% MeCN/water); ES+ve–MS (M+H$^+$) 398 m/z; FAB-HRMS calcd for C$_{25}$H$_{35}$NO$_3$ 398.2695 found (M+H$^+$) 398.2695

Compound 29 HDS02-134-5: Diagnostic signals $^1$H NMR (270 MHz, CDCl$_3$) 0.82 (s, 3H, 18-CH$_3$), 0.91-0.94 (m, 3H), 1.17-1.22 (t, J=7.6 Hz, 3H, CH$_2$—CH$_3$), 1.29-2.43 (m, 15H), 2.53-2.62 (q, J=7.9 Hz, 2H, CH$_2$—CH$_3$), 2.78-2.82 (m, 3H), 3.20-3.25 (m, 1H), 4.82 and 4.89 (2× broad s, 1H, OH), 5.72 and 5.96 (2× broad t, 1H, NH), 6.51 (s, 1H, CH), 7.02 (s, 1H, CH); HPLC>99% (R$_f$=2.96, 70% MeCN/water); ES+ve–MS (M+H$^+$) 412 m/z; FAB-HRMS calcd for C$_{28}$H$_{37}$NO$_3$ 412.2851 found (M+H$^+$) 412.2857

Compound 30 HDS02-134-6: $^1$H NMR (270 MHz, CDCl$_3$) 0.82 and 0.94 (2×s, 3H, 18-CH$_3$), 1.08-1.22 (2×t, J=7.1 and 7.4 Hz, 3H each, 2×CH$_2$—CH$_3$), CH$_2$—CH$_3$), 1.92-2.43 (m, 13H), 2.53-2.62 (q, J=7.6 Hz, 2H, CH$_2$—CH$_3$), 2.78-2.81 (m, 3H), 3.25-3.42 (m, 4H, N—CH$_2$—CH$_3$), 4.77 and 4.81 (broad s, 1H, OH), 6.51 (s, 1H, CH), 7.02 (s, 1H, CH); HPLC>96% (R$_f$=13.41, 5% MeCN/water to 95% MeCN/water); ES+ve–MS (M+H$^+$) 412 m/z; FAB-HRMS calcd for C$_{26}$H$_{37}$NO$_3$ 412.2851 found (M+H$^+$) 412.2854

Compound 31 HDS02-134-7 Mixture of diastereomers $^1$H NMR (270 MHz, CDCl$_3$) 0.79 and 0.93 (2×s, 3H, 18-CH$_3$), 1.12-1.16 (2×d, J=6.3 Hz each, 6H, 2×CH$_3$), 1.19-1.21 (t, J=7.1 Hz, 3H, CH$_2$—CH$_3$), 1.92-2.43 (m, 13H), 2.53-2.62 (m, 2H, CH$_2$—CH$_3$), 2.78-2.85 (m, 3H), 4.04-4.08 (m, 4H, NH—CH—(CH$_3$)$_2$), 5.28 and 5.42 (2×s, 1H, 2×OH), 5.57-5.59 and 5.83-5.86 (2×d, J=7.6 Hz each, 1H, NH), 6.52 (s, 1H, CH), 7.01 (s, 1H, CH); HPLC>84% (R$_f$=3.90, 5% MeCN/water to 95% MeCN/water); ES+ve–MS (M+H$^+$) 398 m/z; FAB-HRMS calcd for C$_{25}$H$_{35}$NO$_3$ 398.2695 found (M+H$^+$) 398.2692

Synthesis of 2-Methoxy Estrone Amide.

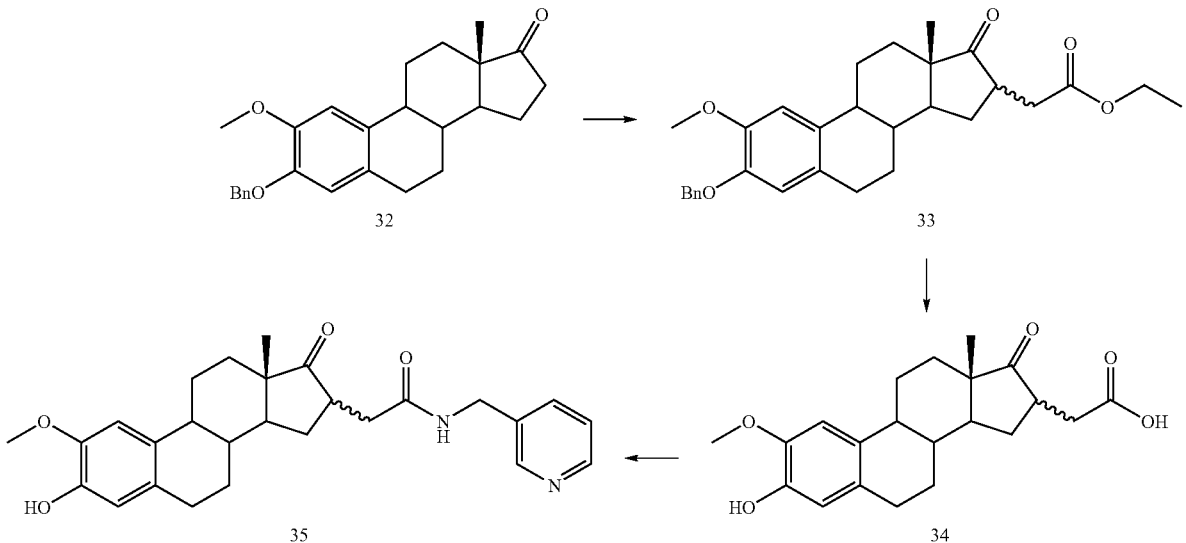

Synthesis of Benzyl Ether (HDS02-170) 32

The 2-Methoxy estrone (0.521 g, 0.00173 mol) was dissolved in anhydrous DMF under nitrogen atmosphere, added K$_2$CO$_3$ (0.718 g, 0.00225 mol) and stirred at r.t. for approximately 40 h. The crude mixture was diluted with EtOAc, washed with water and brine. The organics were dried (MgSO$_4$) and concentrated. The crude product was pre-absorbed onto silica gel, purified using Flash Master-2 system to give the benzylated compound 32 (0.651 g, 96%) as a chalky white solid: TLC (R$_f$ 0.4, EtOAc:Hexane, 3:7); $^1$H NMR (270 MHz, CDCl$_3$) δ 0.90 (s, 3H, 18-CH$_3$ diastereomeric methyl signals), 1.24-1.27 (t, J=3.4 Hz, 3H, CH$_2$—CH$_3$), 1.24-1.29 (t, J=7.1 Hz, 3H, CH$_2$—CH$_3$), 1.39-2.44 (broad m, 12H), 2.44-2.54 (dd, J=18.8 and 8.6 Hz, 1H), 2.77-2.83 (m, 2H), 3.84-3.87 (s, 3H, OMe), 5.0 (s, 2H, PhCH$_2$), 6.6 (s, 1H, aromatic), 6.77 (s, 1H, aromatic), 3.87-3.84 (s, 3H, OMe), 4.10-4.16 (q, J=7.0 Hz, 2H, CH$_3$—CH$_2$—O), 5.09 (s, 2H, CH$_2$-phenyl), 6.61 (s, 1H, 4-CH), 6.82 (s, 1H, aromatic 1-CH), 7.41-7.43 (m, 5H).

Synthesis of the Ethyl Ester (HDS02-174) 33

To a stirred solution of 2-Methoxy benzyl estrone 32 (150 mg, 0.38 mmol) in anhydrous THF under inert conditions was added a solution of LDA (0.234 ml, 1.8 M solution in heptane, THF, and Ethylbenzene) at −10° C. over a period of 20 min. The reaction mixture was cooled to −60° C., stirred 15 min, added ethyl bromoacetate (0.052 ml, 0.46 mmol) drop wise over 10 min. and allowed to warm to rt overnight. Diluted the mixture with DCM, added saturated NH$_4$Cl and extracted with DCM. The organic phases were combined, dried, and concentrated to obtain a yellow solid which was then purified using Flash Master-2 (10 g column, DCM:MeOH, gradient elution) to obtain the pure product (0.120 g, 65% yield) as a colourless glassy solid: $^1$H NMR (270 MHz, CDCl$_3$) δ 0.99 and 0.97 (2×s, 3H, 18-CH$_3$diastereomeric methyl signals), 1.24-1.27 (t, J=3.4 Hz, 3H, CH$_2$—CH$_3$), 1.24-1.29 (t, J=7.1 Hz, 3H, CH$_2$—CH$_3$), 1.47-3.19 (broad m, 15H), 3.87-3.84 (s, 3H, OMe), 4.10-4.16 (q, J=7.0 Hz, 2H, CH$_3$—CH$_2$—O), 5.09

(s, 2H, CH$_2$-phenyl), 6.61 (s, 1H, 4-CH), 6.82 (s, 1H, aromatic 1-CH), 7.41-7.43 (m, 5H).

Synthesis of the Acid (HDS02-182) 34

The estrone ester 33 (0.120 g, 0.252 mmol) was dissolved in a mixture of MeOH:THF (1:1, 6 ml), added. NaOH (4M, 3.0 ml) and stirred at room temperature for 30 h. The completion of the reaction was determined by t.l.c (EtOAc: Hexane 3:7, product-base line spot). The crude mixture was acidified to pH=2 to 3, extracted with DCM, washed with water and brine. The organic phase was dried (MgSO$_4$) and concentrated to obtain the product as a pale yellow solid. This product 33 (0.092 g, 0.205 mmol) was dissolved in a mixture of MeOH:THF (1:1, 7 ml), degassed the mixture using N$_2$, added 5% Pd on C (10 mg) then hydrogenated under a of balloon of Hydrogen for approximately for 15 h. The crude mixture was filtered using a pad of celite, purified (SiO$_2$, EtOAc:hexane gradient elution using Flash Master-2) to obtain the product 34 (0.081 g, 100% ) as a pale yellow solid: The diagnostic signals of the $^1$H NMR (400 MHz, CDCl$_3$) δ 0.93 (s, 3H, 18-CH$_3$), 1.47-2.65 (broad m, 13H), 2.83-2.85 (m, 2H, CH$_2$), 2.96-3.01 (dd, J=16.3 and 4.6 Hz, CH-diestereotopic) 3.89 (s, 3H, OMe), 5.33 (broad s, 1H, OH), 6.69 (s, 1H, aromatic 4-CH), 6.81 (s, 1H, aromatic 1-CH); HPLC>99% (R$_t$=1.59, 70% MeCN in water); ES+ve-MS (M+H$^+$) 357 m/z.

Synthesis of the Amide (HDS02-190) 35 (STX1191).

The starting material acid 34 (0.038 g, 0.106 mmol) was suspended in DCM (5.0 ml), added PyBop (0.062 g, 0.12 mmol), HOBt (0.016 g, 0.12 mmol) stirred for 20 minutes and added DIPEA (0.076 ml) followed by 3-amino methyl pyridine (0.026 g, 0.24 mmol). The reaction was left to stir 20 h, quenched with sat. Na$_2$CO$_3$, washed with brine. The organics were separated, dried concentrated to obtain a pale yellow oil. This crude oil was purified using the Flash Master-2 system to obtain a white solid. The product obtained at this point was re-crystalised with hexane/EtOAc to give the required product amide 35 also as a white solid: The diagnostic signals of the mixture of diastereomers of 35 $^1$H NMR (400 MHz, CDCl$_3$) δ 0.84 and 0.97 (2×s, 3H, 18-CH$_3$), 1.47-2.81 (broad m, 13H), 3.11-3.17 (m, 2H, CH$_2$), 3.84 (s, 3H, OMe), 4.44-4.46 (m, 2H, NH—CH$_2$—), 5.46 (broad s, 1H, OH), 6.61 (s, 1H, aromatic 4-CH), 6.75 (s, 1H, aromatic CH), 7.63 (m, 1H, CH aromatic), 8.53 (m, 2H, 2H); HPLC>90% (R$_t$=1.59, 90% MeCN in water); ES+ve-MS (M+H$^+$) 448 m/z.

Section 4

3-O-Acetyl-estrone (DSF 02124)

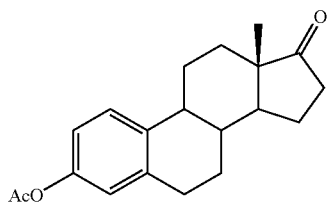

Acetic acid (60 mL, 1.05 mmol) was added dropwise over 45 minutes to a stirred solution of estrone (3 g, 11.1 mmol) in anhydrous pyridine (200 mL) at 0° C. under an atmosphere of N$_2$. The resulting yellow mixture was heated to reflux for 1 hour. After cooling down, this was poured into H$_2$O and ice (300 mL) and acidified with HCl 6M. The organics were extracted with EtOAc (300 mL), washed with H$_2$O (200 mL), aq. NaHCO$_3$ (200 mL), then brine (200 mL), dried (Na$_2$SO$_4$), filtered and concentrated under reduced pressure. The crystalline orange crude (3.88 g) was recrystallized from IPA to give light yellow needles (3.25 g, 94%): TLC (chloroform/EtOAc, 4:1) R$_f$ 0.82 cf. R$_f$ 0.68 (E1); δ$_H$ (CDCl$_3$, 400 MHz) 0.91 (3H, s, C-18-H$_3$), 1.45-2.54 (13H,m), 2.29 (3H, s, OAc), 2.89-2.92 (2H, m, C-6-H$_2$), 6.81 (1H, d, J$_{C-2-H,C-4-H}$=2.6 Hz, C-4-H), 6.85 (1H, dd, J$_{C-1-H,C-2-H}$=8.3 Hz and J$_{C-4-H,C-2-H}$=2.6 Hz, C-2-H) and 7.28 (1H, J$_{C-2-H,C-1-H}$=8.3 Hz, C-1-H).

6-Oxo-3-O-acetyl-estrone (DSF 02128)

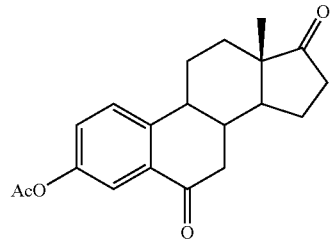

A solution of CrO$_3$ (673 mg, 6.73 mmol) in acetic acid 10% (4 mL) was added dropwise over 2 hours to a stirred solution of 3-O-acetyl-estrone (500 mg, 1.60 mmol) in acetic acid at 10-15° C. in an ice/water bath. The resulting dark brown solution was stirred overnight at room temperature. The solvent was then removed under reduced pressure and H$_2$O (100 mL) added. The organics were extracted with EtOAc (100 mL), washed with H$_2$O (2×30 mL), then brine (2×30 mL), dried (Na$_2$SO$_4$), filtered and concentrated under reduced pressure to give a green foam. This was recrystallized from IPA to give grey crystals (103 mg, 20%): TLC (chloroform/EtOAc, 4:1) R$_f$ 0.53 cf. R$_f$ 0.86; δ$_H$ (CDCl$_3$, 400 MHz) 0.92 (3H, s, C-18-H$_3$), 1.20-2.63 (12H, m), 2.32 (3H, S, OAc), 2.88 (1H, dd, J$_{AB}$=16.8 Hz, J$_{C-8-H,C-7-HB}$=3.1 Hz, C-7-HB), 7.28 (1H, dd, J$_{C-1-H,C-2-H}$=8.6 Hz and J$_{C-4-H,C-2-H}$=2.6 Hz, C-2-H), 7.46 (1H, d, J$_{C-2-H,C-1-H}$=8.6 Hz, C-1-H) and 7.77 (1H, d, J$_{C-2-H,C-4-H}$=2.6 Hz, C-4-H).

6-Oxo-estrone (DSF 02130, STX416)

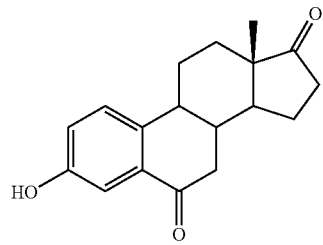

A solution of KOH (247 mg, 4.40 mmol) in MeOH (1.5 mL) was added dropwise to a stirred solution of 6-oxo-3-O-acetyl-estrone (80 mg, 0.24 mmol) in MeOH (1.5 mL). The resulting brown solution was stirred for 2 hours at room temperature. The solvent was then concentrated under reduced pressure and H$_2$O (20 mL) added, followed by HCl 5M. The organics were extracted with EtOAc (50 mL), washed with H$_2$O (20 mL), then brine (2×30 mL), dried (Na$_2$SO$_4$), filtered and concentrated under reduced pressure. The crude product (74 mg) was purified by flash chromatography with chloroform/EtOAc (7:3) as eluent and gave the product as a light pink powder (41 mg, 58%): mp 241-243° C.; TLC (chloroform/EtOAc, 4:1) R$_f$ 0.39 cf. R$_f$ 0.64; IR (KBr) 3345 (br, OH), 2940-2880 (aliph CH), 1720 (C=O), 1680 (C=O), 1610-1495 (arom C=C) cm$^{-1}$; $\delta_H$ (CDCl$_3$, 400 MHz) 0.93 (3H, s, C-18-H$_3$), 1.24-2.59 (12H, m), 2.87 (1H, dd, J$_{C-8-H,C-7-HB}$=3.3 Hz, J$_{AB}$=17.0 Hz, C-7-HB), 5.74 (1H, s, exchanged with D$_2$O, OH), 7.10 (1H, dd, J$_{C-1-H,C-}$2-H=8.5 Hz and J$_{C-4-H,C-2-H}$=2.8 Hz, C-2-H), 7.33 (1H, d, J$_{C-2-H,C-1-H}$=8.5 Hz, C-1-H) and 7.60 (1H, d, J$_{C-2-H,C-4-H}$=2.8 Hz, C-4-H); MS m/z (FAB+) 369.2 [50], 285.1 [95, (M+H)$^+$], 113.1 [68], 84.0 [94]; Acc MS m/z (FAB+) 285.14917, C$_{18}$H$_{21}$O$_3$ requires 285.14907. HPLC (methanol/water, 90:10, $\lambda_{max}$=223.9 nm) Rt=2.34 min, 100%.

6,17-Bis-oxime-estrone (DSF 02169, STX454)

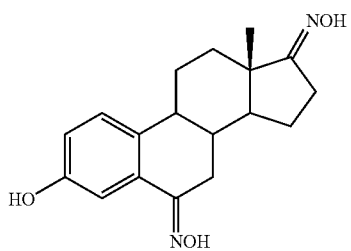

NaOAc (293 mg, 3.58 mmol) followed by hydroxylamine hydrochloride (274 mg, 3.94 mmol) were added to a solution of 6-oxo-estrone (100 mg, 0.35 mmol) in a mixture of MeOH/H$_2$O (5:1, 18 mL). The resulting solution was stirred at room temperature overnight. The solvent was then removed under reduced pressure and H$_2$O added (50 mL). The organics were extracted with EtOAc (50 mL+20 mL), washed with H$_2$O (2×20 mL), then brine (2×20 mL), dried (Na$_2$SO$_4$), filtered and concentrated under reduced pressure to give a light brown crude (120 mg). This was purified by flash chromatography using a gradient of chloroform/EtOAc (7:3 to 1:1) then chloroform/EtOAc/acetone (2:2:1 to 1:1:2) as eluent and gave the product as a creamy powder (46 mg, 41%): mp 341-344° C.; TLC (chloroform/EtOAc, 7:3) R$_f$ 0.11 cf. R$_f$ 0.44; IR (KBr) 3410, 3265-3050 (br, NOH, OH), 2930-2850 (aliph CH), 1705 (C=N), 1580-1495 (arom C=C) cm$^{-1}$; $\delta_H$ (DMSO-d$_6$, 400 MHz) 0.83 (3H, s, C-18-H$_3$), 1.14-2.42 (12H, m), 3.06 (1H, n, C-7-HB), 6.73 (1H, dd, J$_{C-1-H,C-2-H}$=8.3 Hz and J$_{C-4-H,C-2-H}$=2.5 Hz, C-2-H), 7.14 (1H, d, J$_{C-2-H,C-1-H}$=8.3 Hz, C-1-H), 7.29 (1H, d, J$_{C-2-H,C-4-H}$=2.8 Hz, C-4-H) and 9.28, 10.15, 11.08 (each 1H, s, 2×NOH, OH); MS m/z (FAB+) 315.1 [82, (M+H)$^+$], 73 [100]; Acc MS m/z (FAB+) 315.17149, C$_{18}$H$_{23}$N$_2$O$_3$ requires 315.17087.

6,17-Bis-O-methyl-oxime-estrone (DF 02183, STX515)

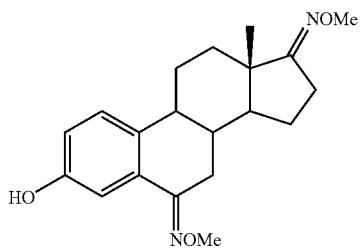

NaOAc (146 mg, 1.79 mmol) followed by O-methyl-hydroxylamine hydrochloride (164 mg, 1.97 mmol) were added to a solution of 6-oxo-estrone (50 mg, 0.18 mmol) in a mixture of MeOH/H$_2$O (5:1, 9 mL). The resulting solution was stirred at room temperature overnight. The solvent was then removed under reduced pressure and H$_2$O added (30 mL). The organics were extracted with EtOAc (20 mL+10 mL), washed with H$_2$O (2×10 mL) then brine (2×10 mL), dried (Na$_2$SO$_4$), filtered and concentrated under reduced pressure. The white crystalline crude was recrystallized from EtOAc/hexane to give the product as white crystals (55 mg, 92%): mp 206-208° C.; TLC (chloroform/EtOAc, 8:2) R$_f$ 0.70 cf. R$_f$ 0.28; IR (KBr) 3134 (br, OH), 2995 (arom CH), 2935-2890 (aliph CH), 1570-1490 (arom C=C) cm$^{-1}$; $\delta_H$ (CDCl$_3$, 400 MHz) 0.92 (3H, s, C-18-H$_3$), 1.24-2.58 (12H, m), 3.12 (1H, dd, J$_{C-8-H,C-7-HB}$=4.5 Hz, J$_{AB}$=18.1 Hz, C-7-HB), 3.84 (3H, s, OMe), 3.99 (3H, s, OMe), 4.85 (1H, br s, exchanged with D$_2$O, OH), 6.84 (1H, dd, J$_{C-1-H,C-2-H}$=8.6 Hz and J$_{C-4-H,C-2-H}$=2.7 Hz, C-2-H), 7.20 (1H, d, J$_{C-2-H,C-1-H}$=8.6 Hz, C-1-H) and 7.29 (1H, d, J$_{C-2-H,C-4-H}$=2.7 Hz, C-4-H); MS m/z (FAB+) 343.2 [100, (M+H)$^+$]; Acc MS m/z (FAB+) 343.20329, C$_{20}$H$_{27}$N$_2$O$_3$ requires 343.20217. Found: C, 70.20; H, 7.57; N, 8.14. C$_{20}$H$_{26}$N$_2$O$_3$ requires: C, 70.15; H. 7.65; N, 8.18.

16-Oximino-estrone (DSF 02036/STX327)

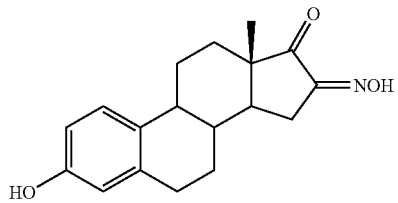

Estrone (200 mg, 740 mmol) was added to a stirred solution of potassium tert-butoxide, freshly prepared by dissolving potassium metal (80 mg, 2.05 mmol) in tert-butanol (2 mL), under an atmosphere of N$_2$. The reaction mixture was stirred for 1 hour at room temperature before addition of isoamyl nitrite (180 μL, 1.34 mmol) in a dropwise manner. The deep red mixture obtained was stirred overnight, then poured into H$_2$O (20 mL). The resulting solution was extracted with ether (2×20 mL) and the aqueous layer was acidified with glacial acetic acid (10 mL) to give a light yellow precipitate. After standing for 2 h, the solid was isolated by filtration to give a yellow powder (140 mg, 63%). For analysis, a sample was recrystallized from acetone to give white crystals: mp 223-225° C. [lit.[1] (aq. MeOH) 214-215° C.]; TLC (chloroform/acetone, 9:1) R$_f$ 0.27 cf. R$_f$ 0.69 (E1); IR (KBr) 3385 (NOH), 2920-2860 (aliph CH), 1735 (C=O), 1605-1500 (arom C=C) cm; 5H (DMSO-d$_6$, 400 MHz) 0.89 (3H, s, C-18-H$_3$), 1.30-2.85 (11H, m), 2.70-2.81 (2H, m, C-6-H$_2$), 6.46 (1H, d, J$_{C-2-H,C-4-H}$=2.3 Hz, C-4-H), 6.52 (1H, dd, J$_{C-1-H,C-2-H}$=8.3 Hz and J$_{C-4-H,C-2-H}$=2.3 Hz, C-2-H), 7.05 (1H, d, J$_{C-2-H,C-1-H}$=8.3 Hz, C-1-H), 9.05 (1H, s, exchanged with D$_2$O, OH) and 12.39 (1H, s, exchanged with D$_2$O, NOH); $\delta_C$ (DMSO-d$_6$, 100.4 MHz) 14.09 (q, C-18), 25.09 (t), 25.46 (t), 26.18 (t), 29.02 (t), 30.92 (t), 37.20 (d), 43.20 (d), 44.59 (d), 48.50 (s, C-13), 112.70 (d), 114.83 (d), 125.82 (d), 129.59 (s), 136.88 (s), 154.84 (s, C-3 or C-16), 155.23 (s, C-3 or C-16) and 204.64 (s, C=O); MS m/z (FAB+) 453.2 [30, (M+H+NBA)$^+$], 300.1 [100, (M+H)$^+$]; MS m/z (FAB−) 451.3 [38, (M−H+NBA)$^−$], 298.2 [100, (M−H)$^−$]; Acc MS m/z (FAB+) 300.15963, C$_{18}$H$_{22}$NO$_3$ requires 300.15997. Found: C, 71.30; H, 7.08; N, 4.35. C$_{18}$H$_{21}$NO$_3$.(AcOH)$_{1/6}$ requires: C, 71.17; H, 7.06; N, 4.53.

[1] Huffman, M. N.; Darby, H. H. *J. Am. Chem. Soc.* 1944, 66, 150

16,17-Bis-oximino-estrone (DSF 02110, STX338)

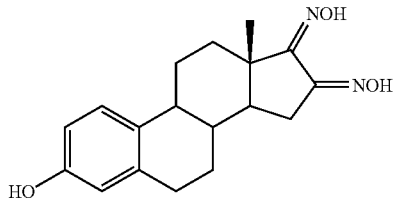

NaOAc (556 mg, 6.79 mmol) followed by hydroxylamine hydrochloride (520 mg, 7.48 mmol) were added to a solution of 16oximino-estrone (200 mg, 0.67 mmol) in a mixture of MeOH/H$_2$O (5:1, 36 mL). The resulting pale yellow solution was stirred at room temperature overnight. The solvent was then removed under reduced pressure and brine added (100 mL). The organics were extracted with EtOAc (100 mL), washed with brine (2×50 mL), dried (Na$_2$SO$_4$), filtered and concentrated under reduced pressure to give the crude product (236 mg). This was recrystallized from acetone to give creamy crystals (109 mg, 52%): mp 245-247° C.; TLC (chloroform/acetone, 8:2) R$_f$ 0.13 cf. R$_f$ 0.50; IR (KBr) 3420-3200 (br, NOH, OH), 3020 (arom CH), 2935-2870 (aliph CH), 1705 (C=N), 1620 (C=N or arom C=C), 1585-1500 (arom C=C) cm$^{-1}$; δ$_H$ (DMSO-d$_6$, 400 MHz) 0.97 (3H, s, C-18-H$_3$), 1.43-2.83 (13H, m), 6.44 (1H, m, C-4-H), 6.51 (1H, dd, J$_{C-1-H,C-2-H}$=8.2 Hz and J$_{C-4-H,C-2-H}$=2.3 Hz, C-2-H), 7.04 (1H, d, J$_{C-2-H,C-1-H}$=8.2 Hz, C-1-H), 9.02 (1H, s, exchanged with D$_2$O, OH), 10.81 (1H, s, exchanged with D$_2$O, NOH) and 11.19 (1H, s, exchanged with D$_2$O, NOH); MS m/z (FAB+) 315.2 [100, (M+H)$^+$], 133.1 [21]; MS m/z (FAB−) 466.2 [66; (M−H−NBA)$^-$], 313.2 [100, (M−H)$^-$], 276.1 [80]; Acc MS m/z (FAB+) 315.17108, C$_{18}$H$_{23}$N$_2$O$_3$ requires 315.17087. HPLC (methanol/water, 70:30, λ$_{max}$=252.1 nm) Rt=2.71 min, 99.2%. Found: C, 67.30; H, 7.41; N, 7.59. C$_{18}$H$_{23}$N$_2$O$_3$.(CH$_3$)$_2$O requires: C, 67.72; H, 7.58; N, 7.52.

17-Oxime-estrone (DSF 03007).

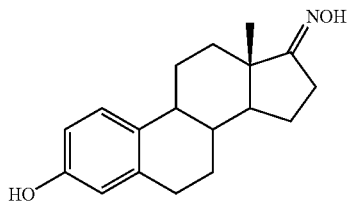

NaOAc (1.5 g, 18.80 mmol) followed by hydroxylamine hydrochloride (1.4 g, 20.72 mmol) were added to a suspension of E1 (500 mg, 1.85 mmol) in a mixture of MeOH/H$_2$O (5:1, 90 mL). The resulting suspension was stirred at room temperature overnight. The solvent was then removed under reduced pressure and H$_2$O added (100 mL). The organics were extracted with EtOAc (100 mL+50 mL), washed with H$_2$O (50 mL), then brine (50 mL), dried (Na$_2$SO$_4$), filtered and concentrated under reduced pressure to give a white crystalline crude product (627 mg). This was recrystallized from MeOH to give white crystals (426 mg, 81%): TLC (chloroform/EtOAc, 4:1) R$_f$ 0.13 cf. R$_f$ 0.55 (E1); IR (KBr) 3415 (NOH), 3270 (OH), 2930 (aliph CH), 1620 (C=N or arom C=C), 1585-1460 (arom C=C) cm$^{-1}$; λ$_H$ (DMSO-d$_6$, 400 MHz) 0.85 (3H, s, C-18-H$_3$), 1.32-2.41 (13H, m), 2.65-2.80 (2H, m, C-6-H$_2$), 6.44 (1H, d, J$_{C-2-H,C-4-H}$=2.6 Hz, C-4-H), 6.50 (1H, dd, J$_{C-1-H,C-2-H}$=8.5 Hz and J$_{C-4-H,C-2-H}$=2.6 Hz, C-2-H), 7.05 (1H, d, J$_{C-2-H,C-1-H}$=8.5 Hz, C-1-H), 9.01 (1H, s, exchanged with D$_2$O, OH) and 10.10 (1H, s, exchanged with D$_2$O, NOH); MS m/z (FAB+) 286.1 [100, (M+H)$^+$], 268.1 [23, (M+H—H$_2$O)$^+$]; Acc MS m/z (FAB+) 286.18093, C$_{18}$H$_{24}$NO$_2$ requires 286.18070.

3-O-Benzyl-Marrianolic Acid (DSF 01042)

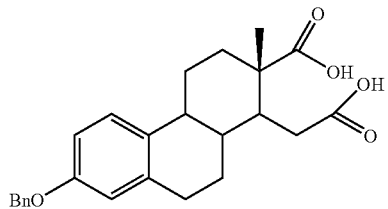

A solution of iodine (7.6 g, 29.9 mmol) in 95 mL of MeOH and a solution of KOH (13.7 g) in 27 mL of H$_2$O and 61 mL of MeOH were added dropwise and alternatively to a stirred solution of 3-O-benzyl-estrone (3.8 g, 10.5 mmol) in MeOH (1 L) so that the colour of the mix remains orange/brown. The addition was carried out over 45 minutes and the resulting light yellow solution was stirred overnight at room temperature under an atmosphere of N$_2$. The resulting clearlight yellow solution was then concentrated under reduced pressure and poured into H$_2$O (800 mL). After acidification with 5M HCl, the organics were extracted with ether (600 mL), washed with aq. Na$_2$S$_2$O$_3$ (4×100 mL), H$_2$O (4×100 mL), dried (MgSO$_4$), filtered and concentrated under reduced pressure. The resulting yellow foam (4.54 g) was then dissolved in a solution of KOH (7.6 g) in MeOH/H$_2$O (1:2, 228 mL) and heated to reflux for 4 hours. The resulting orange solution was poured into H$_2$O (800 mL) and after acidification with 5M HCl the organics were extracted with EtOAc (300 mL). After washing with brine (4×200 mL), the organic layer was dried (MgSO$_4$), filtered and evaporated under reduced pressure to give a yellow residue (4.32 g). This was recrystallized from CHCl$_3$/Hexane 5:3 to give a creamy powder (3.25 g, 75%): mp 212-215° C. [lit.[2] (aq. MeOH) 226-227° C.]; TLC (chloroform/methanol, 5:1) R$_f$ 0.37 cf. R$_f$ 0.88; IR (KBr) 3050-2650 (CO$_2$H), 1700 (C=O), 1600-1500 (arom C=C) cm$^{-1}$; δ$_H$ (DMSO-d$_6$, 400 MHz) 1.02 (3H, s, C-18-H$_3$), 1.20-2.78 (11H, m), 2.72-2.76 (2H, m, C-6-H$_2$), 5.05 (2H, s, OCH$_2$Ar), 6.68 (1H, d, J$_{C-2-H,C-4-H}$=2.5 Hz, C-4-H), 6.75 (1H, dd, J$_{C-1-H,C-2-H}$=8.7 Hz and J$_{C-4-H,C-2-H}$=2.5 Hz, C-2-H), 7.18 (1H, d, J$_{C-2-H,C-1-H}$=8.7 Hz, C-1-H), 7.30-7.42 (5H, m, C$_6$H$_5$) and 12.14 (2H, s, exchanged with D$_2$O, CO$_2$H); □$_C$ (DMSO-d$_6$, 100.4 MHz) 15.37 (q, C-18), 25.84 (t), 26.53 (t), 29.73 (t), 35.77 (t), 36.10 (t), 40.73 (d), 41.84 (d), 42.55 (d), 46.21 (s, C-13), 68.93 (t, OCH$_2$Ar), 112.35 (d), 114.02 (d), 126.32 (d), 127.29 (2×d), 127.49 (d), 128.19 (2×d), 131.64 (s), 137.18 (2×s), 155.96 (s, C-3), 173.93 (s, CO$_2$H) and 178.60 (s, CO$_2$H); MS m/z (FAB+) 408.2 [41, M$^+$], 91.1 [100, (CH$_2$Ar)$^+$]; Acc MS m/z (FAB+) 408.19404, C$_{25}$H$_{28}$O$_5$ requires 408.19367.

[2] Heer, J.; Miescher, K. *Helv. Chim. Acta* 1945, 28, 156.

Marrianolic Acid (DSF 02136, STX417)

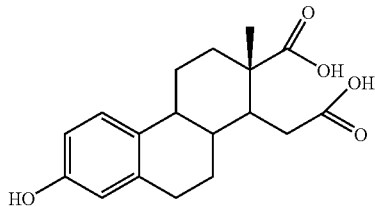

A suspension of Pd—C (10%, 90 mg) in THF (2 mL) was added to a stirred solution of 3-benzyl-O-marrianolic acid (200 mg, 0.61 mmol) in a mixture of MeOH/THF (2:1, 30 mL). The resulting suspension was hydrogenated at room temperature for 2 hours using a hydrogen-filled balloon. After removal of the supported catalyst by filtration and evaporation of the filtrate under reduced pressure, the resulting yellow foam (142 mg) was recrystallized from EtOAc/hexane: mp 211-213° C. [lit.[2] (EtOH), 223-224° C.]; TLC (chloroform/MeOH, 5:1) $R_f$ 0.40 cf. $R_f$ 0.53; IR (KBr) 3600-3350 (br, $CO_2H$), 3080-3005 (arom CH), 2940-2860 (aliph CH), 1715 (C=O), 1695 (C=O), 1610-1450 (arom C=C) cm$^{-1}$; $\delta_H$ (DMSO-d$_6$, 400 MHz) 1.01 (3H, s, C-18-H$_3$), 1.18-2.34 (11H, m), 2.65-2.71 (2H, m, C$_6$—H$_2$), 6.41 (1H, d, $J_{C-2-H,C-4-H}$=2.3 Hz, C-4-H), 6.51 (1H, dd, $J_{C-1-H,C-2-H}$=8.6 Hz and $J_{C-4-H,C-2-H}$=2.3 Hz, C-2-H), 7.06 (1H, d, $J_{C-2-H,C-1-H}$=8.6 Hz, C-1-H), 9.03 (1H, s, exchanged with D$_2$O, OH) and 12.12 (2H, br s, exchanged with D$_2$O, 2×CO$_2$H); MS m/z (FAB+) 318.1 [100, (M+H)$^+$], 301.1 [80, (M−OH)$^+$]; Acc MS m/z (FAB+) 318.14635, C$_{18}$H$_{22}$O$_6$ requires 318.14672.

[2] Heer, J.; Miescher, K. *Helv. Chim. Acta* 1945, 28, 156.

3-tert-Butyl-dimethylsilyl-estrone (DSF 03034)

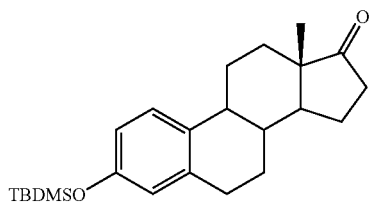

Imidazole (6.3 g, 92.4 mmol) and tert-butyl-dimethylsilyl chloride (7.8 g, 51.8 mmol) were added to a stirred solution of E1 (10 g, 37.0 mmol) in anhydrous DMF (300 mL) at room temperature, under an atmosphere of N$_2$. The resulting solution was stirred overnight to give a white suspension. This was poured into H$_2$O (500 mL) and the organics were extracted with EtOAc (500 mL+300 mL), washed with H$_2$O (2×200 mL), then brine (2×200 mL), dried (Na$_2$SO$_4$), filtered and concentrated under reduced pressure. The crude was recrystallized from EtOH to give white needles (~14 g, 100%): TLC (chloroform/EtOAc, 9:1) $R_f$ 0.91 cf. $R_f$ 0.61 (E1); $\delta_H$ (CDCl$_3$, 400 MHz) 0.19 (6H, s, Si(CH$_3$)$_2$), 0.91 (3H, s, C-18-H$_3$), 0.98 (9H, s, C(CH$_3$)$_3$), 1.37-2.55 (13H, m), 2.81-2.89 (2H, m, C-6-H$_2$), 6.57 (1H, d, $J_{C-2-H,C-4-H}$=2.6 Hz, C-4-H), 6.62 (1H, dd, $J_{C-1-H,C-2-H}$=8.3 Hz and $J_{C-4-H,C-2-H}$=2.6 Hz, C-2-H) and 7.12 (1H, d, $J_{C-2-H,C-1-H}$=8.3 Hz, C-1-H).

3-O-tert-Butyl-dimethylsilyl-16-formyl-estrone (DSF 03066)

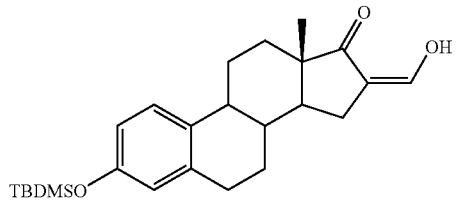

NaOMe (3.8 g, 70.2 mmol) was added portionwise to a stirred solution of 3-tert-butyl-dimethylsilyl-estrone (9 g, 23.4 mmol) in dry toluene (250 mL) at room temperature, under an atmosphere of N$_2$. Ethyl formate (13.2 mL, 164 mmol) was then added and the resulting bright yellow solution stirred overnight. The final thick yellow mixture was poured into H$_2$O (300 mL), acidified with HCl 5M. The organics were extracted with EtOAc (5×500 mL), washed with water (3×200 mL), then brine (2×200 mL), dried (Na$_2$SO$_4$), filtered and concentrated under reduced pressure to give a creamy crude (9.49 g, 98%). For analysis a sample was recrystallized from EtOH to give white crystals: TLC (chloroform/EtOAc, 9:1) $R_f$ 0.61 cf. $R_f$ 0.84; $\delta_H$ (DMSO-d$_6$, 400 MHz) 0.17 (6H, s, Si(CH$_3$)$_2$), 0.83 (3H, s, C-18-H$_3$), 0.96 (9H, s, C(CH$_3$)$_3$), 1.32-2.63 (12H, m), 2.77-2.85 (2H, m, C-6-H$_2$), 6.55 (1H, d, $J_{C-2-H,C-4-H}$=2.6 Hz, C-4-H), 6.61 (1H, dd, $J_{C-1-H,C-2-H}$=8.3 Hz and $J_{C-4-H,C-2-H}$=2.6 Hz, C-2-H), 7.14 (1H, d, $J_{C-2-H,C-1-H}$=8.3 Hz, C-1-H), 7.40 (1H, s, =CH) and 10.69 (1H, s, exchanged with D$_2$O, =COH); MS m/z (FAB+) 413.2 [68, (M+H)$^+$], 355.1 [33, (M−C(CH$_3$)$_3$)$^+$], 72.9 [100]; Acc MS m/z (FAB+) 413.24921, C$_{25}$H$_{37}$O$_3$Si requires 413.25120.

3-Hydroxy-16-formyl-estrone (DSF 03093, STK 486)

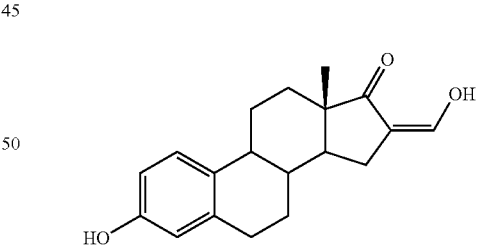

A 1.0 M solution of tetrabutyl ammonium fluoride in dry THF (21.3 mL, 21.3 mmol) was added to a stirred solution of 3-O-tert-butyl-dimethylsilyl-16-hydroxymethylene-estrone (4.4 g, 10.7 mmol) in dry THF (100 mL) at room temperature, under an atmosphere of N$_2$. The mixture was stirred overnight to give a brown solution. After removal of the solvent under reduced pressure, H$_2$O was added (300 mL) and the organics were extracted with EtOAc (2×200 mL), washed with H$_2$O (200 mL), then brine (200 mL), dried (Na$_2$SO$_4$), filtered and concentrated under reduced pressure. The light yellow crude was precipitated from boiling EtOAc, yielding a pale yellow powder (2.21 g, 69%): TLC (chloroform/EtOAc, 8:2) $R_f$ 0.32 cf. $R_f$ 0.68; $\delta_H$ (DMSO-$d_6$, 400 MHz) 0.80 (3H, s, C-18-$H_3$), 1.28-2.61 (11H, m), 2.69-2.78 (2H, m, C-6-$H_2$), 6.44 (1H, d, $J_{C-2-H,C-4-H}$=2.6 Hz, C-4-H), 6.51 (1H, dd, $J_{C-1-H,C-2-H}$=8.5 Hz and $J_{C-4-H,C-2-H}$=2.6 Hz, C-2-H), 7.04 (1H, d; $J_{C-2-H,C-1-H}$=8.5 Hz, C-1-H), 7.38 (1H, s, =CH), 9.02 (1H, s, exchanged with $D_2O$, C-3-OH) and 10.69 (1H, br s, exchanged with $D_2O$, =COH); MS m/z (FAB+) 299.2 [36, (M+H)+], 242.3 [100]; Acc MS m/z (FAB+) 299.16505, $C_{19}H_{23}O_3$ requires 299.16472.

3-Hydroxy-estra-1,3,5(10)-trieno-(17,16-c)--pyrazole (CAB 02156/DSF 03060, STX 509)

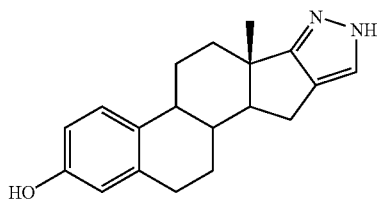

Hydrazine hydrate (48 μL, 1.00 mmol) was added to a solution of 16-hydroxymethylene-estrone (200 mg, 0.67 mmol) in absolute EtOH (10 mL) at room temperature, under an atmosphere of $N_2$. The resulting intense yellow solution was heated to reflux for 30 minutes. The solvent was then removed under reduced pressure, $H_2O$ (50 mL) added and the mixture acidified with HCl 5M. The organics were extracted with EtOAc (100 mL+50 mL), washed with $H_2O$ (2×50 mL), then brine (2×50 mL), dried ($Na_2SO_4$), filtered and concentrated under reduced pressure to give a pale yellow crude (212 mg). This was recrystallized from absolute EtOH to give pale yellow flaky crystals (125 mg, 64%): mp 326-328° C. [lit.[3] 320-328° C.]; TLC (chloroform/EtOAc, 7:3) $R_f$ 0.11 cf. $R_f$ 0.28; $\delta_H$ (DMSO-$d_6$, 400 MHz) 0.90 (3H, s, C-18-$H_3$), 1.32-2.58 (11H, m), 2.69-2.84 (2H, m, C-6-$H_2$), 6.45 (1H, d, $J_{C-2-H,C-4-H}$=2.6 Hz, C-4-H), 6.52 (1H, dd, $J_{C-1-H,C-2-H}$=8.4 Hz and $J_{C-4-H,C-2-H}$=2.6 Hz, C-2-H), 7.06 (1H, d, $J_{C-2-H,C-1-H}$=8.4 Hz, C-1-H), 7.26 (1H, s, C-5'-H), 9.02 (1H, s, exchanged with $D_2O$, C-3-OH) and 12.00 (1H, d, J=3.5 Hz, exchanged with $D_2O$, NH); MS m/z (FAB+) 295.0 [100, (M+H)+]; Acc MS m/z (FAB+) 295.18078, $C_{19}H_{23}N_2O$ requires 295.18104.

[3] Sweet, F; Boyd, J.; Medina, O.; Konderski, L.; Murdock, G. *Biochem. Biophys. Res. Comm.* 1991, 180, 1057-1063

16-Cyano-estradiol (DSF 03019/STX561)

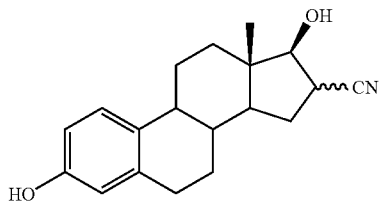

Sodium borohydride (50 mg, 1.32 mmol) was added portionwise to a stirred solution of 16-nitrile-estrone (150 mg, 0.51 mmol) in a mixture of THF/EtOH (3:2, 5 mL) at room temperature. The resulting pale yellow solution was stirred for 30 minutes. The solvent was then removed under reduced pressure, and $H_2O$ added (20 mL). The organics were extracted with EtOAc (20 mL+10 mL), washed with $H_2O$ (20 mL), then brine (20 mL), dried ($Na_2SO_4$), filtered and concentrated under reduced pressure to give a light yellow crude (159 mg). This was recrystallized from IPA/$H_2O$ to give white crystals (16 mg) and a further crop of the product (40 mg) was obtained from the residue of the mother liquor upon recrystallization from absolute EtOH (overall yield 37%): mp 252-254° C.; IR (KBr) 3430-3235 (OH), 2925-2850 (aliph CH), 2255 (CN), 1610-1500 (arom C=C) $cm^{-1}$; $\delta_H$ (DMSO-$d_6$, 400 MHz) 0.79 (3H, s, C-18-$H_3$), 1.10-2.27 (11H, m), 2.66-2.76 (2H, m, C-6-$H_2$), ~3.33 (~1H, m, C-16-H, under solvent peaks), 3.68 (1H, dd, $J_{C-16-H,C-17-H}$=9.4 Hz, $J_{C-17-OH,C-17-H}$=4.7 Hz, C-17-H), 5.50 (1H, d, $J_{C-17-H,C-17-OH}$=4.7 Hz, C-17-OH), 6.43 (1H, d, $J_{C-2-H,C-4-H}$=2.5 Hz, C-4-H), 6.50 (1H, dd, $J_{C-1-H,C-2-H}$=8.5 Hz and $J_{C-4-H,C-2-H}$=2.5 Hz, C-2-H), 7.03 (1H, d, $J_{C-2-H,C-1-H}$=8.5 Hz, C-1-H) and 9.01 (1H, s, exchanged with $D_2O$, C-3-OH); MS m/z (FAB+) 297.1 [100, M+], 242.1 [50]; Acc MS m/z (FAB+) 297.17239, $C_{19}H_{23}NO_2$ requires 297.17288.

16-Isobutylidene-estrone (DSF 03029, STX571)

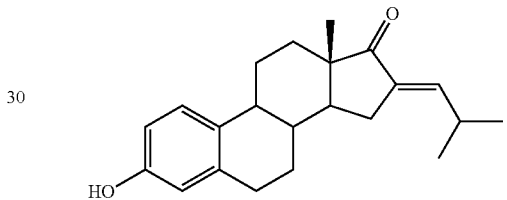

A solution of estrone (420 mg, 1.55 mmol) in dry THF (5 mL) was added dropwise to a stirred solution of LDA (2.47 mL of a 1.8 M solution in heptane/THF/ethyl benzene, 4.44 mmol) in dry THF (2 mL) at −78° C., under an atmosphere of $N_2$. After 2 hours of stirring at −78° C., isobutyraldehyde (185 μL, 2.03 mmol, freshly distilled from $Na_2SO_4$) was added. The resulting mixture was stirred overnight during which it was allowed to warm to room temperature. The solvent was then removed under reduced pressure and $H_2O$ added (50 mL). The organics were extracted with EtOAc (50 mL+20 mL), washed with $H_2O$ (20 mL) then brine (20 mL), dried ($Na_2SO_4$), filtered and concentrated under reduced pressure to give. a crude white foam (602 mg). This was purified by flash chromatography with chloroform/EtOAc (9:1) as eluent and gave the product as a white foam (401 mg, 79%). This was recrystallized from EtOAc/hexane to give white crystals (325 mg, 64%): mp 188-190° C.; TLC (chloroform/EtOAc, 8:2) $R_f$ 0.65 cf. $R_f$ 0.74 (E1); IR (KBr) 3370 (OH), 2930-2890 (aliph CH), 1710 (C=O), 1645-1445 (arom C=C and exocyclic C=C) $cm^{-1}$; $\delta_H$ ($CDCl_3$, 400 MHz) 0.92 (3H, s, C-18-$H_3$), 1.06 (3H, d, $J_{C-2'-H,C-3'-H}$=6.6 Hz, C-3'-$H_3$), 1.04 (3H, d, $J_{C-2'-H,C-4'-H}$=6.6 Hz, C-4'-$H_3$), 1.40-2.70 (12H, m), 2.84-2.90 (2H, m, C-6-$H_2$), 4.67 (1H, s, exchanged with $D_2O$, OH), 6.46 (1H, ddd, $J_{C-2'-H,C-1'-H}$=9.8 Hz, $J_{C-15-H,C-1'-H}$=1.9 Hz, C-1'-H), 6.59 (1H, d, $J_{C-2-H,C-4-H}$=2.7 Hz, C-4-H), 6.64 (1H, dd, $J_{C-1-H,C-2-H}$=8.3 Hz and $J_{C-4-H,C-2-H}$=2.7 Hz, C-2-H) and 7.16 (1H, d, $J_{C-2-H,C-1-H}$=8.3 Hz, C-1-H); $\delta_C$ ($CDCl_3$, 100.4 MHz) 14.99 (q, C-18), 22.34 (2×q), 26.42 (t), 26.44 (t), 27.18 (t), 29.69 (d), 29.94 (t), 31.98 (t), 38.32 (d), 44.38 (d), 48.34 (d), 48.79 (s, C-13), 113.12 (d), 115.54 (d), 126.66 (d), 132.20 (s), 134.73 (s), 138.12 (s), 144.25 (d, C-1'), 153.78 (s, C-3), and 210.04 (s, C=O); MS m/z (FAB+) 325.1 [100, (M+H)⁺]; Acc MS m/z (FAB+) 325.21663, $C_{22}H_{29}O_2$ requires 325.21675. Found: C, 81.30; H, 8.71; N, O. $C_{22}H_{28}O_2$ requires: C, 81.44; H, 8.70; N, 0.

16-Isobutylidene-estradiol (DSF 03046, STX614)

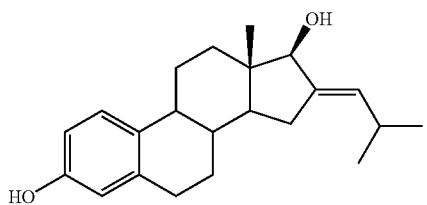

A solution of sodium borohydride (57 mg, 1.51 mmol) in $H_2O$ (3 mL) was added dropwise to a stirred solution of 16-isobutylidene-estrone (100 mg, 0.31 mmol) in a mixture of MeOH/THF (3:1, 9 mL) at 0° C. The resulting solution was stirred at 0° C. for 20 minutes. 5 Drops of AcOH glacial were then added, followed by aq. NaCl (10% solution, 20 mL) and the white precipitate that formed was filtered and dried (102 mg). This was recrystallized from acetone/hexane to give white crystals (60 mg, 60%): TLC (chloroform/EtOAc, 8:2) $R_f$ 0.72 cf. $R_f$ 0.82; IR (KBr) 3435-3325 (OH), 2955-2865 (aliph CH), 1695-1500 (arom C=C and exocyclic C=C) cm⁻¹; $δ_H$ (CDCl₃, 400 MHz) 0.67 (3H, s, C-18-H₃), 0.96 (3H, d, $J_{C-2'-H,C-3'-H}$=6.6 Hz, C-3'-H₃), 0.99 (3H, d, $J_{C-2'-H,C-4'-H}$=6.6 Hz, C-4'-H₃), 1.22-2.02 (14H, m), 2.81-2.87 (2H, m, C-6-H₂), 3.91-3.98 (1H, m, C-17-H), 4.66 (1H, s, exchanged with D₂O, OH), 5.32 (1H, ddd, $J_{C-2'-H,C-1'-H}$=9.4 Hz, $J_{C-15-H,C-1'-H}$=2.3 Hz, C-1'-H), 6.56 (1H, d, $J_{C-2-H,C-4-H}$=2.7 Hz, C-4-H), 6.63 (1H, dd, $J_{C-1-H,C-2-H}$=8.6 Hz and $J_{C-4-H,C-2-H}$=2.7 Hz, C-2-H) and 7.16 (1H, d, $J_{C-2-H,C-1-H}$=8.6 Hz, C-1-H); MS m/z (FAB+) 326.2 [95, M⁺], 309.2 [100, (M−OH)⁺], 283.1 [50, (M−C₃H₇)⁺]; Acc MS m/z (FAB+) 326.22520, $C_{22}H_{30}O_2$ requires 326.22458.

16-(2',2'-Dimethyl)-propylidene-estrone (DSF 03069A/STX748)

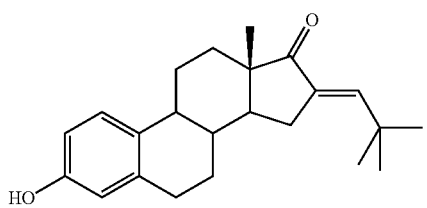

A solution of estrone (500 mg, 1.85 mmol) in dry THF (5 mL) was added dropwise to a stirred solution of LDA (2.47 mL of a 1.8 M solution in heptane/THF/ethyl benzene, 4.44 mmol) in dry THF (2 mL) at −78° C., under an atmosphere of $N_2$. After 2 hours of stirring at −78° C., 2,2-dimethyl-propionaldehyde (261 μL, 2.40 mmol, freshly distilled from Na₂SO₄) was added. The resulting mixture was stirred for 50 hours during which it was allowed to warm to room temperature. The solvent was then removed under reduced pressure and H₂O added (50 mL). The organics were extracted with EtOAc (50 mL+20 mL), washed with H₂O (20 mL), then brine (20 mL), dried (Na₂SO₄), filtered and concentrated under reduced pressure. The light yellow crude was purified by flash chromatography with a gradient of chloroform/EtOAc (9:1 to 8:2) as eluent and gave the product as a white crystalline solid (264 mg, 42%). This was recrystallized from EtOAc to give white crystals (113 mg, 21%): TLC (chloroform/EtOAc; 8:2) $R_f$ 0.71 cf. $R_f$ 0.61 (E1); $δ_H$ (CDCl₃, 400 MHz) 0.90 (3H, s, C-18-H₃), 1.17 (9H, s, C(CH₃)₃), 1.41-2.45 (11H, m), 2.83-2.91 (2H, m, C-6-H₂), 4.72 (1H, s, exchanged with D₂O, OH), 6.59 (1H, d, $J_{C-2-H,C-4-H}$=2.7 Hz, C-4-H), 6.63-6.65 (2H, m, C-2-H and C-1'-H) and 7.16 (1H, d, $J_{C-2-H,C-1-H}$=8.0 Hz, C-1-H); MS m/z (FAB+) 677.5 [54, (2M+H)⁺], 339.2 [100, (M+H)⁺], 492.2 [24, (M+H+NBA)⁺]; Acc MS m/z (FAB+) 339.23256, $C_{23}H_{31}O_2$ requires 339.23241. Found: C, 81.50; H, 8.96; N, O. $C_{23}H_{30}O_2$ requires: C, 81.61; H, 8.93; N, 0.

16-(1'-Hydroxy-propyl)-estrone (DSF 03044B, SIX 665)

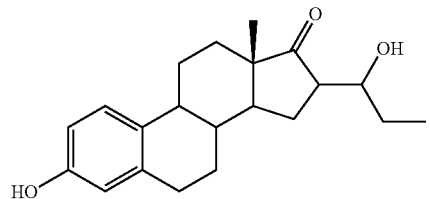

A solution of estrone (500 mg, 1.85 mmol) in dry THF (30 mL) was added dropwise to a stirred solution of LDA (2.47 mL of a 1.8 M solution in heptane/THF/ethyl benzene, 4.44 mmol) in dry THF (20 mL) at −78° C., under an atmosphere of $N_2$. After 2 hours of stirring at −78° C., propionaldehyde (160 μL, 2.40 mmol, dried on CaCl₂ and freshly distilled from Na₂SO₄) was added. The resulting mixture was stirred overnight during which it was allowed to warm to room temperature. The solvent was then removed under reduced pressure and H₂O added (100 mL). The organics were extracted with EtOAc (2×100 mL), washed with H₂O (100 mL), then brine (100 mL), dried (Na₂SO₄), filtered and concentrated under reduced pressure to give a creamy crude oil that crystallizes (971 mg). This was purified by flash chromatography with chloroform/EtOAc (8:2) as eluent and gave the product as a white solid (363 mg, 60%). This was recrystallized from EtOAc to give white crystals (49 mg) and a further crop of the product (170 mg) was obtained from the residue of the mother liquor upon recrystallization from EtOAc/hexane (overall yield 36%): TLC (chloroform/EtOAc, 8:2) $R_f$ 0.38 cf. $R_f$ 0.61 (E1); $δ_H$ (CDCl₃, 400 MHz) 0.94 (3H, s, C-18-H₃), 1.01 (3H, t, $J_{C-2'-H,C-3'-H}$=7.5 Hz, C-3'-H₃), 1.32-2.44 (14H, m), 2.83-2.91 (2H, m, C-6-H₂), 3.65-3.72 (1H, m, C-1'-H), 3.99 (1H, s, OH), 4.69 (1H, s, OH), 6.59 (1H, d, $J_{C-2-H,C-4-H}$=2.7 Hz, C-4-H), 6.65 (1H, dd, $J_{C-1-H,C-2-H}$=8.4 Hz and $J_{C-4-H,C-2-H}$=2.7 Hz, C-2-H) and 7.15 (1H, d, $J_{C-2-H,C-1-H}$=8.4 Hz, C-1-H); MS m/z (FAB+) 329.2 [100, (M+H)⁺], 311.2 [30, (M−OH)⁺]; Acc MS m/z (FAB+) 329.21188, $C_{21}H_{29}O_3$ requires 329.21167.

3-O-Acetyl-16-methylene-estrone (DSF 03023)

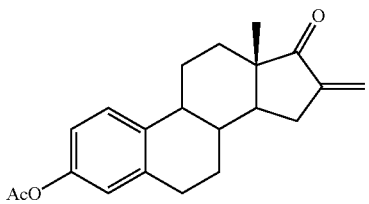

Paraformaldehyde (480 mg, 16.0 mmol for one unit) and dimethylamine hydrochloride (1.6 g, 19.6 mmol) were added to a stirred solution of 3-O-acetyl-estrone in anhydrous isoamyl alcohol (8 mL). The resulting mixture was heated to reflux for 24 hours. The resulting light yellow solution was poured into H$_2$O (30 mL) and acidified with HCl 5M. The organics were extracted with EtOAc (2×50 mL), washed with NaHCO$_3$ sat. (20 mL), H$_2$O (20 mL), then brine (20 mL), dried (Na$_2$SO$_4$), filtered and concentrated under reduced pressure to give a light yellow oil. This was distilled in a kugelrohr until no more isoamyl alcohol was distilled. The oily residue crystallized overnight and was purified by flash chromatography with chloroform/EtOAc (95:5) as eluent to give the product as a white solid (527 mg, 51%). For analysis some crystals were obtained by adding hexane to the distilled oily crude and leaving standing for 1 h: $\delta_H$ (CDCl$_3$, 400 MHz) 0.93 (3H, s, C-18-H$_3$), 1.41-2.72 (11H, m), 2.29 (3H, s, OAc), 2.90-2.95 (2H, m, C-6-H$_2$), 5.41-5.43 (1H, m, C-1'-Htrans), 6.09-6.12 (1H, m, C-1'-Hcis), 6.81 (1H, d, $J_{C-2-H,C-4-H}$=2.5 Hz, C-4-H), 6.86 (1H, dd, $J_{C-1-H,C-2-H}$=8.3 Hz and $J_{C-4-H,C-2-H}$=2.5 Hz, C-2-H) and 7.29 (1H, d, $J_{C-2-H,C-1-H}$=8.3 Hz, C-1-H); MS m/z (FAB+) 325.2 [100, (M+H)$^+$], 282.2 [78, (M+H−CH$_3$CO)$^+$]; Acc MS m/z (FAB+) 325.18224, C$_{21}$H$_{25}$O$_3$ requires 325.18037.

16-Ethoxymethyl-estrone (DSF 030368, STX664)

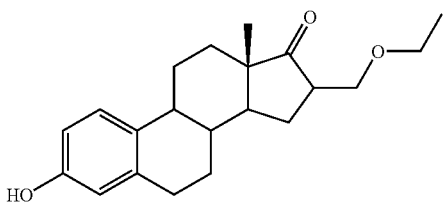

A solution of KOH (41 mg, 0.74 mmol) in H$_2$O (2 mL) was added dropwise to a stirred solution of 16-methylene-estrone (20 mg, 0.62) in absolute EtOH (20 mL) at 0° C. The resulting light yellow solution was stirred for 30 minutes at 0° C. The solvent was then removed under reduced pressure, H$_2$O added (40 mL) followed by a few drops of HCl 5M. The white precipitate that formed was filtered and dried (131 mg). This was purified by flash chromatography with chloroform/EtOAc (95:5) as eluent and gave the product as a light yellow solid (26 mg, 13%). This was recrystallized from EtOH/H$_2$O to give light yellow crystals (13 mg, 6%): mp 208-210° C.; TLC (chloroform/EtOAc, 8:2) R$_f$ 0.40 cf. R$_f$ 0.86; $\delta_H$ (CDCl$_3$, 400 MHz) 0.89 (3H, s, C-18-H$_3$), 1.16 (3H, t, $J_{C-2-H,C-1-H}$=7.0 Hz, C-1-H$_3$), 1.36-2.42 (12H, m), 2.81-2.85 (2H, m, C-6-H2), 3.42-3.50 (2H, m, C-2'-H$_2$), 3.59 (3H, m, C-1'-H$_2$), 4.66 (1H, s, OH), 6.58 (1H, d, $J_{C-2-H,C-4-H}$=2.8 Hz, C-4-H), 6.64 (1H, dd, $J_{C-1-H,C-2-H}$=8.1 Hz and $J_{C-4-H,C-2-H}$=2.8 Hz, C-2-H) and 7.15 (1H, d, $J_{C-2-H,C-1-H}$=8.1 Hz, C-1-H); MS m/z (FAB+) 329.1 [100, (M+H)$^+$]; Acc MS m/z (FAB+) 329.21242, C$_{21}$H$_{29}$O$_3$ requires 329.21167. Found: C, 76.60; H, 8.62; N, O. C$_{21}$H$_{28}$O$_3$ requires: C, 76.79; H, 8.59; N, O.

17-O-Allyl-oxime-estrone (DSF 03048)

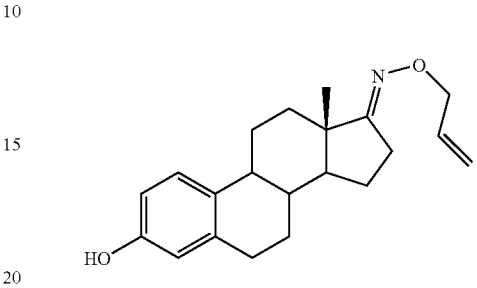

NaOAc (3 g, 10.17 mmol) followed by O-allyl-hydroxylamine hydrochloride (4.5 g, 41.4 mmol) were added to a solution of estrone (1 g, 3.70 mmol) in a mixture of MeOH/H$_2$O (5:1, 180 mL). The resulting solution was stirred at room temperature overnight. The solvent was then removed under reduced pressure and water added (200 mL). The organics were extracted with EtOAc (200 mL+100 mL), washed with water (2×100 mL) then brine (2×100 mL), dried (Na$_2$SO$_4$), filtered and concentrated under reduced pressure to give a white crude (1.37 g). This was recrystallized from MeOH/H$_2$O and gave the product as white crystals (1.13 g, 94%): TLC (chloroform/EtOAc, 8:2) R$_f$ 0.66 cf. R$_f$ 0.56; $\delta_H$ (CDCl$_3$, 400 MHz) 0.94 (3H, s, C-18-H$_3$), 1.35-2.60 (13H, m), 2.80-2.87 (2H, m, C-6-H$_2$), 4.55 (2H, ddd, $J_{AB}$=5.5 Hz, $J_{C-2'-H,C-1'H}$=2.7 Hz and $J_{C-3'-H,C-1'-H}$=1.4 Hz, C-1'-H$_2$), 4.74 (1H, s, exchanged with D$_2$O, OH), 5.19 (1H, ddd, $J_{cis}$=10.3 Hz, $J_{C-1'-H,C-3'-H}$=1.4 Hz, C-3'-Ha), 5.28 (1H, d, $J_{trans}$=17.2 Hz, $J_{C-1'C-3'-H}$=1.6 Hz, C-3'-Hb), 5.59-6.01 (1H, m, C-2'-H), 6.56 (1H, d, $J_{C-2-H,C-4-H}$=2.7 Hz, C-4-H), 6.63 (1H, dd, $J_{C-1-H,C-2-H}$=8.2 Hz and $J_{C-4-H,C-2-H}$=2.7 Hz, C-2-H) and 7.15 (1H, d, $J_{C-2-H,C-4-H}$=8.2 Hz, C-1-H); MS m/z (FAB+) 326.1 [100, (M+H)$^+$], 268.1 [30, OCH$_2$CH=CH$_2^+$]; Acc MS m/z (FAB+) 326.21157, C$_{21}$H$_{28}$NO$_2$ requires 326.21200. Found: C, 76.40; H, 8.24; N, 4.36. C$_{21}$H$_{27}$NO$_2$ requires: C, 76.23; H, 8.50; N, 4.17.

3-Hydroxy-estra-1,3,5(10)-triene-(17,16)-[1]pyrimidine (DSF 03073, STX663)

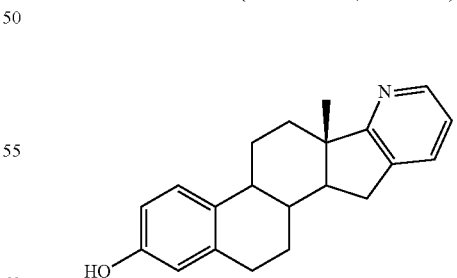

17-O-allyloxime (2.45 g, 7.53 mmol). was stirred and heated to 230° C. (using a sand bath) for 46 hours. The resulting dark brown solid was cooled and EtOH was added until most of the solid was dissolved. The remaining undissolved material was crushed to a fine powder, silica was added and the solvent removed under reduced pressure. The light brown powder was then transferred onto a flash chromatography column (wet packed) and the column eluted with chloroform/EtOAc (9:1). A dark orange solid was recovered (200 mg, 9%) which was purified by performing another flash chromatography with chloroform/EtOAc (95:5) as eluent and gave a light orange powder (146 mg, 6%): TLC (chloroform/EtOAc, 8:2) $R_f$ 0.26 cf. $R_f$ 0.70; $\delta_H$ (CDCl$_3$, 400 MHz) 1.01 (3H, s, C-18-H$_3$), 1.43-2.68 (11H, m), 2.80-2.96 (2H, m, C-6-H$_2$), 6.08 (1H, s, OH), 6.61 (1H, d, $J_{C-2-H,C-4-H}$=2.6 Hz, C-4-H), 6.67 (1H, dd, $J_{C-1-H,C-2-H}$=8.4 Hz and $J_{C-4-H,C-2-H}$=2.5 Hz, C-2-H), 7.04 (1H, dd, $J_{C-4'-H,C-5'-H}$=7.4 Hz and $J_{C-6'-H,C-5'-H}$=4.8 Hz, C-5'-H), 7.18 (1H, d, $J_{C-2-H,C-1-H}$=8.4 Hz, C-1-H), 7.54 (1H, d, $J_{C-5'-H,C-4'-H}$=7.4 Hz, C-4'-H) and 8.33 (1H, d, $J_{C-5'-H,C-6'-H}$=4.8 Hz, C-2'-H); MS m/z (FAB+) 306.1 [85, (M+H)$^+$], 207.0 [95], 114.9 [100]; Acc MS m/z (FAB+) 306.18645, C$_{21}$H$_{24}$NO requires 306.18579.

3-O-Acetyl-16-acetoxymethylene-estrone (DSF 03054)

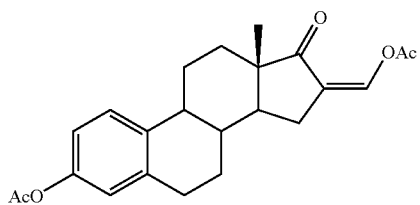

Acetic anhydride (8.34 mL, 88.4 mmol) was added dropwise over 10 minutes to a stirred solution of 16-formyl-estrone (230 mg, 0.77 mmol) in dry pyridine (15 mL) at 0° C., under an atmosphere of N$_2$. The resulting yellow mixture was then heated to reflux for 1 hour. The final brown solution was cooled, then poured into H$_2$O (50 mL) and ice and acidified with HCl 5M. The organics were extracted with EtOAc (2×50 mL), washed with H$_2$O (30 mL), Na$_2$CO$_3$ 10% (30 mL), then brine (30 mL), dried (Na$_2$SO$_4$), filtered and concentrated under reduced pressure to give an orange foam (250 mg). This was purified by flash chromatography with chloroform/EtOAc (95:5) as eluent and gave the product as a pale yellow oil that crystalizes (140 mg, 47%): TLC (chloroform/EtOAc, 9:1) $R_f$ 0.70 cf. $R_f$ 0.30; $\delta_H$ (CDCl$_3$, 400 MHz) 0.93 (3H, s, C-18-H$_3$), 1.42-2.84 (11H, m), 2.24 (3H, s, OAc), 2.29 (3H, s, OAc), 2.89-2.96 (2H, m, C-6-H$_2$), 6.81 (1H, d, $J_{C-2-H,C-4-H}$=2.6 Hz, C-4-H), 6.86 (1H, dd, $J_{C-1-H,C-2-H}$=8.3 Hz and $J_{C-4-H,C-2-H}$=2.6 Hz, C-2-H), 7.29 (1H, d, $J_{C-2-H,C-1-H}$=8.3 Hz, C-1-H) and 8.15 (1H, dd, $J_{C-15-Ha,C-1'-H}$=2.9 Hz, $J_{C-15-H,C-1'-H}$=1.7 Hz, =CH); MS m/z (FAB+) 383.0 [100, (M+H)$^+$], 341.0 [86, (M+H–CH$_2$C=O)$^+$]; Acc MS m/z (FAB+) 383.18523, C$_{23}$H$_{27}$O$_5$ requires 383.18585.

6-Oxo-3-O-acetyl-16-acetoxymethylene-estrone (DSF 03062)

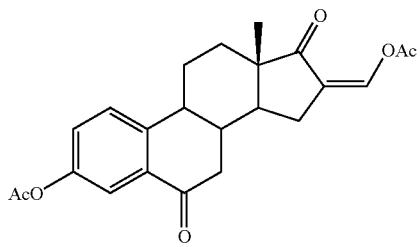

A solution of CrO$_3$ (132 mg, 1.32 mmol) in acetic acid 10% (750 µL) was added dropwise over 30 minutes to a stirred solution of 3-O-acetyl-16-acetoxymethylene-estrone (120 mg, 0.31 mmol) in acetic acid at 10-15° C. in an ice/water bath. The resulting dark brown solution was stirred for 40 hours at room temperature. The solvent was then removed under reduced pressure and H$_2$O (50 mL) and ice added. The organics were extracted with EtOAc (2×50 mL), washed with H$_2$O (2×30 mL), then brine. (2×30 mL), dried (Na$_2$SO$_4$), filtered and concentrated under reduced pressure to give a brown crude. This was purified by flash chromatography with chloroform/EtOAc (8:2) as eluent an gave the product as a light yellow solid (13 mg, 10%): TLC (chloroform/EtOAc, 4:1) $R_f$ 0.40 cf. $R_f$ 0.63; $\delta_H$ (CDCl$_3$, 400 MHz) 0.95 (3H, s, C-18-H$_3$), 1.24-2.92 (11H, m), 2.26 (3H, s, OAc), 2.32 (3H, s, OAc), 7.29 (1H, dd, $J_{C-1-H,C-2-H}$=8.4 Hz and $J_{C-4-H,C-2-H}$=2.6 Hz, C-2-H), 7.46 (1H, d, $J_{C-2-H,C-1-H}$=8.4 Hz, C-1-H), 7.77 (1H, d, $J_{C-2-H,C-4-H}$=2.6 Hz, C-4-H) and 8.17 (1H, dd, $J_{C-15-Ha,C-1'-H}$=2.9 Hz, $J_{C-15-Hb,C-1'-H}$=1.7 Hz, =CH); MS m/z (FAB+) 663.5 [48], 397.2 [38, (M+H)$^+$], 355.2 [30], 73.0 [100]; Acc MS m/z (FAB+) 397.16700, C$_{23}$H$_{25}$O$_6$ requires 397.16511.

6-Oxo-16-ethoxymethylene-estrone (DSF 03083A, STX749)

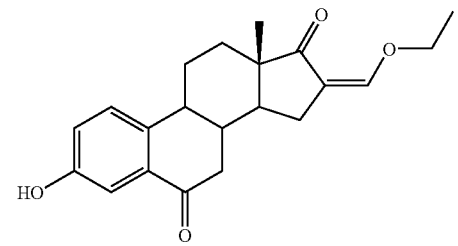

A solution of KOH (27 mg, 0.48 mmol) in H$_2$O (0.8 mL) was added dropwise to a stirred solution of 6-oxo-3-O-acetyl-16-acetoxymethylene-estrone (80 mg, 0.20 mmol) in absolute EtOH at 0° C. The resulting bright yellow mixture was stirred at 0° C. for 30 minutes. The mixture was then acidified with 3 drops of 5M HCl and the solvent removed under reduced pressure. H$_2$O was added (50 mL) and the organics were extracted with EtOAc (2×50 mL), washed with H$_2$O (2×30 mL), then brine (2×30 mL), dried (Na$_2$SO$_4$), filtered and concentrated under reduced pressure to give a pale yellow crude (52 mg). This was purified by flash chromatography with DCM/EtOAc (75:25) as eluent and gave the product as a white solid (12 mg, 18%): mp 314-316° C. (dec.); TLC (chloroform/EtOAc, 8:2) $R_f$ 0.11 cf. $R_f$ 0.82; $\delta_H$ (CDCl$_3$, 270 MHz) 0.94 (3H, s, C-18-H$_3$), 1.10-2.72 (10H, m), 1.35 (3H, t, $J_{C-2'-H,C-3'-H}$=7.0 Hz, C-3'-H$_3$), 2.85 (1H, dd, $J_{C-8-H,C-7-HB}$=3.1 Hz, $J_{AB}$=16.7 Hz, C-7-HB), 4.05-4.13 (2H, m, C-2'-H$_2$), 7.09 (1H, dd, $J_{C-1-H,C-2-H}$=8.6 Hz and $J_{C-4-H,C-2-H}$=2.7 Hz, C-2-H), 7.31 (1H, s, C-1'-H), 7.34 (1H, m, C-1-H) and 7.57 (1H, d, $J_{C-2-H,C-4-H}$=8.4 Hz, C-4-H); MS m/z (FAB+) 341.2 [100, (M+H)$^+$]; Acc MS m/z (FAB+) 341.17466, C$_{21}$H$_{25}$O$_4$ requires 341.17528.

6-Oxo-16-formyl-estrone (DSF 03105, STX784)

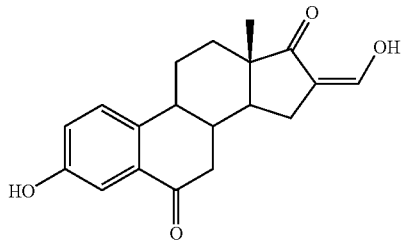

A solution of K$_2$CO$_3$ (63 mg, 0.46 mmol) in H$_2$O (1 mL) was added dropwise to a stirred solution of 6-oxo-3-O-acetyl-16-acetoxymethylene-estrone (30 mg, 0.08 mmol) in MeOH (10 mL). The resulting pale yellow solution was stirred for 45 minutes. The final pale brown mixture was then acidified with 3 drops of HCl 5M and the solvent removed under reduced pressure. H$_2$O was added (30 mL) and the organics were extracted with EtOAc (2×50 mL), washed with H$_2$O (2×30 mL), then brine (2×30 mL), dried (Na$_2$SO$_4$), filtered and concentrated under reduced pressure. The beige crude was recystallized from EtOAc/hexane to give a white powder (13 mg, 54%): mp 224-227° C.; $\delta_H$ (DMSO-d$_6$, 400 MHz) 0.80 (3H, s, C-18-H$_3$), 1.41-2.65 (11H, m), 7.01 (1H, dd, $J_{C\text{-}1\text{-}H,C\text{-}2\text{-}H}$=8.4 Hz and $J_{C\text{-}4\text{-}H,C\text{-}2\text{-}H}$=2.7 Hz, C-2-H), 7.28 (1H, d, $J_{C\text{-}2\text{-}H,C\text{-}4\text{-}H}$2.7 Hz, C-4-H), 7.31 (1H, d, $J_{C\text{-}2\text{-}H,C\text{-}1\text{-}H}$=8.4 Hz, C-1-H), 7.41 (1H, s, C-1'-H), 9.64 (1H, s, exchanged with D$_2$O, C-3-OH) and 10.77 (1H, br s, exchanged with D$_2$O, C-1'-OH); MS m/z (FAB+) 313.2 [6, (M+H)$^+$], 149.1 [100]; MS m/z (FAB−) 311.2 [100, (M−H)$^-$]; Acc MS m/z (FAB+) 313.14503, C$_{19}$H$_{21}$O$_4$ requires 313.14398.

3-O-Benzyl-16-formyl-estrone (DSF 03091)

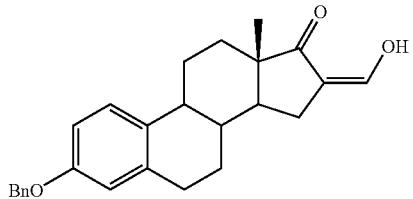

Potassium tert-butoxide (9.4 g, 84.1 mmol) was added portionwise to a stirred solution of 3-O-benzyl-estrone (10 g, 27.7 mmol) in dry toluene (250 mL) at room temperature, under an atmosphere of N$_2$. After stirring for 20 minutes, ethyl formate (14.8 mL, 194 mmol) was added and the resulting suspension stirred for 2.5 hours. The final thick creamy suspension was poured into H$_2$O (300 mL) and ice, and the organics extracted with EtOAc (2×200 mL), washed with H$_2$O (3×100 mL), then brine (2×100 mL), dried (Na$_2$SO$_4$), filtered and concentrated under reduced pressure. The crude was precipitated from boiling EtOAc to give a creamy solid (9.25 g, 86%): TLC (hexane/EtOAc, 1:1) R$_f$ 0.57 cf. R$_f$ 0.78; $\delta_H$ (DMSO-d$_6$, 400 MHz) 0.81 (3H; S, C-18-H$_3$), 1.31-2.62 (11H, m), 2.79-2.85 (2H, m, C-6-H$_2$), 5.05 (2H, s, OCH$_2$Ar), 6.71 (1H, d, $J_{C\text{-}2\text{-}H,C\text{-}4\text{-}H}$=2.7 Hz, C-4-H), 6.75 (1H, dd, $J_{C\text{-}1\text{-}H,C\text{-}2\text{-}H}$=8.4 Hz and $J_{C\text{-}4\text{-}H,C\text{-}2\text{-}H}$=2.7 Hz, C-2-H), 7.16 (1H, d, $J_{C\text{-}2\text{-}H,C\text{-}1\text{-}H}$=8.4 Hz, C-1-H), 7.28-7.33 (1H, m, =CH), 7.35-7.43 (5H, m, C$_6$H$_5$) and 10.6-10.9 (1H, br s, exchanged with D$_2$O, =COH); MS m/z (FAB+) 389.3 [31, (M+H)$^+$], 91.1 [100, (CH$_2$Ar)$^+$]; Acc MS m/z (FAB+) 389.20994, C$_{26}$H$_{29}$O$_3$ requires 389.21167.

3-O-Benzyl-estra-1,3,5(10)-trieno-(17,16-c)-pyrazole (DSF 03095)

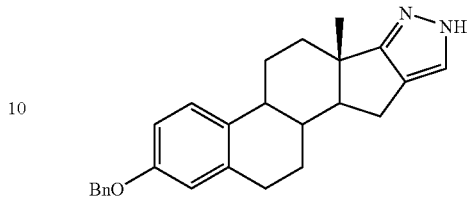

Hydrazine hydrate (751 μL, 15.4 mmol) was added to a suspension of 3-O-benzyl-16-formyl-estrone (4 g, 10.3 mmol) in absolute EtOH (200 mL) at room temperature, under an atmosphere of N$_2$. The resulting yellow solution was heated to reflux for 45 minutes. After acidification with HCl 5M, the solvent was removed under reduced pressure until precipitation of the product. H$_2$O was then added (20 mL) and the creamy precipitate filtered and dried (3.73 g, 94%): TLC (hexane/EtOAc, 1:1) R$_f$ 0.20 cf. R$_f$ 0.66; $\delta_H$ (DMSO-d$_6$, 400 MHz) 0.91 (3H, s, C-18-H$_3$), 1.36-2.58 (11H, m), 2.78-2.87 (2H, m, C-6-H$_2$), 5.05 (2H, s, OCH$_2$Ar), 6.72 (1H, d, $J_{C\text{-}2\text{-}H,C\text{-}4\text{-}H}$=2.7 Hz, C-4-H), 6.76 (1H, dd, $J_{C\text{-}1\text{-}H,C\text{-}2\text{-}H}$=8.6 Hz and $J_{C\text{-}4\text{-}H,C\text{-}2\text{-}H}$=2.7 Hz, C-2-H), 7.18 (1H, d, $J_{C\text{-}2\text{-}H,C\text{-}1\text{-}H}$=8.6 Hz, C-1-H), 7.27 (1H, s, C-5'-H), 7.29-7.44 (5H, m, C$_6$H$_5$) and 12.00 (1H, s, exchanged with D$_2$O, NH); MS m/z (FAB+) 385.3 [75, (M+H)$^+$], 91.1 [100, (CH$_2$Ar)$^+$]; Acc MS m/z (FAB+) 385.22796, C$_{26}$H$_{29}$N$_2$O requires 385.22799.

General Procedure for Alkylation of D-Ring Fused Pyrazoles.

NaH (60% dispersion, 1.5 eq.) was added to a stirred solution of 3-O-benzyl-estra-1,3,5(10)-trieno-(17,16-c)--pyrazole in DMF at 0° C., under an atmosphere of N$_2$. After stirring for 20 minutes at 0° C., the alkylating agent was added (2 eq.) and the mixture was stirred at room temperature until completion of the reaction (followed by TLC). The mixture was then poured into H$_2$O (50 mL) and the organics extracted with EtOAc (2×50 mL), washed with H$_2$O (2×30 mL), then brine (2×30 mL), dried (Na$_2$SO$_4$), filtered and concentrated under reduced pressure. The crude product was purified by flash chromatography using DCM/EtOAc as eluent.

3-O-Benzyl-estra-1,3,5(10)-trieno-(17,16)-N-methyl-pyrazole

Following the general procedure, 3-O-benzyl-estra-1,3,5 (10)-trieno-(17,16-c)--pyrazole (150 mg, 0.39 mmol) was treated with NaH (19 mg, 0.47 mmol) and the subsequent reaction with methyl iodide (57 μL, 0.78 mmol) was complete within 50 minutes. Purification of the crude by flash chromatography with a gradient of DCM/EtOAC (98:2 to 95:5) as eluent gave: 1'-Methyl-3-O-Benzyl-estra-1,3,5(10)-trieno-(17,16-c)-pyrazole, DSF 03098A, as a light yellow oil that crystallized on standing (52 mg, 33%): TLC (hexane/EtOAc, 1:1) R$_f$ 0.52 cf. R$_f$ 0.38; $\delta_H$ (CDCl$_3$, 400 MHz) 1.01 (3H, s, C-18-H$_3$), 1.42-2.67 (11H, m), 2.81-2.99 (2H, m, C-6-H$_2$), 3.84 (3H, s, N—Me), 5.03 (2H, s, OCH$_2$Ar), 6.73 (1H, d, $J_{C\text{-}2\text{-}H,C\text{-}4\text{-}H}$=2.5 Hz, C-4-H), 6.79 (1H, dd, $J_{C\text{-}1\text{-}H,C\text{-}2\text{-}H}$=8.5 Hz and $J_{C\text{-}4\text{-}H,C\text{-}2\text{-}H}$=2.5 Hz, C-2-H), 6.97 (1H, s, C-5'-H), 7.22 (1H, d, $J_{C\text{-}2\text{-}H,C\text{-}1\text{-}H}$=8.5 Hz, C-1-H) and 7.29-7.45 (5H, m, C$_6$H$_5$); MS m/z (FAB+) 399.3 [74, (M+H)$^+$], 91.1 [100, (CH$_2$Ar)$^+$], 73.0 [24]; Acc MS m/z (FAB+) 399.24467, C$_{27}$H$_{31}$N$_2$O requires 399.24364.

2'-Methyl-3-O-Benzyl-estra-1,3,5(10)-trieno-(17,16-c)-pyrazole, DSF 03098B, was obtained as a creamy solid (55 mg, 35%): TLC (hexane/EtOAc, 1:1) $R_f$ 0.46. cf. $R_f$ 0.38; $\delta_H$ (CDCl$_3$, 400 MHz) 1.01 (3H, s, C-18-H$_3$), 1.44-2.64 (11H, m), 2.85-2.98 (2H, m, C-6-H$_2$), 3.82 (3H, S, N—Me), 5.04 (2H, S, OCH$_2$Ar), 6.74 (1H, d, $J_{C-2-H,C-4-H}$=2.8 Hz, C+H), 6.80 (1H, dd, $J_{C-1-H,C-2-H}$=8.6 Hz and $J_{C-4-H,C-2-H}$=2.8 Hz, C-2-H), 7.15 (1H, s, C-3'-H), 7.20 (1H, d, $J_{C-2-H,C-1-H}$=8.6 Hz, C-1-H) and 7.30-7.45 (5H, m, C$_6$H$_5$); MS m/z (FAB+) 399.3 [55, (M+H)$^+$], 91.1 [100, (CH$_2$Ar)$^+$]; Acc MS m/z (FAB+) 399.24341, C$_{27}$H$_{31}$N$_2$O requires 399.24364.

1'-Isobutyl-3-O-Benzyl-estra-1,3,5(10)-trieno-(17,16-c)-pyrazole and 2'-Isobutyl-3-O-Benzyl-estra-1,3,5(10)-trieno-(17,16-c)-pyrazole Following the general procedure, 3-O-benzyl-estra-1,3,5(10)-trieno-(17,16-c)--pyrazole (250 mg, 0.65 mmol) was treated with NaH (31 mg, 0.78 mmol) and the subsequent reaction with 1-bromo-2-methyl-propane (124 μL, 1.30 mmol) was complete within 2 hours. Purification of the crude by flash chromatography with DCM/EtOAC (95:5) as eluent gave: 1'-Isobutyl-3-O-Benzyl-estra-1,3,5(10)-trieno-(17,16-c)-pyrazole, DSF 03111A, as a pale yellow oil (121 mg, 42%): TLC (DCM/EtOAc, 9:1) $R_f$ 0.93 cf. $R_f$ 0.26; $\delta_H$ (CDCl$_3$, 400 MHz) 0.87-0.92 (6H, 2×d, $J_{C-2''-H,C-3''-H}$=6.6 Hz and $J_{C-2''-H,C-4''-H}$=6.6 Hz, C-3''-H$_3$, C-4''-H$_3$), 1.01 (3H, s, C-18-H$_3$), 1.42-2.98 (14H, m), 3.81 (1H, dd, $J_{BA}$=13.8 Hz and $J_{C-2''-H,C-1''-H}$=7.5 Hz, N—CH$_A$H$_B$), 3.86 (1H, dd, $J_{AB}$=13.8 Hz and $J_{C-2''-H,C-1''-H}$=7.5 Hz, N—CH$_A$H$_B$), 5.04 (2H, s, OCH$_2$Ar), 6.71-6.75 (1H, m, C-4-H), 6.79 (1H, dd, $J_{C-1-H,C-2-H}$=8.6 Hz and $J_{C-4-H,C-2-H}$=2.7 Hz, C-2-H), 6.94-6.99 (1H, m, C-5'-H), 7.22 (2H, d, $J_{C-2-H,C-1-H}$=8.6 Hz, C-1-H) and 7.31-7.46 (5H, m, C$_6$H$_5$).

2'-Isobutyl-3-O-Benzyl-estra-1,3,5(10)-trieno-(17,16-c)-pyrazole, DSF 039111B, was obtained as a white crystalline solid (56 mg, 19%): mp 126-128° C.; TLC (DCM/EtOAc, 9:1) $R_f$ 0.64 cf. $R_f$ 0.26; $\delta_H$ (CDCl$_3$, 400 MHz) 0.92 (3H, d, $J_{C-2''-H,C-3''-H}$=6.6 Hz, C-3''-H$_3$), 0.95 (3H, d, $J_{C-2''-H,C-4''-H}$=6.6 Hz, C-4''-H$_3$), 1.02 (3H, s, C-18-H$_3$), 1.46-2.60 (12H, m), 2.89-2.94 (2H, m, C-6-H$_2$), 3.74 (1H, dd, $J_{BA}$=13.3 Hz and $J_{C-2''-H,C-1''-H}$=7.8 Hz, N—CH$_A$H$_B$), 3.85 (1H, dd, $J_{AB}$=13.3 Hz and $J_{C-2''-H,C-1''-H}$=7.4 Hz, N—CH$_A$H$_B$), 5.04 (2H, s, OCH$_2$Ar), 6.74 (1H; d, $J_{C-2-H,C-4-H}$=2.6 Hz, C-4-H), 6.79 (1H, dd, $J_{C-1-H,C-2-H}$=8.6 Hz and $J_{C-1-H,C-2-H}$=2.6 Hz, C-2-H), 7.17-7.21 (2H, m, C-1-H and C-3'-H) and 7.31-7.45 (5H, m, C$_6$H$_5$).

1'-Methylacetate-3-O-Benzyl-estra-1,3,5(10)-trieno-(17,16-c)-pyrazole and 2'-Methylacetate-3-O-Benzyl-estra-1,3,5 (10)-trieno-(17,16-c)-pyrazole Following the general procedure, 3-O-benzyl-estra-1,3,5(10trieno-17,16-c)--pyrazole (300 mg, 0.78 mmol) was treated with NaH (47 mg, 1.17 mmol) and the subsequent reaction with methyl-chloro-acetate (136 μL, 1.56 mmol) was complete within 2.5 hours. Purification of the crude by flash chromatography with a slow gradient of DCM to DCM/EtOAC (8:2) as eluent gave: 1'-Methylacetate-3-O-Benzyl-estra-1,3,5(10)-trieno-(17,16-c)-pyrazole, DSF 03117-2A as a white crystalline solid (173 mg, 48%): TLC (DCM/EtOAc, 9:1) $R_f$ 0.53 cf. $R_f$ 0.09; $\delta_H$ (CDCl$_3$, 400 MHz) 1.03 (3H, s, C-18-H$_3$), 1.44-2.69 (11H, m), 2.85-2.99 (2H, m, C-6-H$_2$), 3.76 (3H, s, OMe), 4.86 (2H, s, N—CH$_2$), 5.04 (2H, s, OCH$_2$Ar), 6.74 (1H, d, $J_{C-2-H,C-4-H}$=2.6 Hz, C-4-H), 6.79 (1H, dd, $J_{C-1-H,C-2-H}$=8.6 Hz and $J_{C-4-H,C-2-H}$=2.6 Hz, C-2-H), 7.07 (1H, s, C-5'-H), 7.22 (1H, d, $J_{C-2-H,C-1-H}$=8.6 Hz, C-1-H) and 7.29-7.44 (5H, m, C$_6$H$_5$); MS m/z (FAB+) 457.3 [55, (M+H)$^+$], 91.1 [100, (CH$_2$Ar)$^+$], 73.0 [72]; Acc MS m/z (FAB+) 457.24954, C$_{29}$H$_{33}$N$_2$O$_3$ requires 457.24912.

2'-Methylacetate-3-O-Benzyl-estra-1,3,5(10)-trieno-(17,16-c)-pyrazole, DSF 03117-2B, was also obtained as a pale yellow oil (70 mg, 20%): TLC (DCM/EtOAc, 9:1) $R_f$ 0.28 cf. $R_f$ 0.09; □$\delta_H$ (CDCl$_3$, 400 MHz) 1.02 (3H, s, C-18-H$_3$), 1.42-2.64 (11H, m), 2.86-2.98 (2H, m, C-6-H$_2$), 3.78 (3H, s, OMe), 4.69-4.88 (2H, m, N—CH$_2$), 5.03 (2H, s, OCH$_2$Ar), 6.74 (1H, d, $J_{C-2-H,C-4-H}$=2.6 Hz, C-4-H), 6.78 (1H, dd, $J_{C-1-H,C-2-H}$=8.6 Hz and $J_{C-4-H,C-2-H}$=2.6 Hz, C-2-H), 7.18 (1H, d, $J_{C-2-H,C-1-H}$=8.6 Hz, C-1-H), 7.25 (1H, s, C-3'-H), and 7.31-7.44 (5H, m, C$_6$H$_5$); MS m/z (FAB+) 457.3-[64, (M+H)$^+$], 91.1 [100, (CH$_2$Ar)$^+$], 73.0 [27]; Acc MS m/z (FAB+) 457.25071, C$_{29}$H$_{33}$N$_2$O$_3$ requires 457.24912.

1'-(2-Methoxyethyl)-3-O-Benzyl-estra-1,3,5(10)-trieno(17,16-c)-pyrazole, DSF 03117-3A and 2'-(2-Methoxyethyl)-3-O-Benzyl-estra-1,3,5(10)-trieno-(17,16-c)-pyrazole, DSF 03117-3B Following the general procedure, 3-O-benzyl-estra-1,3,5(10)trieno-(17,16-c)-pyrazole (300 mg, 0.78 mmol) was treated with NaH (47 mg, 1.17 mmol) and the subsequent reaction with 1-chloro-2-methoxy-ethane (142 μL, 1.56 mmol) was complete within 4 hours. Purification of the crude by flash chromatography with DCM/EtOAC (9:1) as eluent gave: 1'-(2-Methoxyethyl)-3-O-Benzyl-estra-1,3,5(10)-trieno-(17,16-c)-pyrazole, DSF 03117-3A as a creamy solid (92 mg, 27%): TLC (DCM/EtOAc, 9:1) $R_f$ 0.38 cf. $R_t$ 0.12; $\delta_H$ (CDCl$_3$, 400 MHz) 1.01 (3H, s, C-18-H$_3$), 1.46-2.66 (11H, m), 2.84-2.99 (2H, m, C-6-H$_2$), 3.33 (~3H, s, OMe), 3.72 (2H, dt, J=5.3 Hz, J 1.3 Hz, C-1-''-H$_2$ or C-2''-H$_2$), 4.23 (2H, t, J=5.2 Hz, C-1''-H$_2$ or C-2''-H$_2$), 5.04 (2H, s, OCH$_2$Ar), 6.74 (1H, d, $J_{C-2-H,C-4-H}$=2.8 Hz, C-4-H), 6.80 (1H, dd, $J_{C-1-H,C-2-H}$=8.3 Hz and $J_{C-4-H,C-2-H}$=2.8 Hz, C-2-H), 7.09 (1H, s, C-5'-H), 7.23 (1H, d, $J_{C-2-H,C-1-H}$=8.3 Hz, C-1-H) and 7.31-7.45 (5H, m, C$_6$H$_5$); MS m/z (FAB+) 443.3 [100, (M+H)$^+$], 91.1 [80, (CH$_2$Ar)$^+$]; Acc MS m/z (FAB+) 443.27119, C$_{29}$H$_{35}$N$_2$O$_2$ requires 443.26985.

2'-(2-Methoxyethyl)-3-O-Benzyl-estra-1,3,5(10)-trieno-(17,16-c)-pyrazole DSF 03117-3B, was obtained as a creamy solid (80 mg, 23%): TLC (DCM/EtOAc, 9:1) $R_f$ 0.29 cf. $R_f$ 0.12; $\delta_H$ (CDCl$_3$, 400 MHz) 1.04 (3H, s, C-18-H$_3$), 1.42-2.66 (11H, m), 2.84-2.99 (2H, m, C-6-H$_2$), 3.32 (~3H, s, OMe), 3.78 (2H, m, C-1''-H$_2$ or C-2''-H$_2$), 4.19 (2H, dt, J=5.7 Hz, J=2.9 Hz, C-1''-H$_2$ or C-2''-H$_2$), 5.04 (2H, s, OCH$_2$Ar), 6.74 (1H, d, $J_{C-2-H,C-4-H}$=2.7 Hz, C-4-H), 6.79 (1H, dd, $J_{C-1-H,C-2-H}$=8.6 Hz and $J_{C-4-H,C-2-H}$=2.7 Hz, C-2-H), 7.19-7.21 (2H, m, C-1-H and C-3'-H) and 7.30-7.44 (5H, m, C$_6$H$_5$); MS m/z (FAB+) 443.3 [100, (M+H)$^+$], 91.1 [95, (CH$_2$Ar)$^+$], 73.1 [44]; Acc MS m/z (FAB+) 443.26964, C$_{29}$H$_{35}$N$_2$O$_2$ requires 443.26985.

General Procedure for Hydrogenation of Benzylated Derivatives.

A suspension of Pd—C (10%) in THF (2 mL) was added to a stirred solution of the benzylated precursor in MeOH/THF (2:1, 30 mL) and the resulting suspension hydrogenated at room temperature using a hydrogen-filled balloon. After removal of the supported catalyst by filtration and evaporation of the filtrate in vacuo, the product obtained was purified by recrystallization to give the parent compound.

1'-Methyl-3-Hydroxy-estra-1,3,5(10)-trieno(17,16-c)-pyrazole (DSF 03100, STX 785)

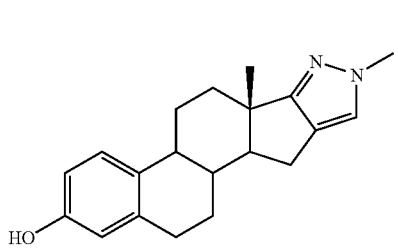

Following the hydrogenation conditions, a suspension of 3-O-benzyl-estra-1,3,5(10)-trieno-(17,16-c)--N-methyl-pyrazole (50 mg, 0.12 mmol) and Pd—C (20 mg) was hydrogenated overnight to give the product as a pale yellow solid (31 mg). This was recrystallized from EtOH/H$_2$O to give creamy crystals (26 mg, 68%): TLC (chloroform/EtOAc, 9:1) R$_f$ 0.16 cf. R$_f$ 0.50; δ$_H$ (DMSO-d$_6$, 400 MHz) 0.89 (3H, s, C-18-H$_3$), 1.32-2.57 (11H, m), 2.69-2.83 (2H, m, C-6-H$_2$), 3.73 (3H, s, N—Me), 6.45 (1H, d, J$_{C-2-H,C-4-H}$=2.4 Hz, C-4-H), 6.52 (1H, dd, J$_{C-1-H,C-2-H}$=8.5 Hz and J$_{C-4-H,C-2-H}$=2.4. Hz, C-2-H), 7.06 (1H, d, J$_{C-2-H,C-1-H}$=8.5 Hz, C-1-H), 7.24 (1H, s, C-5'-H) and 9.02 (1H, s, OH); MS m/z (FAB+) 309.2 [100, (M+H)$^+$], 219.2 [52]; Acc MS m/z (FAB+) 309.19747, C$_{20}$H$_{25}$N$_2$O requires 309.19669.

2'-Methyl-3-Hydroxy-estra-1,3,5(10)-trieno-(17,16-c)-pyrazole (DSF 03102, STX 786)

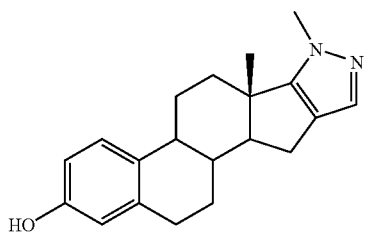

Following the hydrogenation conditions, a suspension of 3-O-benzyl-estra-1,3,5(10)-trieno-(17,16-c)--N-methyl-pyrazole (50 mg, 0.12 mmol) and Pd—C (20 mg) was hydrogenated overnight to give the product as a white solid (40 mg). This was recrystallized from EtOH to give white crystals (20 mg, 53%): TLC (chloroform/EtOAc, 9:1) R$_f$ 0.13 cf. R$_f$ 0.32; δ$_H$ (DMSO-d$_6$, 400 MHz) 0.95 (3H, s, C-18-H$_3$), 1.32-2.52 (11H, m), 2.69-2.83 (2H, m, C-6-H$_2$), 3.73 (3H, s, N—Me), 6.45 (1H, d, J$_{C-2-H,C-4-H}$=2.6 Hz, C-4-H), 6.52 (1H, dd, J$_{C-1-H,C-2-H}$=8.4 Hz and J$_{C-4-H,C-2-H}$=2.6 Hz, C-2-H), 7.04 (1H, s, C-3'-H), 7.06 (1H, d, J$_{C-2-H,C-1-H}$=8.4 Hz, C-1-H) and 9.03 (1H, s, OH); MS m/z (FAB+) 663.5 [24], 391.3 [28], 309.2 [100, (M+H)$^+$]; Acc MS m/z (FAB+) 309.19737, C$_{20}$H$_{25}$N$_2$O requires 309.19669.

2'-Isobutyl-3-Hydroxy-estra-1,3,5(10)-trieno-(17,16-c)-pyrazole (DSF 03113, STX 813)

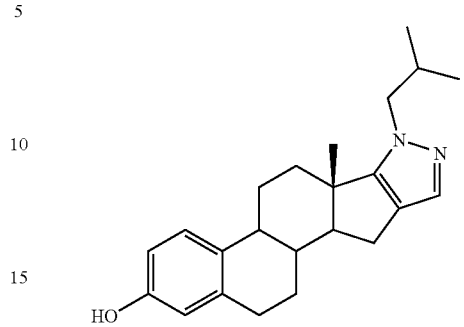

Following the hydrogenation conditions, a suspension of 3-O-benzyl-estra-1,3,5(10)-trieno-(17,16-c)--N-isobutyl-pyrazole (45 mg, 0.10 mmol) and Pd—C (20 mg) was hydrogenated overnight to give the product as a light yellow solid (103 mg). This was recrystallized from EtOAc/hexane to give creamy crystals (33 mg, 92%): TLC (chloroform/EtOAc, 9:1) R$_f$ 0.30 cf. R$_f$ 0.57; δ$_H$ (CDCl$_3$, 400 MHz) 0.92 (3H, d, J$_{C-2''-H,C-3''-H}$=6.6 Hz, C-3''-H$_3$), 0.95 (3H, d, J$_{C-2''-H,C-4''-H}$=6.6 Hz, C-4''-H$_3$), 1.03 (3H, s, C-18-H$_3$), 1.41-2.63 (12H, m), 2.84-2.91 (2H; m, C-6-H$_2$), 3.77 (1H, dd, J$_{BA}$=13.4 Hz and J$_{C-2''-H,C-1''-H}$=8.2 Hz, N—CH$_A$H$_B$), 3.89 (1H, dd, J$_{AB}$=13.4 Hz and J$_{C-2''-H,C-1''-H}$=7.6 Hz, N—CH$_A$H$_B$), ~5.50 (~1H, br s, exchanged with D$_2$O, OH), 6.60 (1H, d, J$_{C-2-H,C-4-H}$=2.6 Hz, C-4-H), 6.66 (1H, dd, J$_{C-1-H,C-2-H}$=8.4 Hz and J$_{C-4-H,C-2-H}$=2.6 Hz, C-2-H), 7.14 (1H, d, J$_{C-2-H,C-1-H}$=8.4 Hz, C-1-H) and 7.22 (1H, s, C-5'-H); MS m/z (FAB+) 351.3 [100, (M+H)$^+$]; Acc MS m/z (FAB+) 351.24437, C$_{23}$H$_{31}$N$_2$O requires 351.24364.

1'-Isobutyl-3-Hydroxy-estra-1,3,5(10)-trieno-(17,16-c)-pyrazole (DSF 03115, STX 812)

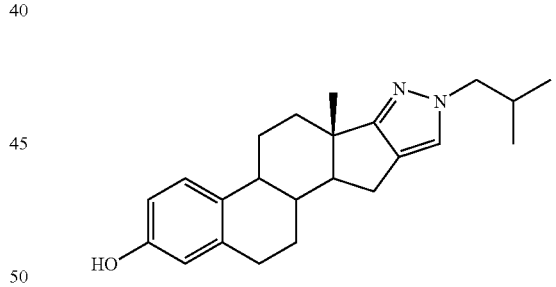

Following the hydrogenation conditions, a suspension of 3-O-benzyl-estra-1,3,5(10)-trieno-(17,16-c)--N-isobutyl-pyrazole (110 mg, 0.25 mmol) and Pd—C (40 mg) was hydrogenated overnight to give the product as a white solid (78 mg). This was recrystallized from MeOH to give colourless crystals (42 mg, 48%): mp 122-123° C.; TLC (chloroform/EtOAc, 9:1) R$_f$ 0.29 cf. R$_f$ 0.72; δ$_H$ (CDCl$_3$, 400 MHz) 0.87 (3H, d, J$_{C-2''-H,C-3''H}$=6.4 Hz, C-3''-H$_3$), 0.89 (3H, d, J$_{C-2''-H,C-4''-H}$=6.4 Hz, C-4''-H$_3$), 1.01 (3H, s, C-18-H3), 1.42-2.65 (12H, m), 2.81-2.95 (2H, m, C-6-H$_2$), 3.81 (1H, dd, J$_{BA}$=13.7 Hz and J$_{C-2''-H,C-1''-H}$=7.4 Hz, N—CH$_A$H$_B$), 3.86 (1H, dd, J$_{AB}$=13.7 Hz and J$_{C-2''H,C-1'-H}$=7.4 Hz, N—CH$_A$H$_B$), 5.61 (1H, s, exchanged with D$_2$O, OH), 6.59 (1H, d, J$_{C-2-H,C-4-H}$=2.6 Hz, C-4-H), 6.65 (1H, dd, J$_{C-1-H,C-2-H}$=8.4 Hz and J$_{C-4-H,C-2-H}$=2.6 Hz, C-2-H), 6.97 (1H, s, C-3'-H) and 7.16 (1H, d, J$_{C-2-H,C-1-H}$=8.4 Hz, C-1-H); MS m/z (FAB+)

351.3 [100, (M+H)⁺]; Acc MS m/z (FAB+) 351.24485, $C_{23}H_{31}N_2O$ requires 351.24364. Found: C, 75.20; H, 8.79; N, 7.42. $C_{23}H_{30}N_2O \cdot MeOH$ requires: C, 75.35; H, 8.96; N, 7.32.

1'-Methylacetate-3-Hydroxy-estra-1,3,5(10)-trieno-(17,16-c)-pyrazole (DSF 03129, STX806)

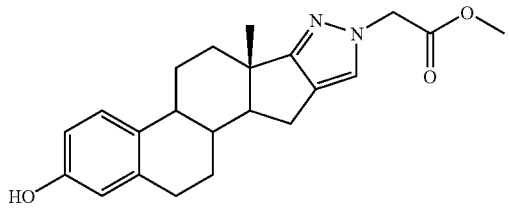

Following the hydrogenation conditions, a suspension of 3-O-benzyl-estra-1,3,5(10)-trieno-(17,16-c)--N-methylacetate-pyrazole (90 mg, 0.20 mmol) and Pd—C (40 mg) was hydrogenated for 6 hours to give the product as a white solid (66 mg). This was recrystallized from MeOH to give colourless crystals (49 mg, 68%): TLC (DCM/EtOAc, 9:1) $R_f$ 0.15 cf. $R_f$ 0.55; $\delta_H$ (CDCl$_3$, 400 MHz) 1.03 (3H, s, C-18-H$_3$), 1.41-2.69 (11H, m), 2.81-2.96 (2H, m, C-6-H$_2$), 3.75 (3H, s, OMe), 4.83 (1H, d, $J_{BA}$=17.6 Hz, N—CH$_A$H$_B$), 4.88 (1H, d, $J_{AB}$=17.6 Hz, N—CH$_A$H$_B$), 5.04 (1H, s, OH), 6.58 (1H, d, $J_{C-2-H,C-4-H}$=2.7 Hz, C-4-H) and 6.64 (1H, dd, $J_{C-1-H,C-2-H}$=8.4 Hz and $J_{C-4-H,C-2-H}$=2.7 Hz, C-2-H), 7.07 (1H, s, C-5'-H), 7.16 (1H, d, $J_{C-2-H,C-1-H}$=8.4 Hz, C-1-H); MS m/z (FAB+) 367.3 [100, (M+H)⁺], 176.1 [23], 73.1 [292]; Acc MS m/z (FAB+) 367.20383, $C_{22}H_{27}N_2O_3$ requires 367.20217.

2'-Methylacetate-3-Hydroxy-estra-1,3,5(10)-trieno-(17,16-c)-pyrazole (DSF 03131, STX807)

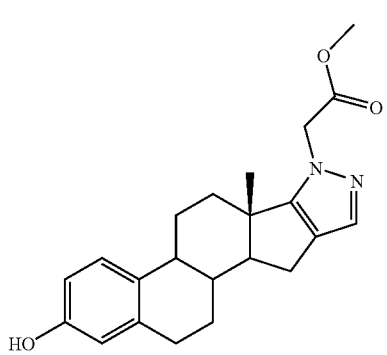

Following the hydrogenation conditions, a suspension of 3-O-benzyl-estra-1,3,5(10)-trieno-17,16-c)--N-methylacetate-pyrazole (60 mg, 0.13 mmol) and Pd—C (25 mg) was hydrogenated overnight to give the product as a light brown foam (34 mg). This was purified by flash chromatography with DCM/EtOAc (8:2) as eluent and gave the product as a light yellow foam (18 mg, 37%): TLC (DCM/EtOAc, 9:1) $R_f$ 0.18 cf. $R_f$ 0.37; □$\delta_H$ (CDCl$_3$, 400 MHz) 1.02 (3H, s, C-18-H$_3$), 1.42-2.64 (12H, m), 2.84-2.91 (2H, m, C-6-H$_2$), 3.77 (3H, s, OMe), 4.81 (1H, d, $J_{BA}$=17.4 Hz, N—CH$_A$H$_B$), 4.87 (1H, d, $J_{AB}$=17.4 Hz, N—CH$_A$H$_B$), 6.59 (1H, d, $J_{C-2-H,C-4-H}$=2.7 Hz, C-4-H), 6.64 (1H, dd, $J_{C-1-H,C-2-H}$=8.6 Hz and $J_{C-4-H,C-2-H}$=2.7 Hz, C-2-H), 7.12 (1H, d, $J_{C-2-H,C-1-H}$=8.6 Hz, C-1-H) and ~7.25 (~1H, s, C-3'-H, under solvent peaky.

1-(2-Methoxyethyl)-3-Hydroxy-estra-1,3,5(10)-trieno-(17,16-c)-pyrazole (DSF 03133, STX808)

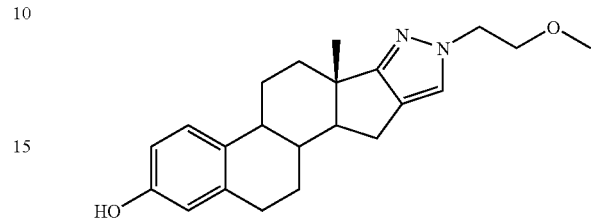

Following the hydrogenation conditions, a suspension of 3-O-benzyl-estra-1,3,5(10)-trieno-(17,16-c)-N(2-methoxyethyl)-pyrazole (80 mg, 0.18 mmol) and Pd—C (35 mg) was hydrogenated for 6 hours to give the product as a white crystalline solid (58 mg). This was recrystallized from MeOH to give white crystals (32 mg, 50%): TLC (DCM/EtOAc, 9:1) $R_f$ 0.11 cf. $R_f$ 0.28; $\delta_H$ (CDCl$_3$, 400 MHz) 1.02 (3H, s, C-18-H$_3$), 1.43-2.66 (11H, m), 2.81-2.93 (2H, m, C-6-H$_2$), 3.33 (3H, s, OMe), 3.71 (2H, td, J=5.5 Hz, J~1 Hz, C-1"-H$_2$ or C-2"-H$_2$), 4.23 (2H, app t, J~5 Hz, C-1"-H$_2$ or C-2"-H$_2$), 5.57 (1H, br s, OH), 6.59 (1H, d, $J_{C-2-H,C-4-H}$=2.7 Hz, C-4-H), 6.64 (1H, dd, $J_{C-1-H,C-2-H}$=8.4 Hz and $J_{C-4-H,C-2-H}$=2.7 Hz, C-2-H), 7.09 (1H, s, C-5'-H) and 7.16 (1H, d, $J_{C-2-H,C-1-H}$=8.4 Hz, C-1-H); MS m/z (FAB+) 353.3 [100, (M+H)⁺].

2'-(2-Methoxyethyl)-3-Hydroxy-estra-1,3,5(10)-trieno-(17,16-c)-pyrazole (DSF 03135, STX800)

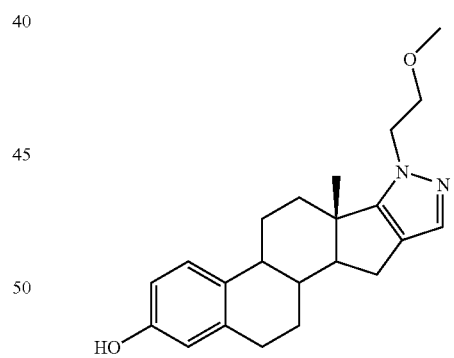

Following the hydrogenation conditions, a suspension of 3-O-benzyl-estra-1,3,5(10)-trieno-(17,16-c)-N-(2-methoxyethyl)-pyrazole (70 mg, 0.16 mmol) and Pd—C (30 mg) was hydrogenated for overnight to give the product as a creamy foam (50 mg). This was purified by flash chromatography using DCM/EtOAc (8:2) as eluent and gave the product as a creamy oil (25 mg, 45%): TLC (DCM/EtOAc, 9:1) $R_f$ 0.15 cf. $R_f$ 0.27; $\delta_H$ (CDCl$_3$, 400 MHz) 1.05 (3H, s, C-18-H$_3$), 1.42-2.61 (12H, m), 2.82-2.95 (2H, m, C-6-H$_2$), 3.31 (3H, s, OMe), 3.74-3.82 (2H, m, C-1"-H$_2$ or C-2"-H$_2$), 4.15-4.24 (2H, m, C-1"-H$_2$ or C-2"-H$_2$), 6.60 (1H, d, $J_{C-2-H,C-4-H}$=2.6 Hz, C-4-H), 6.66 (1H, dd, $J_{C-1-H,C-2-H}$=8.6 Hz and $J_{C-4-H,C-2-H}$=2.6 Hz, C-2-H), 7.14 (1H, d, $J_{C-2-H,C-1-H}$=8.6 Hz, C-1-H) and 7.23 (1H, s, C-3'-H); MS m/z (FAB+) 353.3 [100, (M+H)+]; Acc MS m/z (FAB+) 353.22359, $C_{22}H_{29}N_2O_2$ requires 353.22290.

3-Benzyloxy-16-nitrile,16-methyl-estrone (DSF03151/DSF03163)

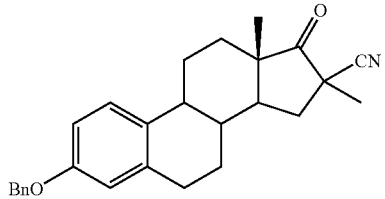

NaH (60% dispersion in mineral oil, 1.2 eq., 0.248 mmol, 10 mg) was added to a stirred solution of 3-benzyloxy-16-nitrile-estrone (0.207 mmol, 80 mg) in anhydrous DMF (5 mL) at 0° C. under an atmosphere of $N_2$. After 30 minutes of stirring, methyl iodide (0.310 mmol, 19 μL) was added to the white suspension and the mixture was stirred for 3 h, in which time it was allowed to warm to room temperature. The resulting light yellow solution was then poured into water (50 mL) and the organics were extracted with EtOAc (3×20 mL), washed with brine (2×20 mL), dried ($Na_2SO_4$), filtered and evaporated in vacuo. The crude product was purified by flash chromatography with $CH_2Cl_2$/hexane (3:2) as eluent to give the product as a crystalline light yellow solid (60 mg, 72%): $δ_H$ (DMSO-$d_6$, 270 MHz) 1.02 (3H, s, C-18-$H_3$), 1.25-2.54 (11H, m), 1.46 (~3H, s, C-16-$H_3$), 2.79-2.83 (2H, m, C-6-$H_2$), 5.06 (2H, s, OC$H_2$Ar), 6.73-6.80 (2H, m, C-4-H and C-2-H), 7.18 (1H, d, $J_{C-2-H,C-1-H}$=8.4 Hz, C-1-H), 7.29-7.46 (5H, m, $C_6H_5$); Found: C, 80.80; H, 7.45; N, 3.45. $C_{27}H_{29}NO_2$ requires: C, 81.17; H, 7.32; N, 3.51.

16-Nitrile,16-methyl-estrone (DSF03170, STX924)

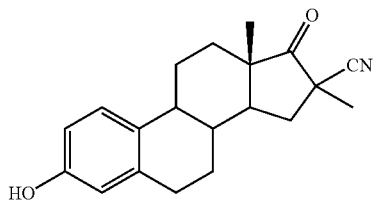

Pd/C (10%, 40 mg) was added to a stirred solution of 3-benzyloxy-16-nitrile,16-methyl-estrone (90 mg, 0.225 mmol) in a mixture of MeOH/THF (1:1, 40 mL). The resulting suspension was hydrogenated at room temperature overnight using a hydrogen-filled balloon. The final mixture was then filtered, the filter cake washed several times with boiling MeOH and THF, and concentrated in vacuo to give a crude white foam. This was purified by flash chromatography with $CH_2Cl_2$/EtOAc (9:1) as eluent to give the product as a white foam (46 mg, 66%). A sample was then triturated in hexane to give a creamy powder: $δ_H$ (CDCl$_3$, 270 MHz) 1.12 (3H, s, C-18-$H_3$), 1.32-2.48 (11H, m), 1.51 (~3H, s; C-16-$H_3$), 2.82-2.92 (2H, m, C-6-$H_2$), 4.55 (1H, s, C-3-OH), 6.73-6.58 (1H, app d, C-4-H), 6.63 (1H, dd, $J_{C-1-H,C-2-H}$=8.5 Hz, $J_{C-4-H,C-2-H}$=2.5 Hz, C-2-H), 7.13 (1H, d, $J_{C-2-H,C-1-H}$=8.5 Hz, C-1-H); MS m/z (FAB+) 309.1 [60, M+], 97.1 [50], 83.0 [65]; Acc MS m/z (FAB+) 309.12761, $C_{20}H_{23}NO_2$ requires 309.12788. HPLC (methanol/water, 80:20, $λ_{max}$=280.5 nm) Rt=2.53 min, 98%.

1'-Propionitrile-3-O-tert-Butyl-dimethylsilyl-estra-1,3,5(10)-trieno-(17,16c)-pyrazole (DSF03145A)

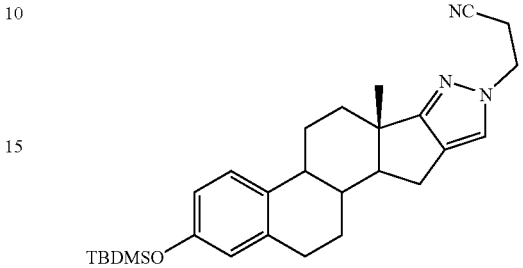

KOC(CH$_3$)$_3$ (0.807 mmol, 91 mg) was added to a stirred solution of 3-O-tert-butyl-dimethylsilyl-estra-1,3,5(10)-trieno-17,16-c)--pyrazole (0.734 mmol, 300 mg) in anhydrous THF (10 mL) at 0° C. under an atmosphere of $N_2$. After 20 minutes of stirring, acrylonitrile (0.881 mmol, 58 μL) was added and the resulting bright orange solution was stirred for 5 h, in which time at room temperature. The resulting dark orange cloudy mixture was then concentrated in vacuo and water (50 mL) was added. The organics were extracted with EtOAc (2×50 mL), washed with water (2×30 mL), then brine (2×30 mL), dried ($Na_2SO_4$), filtered and evaporated in vacuo. The crude product was purified by flash chromatography with $CH_2Cl_2$/EtOAc (9:1) as eluent to give two products, one of which was DSF03145A, as a light yellow solid (29 mg, 8%): $δ_H$ (CDCl$_3$, 400 MHz) 0.20 (6H, s, Si(CH$_3$)$_2$), 0.98 (9H, s, C(CH$_3$)$_3$), 1.02 (3H, s, C-18-$H_3$), 1.42-2.67 (11H, m), 2.82-2.91 (4H, m, C-6-$H_2$ and CH$_2$CN), 4.28-4.40 (2H, m, NCH$_2$), 6.57 (1H, d, $J_{C-2-H,C-4-H}$=2.6 Hz), 6.63 (1H, dd, $J_{C-1-H,C-2-H}$=8.5 Hz, $J_{C-4-H,C-2-H}$=2.6 Hz, C-2-H), 7.10 (1H, s, C-5'-H), 7.14 (1H, d, $J_{C-2-H,C-1-H}$=8.5 Hz, C-1-H).

3-Hydroxy-estra-1,3,5(10)-trieno-(17,16-c)-N-propionitrile-pyrazole (DSF03153, STX921)

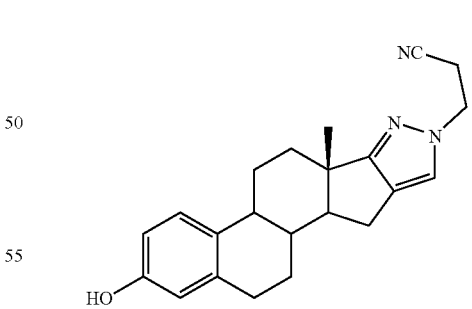

TBAF (0.110 mmol, 0.11 mL) was added to a stirred solution of 3-TBDMS-N-propionitrile (25 mg, 0.050 mmol) in anhydrous THF (5 mL) at room temperature under an atmosphere of $N_2$. The mixture was stirred for 3 h at room temperature. The solvent was then removed in vacuo and water added (50 mL). The organics were extracted with EtOAc (50 mL+20 mL), washed with water (20 mL), then brine (20 mL), dried ($Na_2SO_4$), filtered and evaporated in vacuo. The crude yellow oil was purified by flash chromatography with CH$_2$Cl$_2$/EtOAc (8:2) as eluent to give a light yellow oil (12 mg, 63%). This was then precipitated from EtOAc/Hexane to give a light yellow powder (8 mg): $\delta_H$ (CDCl$_3$, 400 MHz) 0.94 (3H, s, C-18-H$_3$), 1.34-2.60 (H, m), 2.76-2.86 (4H, m, C-6-H$_2$ and CH$_2$CN), 4.19-4.31 (2H, m, NCH$_2$), 4.92 (1H, br s, exchanged with D$_2$O, C-3-OH), 6.50 (1H, d, J$_{C-2-H,C-4-H}$=2.7 Hz), 6.55 (1H, dd, J$_{C-1-H,C-2-H}$=8.4 Hz, J$_{C-4-H,C-2-H}$=2.7 Hz, C-2-H), 7.02 (1H, s, C-5'-H), 7.08 (1H, d, J$_{C-2-H,C-1-H}$=8.4 Hz, C-1-H); MS m/z (APCI) 348.3 [32, (M+H)$^+$], 141.0 [20]. HPLC (methanol/water, 90:10, $\lambda_{max}$=229.8 nm) Rt=2.27 min, 96%.

16-(2',2'-Dimethyl-propylidene)-estradiol (STX948)

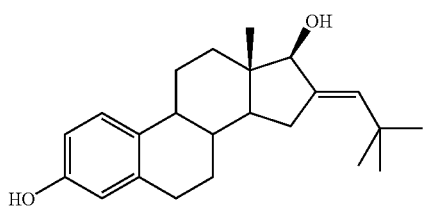

A solution of NaBH$_4$ (44 mg, 1.16 mmol) in H$_2$O (2.5 mL) was added to a stirred solution of STX748 in a mixture of MeOH/THF (2:1, 15 mL) at 0° C. The colourless solution was stirred for 1 hour at 0° C., after which AcOH glacial (4 drops) was added, followed by 10% aq. NaCl solution (15 mL). The resulting white precipitate was filtered, dried (79 mg) and recrystallised from EtOAc/Hexane (1:8) to give 68 as white crystals (63 mg, 79%): mp 219-222° C.; IR (KBr) 3550, 3410 (OH), 2960-2875 (aliph CH), 1610, 1505 (aliph C=C and arom C=C) cm$^{-1}$; $\delta_H$, (CDCl$_3$, 400 MHz) 0.65 (3H, s, C-18-H$_3$), 1.10 (9H, s, C(CH$_3$)$_3$), 1.18-2.59 (12H, m), 2.82-2.88 (2H, m, C-6-H$_2$), 3.85-3.90 (1H, app d, J=9.4 Hz, C-17-H), 4.60 (1H, s, exchanged with D$_2$O, OH), 5.46 (1H, dd, J=4.9 Hz, J=2.5 Hz, C-1'-H), 6.55 (1H, d, J=2.8 Hz, C-4-H), 6.61 (1H, dd, J=8.5 Hz, J=2.8 Hz, C-2-H) and 7.14 (1H, d, J=8.5 Hz, C-1-H); $\delta_C$ (CDCl$_3$, 100.4 MHz) 11.4 (q, C-18), 26.8 (t), 27.8 (t), 29.1 (t), 30.0 (t), 30.8 (3×q, C(CH$_3$)$_3$), 33.5 (s, C(CH$_3$)$_3$), 36.8 (t), 38.7 (d), 42.9 (s, C-13), 44.4 (d), 47.5 (d), 85.0 (di C-17), 113.0 (d), 115.5 (d), 126.7 (d), 132.7 (s), 133.7 (d, C-1'), 138.3 (s), 140.2 (s) and 153.6 (s, C-3); MS m/z (FAB+) 340.2 [49, M$^+$], 323.2 [100, (M−OH)$^+$], 283.2 [92, (M−C(CH$_3$)$_3$)$^+$]; Acc MS m/z (FAB+) 340.2390, C$_{23}$H$_{32}$O$_2$ requires 340.2402. HPLC (MeOH/H$_2$O, 96:4, $\lambda_{max}$, 280.5 nm) Rt=2.54 min, 99.5%. Found: C, 81.00; H, 9.54. C$_{23}$H$_{32}$O$_2$ requires: C, 81.13; H, 9.47%.

Synthesis of N-propionitrile [17-16-c]-pyrazole Derivatives

3-O-tert-Butyl-dimethylsilyl-estrone (1)

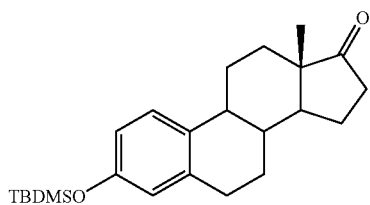

Imidazole (6.3 g, 92.4 mmol) and tert-butyl-dimethylsilyl chloride (7.8 g, 51.8 mmol) were added to a stirred solution of E1 (10.0 g, 37.0 mmol) in anhydrous DMF (300 mL) at room temperature, under an atmosphere of N$_2$. After stirring overnight, the resulting white suspension was poured into H$_2$O (500 mL). The organics were extracted with EtOAc (500 mL+300 mL), washed with H$_2$O (2×200 mL), then brine (2×200 mL), dried (Na$_2$SO$_4$), filtered and concentrated under reduced, pressure. The crude product was recrystallised from EtOH to give 1 as white needles (14.0 g, 98%): mp 171-173° C. [lit.{Fevig, 1987} (EtOH) 170-172° C.]; IR (KBr) 2960-2855 (aliph CH), 1730 (C=O), 1605, 1495 (arom C=C) cm$^{-1}$; $\delta_H$ (CDCl$_3$, 400 MHz) 0.19 (6H, s, Si(CH$_3$)$_2$), 0.91 (3H, s, C-18-H$_3$), 0.98 (9H, s, C(CH$_3$)$_3$), 1.37-2.55 (13H, m), 2.81-2.89 (2H, m, C-6-H$_2$), 6.57 (1H, d, J=2.6 Hz, C-4-H), 6.62 (1H, dd, J=8.3 Hz, J=2.6 Hz, C-2-H) and 7.12 (1H, d, J=8.3 Hz, C-1-H); MS m/z (FAB+) 384.2 [100, M$^+$], 327.2 [44, (M−C(CH$_3$)$_3$)$^+$], 73.0 [44]; Acc MS m/z (FAB+) 384.2477, C$_{24}$H$_{36}$O$_2$Si requires 384.2485.

3-O-tert-Butyl-dimethylsilyl-16-hydroxymethylene-estrone (2)

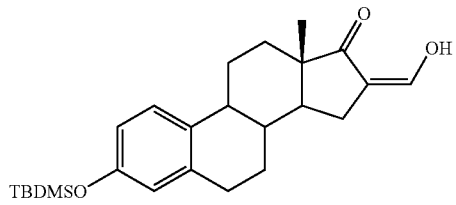

NaOMe (4.8 g, 70.2 mmol) was added portionwise to a stirred solution of 1 (9 g, 23.4 mmol) in anhydrous toluene (250 mL) at room temperature, under an atmosphere of N$_2$. After stirring for 20 minutes, ethyl formate (13.2 mL, 164 mmol) was added and the resulting bright yellow solution was stirred overnight. The final thick yellow suspension was poured into H$_2$O (300 mL) and acidified with 5M HCl. The organics were extracted with EtOAc (2×500 mL), washed with H$_2$O (3×200 mL), then brine (2×200 mL), dried (Na$_2$SO$_4$), filtered and concentrated under reduced pressure to give an off-white crude product (9.49 g, 98%). For analysis a sample was recrystallised from EtOH to give 2 as white crystals: mp 168-171° C.; IR (KBr) 2930-2855 (aliph CH), 1710 (C=O), 1695-1500, 1495 (C=C and arom C=C) cm$^{-1}$; $\delta_H$ (DMSO-d$_6$, 400 MHz) 0.17 (6H, s, Si(CH$_3$)$_2$), 0.83 (3H, s, C-18-H$_3$), 0.96 (9H, s, C(CH$_3$)$_3$), 1.32-2.63 (11H, m), 2.77-2.85 (2H, m, C-6-H$_2$), 6.55 (1H, d, J=2.6 Hz, C-4-H), 6.61 (1H, dd, J=8.3 Hz, J=2.6 Hz, C-2-H), 7.14 (1H, d, J=8.3 Hz, C-1-H), 7.40 (1H, s, =CHOH) and 10.69 (1H, s, exchanged with D$_2$O, =CHOH); $\delta_C$ (DMSO-d$_6$, 100.4 MHz) −4.3 (2×q, Si(CH$_3$)$_2$), 14.5 (q, C-18), 18.0 (s, C(CH$_3$)$_3$), 24.1 (t), 25.6 (t and 3×q, C(CH$_3$)$_3$), 26.2 (t), 29.0 (t), 31.5 (t), 37.3 (d), 43.6 (d), 47.7 (s, C-13), 48.4 (d), 113.0 (s, C-16), 116.9 (d), 119.4 (d), 125.9 (d), 132.5 (s), 137.3 (s), 149.9 (d, C-1'), 152.5 (s, C-3) and 208.2 (s, C=O); MS m/z (FAB+) 413.2 [68, (M+H)$^+$], 355.1 [33, (M−C(CH$_3$)$_3$)$^+$], 72.9 [100]; Acc MS m/z (FAB+) 413.2492, C$_{25}$H$_{37}$O$_3$Si requires 413.2512. Found: C, 72.77; H, 8.79. C$_{25}$H$_{36}$O$_3$Si requires: C, 72.40; H, 8.90%.

3-O-tert-Butyl-dimethylethyl-estra-1,3,5(10)-triene [17,16-c]-pyrazole (3)

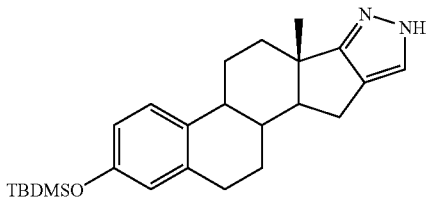

Hydrazine hydrate (440 µL, 9.1 mmol) was added to a suspension of 2 (2.5 g, 6.1 mmol) in EtOH (125 mL) at room temperature, under an atmosphere of $N_2$. The resulting mixture was heated to reflux for 45 minutes. After cooling down, the solvent was removed under reduced pressure, $H_2O$ (200 mL) added and the mixture acidified with 5M HCl. The organics were extracted with EtOAc (2×10 mL), washed with $H_2O$ (2×50 mL), then brine (2×50 mL), dried ($Na_2SO_4$), filtered and concentrated under reduced pressure to give a yellow foam (2.9 g). This was recrystallised from EtOH/$H_2O$ to give 3 as yellow crystals (2.0 g, 81%): mp 122-124° C.; IR (KBr) 3190 (arom CH), 2930-2855 (aliph CH), 1605-1495 (C=N and arom C=C) cm$^-$; $\delta_H$ (DMSO-d$_6$, 400 MHz) 0.18 (6H, s, Si(CH$_3$)$_2$), 0.95 (3H, s, C-18-H$_3$), 0.96 (9H, s, C(CH$_3$)$_3$), 1.36-2.61 (11H, m), 2.79-2.87 (2H, m, C-6-H$_2$), 6.55 (1H, d, J=2.3 Hz, C-4-H), 6.62 (1H, dd, J=8.5 Hz, J=2.3 Hz, C-2-H), 7.16 (1H, d, J=8.5 Hz, C-1-H), 7.28 (1H, s, C-5'-H) and 12.02 (1H, s, exchanged with D$_2$O, NH); $\delta_C$ (CDCl$_3$, 100.4 MHz) −3.8 (2×q, Si(CH$_3$)$_2$), 18.6 (s, C(CH$_3$)$_3$), 18.8 (q, C-18), 24.3 (t), 26.2 (3×q, C(CH$_3$)$_3$), 26.6 (t), 27.9 (t), 30.0 (t), 34.5 (t), 38.0 (d), 41.1 (s, C-13), 44.9 (d), 61.9 (d), 117.4 (d), 120.2 (d), 121.8 (s), 123.2 (s), 126.2 (d), 133.2 (s), 137.8 (s), 153.5 (s) and 168.6 (s); MS m/z (FAB+) 409.2 [100, (M+H)$^+$], 73.0 [33]; Acc MS m/z (FAB+) 409.2662, C$_{25}$H$_{37}$N$_2$OSi requires 409.2675. Found: C, 71.40; H, 8.93; N, 6.53. C$_{25}$H$_{36}$N$_2$OSi.(H$_2$O)$_{2/3}$ requires: C, 71.38; H, 8.95; N, 6.66%.

3-O-tert-Butyl-dimethylsilyl-estra-1,3,5(10)-triene-[17,16-c]-(1'-propionitrile)-pyrazole (4) and 3-O-tert-Butyl-dimethylsilyl-estra-1,3,5(10)-triene-[17,16-c]-(2'-propionitrile)-pyrazole (5)

$^t$BuOK (91 mg, 807 µmol) was added to a stirred solution of 3 (300 mg, 734 µmol) in anhydrous THF (10 mL) at 0° C., under an atmosphere of N$_2$. After 20 minutes of stirring, acrylonitrile (58 µL, 881 µmol) was added and the resulting bright orange solution was stirred for 5 hours at room temperature. The resulting dark orange mixture was then concentrated under reduced pressure and H$_2$O (50 mL) was added. The organics were extracted with EtOAc (2×50 mL), washed with H$_2$O (2×30 mL), then brine (2×30 mL), dried (Na$_2$SO$_4$), filtered and concentrated under reduced pressure. The crude product was purified by flash chromatography (DCM/EtOAc, 9:1) to give two products:

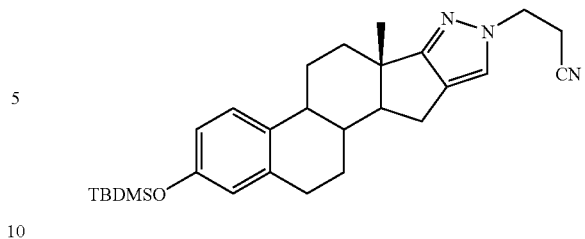

The less polar fraction gave 4 as a light yellow oil (29 mg, 8%): IR (KBr) 2930-2860 (aliph CH), 2250 (CN), 1640-1495 (C=N and arrow C=C), 1250 (C—O or Si(CH$_3$)$_2$) cm$^{-1}$; $\delta_H$ (CDCl$_3$, 400 MHz), 0.20 (6H, s, Si(CH$_3$)$_2$), 0.98 (9H, s, C(CH$_3$)$_3$), 1.02 (3H, s, C-18-H$_3$), 1.42-2.67 (11H, m), 2.82-2.91 (4H, m, C-6-H$_2$ and CH$_2$CN), 4.28-4.40 (2H, m, N—CH$_2$), 6.57 (1H, d, J=2.6 Hz, C-4-H), 6.63 (1H, dd, J=8.5 Hz, J=2.6 Hz, C-2-H), 7.10 (1H, s, C-5'-H) and 7.14 (1H, d, J=8.5 Hz, C-1-H); MS m/z (FAB+) 462.2 [100, (M+H)$^+$], 73.0 [55]; Acc MS m/z (FAB+) 462.2914, C$_{28}$H$_{40}$N$_3$OSi requires 462.2941.

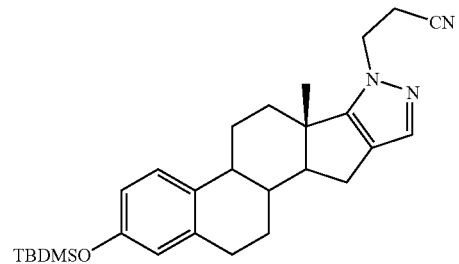

The more polar fraction gave 5 as a light brown oil that crystallises on standing (42 mg, 12%): mp 80-82° C.; IR (KBr) 2930-2855 (aliph CH), 2255 (CN), 1705-1445 (C=N and arom C=C), 1285, 1250 (C—O or Si(CH$_3$)$_2$) cm$^{-1}$; $\delta_H$ (CDCl$_3$, 400 MHz), 0.20 (6H, s, Si(CH$_3$)$_2$), 0.98 (9H, s, C(CH$_3$)$_3$), 1.07 (3H; s, C-18-H$_3$), 1.41-2.91 (13H, m), 2.99 (2H, t, J=6.6 Hz, CH$_2$CN), 4.21-4.38 (2H, m, N—CH$_2$), 6.57 (1H, d, J=2.4 Hz, C-4-H), 6.63 (1H, dd, J=8.7 Hz, J=2.4 Hz, C-2-H), 7.11 (1H, d, J=8.7 Hz, C-1-H), and 7.25 (1H, s, C-5'-H); MS m/z (FAB+) 462.1 [100, (M+H)$^+$], 73.0 [79]; Acc MS m/z (FAB+) 462.2922, C$_{28}$H$_{40}$N$_3$OSi requires 462.2941.

3-Hydroxy-estra-1,3,5(10)-triene-[17,16-c-]-(1'-propionitrile)-pyrazole (STX921)

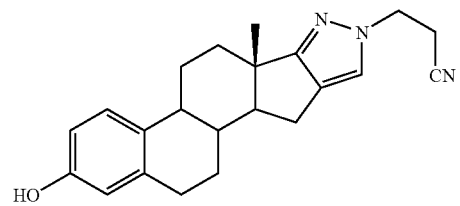

A 1.0 M solution of TBAF in anhydrous THF (110 µl, 110 µmol) was added to a stirred solution of 4 (25 mg, 50 µmol) in anhydrous THF (5 mL) at room temperature, under an atmosphere of N$_2$. The mixture was stirred for 3 hours at room temperature, after which the solvent was removed under reduced pressure and H$_2$O added (50 mL). The organics were extracted with EtOAc (70 mL), washed with H$_2$O (20 mL), then brine (20 mL), dried (Na$_2$SO$_4$), filtered and concentrated under reduced pressure. The crude yellow oil was purified by flash chromatography (DCM/EtOAc, 8:2) to give STX921 as a light yellow oil (12 mg, 63%). This was then triturated with EtOAc/hexane to give a light yellow powder (8 mg): mp 92-94° C.; IR (KBr) 3230 (OH), 3095 (arom CH), 2925-2860 (aliph CH), 2265 (CN), 1665-1500 (C=N and arom C=C), 1245 (C—O) cm$^{-1}$; δ$_H$ (CDCl$_3$, 400 MHz), 0.94 (3H, s, C-18-H$_3$), 1.34-2.60 (11H, m), 2.76-2.86 (4H, m, C-6-H$_2$ and CH$_2$CN), 4.19-4.31 (2H, m, N—CH$_2$), 4.92 (1H, br s, exchanged with D$_2$O, OH), 6.50 (1H, d, J=2.7 Hz, C-4-H), 6.55 (1H, dd, J=8.4 Hz, J=2.7 Hz, C-2-H), 7.02 (1H, s, C-5'-H) and 7.08 (1H, d, J=8.4 Hz, C-1-H); MS m/z (FAB+) 348.1 [90, (M+H)$^+$], 147.1 [64], 73.0 [100]; Acc MS m/z (FAB+) 348.2072, C$_{22}$H$_{26}$N$_3$O requires 348.2076. HPLC (MeOH/H$_2$O, 90:10, λ$_{max}$=229.8 nm) Rt=2.27 min, 96%.

3-Hydroxy-estra-1,3,5(10)-triene-[17,16-c]-(2'-propionitrile)-pyrazole

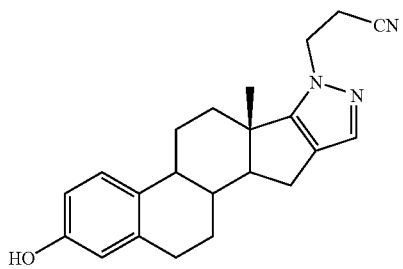

Method A: A 1.0 M solution of TBAF in anhydrous THF (150 μL, 150 μmol) was added to a stirred solution of 5 (35 mg, 76 μmol) in anhydrous THF (5 mL) at room temperature, under an atmosphere of N$_2$. The mixture was stirred for 3 hours at room temperature, after which the solvent was removed under reduced pressure and H$_2$O added (50 mL). The organics were extracted with EtOAc (70 mL), washed with H$_2$O (20 mL), then brine (20 mL), dried (Na$_2$SO$_4$), filtered and concentrated under reduced pressure. The crude brown oil was purified by flash chromatography (DCM/EtOAc, 8:2) to give 3-Hydroxy-estra-1,3,5(10)-triene-[17,16-c]-(2'-propionitrile)-pyrazole as a light brown oil (10 mg, 38%).

Method B: A 1.0 M solution of TBAF in anhydrous THF (916 μL, 916 μmol) was added to a stirred solution of 6 (220 mg, 458 μmol) in anhydrous THF (20 mL) at room temperature, under an atmosphere of N$_2$. The mixture was stirred overnight at room temperature after which the solvent was removed under reduced pressure and H$_2$O added (50 mL). The organics were extracted with EtOAc (2×50 mL), washed with H$_2$O (2×30 mL), then brine (2×30 mL), dried (Na$_2$SO$_4$), filtered and concentrated under reduced pressure. The crude product was purified by flash chromatography (EtOAc/CHCl$_3$, 9:1) to give 3-Hydroxy-estra-1,3,5(10)-triene-[17,16-c]-(2'-propionitrile)-pyrazole as a pale pink foam (136 mg, 85%). This was then triturated with EtOAc/Hexane to give white crystals (99 mg, 62%): mp 198-200° C.; IR (KBr) 3160 (br, OH), 2925-2860 (aliph CH), 2250 (CN), 1610-1500 (arom C=C) cm$^{-1}$; δ$_H$ (CDCl$_3$, 400 MHz), 1.06 (3H, s, C-18-H$_3$), 1.41-2.63 (11H, m), 2.82-2.91 (2H, m, C-6-H$_2$), 2.99 (2H, app. td, J=6.8 Hz, J=3.5 Hz, CH$_2$CN), 4.22-4.34 (2H, m, N—CH$_2$), 5.42 (1H, br s, exchanged with D$_2$O, OH), 6.57 (1H, d, J=2.4 Hz, C-4-H), 6.64 (1H, dd, J=8.3 Hz, J=2.4 Hz, C-2-H), 7.12 (1H, d, J=8.3 Hz, C-1-H) and 7.25 (1H, s, C-5'-H); δ$_C$ (CDCl$_3$, 100.4 MHz), 18.6 (q, C-18), 19.7 (t, CH$_2$CN), 24.5 (t), 26.5 (t), 27.6 (t), 29.8 (t), 34.8 (t), 37.7 (d), 42.4 (s, C-13), 44.4 (d), 45.9 (t, N—CH$_2$), 62.2 (d), 113.1 (d), 115.7 (d), 117.4 (s), 124.3 (s), 126.4 (d), 132.0 (s), 135.2 (d), 138.2 (s), 154.1 (s) and 157.98, (s); MS m/z (FAB+) 348.1 [100, (M+H)$^+$], 147.0 [50], 85.1 [75], 73.0 [94]; Acc MS m/z (FAB+) 348.2060, C$_{22}$H$_{26}$N$_3$O requires 348.2076. Found: C, 75.90; H, 7.17; N, 12.10. C$_{22}$H$_{25}$N$_3$O requires: C, 76.05; H, 7.25; N, 12.09%.

3-O-tert-Butyl-dimethylsilyl-estra-1,3,5(10)-triene-[17,16-c]-(2'-propionitrile-3',4'-dihydro)-pyrazol-3'-ol (6)

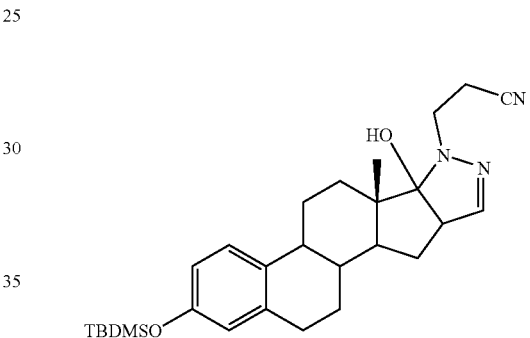

Cyanoethylhydrazine (177 μL, 2.18 mmol) was added to a stirred solution of 2 (600 mg, 1.45 mmol) in EtOH (50 mL) under an atmosphere of N$_2$. After 4 hours of stirring at room temperature, the resulting orange mixture was concentrated under reduced pressure and H$_2$O (100 mL) added, followed by 5M HCl. The organics were extracted with EtOAc (2×100 mL), washed with H$_2$O (50 mL), then brine (50 mL), dried (Na$_2$SO$_4$), filtered and concentrated under reduced pressure. The crude product was purified by flash chromatography (CHCl$_3$/EtOAc, 7:3) to give 6 as a pale yellow solid (510 mg, 73%). This was recrystallised from EtOH to give white needles (240 mg, 34%): IR (KBr) 3380 (OH), 2950-2860 (aliph CH), 2260 (CN), 1610, 1495 (C=N and arom C=C) cm$^{-1}$; δ$_H$ (DMSO-d$_6$, 400 MHz), 0.15 (6H, s, Si(CH$_3$)$_2$), 0.88 (3H, s, C-18-H$_3$), 0.93 (9H, s, C(CH$_3$)$_3$), 1.19-3.16 (11H, m), 2.70-3.16 (7H, m), 5.97 (1H, s, exchanged with D$_2$O, OH), 6.48 (1H, d, J=2.7 Hz, C-4-H), 6.56 (1H, dd, J=8.2 Hz, J=2.7 Hz, C-2-H), 6.74 (1H, d, J=1.9 Hz, C-5'-H) and 7.10 (1H, d, J=8.2 Hz, C-1-H); δ$_C$ (CDCl$_3$, 100.4 MHz), −4.4 (2×q, Si(CH$_3$)$_2$), 15.6 (q, C-18), 17.1 (t, CH$_2$CN), 18.0 (s, C(CH$_3$)$_3$), 25.6 (3×q, C(CH$_3$)$_3$), 25.8 (t), 27.0 (t), 29.1 (t), 29.4 (t), 31.4 (t), 38.6 (d), 43.2 (d), 43.9 (t, N—CH$_2$), 47.1 (s, C-13), 49.5 (d), 56.7 (d), 104.2 (s), 116.8 (d), 119.4 (d), 119.9 (s, CN), 126.0 (d), 132.5 (s), 137.3 (s), 144.6 (s) and 152.4 (s); MS m/z (FAB+) 480.1 [100, (M+H)$^+$], 462.1 [63, (M+H−H$_2$O)$^+$], 72.9 [77]; MS m/z (FAB−) 632.3 [32, (M+NBA)$^−$]; Acc MS m/z (FAB+) 480.3038 C$_{28}$H$_{42}$N$_3$O$_2$Si requires 480.3046.

Synthesis of 16-hydroxymethylene Derivatives and Corresponding 5'-alkylated [17,16c]-pyrazoles

3-Benzyloxy-16-(1'-hydroxy-ethylidene)-estrone (99)

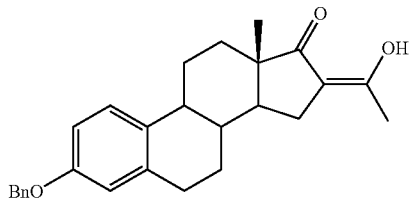

ᵗBuOK (438 mg, 4.14 mmol) was added to a stirred solution of 3-benzyloxy-estrone (500 mg, 1.38 mmol) in anhydrous toluene (6 mL) and anhydrous DMSO (1.5 mL) at 0° C., under an atmosphere of $N_2$. Ethyl acetate (1.27 mL, 17.94 mmol) was then added and the mixture was heated to reflux for 1 hour. After cooling down, the resulting brown solution was poured into $H_2O$ (200 mL) and acidified with 5M HCl. The organics were extracted with EtOAc (2×150 mL), washed with $H_2O$ (2×100 mL), then brine (2×100 mL), dried ($Na_2SO_4$), filtered and concentrated under reduced pressure. The crude product was purified by flash chromatography (DCM) to give 99 as a light yellow crystalline solid (447 mg, 80%). This was recrystallised from EtOH to give yellow crystals (351 mg, 63%): mp 126-128° C.; IR (KBr) 2930-2860 (aliph CH), 1660 (C=O), 1615-1455 (C=C and arom C=C) Cm$^{-1}$; $\delta_H$ (CDCl$_3$, 400 MHz), 0.83, 0.95 (3H, 2×s, C-18-H$_3$), 1.38-2.49 (11H, m), 1.97, 2.37 (3H, 2×s, C-2'-H$_3$), 2.87-2.92 (2H, m, C-6-H$_2$), 3.43 (app, dd, J=9.4 Hz, J=8.2 Hz, C-16-H), 5.02 (2H, s, OCH$_2$Ar), 6.71 (1H, d, J=2.8 Hz, C-4-H), 6.77 (1H, dd, J=8.3 Hz, J=2.8 Hz, C-2-H), 7.17 (1H, d, J=8.3 Hz, C-1-H), 7.28-7.42 (5H, m, C$_6$H$_5$) and 12.91 (br s, exchanged with D$_2$O, C-1'-OH); MS m/z (FAB+) 403.1 [68, (M+H)$^+$], 91.0 [100, (CH$_2$Ar)$^+$]; Acc MS m/z (FAB+) 403.2246, C$_{27}$H$_{31}$O$_3$ requires 403.2273. Found: C, 80.20; H, 7.56. C$_{27}$H$_{30}$O$_3$ requires: C, 80.56; H, 7.51%.

3-O-tert-Butyl-dimethylsilyl-16-(1'-hydroxy-2',2',2'-trifluoro-ethylidene)-estrone (100)

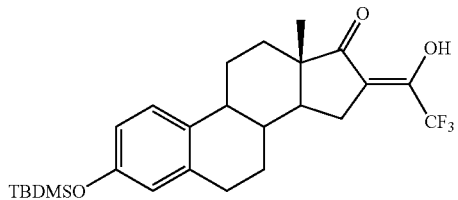

ᵗBuOK (875 mg, 7.80 mmol) was added to a stirred solution of 1 (1.0 g, 2.60 mmol) in anhydrous toluene (20 mL) at 0° C., under an atmosphere of $N_2$. After 20 minutes of stirring, ethyl trifluoroacetate (2.16 mL, 18.2 mmol) was added and the mixture heated to reflux for 2 hours. After cooling down, the resulting dark orange suspension was poured into $H_2O$ (50 mL) and acidified with 5M HCl. The organics were extracted with EtOAc (2×50 mL), washed with $H_2O$ (2×30 mL), then brine (2×30 mL), dried ($Na_2SO_4$), filtered and concentrated under reduced pressure. The crude orange oil that crystallises on standing was used without further purification (1.4 g, quant.). An analytical sample was recrystallised from EtOH to give 100 as light yellow crystals: mp 145-146° C.; IR (KBr) 2930-2860 (aliph CH), 1690 (C=O), 1640-1495 (C=C and arom C=C) cm$^{-1}$; $\delta_H$ (CDCl$_3$, 400 MHz), 0.19 (6H, s, Si(CH$_3$)$_2$), 0.98 (9H, s, C(CH$_3$)$_3$), 0.99 (3H, s, C-18-H$_3$), 1.42-2.90 (13H, m), 6.57 (1H, d, J=2.6 Hz, C-4-H), 6.63 (1H, dd, J=8.4 Hz, J=2.6 Hz, C-2-H) and 7.11 (1H, d, J=8.4 Hz, C-1-H), C-1'-OH not seen; $\delta_C$ (CDCl$_3$, 100.4 MHz), -4.4 (2×q, Si(CH$_3$)$_2$), 14.8 (q, C-18), 18.1 (s, C(CH$_3$)$_3$), 25.2 (t), 25.6 (t), 25.7 (3×q, C(CH$_3$)$_3$), 26.7 (t), 29.3 (t), 31.0 (t), 37.5 (d), 43.9 (d), 48.5 (s, C-13), 49.5 (d), 110.9 (s, C-16), 117.4 (d), ~119 (app d, J=272 Hz, CF$_3$), 120.0 (d), 126.0 (d), 132.0 (s), 137.4 (s), 153.6 (s, C-3), ~154 (app d, J=38 Hz, C-1') and 216.0 (s, C=O); MS m/z (FAB+) 480.1 [47, M$^+$], 423.0 [38, (M-F$_3$)$^+$], 73.0 [100]; Acc MS m/z (FAB+) 480.2296, C$_{26}$H$_{35}$F$_3$O$_3$Si requires 480.2308. Found: C, 64.90; H, 7.13. C$_{26}$H$_{35}$F$_3$O$_3$Si requires: C, 64.97; H, 7.34%.

3-O-tert-Butyl-dimethylsilyl-16-(1'-hydroxy-1''-pyridin-3''-ylmethylene)-estrone (101)

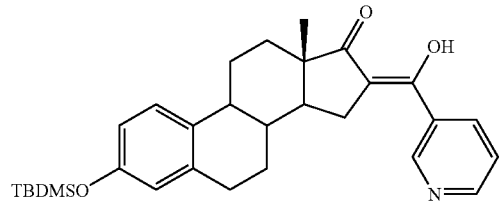

ᵗBuOK (875 mg, 7.80 mmol) was added to a stirred solution of 1 (1.0 g, 2.60 mmol) in anhydrous toluene (30 mL) at 0° C., under an atmosphere of $N_2$. After 20 minutes of stirring, ethyl nicotinate (2.48 mL, 18.2 mmol) was added and the mixture was heated to reflux for 1.5 hours. After cooling down, the resulting dark red suspension was poured into $H_2O$ (200 mL) and acidified with 5M HCl. The organics were extracted with EtOAc (2×100 mL), washed with $H_2O$ (100 mL), then brine (2×100 mL), dried ($Na_2SO_4$), filtered and concentrated under reduced pressure. The crude yellow solid was recrystallised from EtOH to give 101 as white flaky crystals (985 mg, 77%): mp 169-170° C.; IR (KBr) 2930-2855 (aliph CH), 1660 (C=O), 1605, 1495 (C=C and arom C=C) cm$^{-1}$; $\delta_H$ (CDCl$_3$, 400 MHz), 0.21 (6H, s, Si(CH$_3$)$_2$), 0.99 (9H, s, C(CH$_3$)$_3$), 1.11 (3H, s, C-18-H$_3$), 1.38-2.77 (11H, m), 2.81-2.95 (2H, m, C-6-H$_2$), 6.58 (1H, d, J=2.6 Hz, C-4-H), 6.63 (1H, dd, J=8.5 Hz, J=2.6 Hz, C-2-H), 7.12 (1H, d, J=8.5 Hz, C-1-H), 7.41 (1H, ddd, J=8.1 Hz, J=4.9 Hz, J=0.8 Hz, C-5'-H), 8.09 (1H, app dt, J=8.1 Hz, J=2.0 Hz, C-4''-H), 8.69 (1H, dd, J=4.9 Hz, J=1.9 Hz, C-6''-H), 8.97 (1H, app dd, J=2.1 Hz, J=0.8 Hz, C-2''-H) and 13.63 (1H, s, exchanged with D$_2$O, C-1'-OH); MS m/z (FAB+) 490.1 [100, (M+H)$^+$]; Acc MS m/z (FAB+) 490.2775, C$_{30}$H$_{40}$NO$_3$Si requires 490.2777. Found: C, 64.90; H, 7.13. C$_{26}$H$_{35}$F$_3$O$_3$Si requires: C, 64.97; H, 7.34%.

16-(1'-hydroxy-ethylidene)-estrone (102)

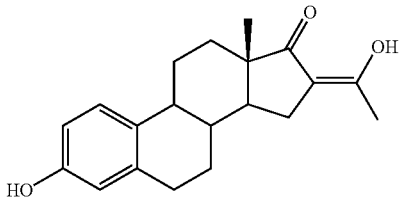

Following method 2, a suspension of 99 (200 mg, 497 µmol) and Pd—C (10%, 80 mg) in MeOH/THF 2:1 (30 mL) was hydrogenated for 2 hours to give 102 as a white solid (98 mg, 63%). This was recrystallised from acetone/hexane to give white crystals (72 mg, 46%): mp 211-214° C.; IR (KBr) 3450 (OH), 2915-2860 (aliph CH), 1705 (C=O), 1655-1510 (C=O, C=C and arom C=C) cm$^{-1}$; $\delta_H$ (CDCl$_3$, 400 MHz), 0.83, 0.96 (3H, 2×s, C-18-H$_3$), 1.39-2.40 (11H, m), 1.98, 2.37 (3H, 2×s, C-2'-H$_3$), 2.83-2.89 (2H, m, C-6-H$_2$), 3.43 (dd, J=9.4 Hz, J=8.2 Hz, C-16-H), 4.70 (br s, exchanged with D$_2$O, OH), 6.55-6.57 (1H, m, C-4-H), 6.62 (1H, dd, J=8.0 Hz, J=2.7 Hz, C-2-H) and 7.11 (1H, d, J=8.0 Hz, C-1-H), 1×OH not seen; MS m/z (FAB+) 313.1 (100, (M+H)$^+$, 73.0 [19]; Acc MS m/z (FAB+) 313.1799, C$_{20}$H$_{25}$O$_3$ requires 313.1804. Found: C, 76.60; H, 7.82. C$_{20}$H$_{24}$O$_3$ requires: C, 76.89; H, 7.74%.

16-(1'-hydroxy-2',2',2'-trifluoro-ethylidene)-estrone (103, STX 946)

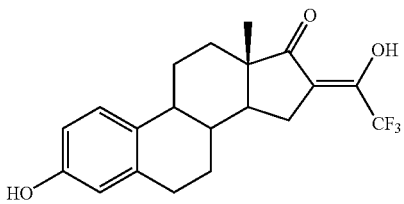

A 1.0 M solution of TBAF in anhydrous THF (4.90 mL, 4.90 mmol) was added to a stirred solution of 100 (1.18 g, 2.45 mmol, crude product) in anhydrous THF (50 mL) under an atmosphere of N$_2$. The resulting light brown solution was stirred at room temperature for 4 hours, after which the solvent was removed under reduced pressure and H$_2$O added (100 mL). The organics were extracted with EtOAc (2×100 mL), washed with H$_2$O (2×80 mL), then brine (2×80 mL), dried (Na$_2$SO$_4$), filtered and concentrated under reduced pressure. The crude brown oil was purified by flash chromatography (DCM) to give 103 as a light brown oil (535 mg, 60%). This was crystallised from cold DCM to give white crystals (249 mg, 28%): mp 91-93° C.; IR (KBr) 3430 (OH), 2930-2860 (aliph CH), 1685 (C=O), 1610, 1500 (C=C and arom C=C) cm$^{-1}$; $\delta_H$ (CDCl$_3$, 400 MHz), 1.02 (3H, s, C-18-H$_3$), 1.43-2.91 (13H, m), 6.58 (1H, d, J=2.7 Hz, C-4-H), 6.64 (1H, dd, J=8.4 Hz, J=2.7 Hz, C-2-H) and 7.14 (1H, d, J=8.4 Hz, C-1-H), C-3-OH and C-1'-OH not seen; MS m/z (FAB+) 366.1 [100, M$^+$]; Acc MS m/z (FAB+) 366.1476, C$_{20}$H$_{21}$F$_3$O$_3$ requires 366.1443. HPLC (MeOH/H$_2$O, 96:4, $\lambda_{max}$=280.5 nm) Rt=1.66 min, 100%. Found: C, 57.60; H, 5.37. C$_{20}$H$_{21}$F$_3$O$_3$.(CH$_2$Cl$_2$)$_{3/4}$ requires: C, 57.95; H, 5.27%.

16-(1'-hydroxy-1"-pyridin-3"-ylmethylene)-estrone (104)

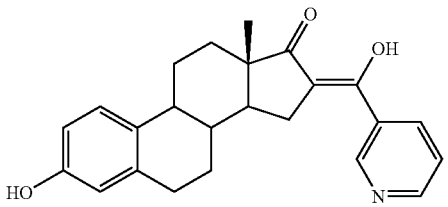

A 1.0 M solution of TBAF in anhydrous THF (1.43 mL, 1.43 mmol) was added to a stirred solution of 101 (350 mg, 716 µmol) in anhydrous THF (10 mL) under an atmosphere of N$_2$. The resulting light brown solution was stirred at room temperature for 3 hours, after which the solvent was removed under reduced pressure and H$_2$O added (100 mL), followed by a few drops of AcOH glacial. The organics were extracted with EtOAc (100 mL), Et$_2$O (100 mL) and CHCl$_3$ (100 mL), washed with H$_2$O (100 mL), then brine (100 mL), dried (Na$_2$SO$_4$), filtered and concentrated under reduced pressure. The crude product was triturated with boiling EtOH to give 104 as a pale yellow solid (125 mg, 50%): mp 275-278° C.; IR (KBr) 2950-2855 (aliph CH), 645 (C=O), 1610-1500 (C=C and arom C=C) cm$^{-1}$; $\delta_H$ (CDCl$_3$, 400 MHz), 1.09 (3H, s, C-18-H$_3$), 1.39-2.76 (11H, m), 2.85-2.91 (2H, m, C-6-H$_2$), 5.48 (1H, s, exchanged with D$_2$O, C-3-OH), 6.59 (1H, d, J=2.7 Hz, C-4-H), 6.65 (1H, dd, J=8.4 Hz, J=2.7 Hz, C-2-H), 7.15 (1H, d, J=8.4 Hz, C-1-H), 7.41 (1H, ddd, J=8.1 Hz, J=4.9 Hz, J=0.8 Hz, C-5"-H), 8.09 (1H, dt, J=8.1 Hz, J=1.8 Hz, C-4"-H), 8.67 (1H, dd, J=4.9 Hz, J=1.8 Hz, C-6"-H), 8.94 (1H, app d, J=1.8 Hz, C-2"-H) and 13.58 (1H, s, exchanged with D$_2$O, C-1'-OH); MS m/z (FAB+) 376.0 [100, (M+H)$^+$], 242.1 [54]; Acc MS m/z (FAB+) 376.1903, C$_{24}$H$_{26}$NO$_3$ requires 376.1913. Found: C, 74.70; H, 6.80; N, 3.51. C$_{24}$H$_{25}$NO$_3$.(H$_2$O)$_{1/2}$ requires: C, 74.98; H, 6.82; N, 3.64%.

3-O-tert-Butyl-dimethylsilyl-estra-1,3,5(10)-triene-[17,16-c]-[5'-(1"-pyridin-3"-yl)-3',4'-dihydro)]-pyrazol-3'-ol (105)

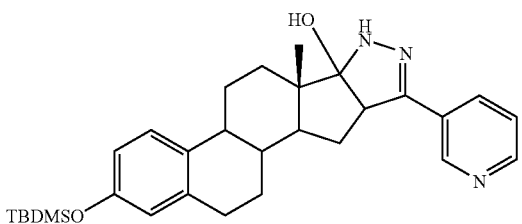

Hydrazine hydrate (75 µL, 1.53 mmol) was added to a refluxing solution of 101 (500 mg, 1.02 mmol) in EtOH (20 mL), under an atmosphere of N$_2$. The resulting pale yellow solution was heated to reflux for 1 hour, after which the solvent was partially removed under reduced pressure and H$_2$O (100 mL) added. The resulting white precipitate was filtered and dried (460 mg, 89%) and an analytical sample was recrystallised from EtOH/H$_2$O to give 101 as white crystals: mp 144-145° C.; IR (KBr) 3480, 3330, 3190 (NH and OH), 2940-2860 (aliph CH), 1610-1495 (C=N and arom C=C) cm$^{-1}$; $\delta_H$ (DMSO-d$_6$, 400 MHz), 0.14 (6H, s, Si (CH$_3$)$_2$), 0.92 (9H, s, C(CH$_3$)$_3$), 0.94 (3H, s, C-18-H$_3$), 1.12-2.31 (11H, m), 2.63-2.71 (2H, m, C-6-H$_2$), 3.43 (1H, app d, J=9.0 Hz, C-16-H), 5.97 (1H, s, exchanged with D$_2$O, C-17-OH), 6.46 (1H, d, J=2.5 Hz, C-4-H), 6.55 (1H, dd, J=8.4 Hz, J=2.5 Hz, C-2-H), 7.10 (1H, d, J=8.4 Hz, C-1-H), 7.26 (1H, s, exchanged with D$_2$O, NH), 7.35 (1H, app ddd, J=8.1 Hz, J=4.6 Hz, J=0.8 Hz, C-5"-H), 7.91 (1H, app dt, J=8.1 Hz, J=1.7 Hz, C-4"-H), 8.43 (1H, dd, J=4.6 Hz, J=1.7 Hz, C-6"-H) and 8.74 (1H, app d, J=1.7 Hz, C-2"-H); MS m/z (FAB+) 504.1 [100, (M+H)$^+$]; 486.1 [27, (M+H–H$_2$O)$^+$]; Acc MS m/z (FAB+) 504.3045, C$_{30}$H$_{42}$N$_3$O$_2$Si requires 504:3046.

3-Hydroxy-estra-1,3,5(10)-triene-[17,16-c]-(5'-methyl)-pyrazole (106)

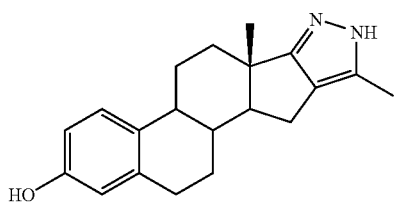

Hydrazine hydrate (56 µL, 1.15 mmol) was added to a refluxing solution of 102 (240 mg, 768 µmol) in EtOH (15 mL), under an atmosphere of N$_2$. The resulting pale yellow solution was heated to reflux for 45 minutes, after which the solvent was removed under reduced pressure, H$_2$O (50 mL) added and the mixture acidified with 5M HCl. The organics were extracted with EtOAc (2×50 mL), washed with H$_2$O (30 mL), then brine (2×30 mL), dried (Na$_2$SO$_4$), filtered and concentrated under reduced pressure. The crude product was purified by flash chromatography (DCM/EtOAc, 8:2) to give 106 as a pale brown solid (84 mg, 35%). This was triturated with acetone to give a creamy solid (32 mg, 13%): mp 234-236° C.; IR (KBr) 3295 (OH), 2930-2860 (aliph CH), 1620-1500 (C=N and arom C=C) cm$^{-1}$; $\delta_H$ (DMSO-d$_6$, 400 MHz), 1.01 (3H, s, C-18-H$_3$), 1.34-2.64 (11H, m), 2.71-2.85 (2H, m, C-6-H$_2$), 2.28 (3H, s, C-1"-H$_3$), 6.45 (1H, d, J=2.6 Hz, C-4-H), 6.52 (1H, dd, J=8.6 Hz, J=2.6 Hz, C-2-H), 7.04 (1H, d, J=8.6 Hz, C-1-H) and 9.04 (1H, s, exchanged with D$_2$O, NH or OH), NH or OH not seen; MS m/z (FAB+) 309.2 [100, (M+H)$^+$], 95.1 [33], 69.0 [39]; Acc MS m/z (FAB+) 309.1978, C$_{20}$H$_{25}$N$_2$O requires 309.1967. HPLC (MeOH/H$_2$O, 96:4, $\lambda_{max}$=280.5 nm) Rt=1.98 min, 99%.

3-Hydroxy-estra-1,3,5(10)-triene-[17,16-c]-(5'-trifluoro-methyl)-pyrazole (107, STX949)

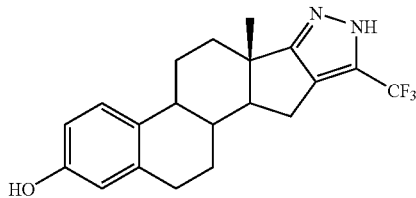

Hydrazine hydrate (32 µL, 655 µmol) was added to a refluxing solution of 103 (160 mg, 437 µmol) in EtOH (15 mL), under an atmosphere of N$_2$. The resulting pale yellow solution was heated to reflux for 3 hours, after which p-toluene sulfonic acid (~10 mg) was added. The mixture was then heated to reflux overnight and after cooling down, the solvent was removed under reduced pressure, H$_2$O (50 mL) added, followed by 5M HCl. The organics were extracted with EtOAc (2×50 mL), washed with H$_2$O (30 mL), then brine (2×30 mL), dried (Na$_2$SO$_4$), filtered and concentrated under reduced pressure. The crude product was purified by flash chromatography (DCM/EtOAc, 8:2) to give 107 as a pale yellow solid (95 mg, 60%). This was precipitated from DCM/Hexane (1:5) to give an off-white solid (51 mg, 32%): mp 152-155° C.; IR (KBr) 3220 (br, OH), 2930-2860 (aliph CH), 1610-1500 (C=N and arom C=C) cm$^{-1}$; $\delta_H$ (CDCl$_3$, 400 MHz), 1.01 (3H, s, C-18-H$_3$), 1.40-2.74 (11H, m), 2.78-2.89 (2H, m, C-6-H$_2$), 4.63 (1H, s, exchanged with D$_2$O, C-3-OH), 6.53 (1H, d, J=2.7 Hz, C-4-H), 6.59 (1H, dd, J=8.2 Hz, J=2.7 Hz, C-2-H) and 7.08 (1H, d, J=8.2 Hz, C-1-H), NH not seen; MS m/z (FAB+) 363.1 [100, (M+H)$^+$]; Acc MS m/z (FAB+) 363.1689, C$_{20}$H$_{22}$N$_2$F$_3$O requires 363.1684. HPLC (MeOH/H$_2$O, 85:15, $\lambda_{max}$=280.5 nm) Rt=2.43 min, 98%.

3-Hydroxy-estra-1,3,5(10)-triene-[17,16-c]-[5'-(1"-pyridin-3"-yl)]-pyrazole (108)

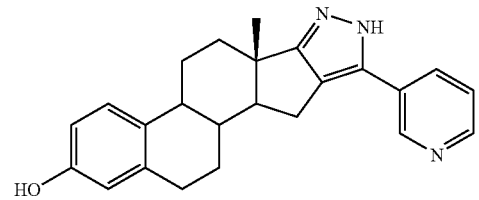

A 1.0 M solution of TBAF in anhydrous THF (436 µL, 436 µmol) was added to a stirred solution of 105 (110 mg, 218 µmol) in anhydrous THF (10 mL) at room temperature, under an atmosphere of N$_2$. The resulting light brown solution was stirred overnight at room temperature, after which the solvent was removed under reduced pressure and H$_2$O added (50 mL). The organics were extracted with EtOAc (2×50 mL), washed with H$_2$O (2×30 mL), then brine (2×30 mL), dried (Na$_2$SO$_4$), filtered and concentrated under reduced pressure. The crude foam was triturated with boiling EtOAc/CHCl$_3$ (1:1) to give 108 as a white powder (61 mg, 75%): mp 298-300° C. (dec.); IR (KBr) 2980-2840 (aliph CH), 1610-1495 (C=N and arom C=C) cm$^{-1}$; $\delta_H$ (DMSO-d$_6$, 400 MHz) 0.98 (3H, s, C-18-H$_3$), 1.37-2.87 (13H, m), 6.45 (1H, d, J=2.6 Hz, C-4-H), 6.51 (1H, dd, J=8.5 Hz, J=2.6 Hz, C-2-H), 7.05 (1H, d, J=8.5 Hz, C-1-H), 7.37-7.48 (1H, m, C-4"-H or C-5"-H), 7.97-8.06 (1H, m, C-4"-H or C-5"-H), 8.42-8.49 (1H, m, C-2"-H or C-6"-H) and 8.84-8.89 (1H, m, C-2"-H or C-6"-H), 9.01 (1H, s, exchanged with D$_2$O, OH), 12.65 and 12.72 (total 1H, 2×s, NH); MS m/z (FAB+) 372.0 [100, (M+H)$^+$]; Acc MS m/z (FAB+) 372.2080, C$_{24}$H$_{26}$N$_3$O requires 372.2076.

3-O-tert-butyl-dimethylsilyl-estra-1,3,5(10)-triene-[17,16-c]-(5'-trifluoromethyl-3',4'-dihydro)-pyrazol-3'-ol (109)

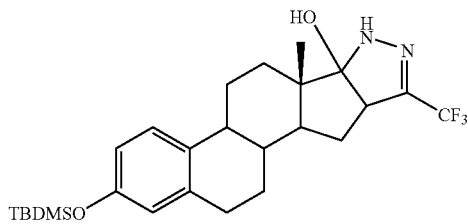

Hydrazine hydrate (22 μL, 468 μmol) was added to a refluxing solution of 100 (150 mg, 312 μmol) in absolute EtOH (8 mL), under an atmosphere of $N_2$. The resulting pale yellow solution was heated to reflux for 1 hour, after which the solvent was removed in vacuo and $H_2O$ (50 mL) added, followed by HCl 5M (4 drops). The organics were extracted with EtOAc (3×30 mL), washed with $H_2O$ (2×30 mL), then brine (2×30 mL), dried ($Na_2SO_4$), filtered and concentrated under reduced pressure. The crude product was purified by flash chromatography ($CH_2C_2$ to $CH_2Cl_2$/EtOAc, 98:2, gradient, flashmaster) to give a light brown crystalline solid (65 mg, 42%). This was recrystallised from EtOH/$H_2O$ to give creamy crystals (26 mg, 18%): mp 235-238° C.; IR (KBr) 3335 (NH), 3170 (br, OH), 2930-2860 (aliph CH), 1664, 1605, 1495 (C=N and arom C=C) cm$^{-1}$; $\delta_H$ (DMSO-d$_6$, 400 MHz), 0.18 (6H, s, SiMe$_2$), 0.96 (9H, s, C(CH$_3$)$_3$), 1.04 (3H, s, C-18-H$_3$), 1.32-2.39 (11H, m), 2.76-2.81 (2H, m, C-6-H$_2$), 3.53-3.57 (1H, m, C-16-H), 6.53 (1H, d, $J_{C-2-H,C-4-H}$=2.7 Hz, C-4-H), 6.60 (1H, dd, $J_{C-1-H,C-2-H}$=8.4 Hz, $J_{C-4-H,C-2-H}$=2.7 Hz, C-2-H), 6.63 (~2H, s, exchanged with D$_2$O, OH and NH) and 7.14 (1H, d, $J_{C-2-H,C-1-H}$=8.4 Hz, C-1-H); MS m/z (FAB+) 495.0 [69, (M+H)$^+$], 453.0 [54], 437.0 [51, (M-F$_3$)$^+$9, 73.0 [100]; Acc MS m/z (FAB+) 495.26311, C$_{26}$H$_{38}$N$_2$F$_3$O$_2$Si requires 495.26547.

3-Hydroxy-estra-1,3,5(10)-triene-(17,16 -c)-3'-trifluoromethyl-5'-hydroxy-pyrazole (110, STX947)

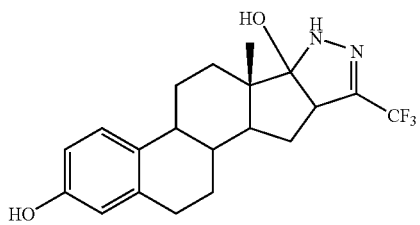

A 1.0 M solution of tetrabutyl ammonium fluoride in dry THF (404 μL, 404 μmol) was added to a stirred solution of 109 (100 mg, 202 μmol) in THF (20 mL) at room temperature, under an atmosphere of $N_2$. The resulting light brown solution was stirred for 4 hours at room temperature, after which the solvent was removed in vacuo and $H_2O$ added (50 mL). The organics were extracted with EtOAc (2×50 mL), washed with $H_2O$ (2×30 mL), then brine (2×30 mL), dried ($Na_2SO_4$), filtered and concentrated under reduced pressure. The light brown crude oil was purified by flash chromatography ($CH_2Cl_2$/EtOAc, 9:1, flashmaster) to give a pale yellow oil (51 mg, 66%). This was then precipitated from Et$_2$O/Hexane (1:5) to give a light yellow powder (7 mg): IR (KBr) 3470, 3415 (OH), 2930-2870 (aliph CH), 1640, 1615, 1500 (C=N and arom C=C) cm$^{-1}$; $\delta_H$ (CDCl$_3$, 400 MHz), 1.06 (3H, s, C-18-H$_3$), 1.16-2.26 (11H, m), 2.70-2.84 (2H, m, C-6-H$_2$), 3.64-3.71 (1H, app d, C-16-H), 4.39 (1H, br s, OH or NH), 5.88 (1H, s, OH or NH), 6.53 (1H, d, $J_{C-2-H,C-4-H}$=2.6 Hz, C-4-H), 6.61-6.65 (1H, app dd, C-2-H) and 7.03 (1H, d, $J_{C-2-H,C-1-H}$=8.8 Hz, C-1-H); MS m/z (FAB+) 381.1 [100, (M+H)$^+$], 85.1 [87]; MS m/z (FAB-) 533.3 [100, (M+NBA)$^-$], 379.2 [98, (M-H)$^-$]; Acc MS m/z (FAB+) 381.17967, C$_{20}$H$_{24}$N$_2$O$_2$F$_3$ requires 381.17899. HPLC (methanol/water, 96:4, $\lambda_{max}$=280.5 nm) Rt=1.66 min, 100%.

New Pathway to STX664

3-Benzyloxy-16-ethoxymethylene-estrone (127)

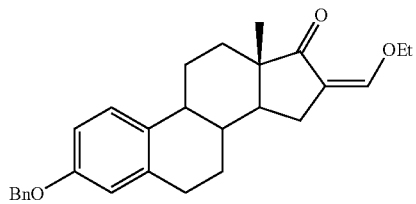

K$_2$CO$_3$ (595 mg, 4.31 mmol) was added portionwise to a stirred suspension of 3-benzyloxy-16-hydroxymethylene-estrone (250 mg, 643 mmol) in acetone (20 mL) at room temperature, under an atmosphere of $N_2$. After 10 minutes of stirring, ethyl iodide (296 μL, 3.70 mmol) was added and the resulting mixture was stirred for 36 hours at room temperature. $H_2O$ was then added (100 mL) and the organics were extracted with DCM (3×50 mL), washed with $H_2O$ (50 mL), then brine (2×50 mL), dried (Na$_2$SO$_4$), filtered and concentrated under reduced pressure. The crude product was purified by flash chromatography (EtOAc/hexane, 1:3) to give 127 as a white solid (215 mg, 80%). This was recrystallised from EtOAc to give white crystals (139 mg, 52%): mp 158-160° C.; IR (KBr) 2935-2850 (aliph CH), 1710 (C=O), 1640-1500 (aliph and arom C=C), 1235 (C—O) cm$^{-1}$; $\delta_H$ (CDCl$_3$, 400 MHz), 0.92 (3H, s, C-18-H$_3$), 1.34 (3H, t, J=7.2 Hz, C-3'-H$_3$), 1.38-2.71 (11H, m), 2.84-2.93 (2H, m, C-6-H$_2$), 4.02-4.10 (2H, m, C-2'-H$_2$), 5.02 (2H, s, OCH$_2$Ar), 6.71 (1H, d, J=2.6 Hz, C-4-H), 6.77 (1H, dd, J=8.6 Hz, J=2.6 Hz, C-2-H), 7.18 (1H, d, J=8.6 Hz, C-1-H) and 7.26-7.43 (6H, m, C-1'-H and C$_6$H$_5$); MS m/z (FAB+) 417.0 [100, (M+H)$^+$]; Acc MS m/z (FAB+) 417.2425, C$_{28}$H$_{33}$O$_3$ requires 417.2430.

16β-Ethoxymethyl-estrone (STX664)

A suspension of 127 (640, mg -1.54 mmol) and Pd—C (10%, 200 mg) in MeOH/THF (1:1, 60 mL) was hydrogenated (H$_2$-filled balloon) at room temperature for 48 hours. After removal of the supported catalyst by filtration through celite and concentration of the filtrate under reduced pressure, the product obtained was purified by flash chromatography (EtOAc/hexane, 3:7) to give STX664 as a white crystalline solid (232 mg, 46%). An analytical sample was recrystallised from EtOH: mp 208-210° C.; IR (KBr) 3370 (OH), 2970-2855 (aliph CH), 1730 (C=O), 1610, 1505 (arom C=C), 1225 (C—) cm$^{-1}$; $\delta_H$ (CDCl$_3$, 400 MHz), 0.89 (3H, s, C-18-H$_3$), 1.16 (3H, t, $J_{C-2'-H,C-3'-H}$=7.0 Hz, C-3'-H$_3$), 1.36-2.42 (12H, m), 2.81-2.85 (2H, m, C-6-H$_2$), 3.42-3.50 (2H, m, C-2'-H₂), 3.61 (1H, dd, $J_{AB}$=9.4 Hz, J=3.9 Hz, C-1'-$H_AH_B$), 3.65 (1H, dd, $J_{BA}$=9.4 Hz, J=5.5 Hz, C-1'-$H_AH_B$), 4.59 (1H, s, exchanged with D₂O, OH), 6.56 (1H, d, J=2.8 Hz, C-4-H), 6.62 (1H, dd, J=8.5 Hz, J=2.8 Hz, C-2-H) and 7.13 (1H, d, J=8.5 Hz, C-1-H); $\delta_C$ (CDCl₃, 100.4 MHz), 12.9 (q, C-3'), 15.0 (q, C-18), 25.8 (t), 25.9 (t), 26.6 (t), 29.4 (t), 32.0 (t), 37.7 (d), 44.0 (d), 48.2 (s, C-13), 48.9 (d), 50.2 (d), 66.4 (t, C-1' or C-2'), 69.3 (t, C-1' or C-2'), 112.5 (d), 115.0 (d), 126.2 (d), 131.9 (s), 137.8 (s) and 153.0 (s, C-3), C=O not seen; MS m/z (FAB+) 329.1 [100; (M+H)⁺]; Acc MS m/z (FAB+) 329.2124, $C_{21}9O_3$ requires 329.2117. HPLC (MeOH/H₂O, 90:10, $\lambda_{max}$=279.3 nm) Rt=2.37 min, 98%. Found: C, 76.60; H, 8.62. $C_{21}H_{28}O_3$ requires: C, 76.79; H, 8.59%.

Sulfamates

3-Sulfamoyloxy-16β-ethoxymethyl-estrone (20)

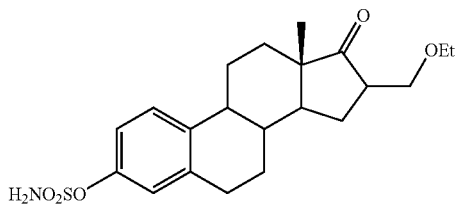

Anhydrous DMA (1.5 mL) was added to a freshly concentrated solution of sulfamoyl chloride (2.2 eq.) cooled to 0° C. under an atmosphere of N₂. STX664 (100 mg, 304 μmol) was then added and the resulting mixture was stirred at room temperature for 3 hours. The mixture was then poured into cold brine (15 mL), and the organics were extracted with EtOAc (2×20 mL), washed with brine (5×20 mL), dried (MgSO₄), filtered and concentrated under reduced pressure. The crude product was purified by flash chromatography (CHCl₃/EtOAc, 8:2) to give 20 as a colourless oil (124 mg, 100%): IR (KBr) 3380, 3285 (br, NH₂), 2970-2865 (aliph CH), 1730 (C=O), 1605-1495 (arom C=C), 1380, 1190 (SO₂) cm⁻¹; $\delta_H$(CDCl₃, 400 MHz), 0.89 (3H, s, C-18-H₃), 1.16 (3H, t, J=7.0 Hz, C-3'-H₃), 1.40-2.43 (12H, m), 2.89-2.94 (2H, m, C-6-H₂), 3.43-3.50 (2H, m, C-2'-H₂), 3.61 (1H, dd, $J_{AB}$=9.4 Hz, J=3.7 Hz, C-1'-$H_AH_B$), 3.66 (1H, dd, $J_{BA}$=9.4 Hz, J=5.5 Hz, C-1'-$H_AH_B$), 4.87 (2H, s, exchanged with D₂O, SO₂NH₂), 7.04 (1H, d, J=2.4 Hz, C-4-H), 7.07 (1H, dd, J=8.4 Hz, J=2.4 Hz, C-2-H) and 7.29 (1H, d, J=8.4 Hz, C-1-H); $\delta_C$ (CDCl₃, 100.4 MHz), 12.9 (q, C-3'), 15.1 (q, C-18), 25.8 (2×t), 26.4 (t), 29.4 (t), 32.0 (t), 37.4 (d), 44.3 (d), 48.2 (s, C-13), 49.0 (d), 50.3 (d), 66.6 (t, C-1' or C-2'), 69.3 (t, C-1' or C-2'), 119.1 (d), 122.1 (d), 126.8 (d), 138.8 (s), 139.1 (s), 148.0 (s, C-3) and 220.8 (s, C=O); MS m/z (FAB+) 408.3 [39, (M+H)⁺], 145.1 [63], 131.1 [61], 117.1 [57], 85.1 [100], 68.0 [50]; Acc MS m/z (FAB+) 408.1841, $C_{21}H_{30}NO_5S$ requires 408.1845. HPLC (MeOH/H₂O, 90:10, $\lambda_{max}$=267.5 nm) Rt=2.28 min, 99%. Found: C, 59.65; H, 6.84; N, 3.36. $C_{21}H_{29}NO_5S\cdot(CHCl_3)_{1/6}$ requires: C, 59.48; H, 6.88; N, 3.28%.

3-Sulfamoyloxy-16-oximino-estrone (21)

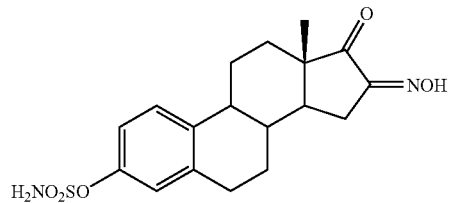

Following an analogous procedure to that described for the preparation of 20, reaction of 16-oximino-estrone (200 mg, 668 μmol) with sulfamoyl chloride in DMA (1.5 mL) was complete within 3 hours. The crude product was purified by flash chromatography (CHCl₃/acetone, 8:2) to give a white foam (93 mg, 37%). This was triturated with hexane to give 21 as a white powder (36 mg, 14%): mp 88-91° C.; IR (KBr) 3370-3250 (NH₂, NOH), 2930-2850 (aliph CH), 1740 (C=O), 1635-1495 (C=N and arom C=C), 1380, 1185 (SO₂) cm⁻¹; $\delta_H$ (DMSO-d₆, 400 MHz), 0.90 (3H, s, C-18-H₃), 1.32-2.48 (11H, m), 2.78-2.94 (2H, m, C-6-H₂), 7.00 (1H, m, C-4-H), 7.03 (1H, dd, J=8.6 Hz, J=2.3 Hz, C-2-H), 7.36 (1H, d, J=8.6 Hz, C-1-H), 7.92 (2H, s, exchanged with D₂O, SO₂NH₂) and 12.41 (1H, s, exchanged with D₂O, NOH); MS m/z (FAB+) 532.2 [32, (M+H+NBA)⁺], 379.1 [100, (M+H)⁺]; MS m/z (FAB−) 531.1 [40, (M+NBA)⁻], 377.1 [100, (M−H)⁻]; Acc MS m/z (FAB+) 379.1320, $C_{18}H_{23}N_2O_5S$ requires 379.1328. Found: C, 56.70; H, 6.02; N, 6.83. $C_{18}H_{22}N_2O_5S$ requires: C, 57.13; H, 5.86; N, 7.40%.

3,1'-Bis-sulfamoyloxy-estra-1,3,5(10)-triene-[17,16-c]-pyrazole (21) and 3-Sulfamoyloxy-estra-1,3,5(10)-triene-[17,16-c]-pyrazole (22)

Following an analogous procedure to that described for the preparation of 20, reaction of 3-hydroxy-estra-1,3,5(10)-triene-[17,16-c]-pyrazole (170 mg, 577 μmol) with sulfamoyl chloride in DMA (2 mL) was complete within 4 hours. The crude product was purified by flash chromatography (CHCl₃/EtOAc, 1:1) to give two products:

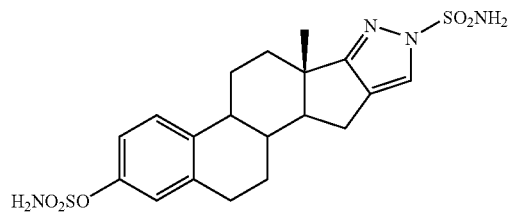

The less polar fraction gave 21 as a pale yellow solid (85 mg, 32%): IR (KBr) 3440, 3410 (NH₂), 2930-2860 (aliph CH), 1635-1495 (C=N and arom C=C), 1385, 1185 (SO₂) cm⁻¹; $\delta_H$ (DMSO-d₆, 400 MHz), 0.99 (3H, s, C-18-H₃), 1.40-2.68 (11H, m), 2.85-2.90 (2H, m, C-6-H₂), 6.97 (1H, d, J=2.3 Hz, C-4-H), 7.02 (1H, dd, J=8.6 Hz, J=2.3 Hz, C-2-H), 7.35 (1H, d, J=8.6 Hz, C-1-H), 7.70 (1H, s, C-5'-H), 7.88 (2H, s, exchanged with D₂O, SO₂NH₂) and 8.30 (2H, s, exchanged with D₂O, SO₂NH₂); MS m/z (FAB+) 452.8 100, M⁺], 373.9 [80, (M+H−SO₂NH₂)⁺], 171.0 [26], 116.0 [29]; Acc MS m/z (FAB+) 452.1164, $C_{19}H_{24}N_4O_5S_2$ requires 452.1188. HPLC (MeOH/H₂O, 80:20, $\lambda_{max}$=220.4 nm) Rt=1.95 min, 97%.

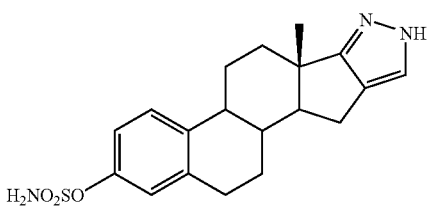

The more polar fraction gave 22 as a white solid (123 mg, 57%): IR (KBr) 3370, 3305 (NH$_2$), 2975-2860 (aliph CH), 1590, 1495 (C=N and arom C=C), 1370, 11.95 (SO$_2$) cm$^{-1}$; $\delta_H$ (DMSO-d$_8$, 400 MHz, 1.17 (3H, s, C-18-H$_3$), 1.38-2.59 (11H, m), 2.85-2.90 (2H, m, C-6-H$_2$), 6.97 (1H, d, J=2.7 Hz, C-4-H), 7.02 (1H, dd, J=8.6 Hz, J=2.7 Hz, C-2-H), 7.25 (1H, s, C-5'-H), 7.35 (1H, d, J=8.6 Hz, C-1-H), 7.89 (2H, s, exchanged with D$_2$O, SO$_2$NH$_2$) and 11.99 (1H, br s, exchanged with D$_2$O, NH); MS m/z (FAB+) 747.3 [38, (2M+H)$^+$], 527.2 [80, (M+H+NBA)$^+$], 509.2 [30], 443.2 [28], 374.2 [100, (M+H)$^+$]; Acc MS m/z (FAB+) 374.1544, C$_{19}$H$_{24}$N$_3$O$_3$S requires 374.1538. HPLC (MeOH/H$_2$O, 80:20, $\lambda_{max}$=218.0 nm) Rt=2.04 min, 100%.

Section 5

3-tert-Butyl-dimethyl-silanyloxy)-13-methyl-17oxo-7,8,9,11,12,13,14,15,16,17-decahydro-6H-cyclopenta[a]phenanthrene-16-carbonitrile-(3-(tert-Butyl-dimethyl)silyl-16-cyano estrone) (CAB01044):

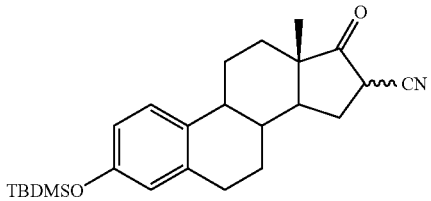

O,N-bistrifluoroacetyl-hydroxylamine (1.35 g, 6.0 mmol) was added to a solution of 3-(tert-butyl-dimethyl)silyl-16-hydroxymethylene estrone (820 mg, 2.0 mmol, CAB01042) and pyridine (1.0 mL) in toluene (50 mL). The mixture was heated to reflux for 1 hour (120° C. oil bath temperature) and then allowed to cool to room temperature (TLC-control). Ethyl acetate (50 mL) was added and the mixture was transferred into separation funnel, washed with water (50 mL) and brine (30 mL), dried over Na$_2$SO$_4$ and concentrated under reduced pressure. The residue was purified by column chromatography on silica (eluent: ethyl acetate/hexane 1:2, Rf: 0.38) to give a light yellow oil, which was dissolved in a small amount of acetone (2 mL) and precipitated by addition of hexane. The light yellow solid was filtered off and dried under high vacuum. Yield: 585 mg (71%), mixture of 16α-cyano and 16β-cyano diastereomers). $^1$H-NMR (CDCl$_3$, 400 MHz), δ: 0.19 (s, 6H), 0.98 (s, 9H, —C(CH$_3$)$_3$), 0.99 (s, ca. 1H, CH$_3$-group of minor isomer), 1.02 (s, ca. 2H, CH$_3$-group of major isomer), 1.40-1.71 (m, 5H), 1.94-2.10 (m, 3H), 2.23-2.34 (m, 1H), 2.38-2.48 (m, 1H), 2.54-2.64 (m, 1H), 2.82-2.90 (m, 2H), 3.12 (dd, J=9.8, 8.6 Hz, ca. 0.65 H, H-16 of major isomer), 3.58 (dd, J=10.2, 1.6 Hz, ca. 0.35 H, H-16 of minor isomer), 6.58 (d, J=2.3 Hz, 1H), 6.63 (dd, J=8.6, 2.3 Hz, 1H), 7.10 (d, J=8.6 Hz, 1H). LRMS (FAB+): 73.1 (100), 352.2 (65), 409.3 (85, [M]$^+$). LRMS (FAB-): 408.3 (100, [M-H]$^-$). HRMS (FAB+) 409.243294 C$_{25}$H$_{35}$NO$_2$Si requires 409.243708

3-(tert-Butyl-dimethyl-silanyloxy)-2-methoxy-13-methyl-17-oxo-7,8,9,11,12,13,14,15,16,17-decahydro-6H-cyclopenta[a]phenanthrene-16-carbonitrile (3-(tert-Butyl-dimethyl)silyl-2-methoxy-16-cyano estrone) (CAB01066):

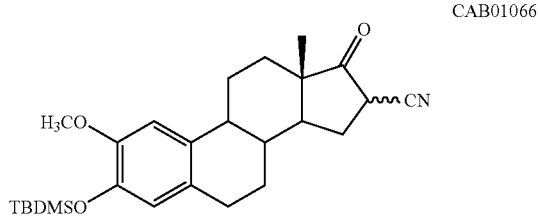

Sodium ethoxide (340 mg, 5.0 mmol) was added to a solution of 2-methoxy-3-tert-butyl-dimethyl)silyl estrone (829 mg, 2.0 mmol) and ethyl formate (2.0 mL) in toluene (20 mL). The mixture was stirred for 2 hours at room temperature (TLC-control) and acetic acid (1 mL) and ethyl acetate (60 mL) were added. The mixture was transferred into a separation funnel and washed with water (2×30 mL) and brine (30 mL). The organic layer was dried over Na$_2$SO$_4$ and concentrated under reduced pressure. The crude 2-methoxy-3-(tert-butyl-dimethylsilyl)-16-hydroxymethylene estrone (785 mg, 1.773 mmol), that was obtained was dissolved in toluene (50 mL) and pyridine (1 mL) and O,N-bistrifluoroacetyl-hydroxylamine (675 mg, 3.0 mmol) were added. The mixture was heated to reflux for 1 hour and then allowed to cool to room temperature (TLC-control). The reaction mixture was diluted with ethyl acetate (50 mL), transferred into a separation funnel, washed with water (2×50 mL) and brine (30 mL), dried over Na$_2$SO$_4$ and concentrated under reduced pressure. The residue was purified by column chromatography on silica (eluent: ethyl acetate/hexane 1:2, Rf: 0.38) to give a pale yellow solid, which was dissolved in a small amount of acetone (2 mL) and precipitated by addition of hexane. The light yellow solid was filtered off and dried under high vacuum. Yield: 620 mg (71%, ca. 2 to 1 mixture of 16α-cyano and 16β-cyano diastereomers). $^1$H-NMR (CDCl$_3$, 400 MHz), δ: 0.15 (s, 6H), 0.98 (s, 9H, —C(CH$_3$)$_3$), 0.99 (s, ca. 1H, CH$_3$-group of minor isomer), 1.08 (s, ca. 2H, CH$_3$-group of major isomer), 1.36-1.70 (m, 5H), 1.90-2.08 (m, 3H), 2.21-2.30 (m, 1H), 2.34-2.42 (m, 1H), 2.54-2.62 (m, 1H), 2.76-2.81 (m, 2H), 3.13 (dd, J=9.8, 8.6 Hz, ca. 0.65 H, H-16 of major isomer), 3.60 (dd, J=10.2, 1.6 Hz, ca. 0.35 H, H-16 of minor isomer), 3.77 (s, 3H, —OCH$_3$), 6.57 (s, 1H), 6.73 (s, 1H). LRMS (FAB+): 73.1 (100), 382.3 (65), 440.3 (20, [M+H]$^+$). LRMS (FAB-): 438.4 (100, [M-H]$^-$). HRMS (FAB+) 440.260025 C$_{26}$H$_{38}$NO$_3$Si requires 440.262098.

STX207 3-Hydroxy-13-methyl-17-oxo-7,8,9,11,12,13,14,15,16,17-decahydro-6H-cyclopenta[a]phenanthrene-16-carbonitrile (16-cyano-estrone, mixture of 16α and 16β diastereomers) (CAB01058):

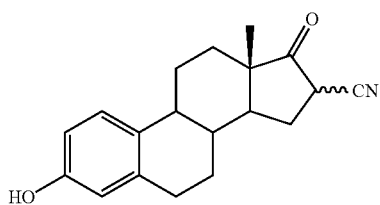

CAB01058

Tetrabutyl ammonium fluoride (1.0 mL, 1M in THF, 1.0 mmol) was added to a solution of 3-(tert-Butyl-dimethyl)silyl-16cyano estrone (350 mg, 0.856 mmol, CAB01044) in THF (20 mL) at 0° C. (icebath). The mixture was stirred for 30 minutes at this temperature, acetic acid (0.5 mL) and ethyl acetate (80 mL) were added and the mixture was transferred into a separation funnel. The organic phase was washed with water (2×25 mL) and brine (25 mL), dried over Na2SO4 and concentrated under reduced pressure. The solid residue was dissolved in ethyl acetate and precipitated by addition of hexane. The pale yellow solid was filtered off and dried under high vacuum. Yield: 223 mg (88%, ca. 2 to 1 mixture of 16α-cyano and 16β-cyano diastereomers). $^1$H-NMR (CDCl$_3$, 400 MHz), δ: 0.97 (s, ca. 1H, CH$_3$-group of minor isomer), 1.07 (s, ca. 2H, CH$_3$-group of major isomer), 1.36-1.70 (m, 5H), 1.90-2.16 (m, 3H), 2.22-2.34 (m, 1H), 2.38-2.46 (m, 1H), 2.56-2.62 (m, 1H), 2.85-2.92 (m, 2H), 3.12,(dd, J=9.8, 8.6 Hz, ca. 0.65 H, H-16 of major isomer), 3.60 (dd, J=10.2, 1.6 Hz, ca. 0.35 H, H-16 of minor isomer),4.76 (bs, 1H, —OH), 6.59 (d, J=2.3 Hz, 1H), 6.65 (dd, J=8.6, 2.3 Hz, 1H), 7.14 (d, J=8.6 Hz, 1H). LRMS (FAB+): 295.2 (100, [M+H]$^+$).

STX208 3-Hydroxy-2-methoxy-13-methyl-17-oxo-7,8,9,11,12,13,14,15,16,17-decahydro-6H-cyclopenta[a]phenanthrene-16-carbonitrile (2-methoxy-16-cyano-estrone, mixture of 16α and 16β diastereomers) (CAB01068).

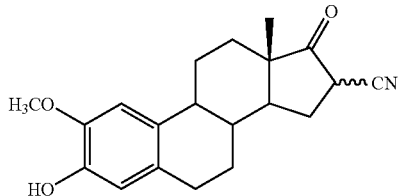

CAB01068

Tetrabutyl ammonium fluoride (1.0 mL, 1M in THF, 1.0 mmol) was added to a solution of 3-(tert-Butyl-dimethyl)silyl-2-methoxy-16-cyano estrone (440 mg, 1.0 mmol, CAB01066) in THF (20 mL) at 0° C. (icebath). The mixture was stirred for 30 minutes at this temperature, acetic acid (0.5 mL) and ethyl acetate (80 mL) were added and the mixture was transferred into a separation funnel. The organic phase was washed with water (2×25 mL) and brine (25 mL), dried over Na2SO4 and concentrated under reduced pressure. The solid residue was dissolved in ethyl acetate (ca. 2 mL) and precipitated by addition of hexane. The pale yellow solid was filtered off and dried under high vacuum. Yield: 233 mg (72%, ca. 2 to 1 mixture of 16α-cyano and 16β-cyano diastereomers). $^1$H-NMR (CDCl$_3$, 400 MHz), δ: 0.98 (s, ca. 1H, CH$_3$-group of minor isomer), 1.07 (s, ca. 2H, CH$_3$-group of major isomer), 1.38-1.68 (m, 5H), 1.92-2.12 (m, 3H), 2.24-2.32 (m, 1H), 2.38-2.44 (m, 1H), 2.54-2.62 (m, 1H), 2.74-2.86 (m, 2H), 3.13 (dd, J=9.8, 8.6 Hz, ca. 0.65 H, H-16 of major isomer), 3.60 (dd, J=10.2, 1.6 Hz, ca. 0.35 H, H-16 of minor isomer), 3.86 (s, 3H, —OCH$_3$), 5.48 (s, 1H, —OH), 6.57 (s, 1H), 6.73 (s, 1H). LRMS (FAB+): 325.3 (100, [M]$^+$). LRMS (FAB−): 324.3 (100, [M−H]$^-$). HRMS (FAB+): 325.168983 C$_{20}$H$_{23}$NO$_3$S requires 325.167794

STX209 Sulfamic acid 16-cyano-13-methyl-17-oxo-7,8,9,11,12,13,14,15,16,17-decahydro-6H-cyclopenta[a]phenanthren-3-yl ester (3-sulphamoyl-16-cyano-estrone, mixture of 16α and 16β diastereomers) (CAB01062):

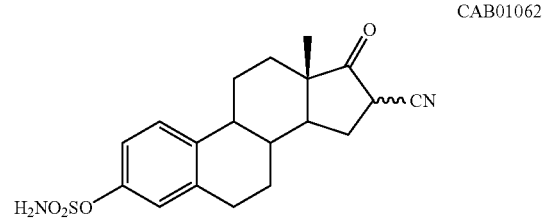

CAB01062

Sulphamoyl chloride solution (1.0 mL, 0.7M, 0.7 mmol) in toluene was concentrated under reduced pressure (30° C. waterbath temperature) to ca. 0.5 mL volume. The residue was cooled to 0° C. (icebath) and DMA (1.5 mL) was added to give a colourless solution. 16-cyano-estrone (89 mg, 0.30 mmol, CAB01058) was added at 0° C., the solution was allowed to warm to room temperature and was stirred overnight at this temperature. Ethyl acetate (50 mL) and water (25 mL) were added, the organic layer was separated and washed with water (2×25 mL) and brine (25 mL), dried over Na$_2$SO$_4$ and concentrated under reduced pressure. The residue was dissolved in acetone (ca. 2 mL) and precipitated by addition of hexane. The white solid was filtered off and dried under high vacuum. Yield: 94 mg (84%, ca. 2 to 1 mixture of 16α-cyano and 16β-cyano diastereomers). $^1$H-NMR (CDCl$_3$, 400 MHz), δ: 0.97 (s, ca. 1H, CH$_3$-group of minor isomer), 1.07 (s, ca. 2H, CH$_3$-group of major isomer), 1.42-1.70 (m, 5H), 1.94-2.18 (m, 3H), 2.26-2.38 (m, 1H), 2.40-2.48 (m, 1H), 2.56-2.64 (m, 1H), 2.88-3.00 (m, 2H), 3.14 (dd, J=9.8, 8.6 Hz, ca. 0.65 H, H-16 of major isomer), 3.60 (dd, J=10.2, 1.6 Hz, ca. 0.35 H, H-16 of minor isomer),4.92 (bs, 2H, —NH$_2$), 7.07 (d, J=2.3 Hz, 1H), 7.11 (dd, J=8.6, 2.3 Hz, 1H), 7.30 (d, J=8.6 Hz, 1H). LRMS (FAB+): 375.1 (100, [M]$^+$).

STX210 Sulfamic acid 16-cyano-2-methoxy-13-methyl-17-oxo-7,8,9,11,12,13,14,15,16,17-decahydro-6H-cyclopenta[a]phenanthren-3-yl ester (2-methoxy-3-sulphamoyl-16-cyano-estrone, mixture of 16α and 16β diastereomers) (CAB01070):

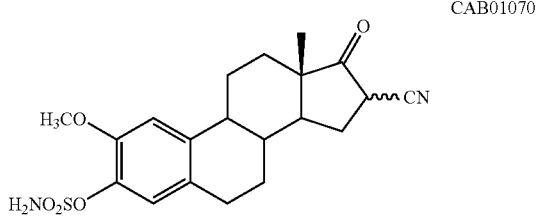

Sulphamoyl chloride solution (1.0 mL, 0.7M, 0.7 mmol) in toluene was concentrated under reduced pressure (30° C. waterbath temperature) to ca. 0.5 mL volume. The residue was cooled to 0° C. (icebath) and DMA (1.5 mL) was added to give a colourless solution. 2-methoxy-16-cyano-estrone (89 mg, 0.30 mmol, CAB01068) was added at 0° C., the solution was allowed to warm to room temperature and was stirred overnight at this temperature. Ethyl acetate (50 mL) and water (25 mL) were added, the organic layer was separated and washed with water (2×25 mL) and brine (25 mL), dried over Na$_2$SO$_4$ and concentrated under reduced pressure. The residue was dissolved in acetone (ca. 2 mL) and precipitated by addition of hexane. The white solid was filtered off and dried under high vacuum. Yield: 102 mg (82%, ca. 2 to 1 mixture of 16α-cyano and 16β-cyano diastereomers). $^1$H-NMR (CDCl$_3$, 400 MHz), δ: 0.98 (s, ca. 1H, CH$_3$-group of minor isomer), 1.07 (s, ca. 2H, CH$_3$-group of major isomer), 1.38-1.70 (m, 5H), 1.90-2.16 (m, 3H), 2.22-2.48 (m, 2H), 2.56-2.64 (m, 1H), 2.79-2.90 (m, 2H), 3.15 (dd, J=9.8, 8.6 Hz, ca. 0.65 H, H-16 of major isomer), 3.62 (dd, J=10.2, 1.6 Hz, ca. 0.35 H, H-16 of minor isomer), 3.88 (s, 3H, —OCH$_3$), 5.07 (s, 2H, —NH$_2$), 6.91 (s, 1H), 7.06 (s, 1H). LRMS (FAB+): 405.1 (100, [M]$^+$).

(3-Benzyloxy-13-methyl-17-oxo-6,7,8,9,11,12,13,14,15,17-decahydro-cyclopenta[a]phenanthren-16-ylidene)-hydroxy-acetic acid ethyl ester (CAB03048):

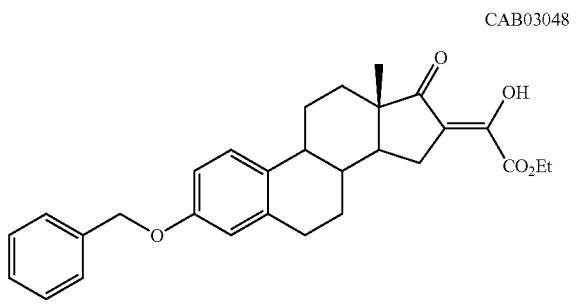

Potassium tert.-butoxide (2.24 g, 20.0. mmol) was added to a solution of 3-benzyl-estrone (5.77 g, 16.0 mmol) and diethyl oxalate (5 mL) in toluene (100 mL). The resulting clear yellow solution was stirred overnight at room temperature. Acetic acid (5 mL) was added (colour changes from dark yellow to light yellow), the mixture was transferred into a separation funnel and ethyl acetate (50 mL) and water (100 mL) were added. The organic layer was separated and washed with water (100 mL) and brine (50 mL), dried over Na$_2$SO$_4$ and concentrated under reduced pressure. The light yellow solid residue was suspended in ethanol (50 mL) and heated to reflux for 5 minutes. The colourless crystalline solid was filtered off after cooling to room temperature and dried under high vacuum. Yield: 7.28 g (99%). $^1$H-NMR (CDCl$_3$, 400 MHz), δ: 1.01 (s, 3H), 1.41 (t, J=7.0 Hz, 3H), 1.44-1.72 (m, 5H), 1.98-2.08 (m, 2H), 2.26-2.35 (m, 1H), 2.40-2.50 (m, 2H), 2.89-2.98 (m, 2H), 3.10 (dd, J=16.0, 5.9 Hz, 1H), 4.37 (q, J=7.0 Hz, 2H), 5.05 (s, 2H), 6.75 (d, J=2.7 Hz, 1H), 6.80 (dd, J=8.6, 2.7 Hz, 1H), 7.20 (d, J=8.6 Hz, 1H), 7.30-7.46 (m, 5H), 12.48 (S, 1H). LRMS (FAB+): 461.2 (100, [M+H]$^+$).

2-Benzyloxy-6α-methyl-4b,5,6, 6a,8,10,10a,10b,11,12-decahydro-7,8-diaza-pentaleno[2,1-a]phenanthrene-9-carboxylic acid ethyl ester (CAB03049).

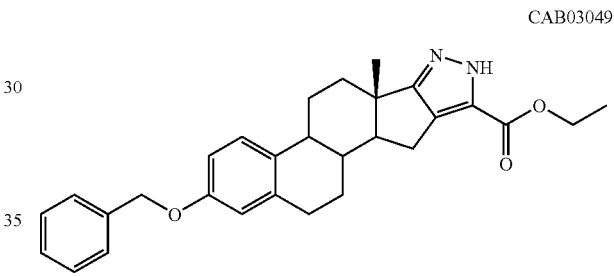

Hydrazine hydrate (0.75, ca. 15 mmol) was added to a suspension of (3-Benzyloxy-13-methyl-17-oxo-6,7,8,9,11,12,13,14,15,17-decahydro-cyclopenta[a]phenanthren-16-ylidene)-hydroxy-acetic acid ethyl ester (6.91 g, 15.0 mmol, CAB03048) in ethanol (100 mL) and dichloromethane (20 mL). The suspension turned into a clear, pale yellow solution after a few minutes, which was refluxed for 15 minutes and stirred overnight at room temperature. The solvents were removed under reduced pressure to give a white solid, which was dissolved in ethanol (50 mL) and p-toluene sulphonic hydrate (200 mg) was added. The mixture was heated to reflux for 5 minutes and transferred into a separation funnel after cooling to room temperature. Ethyl acetate (120 mL) and water (50 mL) were added, the organic layer was separated, washed with concentrated NaHCO$_3$-solution (30 mL) and brine (30 mL), dried over Na$_2$SO$_4$ and concentrated under reduced pressure. The residue was crystallised from ethyl acetate/hexane. Yield: 5.43 g (79%) fine colourless crystals. $^1$H-NMR (CDCl$_3$, 400 MHz), δ: 1.05 (s, 3H, —CH$_3$), 1.39 (t, J=7.0 Hz, 3H, OCH$_2$CH$_3$), 1.44-1.72 (m, 4H), 1.98-2.06 (m, 1H), 2.10-2.20 (m, 1H), 2.30-2.42 (m, 4H), 2.82-3.00 (m, 3H), 4.37 (q, J=7.0 Hz, 2H, OCH$_2$CH$_3$), 5.05 (s, 2H, OCH$_2$Ph), 6.73.(d, J=2.3 Hz, 1H), 6.81 (dd, J=8.6, 2.3 Hz, 1H), 7.23 (d, J=8.6 Hz, 1H), 7.30-7.46 (m, 5H) NH-proton not visible, probably very broad signal at 11 ppm. LRMS (FAB+): 457.4 (100, [M+H]$^+$).

2-Benzyloxy-6a-methyl-4b,5,6,6a,8,10,10a,10b,11, 12-decahydro-7,8-diaza-pentaleno[2,1-a]phenan-threne-9-carboxylic acid ethyl ester (CAB03051).

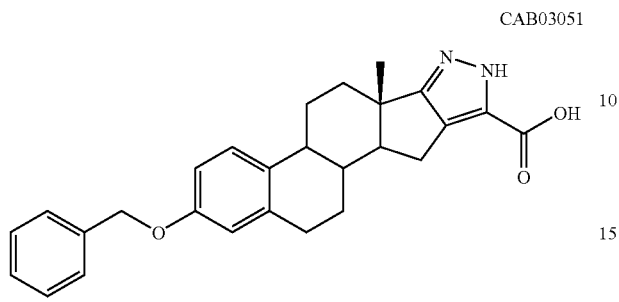

CAB03051

Sodium hydroxide solution (7.5 mL, 2N NaOH, 15 mmol) was added to a suspension of 2-Benzyloxy-6a-methyl-4b,5, 6,6a,8,10,10a,10b,11,12-decahydro-7,8-diaza-pentaleno[2, 1-a]phenanthrene-9-carboxylic acid ethyl ester (2.283 g, 5.0 mmol, CAB03049) in ethanol (40 mL). The mixture was heated to reflux for 30 minutes. Acetic acid (5 mL) was added after cooling to room temperature and the mixture was stirred for 2 hours, while the product precipitated. The product was filtered off, washed with water (50 mL) and ethanol (20 mL) and dried under high vacuum for 2 days. Yield: 2.130 g (99%) white powder. $^1$H-NMR (DMSO-d6, 400 MHz), δ: 0.95 (s, 3H, —CH$_3$), 1.36-1.82 (m, 5H), 1.88-1.98 (m, 1H), 2.00-2.10 (m, 1H), 2.12-2.20 (m, 1H), 2.26-2.46 (m, 4H), 2.70 (dd, J=14.6, 6.2 Hz, 1H), 2.80-2.94 (m, 2H), 5.06 (s, 2H, OCH$_2$Ph), 6.73 (d, J=2.3 Hz, 1H), 6.78 (dd, J=8.6, 2.3 Hz, 1H), 7.20 (d, J=8.6 Hz, 1H), 7.30-7.45 (m, 5H), 12.90 (bs, 2H, NH+OH). LRMS (FAB+): 429.2 (100, [M+H]$^+$).

STX782 2-Hydroxy-6a-methyl-4b,5, 6,6a,8,10,10a, 10b,11,12-decahydro-7,8-diaza-pentaleno[2,1-a] phenanthrene-9-carboxylic acid ethyl ester (CAB03052):

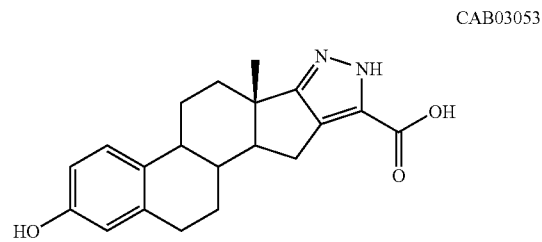

CAB03052

Palladium on charcoal (100 mg, 5%Pd) was added to a solution of 2-Benzyloxy-6a-methyl-4b,5,6,6a,8,10,10a,10b, 11,12-decahydro-7,8-diaza-pentaleno[2,1-a]phenanthrene-9-carboxylic acid ethyl ester (913 mg, 2.0 mmol, CAB03049) in THF (30 mL) and ethanol (30 mL). The resulting mixture was stirred under a hydrogen-atmosphere (balloon) for 72 hours, filtered through a 3 cm layer of celite and concentrated under reduced pressure. The residue was crystallised from acetone/cyclohexane. Yield: 602 mg (82%) pale yellow crystals. $^1$H-NMR (DMSO-d6, 400 MHz), δ: 0.92 (s, 3H, —CH$_3$), 1.12-2.84 (m, 16H), 4.14-4.40 (m, 2H, OCH$_2$CH$_3$), 6.45 (d, J=2.3 Hz, 1H), 6.50 (dd, J=8.6, 2.3 Hz, 1H), 7.05,(d, J=8.6 Hz, 1H), 9.01 (s, 1H, —OH), 13.07 (s, 1H, NH). LRMS (FAB+): 367.2 (100, [M+H]$^+$). HRMS (FAB+): 367.203796 C$_{22}$H$_{27}$N$_2$O$_3$ requires 367.202168

STX783 2-Hydroxy-6a-methyl-4b,5,6,6a,8,10,10a, 10b,11,12-decahydro-7,8-diaza-pentaleno[2,1-a] phenanthrene-9-carboxylic acid (CAB03053): ):

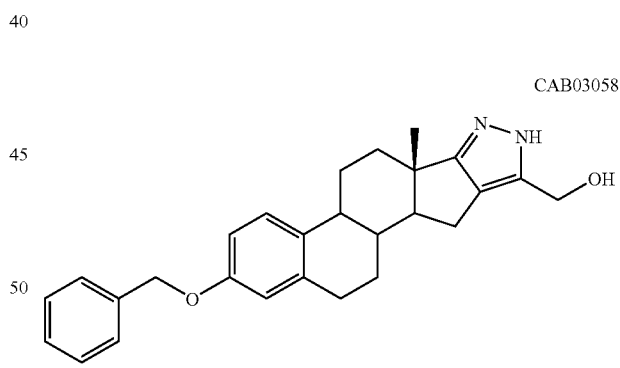

CAB03053

Palladium on charcoal (50 mg, 5% Pd) was added to a solution 2-Benzyloxy-6a-methyl-4b,5,6,6a,8,10,10a,10b,11, 12-decahydro-7,8-diaza-pentaleno[2,1-a]phenanthrene-9-carboxylic acid ethyl ester(214 mg, 0.5 mmol, CAB03051) in THF (15 mL) and ethanol (15 mL). The resulting mixture was stirred under a hydrogen-atmosphere (balloon) for 24 hours, filtered through a 3 cm layer of celite and concentrated under reduced pressure. The residue was dried under high vacuum. Yield: 165 mg (98%) light grey solid. $^1$H-NMR (DMSO-d6, 400 MHz), δ: 0.92 (s, 3H, —CH$_3$), 1.30-2.86 (m, 13H), 6.44 (d, J=2.3 Hz, 1H), 6.52 (dd, J=8.6, 2.3 Hz, 1H), 7.05 (d, J=8.6 Hz, 1H), 9.02 (s, 1H, —OH), 12.90 (bs, 2H, —COOH and NH). LRMS (FAB+): 176.0 (100), 329.1 (45, [M+H]$^+$). HRMS (FAB+): 339.171135 C$_{20}$H$_{23}$N$_2$O$_3$ requires 339.170868

(2-Benzyloxy-6a-methyl-4b,5,6,6a,8,10,10a,10b,11, 12-decahydro-7,8-diaza-pentaleno[2,1-a]phenan-thren-9-yl)-methanol (CAB03058):

CAB03058

2-Benzyloxy-6a-methyl-4b,5,6,6a,8,10,10a,10b,11,12-decahydro-7,8diaza-pentaleno[2,1-a]phenanthrene-9-carboxylic acid ethyl ester (457 mg, 1.0 mmol, CAB03049) was added to a suspension of LiAlH$_4$ (100 mg) in THF (20 mL). The mixture was stirred for 30 minutes at room temperature, then water (1 mL) was added (to destroy the excess of LiAlH$_4$). Stirring was continued for 1 hour (light yellowgreen suspension), acetic acid (0.5 mL) was added, the inorganic solids were filtered of and washed carefully with THF (ca. 50 mL).The combined organic layers were dried over Na$_2$SO$_4$ and concentrated under reduced pressure. The residue was crystallised from ethyl acetate/diethyl ether. Yield: 215 mg (52%) colorless crystals. $^1$H-NMR (CDCl$_3$, 400 MHz), δ:

1.01 (s, 3H, —CH$_3$), 1.40-2.46 (m, 10 H), 2.60 (dd, J=13.7, 6.3 Hz, 1H), 2.82-3.00 (m, 2H), 4.69 (s, 2H, —CH$_2$OH), 5.04 (s, 2H, —CH$_2$Ph), 6.28 (bs, 2H, —OH and NH), 6.73 (d, J=2.3 Hz, 1H), 6.80 (dd, J=8.6, 2.3 Hz, 1H), 7.21 (d, J=8.6 Hz, 1H), 7.30-7.45, (m, 5H). LRMS (FAB+): 91.1 (100), 415.3 (60, [M+H]$^+$). HRMS (FAB+): 415.238434 C$_{27}$H$_{31}$N$_2$O$_2$ requires 415.238554

STX804 9-Hydroxymethyl-6a-methyl-4b,5,6,6a,8,10,10a,10b,11,12-decahydro-7,8-diaza-pentaleno[2,1-a]phenanthren-2-ol (CAB03065):):

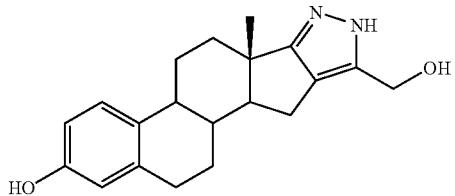

CAB03065

Palladium on charcoal (50 mg, 5% Pd) was added to a solution (2-Benzyloxy-6a-methyl-4b,5,6,6a,8,10,10a,10b,11,12-decahydro-7,8-diaza-pentaleno[2,1-a]phenanthren-9-yl)-methanol (120 mg, 0.289 mmol, CAB03058) in THF (20 mL) and ethanol (20 mL). The resulting mixture was stirred under a hydrogen-atmosphere (balloon) for 24 hours, filtered through a 3 cm layer of celite and concentrated under reduced pressure. The residue was dried under high vacuum. Yield: 93 mg (99%) white solid. $^1$H-NMR (DMSO-d6, 270 MHz), δ: 0.82 (s, 3H, —CH$_3$), 1.20-2.80 (m, 13H), 4.31 (s, 2H, —CH$_2$OH), 4.95 (bs, 1H, —OH), 6.37 (s, 1H), 6.44 (d, J=8.5 Hz, 1H), 6.97 (d, J=8.5 Hz, 1H), 8.92 (s, 1H, —OH), 11.78 (bs, 1H, NH). LRMS (FAB+): 3.25.2 (100, [M]$^+$). HRMS (FAB+): 325.192528 C$_{20}$H$_{25}$N$_2$O$_2$ requires 325.191603.

STX319 3-Hydroxy-13-methyl-16-pyridin-2-ylmethylene-6,7,8,9,11,12,13,14,15,16-decahydro-cyclopenta[a]phenanthren-17-one (CAB01150):

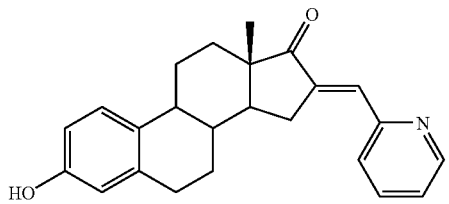

CAB01150

Sodium hydroxide (1.0 g, 25 mmol) was added to a suspension of estrone (1.35 g, 5.0 mmol) and pyridine-2-carbaldehyde (595 mg, 5.0 mmol) in ethanol (40 mL) at room temperature. The resulting dark orange solution was stirred at room temperature for 4 hours. Then glacial acetic (ca. 10 mL) acid was added with stirring. The colour changed to light yellow and a light yellow solid precipitated. The solid was filtered off and washed with water (50 mL), ethanol (20 mL), diethyl ether (50 mL) and hexane (50 mL) and dried under high vacuum. Yield: 1.638 g (91%) yellow powder.

$^1$H-NMR (DMSO-d6, 400 MHz), δ: 0.89 (s, 3H, —CH$_3$), 1.30-1.65 (m, 5H), 1.84-1.90 (m, 1H), 1.93-2.00 (m, 1H), 2.14-2.23 (m, 1H), 2.30-2.38 (m, 1H), 2.52-2.60 (m, 1H), 2.70-2.86 (m, 1H), 3.24-3.32 (m, 2H), 6.46 (d, J=2.3 Hz, 1H), 6.52 (dd, J=8.6, 2.3 Hz, 1H), 7.05 (d, J=8.6 Hz, 1H), 7.30 (s, 1H), 7.36 (dd, J=6.6, 4.7 Hz, 1H), 7.71 (d, J=7.8 Hz, 1H), 7.86 (dt, J=7.4, 1.6 Hz, 1H), 8.70 (d, J=3.9 Hz, 1H), 9.05 (s, 1H, —OH). LRMS (FAB+): 360.2 (100, [M+H]$^+$). LRMS (FAB−): 358.2 (100, [M—H]$^-$). HRMS (FAB+): 360.196640 C$_{24}$H$_{26}$NO$_2$ requires 360.196354.

C$_{24}$H$_{25}$NO$_2$ (359.46) calculated: C 80.19% H 7.01% N 3.90% found: C 79.8% H 7.00% N 3.92%

STX321 3-Hydroxy-13-methyl-16-pyridin-4-ylmethylene-6,7,8,9,11,12,13,14,15,16-decahydro-cyclopenta[a]phenanthren-17-one (CAB01154):

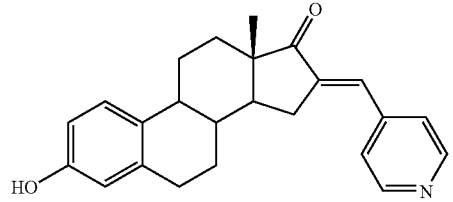

CAB01154

Sodium hydroxide (1.0 g, 25 mmol) was added to a suspension of estrone (1.35 g, 5.0 mmol) and pyridine-4-carbaldehyde (595 mg, 5.0 mmol) in ethanol (40 mL) at room temperature. The resulting dark orange solution was stirred at room temperature for 4 hours. Then glacial acetic (ca. 10 mL) acid was added with stirring. The colour changed to light yellow and a light yellow solid precipitated. The solid was filtered off and washed with water (50 mL), ethanol (20 mL), diethyl ether (50 mL) and hexane (50 mL) and dried under high vacuum. Yield: 1.588 g (88%) light yellow solid. $^1$H-NMR (DMSO-d6, 400 MHz), δ: 0.92 (s, 3H, —CH$_3$), 1.30-1.68 (m, 5H), 1.82-1.92 (m, 1H), 1.96-2.04 (m, 1H), 2.14-2.24 (m, 1H), 2.31-2.38 (m, 1H), 2.61-2.69 (m, 1H), 2.71-2.84 (m, 2H), 2.87-2.96 (m, 1H), 6.47 (d, J=2.3 Hz, 1H), 6.53 (dd, J=8.6, 2.3 Hz, 1H), 7.06 (d, J=8.6 Hz, 1H), 7.28 (s, 1H), 7.60 (d, J=6.2 Hz, 2H), 8.65 (d, J=6.2 Hz, 2H), 9.05 (s, 1H, —OH). LRMS (FAB+): 360.2 (100, [M+H]$^+$). LRMS (FAB−): 358.2 (100, [M−H]$^-$). HRMS (FAB+): 360.196986 C$_{24}$H$_{26}$NO$_2$ requires 360.196354.

C$_{24}$H$_{25}$NO$_2$ (359.46) calculated: C 80.19% H 7.01% N 3.90%.

found: C 80.1% H 6.90% N 3.96%

STX320 3-Hydroxy-13-methyl-16-pyridin-3-ylmethylene-6,7,8,9,11,12,13,14,15,16-decahydro-cyclopenta[a]phenanthren-17-one (CAB01156):

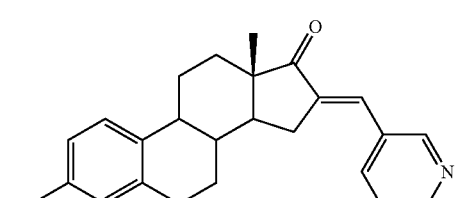

CAB01156

Sodium hydroxide (1.0 g, 25 mmol) was added to a suspension of estrone (1.35 g, 5.0 mmol) and pyridine-3-carbaldehyde (595 mg, 5.0 mmol) in ethanol (40 mL) at room temperature. The resulting dark orange solution was stirred at room temperature for 4 hours. Then glacial acetic (ca. 10 mL) acid was added with stirring. The colour changed to light yellow and a light yellow solid precipitated. The solid was filtered off and washed with water (50 mL), ethanol (20 mL), diethyl ether (50 mL) and hexane (50 mL) and dried under high vacuum. Yield: 1.6313 g (90%) yellow powder. $^1$H-NMR (DMSO-d6, 400 MHz), δ: 0.90 (s, 3H, —CH$_3$), 1.26-1.66 (m, 5H), 1.82-1.90 (m, 1H), 1.95-2.02 (m, 1H), 2.14-2.22 (m, 1H), 2.30-2.38 (m, 1H), 2.57-2.66 (m, 1H), 2.70-2.81 (m, 2H), 2.83-2.92 (m, 1H), 6.45 (d, J=2.3 Hz, 1H), 6.51 (dd, J=8.2, 2.3 Hz, 1H), 7.04 (d, J=8.2 Hz, 1H), 7.34 (s, 1H), 7.47 (dd, J=8.2, 5.1 Hz, 1H), 8.06 (d, J=8.2 Hz, 1H), 8.56 (dd, J=4.7, 1.2 Hz, 1H), 8.82 (d, J=1.6 Hz, 1H), 9,03 (s, 1H, —OH). LRMS (FAB+): 360.2 (100, [M+H]$^+$). LRMS (FAB−): 276.1 (100), 358.2 (90, [M−H]$^−$). HRMS (FAB+): 360.196434 C$_{24}$H$_{26}$NO$_2$ requires 360.196354

STX324 13-ethyl-16-pyridin-4-ylmethylene-7,8,9,11,12,13,14,15,16,17-decahydro-6H-cyclopenta[a]phenanthrene-3,17-diol (CAB01158):

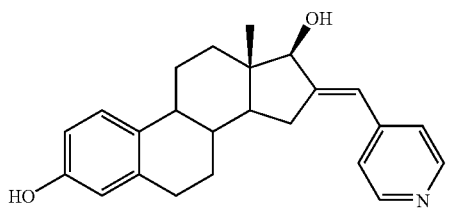

CAB01158

16-(pyridin-4-yl)methylene estrone (360 mg, 1.0 mmol, CAB01154) was dissolved in ethanol (20 mL) and THF (20 mL). The solution was cooled to 0° C. (icebath) and sodium borohydride (100 mg) was added. The reaction mixture was allowed to warm to room temperature and was stirred overnight at this temperature. The clear and colourless solution was concentrated under reduced pressure to ca. 20 mL volume and water (50 mL) was added. The product was filtered off and washed with water (50 mL), ethanol (20 mL) and diethylether (20 mL) and dried under high vacuum. Yield: 312 mg (86%) white powder. $^1$H-NMR (DMSO-d6, 400 MHz), δ: 0.58 (s, 3H, —CH$_3$), 1.30-1.40 (m, 5H), 1.84-1.98 (m, 2H), 2.12-2.34 (m, 3H), 2.64-2.78 (m, 3H), 3.97-4.03 (m, 1H, H-17), 5.30 (d, J=5.9 Hz, 1H, —OH), 6.38 (s, 1H) 6.44 (s, 1H), 6.50 (dd, J=8.2, 2.4 Hz, 1H), 7.03 (d, J=8.2 Hz, 1H), 7.33 (d, J=5.5 Hz, 2H), 8.47 (d, J=5.5 Hz, 2H), 9.00 (s, 1H, —OH). LRMS (FAB+): 362.2 (100, [M+H]$^+$).

STX322 13-Methyl-16-pyridin-2-ylmethylene-7,8,9,11,12,13,14,15,16,17-decahydro-6H-cyclopenta[a]phenanthrene-3,17-diol (CAB01160):

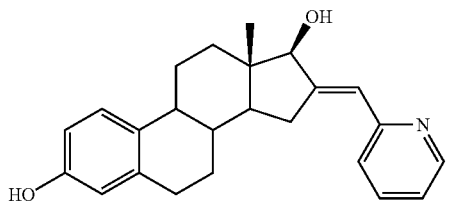

CAB01160

16-(pyridin-2-yl)methylene estrone (360 mg, 1.0 mmol, CAB01150) was dissolved in ethanol (20 mL) and THF (20 mL). The solution was cooled to 0° C. (icebath) and sodium borohydride (100 mg) was added. The reaction mixture was allowed to warm to room temperature and was stirred overnight at this temperature. The clear and colourless solution was concentrated under reduced pressure to ca. 20 mL volume and water (50 mL) was added. The product was filtered off and washed with water (50 mL), methanol (20 mL) and diethylether (50 mL) and dried under high vacuum. Yield: 328 mg (91%) white powder. $^1$H-NMR (DMSO-d6, 400 MHz), δ: 0.58 (s, 3H, —CH$_3$), 1.23-1.45 (m, 5H), 1.81-1.92 (m, 2H), 2.10-2.18 (m, 1H), 2.23-2.37 (m, 2H), 2.66-2.89 (m, 3H), 3.97-4.03 (m, 1H, H-17), 5.21 (d, J=5.9 Hz, 1H, —OH), 6.41 (d, J=1.3 Hz, 1H), 6.48-6.51 (m, 2H), 7.04(d, J=8.6 Hz, 1H), 7.11 (dd, J=7.0, 4.7 Hz, 1H), 7.34 (d, J=7.8 Hz, 1H), 7.69 (dt, J=7.8, 2.0 Hz, 1H), 8.53 (d, J=3.5 Hz, 1H), 9.00 (s, 1H, —OH). LRMS (FAB+): 362.2 (100, [M+H]$^+$). LRMS (FAB−): 360.2 (1000, [M−H]$^−$).

STX323 13-Methyl-16-pyridin-3-ylmethylene-7,8,9,11,12,13,14,15,16,17-decahydro-6H-cyclopenta[a]phenanthrene-3,17-diol (CAB01162):

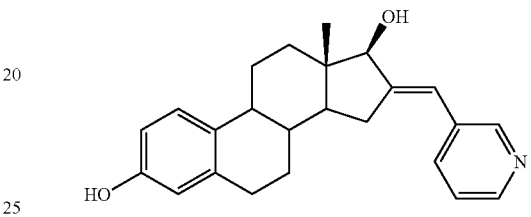

CAB01162

16-(pyridin-3-yl)methylene estrone (360 mg, 1.0 mmol, CAB01156) was dissolved in ethanol (20 mL) and THF (20 mL). The solution was cooled to 0° C. (icebath) and sodium borohydride (100 mg) was added. The reaction mixture was allowed to warm to room temperature and was stirred overnight at this temperature. The clear and colourless solution was concentrated under reduced pressure to ca. 20 mL volume and water (50 mL) was added. The product was filtered off and washed with water (50 mL), methanol (20 mL) and diethylether (50 mL) and dried under high vacuum. Yield: 333 mg (92%) white powder. $^1$H-NMR (DMSO-d6, 400 MHz), δ: 0.58 (s, 3H, —CH$_3$), 1.15-1.43 (m, 5H), 1.83-1.96 (m, 2H), 2.12-2.31 (m, 3H), 2.62-2.80 (m, 3H), 3.99 (bs, 1H, H-17), 5.25 (bs, 1H, —OH), 6.41 (d, J=2.0 Hz, 1H), 6.43 (d, J=2.3 Hz, 1H), 6.49 (dd, J=8.6, 2.3 Hz, 1H), 7.04 (d, J=8.6 Hz, 1H), 7.34 (dd, J=8.2, 5.1 Hz, 1H), 7.80 (d, J=8.2 Hz, 1H), 8.36 (dd, J=4.7, 1.2 Hz, 1H), 8.56 (d, J=2.0 Hz, 1H), 9.00 (bs, 1H, —OH). LRMS (FAB+): 362.2 (100, [M+H]$^+$). LRMS (FAB−): 360.2 (1000, [M−H]$^−$). HRMS (FAB+): 362.211723 C$_{24}$H$_{28}$NO$_2$ requires 362.212004

STX452 Sulfamic acid 13-methyl-17-oxo-16-pyridin-4-ylmethylene-7,8,9,11,12,13,14,15,16,17-decahydro-6H-cyclopenta[a]phenanthren-3-yl ester (CAB02078):

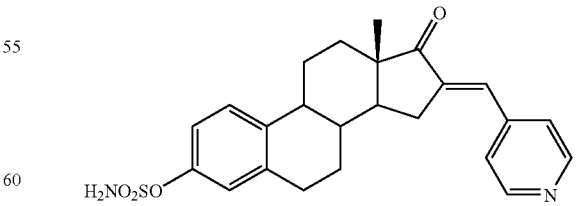

CAB02078

A solution of sulphamoyl chloride (5 mL, 0.7M, 3.5 mmol) in toluene was concentrated under reduced pressure (water-bath temperature 30° C.). The residue was cooled to 0° C. and DMA (5 mL) was added. The resulting colourless solution was stirred for 5 minutes and 16-(pyridin-4-yl)methylene estrone (360 mg, 1.0 mmol, CAB01154) was added. The mixture was stirred overnight at room temperature and the product was precipitated by addition of diethyl ether (20 mL) and ethyl acetate (20 mL). The yellow solid was filtered off and purified by heating it with acetone (30 mL) to reflux (the product did not dissolve completely). After cooling to room temperature the solid was filtered off and dried under high vacuum. Yield: 341 mg (78%) yellow powder. $^1$H-NMR (DMSO-d6, 400 MHz), δ: 0.94 (s, 3H, —CH$_3$), 1.37-1.70 (m, 5H), 2.01-2.06 (m, 1H), 2.29-2.34 (m, 1H), 2.41-2.48 (m, 2H), 2.73-3.02 (m, 4H), 6.98 (d, J=1.8 Hz, 1H), 7.02 (dd, J=8.4, 1.8 Hz, 1H), 7.34 (d, J=8.4 Hz, 1H), 7.45 (s, 1H), 7.92 (s, 2H, —NH$_2$), 8.18 (d, J=6.2 Hz, 2H), 8.89 (d, J=6.2 Hz, 2H). LRMS (FAB+): 439.1 (100, [M+H$^1$]).

STX453 Sulfamic acid 13-methyl-17-oxo-16-pyridin-3-ylmethylene-7,8,9,11,12,13,14,15,16,17-decahydro-6H-cyclopenta[a]phenanthren-3-yl ester (CAB02085):

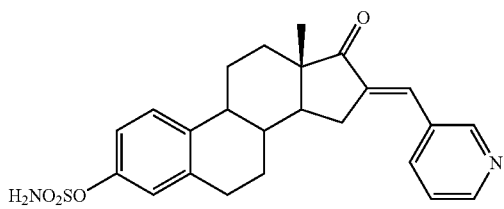

CAB02085

A solution of sulphamoyl chloride (5 mL, 0.7M, 3.5 mmol) in toluene was concentrated under reduced pressure (water-bath temperature 30° C.). The residue was cooled to 0° C. and DMA (8 mL) was added. The resulting colourless solution was stirred for 5 minutes and 16-(pyridin-3-yl)methylene estrone (360 mg, 1.0 mmol, CAB01156) was added. The mixture was stirred overnight at room temperature and the product was precipitated by addition of diethyl ether (20 mL) and ethyl acetate (20 mL). The yellow solid was filtered off and purified by heating it with acetone (30 mL) to reflux (the product did not dissolve completely). After cooling to room temperature the solid was filtered off and dried under high vacuum. Yield: 333 mg (76%) yellow powder. $^1$H-NMR (DMSO-d6, 400 MHz) δ: 0.93 (s, 3H, —CH$_3$), 1.34-1.74 (m, 5H), 1.86-1.96 (m, 1H), 2.00-2.09 (m, 1H), 2.26-2.36 (m, 1H), 2.38-2.46 (m, 1H), 2.66-2.76 (m, 1H), 2.82-3.00 (m, 3H), 6.99 (d, J=2.3 Hz, 1H), 7.02 (dd, J=8.6, 2.3 Hz, 1H), 7.35 (d, J=8.6 Hz, 1H), 7.45 (s, 1H), 7.94 (s, 2H, —NH$_2$), 8.01 (dd, J=8.2, 5.5 Hz, 1H), 8.68 (d, J=8.2 Hz, 1H), 8.83 (d, J=5.5 Hz, 1H), 9.12 (s, 1H). LRMS (FAB+): 439.1 (100, [M+H]$^+$).

STX474 16-Furan-2-ylmethylene-3-hydroxy-13-methyl-6,7,8,9,11,12,13,14,15,16-decahydro-cyclopenta[a]phenanthren-17-one (CAB02072):

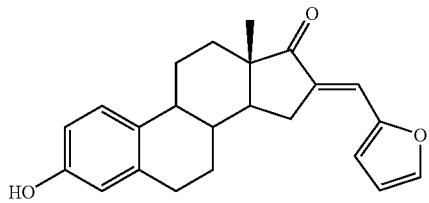

CAB02072

Potassium hydroxide (2.0 g) was added to a suspension of estrone (2.704 g, 10 mmol) and furfuraldehyde (2 mL, ca. 20 mmol) in ethanol (40 mL). The resulting dark brown solution was stirred for 4 hours at room temperature, then acetic acid (5 mL) and water (5 ml) were added. After a few minutes the product started to precipitate. The precipitation was completed by addition of more water (ca. 10 mL). The yellow solid was filtered off, washed with water, dissolved in chloroform and dried over Na$_2$SO$_4$. The solvent was removed under reduced pressure and the residue was crystallised from ethyl acetate/hexane. Yield: 3.24 g (93%) light yellow crystals. $^1$H-NMR (CDCl$_3$, 400 MHz) δ: 0.97 (s, 3H, —CH$_3$), 1.42-1.76 (m, 5H), 2.00-2.20 (m, 2H), 2.22-2.35 (m, 1H), 2.36-2.51 (m, 2H), 2.82-3.00 (m, 2H), 3.14 (ddd, J=15.2, 6.6, 1.6 Hz, 1H), 5.08 (s, 1H, —OH),6.52 (dd, J=3.1, 1.6 Hz, 1H),6.62 (d, J=2.7 Hz, 1H),6.64-6.70 (m, 2H),7.16 (d, J=8.2 Hz, 1H), 7.22-7.27 (m, 1H), 7.57 (d, J=1.6 Hz, 1H). LRMS (FAB+): 349.2 (100, [M+H]$^+$).

STX475 3-Hydroxy-13-methyl-16-thiophen-2-ylmethylene-6,7,8,9,11,12,13,14,15,16-decahydro-cyclopenta[a]phenanthren-17-one (CAB02073):

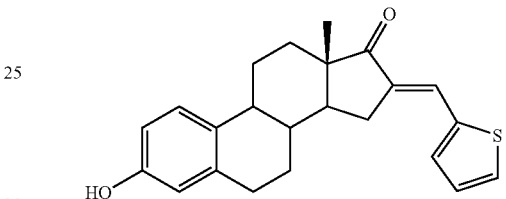

CAB02073

Potassium hydroxide (2.0 g) was added to a suspension of estrone (1.352 g, 5.0 mmol) and thiophene-2-carboxaldehyde (561 mg, 5.0 mmol) in ethanol (40 mL). The resulting dark brown solution was stirred for 4 hours at room temperature, then acetic acid (5 mL) and water (5 ml) were added, the product started to precipitate after a few minutes and was filtered off, washed with water (20 mL), ethanol (10 mL) and diethyl ether (10 mL) and dried under high vacuum. Yield: 1.614 g (89%) yellow solid. $^1$H-NMR (CDCl$_3$, 400 MHz) δ: 0.98 (s, 3H, —CH$_3$), 1.44-1.78 (m, 5H), 2.02-2.14 (m, 2H), 2.26-2.46 (m, 3H), 2.84-3.02 (m, 3H), 4.98 (s, 1H, —OH), 6.62 (d, J=2.7 Hz, 1H), 6.67 (dd, J=8.6, 2.7 Hz, 1H), 7.14 (dd, J=5.1, 3.5 Hz, 1H), 7.17 (d, J=8.6 Hz, 1H), 7.35 (d, J=3.5 Hz, 1H), 7.53 (d, J=5.1 Hz, 1H), 7.67 (s, 1H). LRMS (FAB+): 365.2 (100, [M+H]$^+$).

STX507 13-Methyl-16-thiophen-2-ylmethylene-7,8,9,11,12,13,14,15,16,17-decahydro-6H-cyclopenta[a]phenanthrene-3,17-diol (CAB02076):

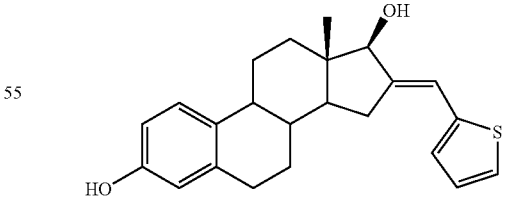

CAB02076

Sodium borohydride (100 mg) was added to a solution of 16-(thiophenen-2-yl)methylene estrone (365 mg, 1.0 mmol, CAB02073) in THF (20 mL) and ethanol (40 mL) at 0° C. The solution was stirred overnight at room temperature and concentrated under reduced pressure. The residue was dissolved in ethyl acetate (40 mL), the organic layer was washed with water (40 mL) and brine (20 mL), dried over NA2SO4 and concentrated under reduced pressure. The white crude product was crystallised from ethyl acetate/hexane. Yield: 208 mg (57%) colourless crystals. $^1$H-NMR (CDCl$_3$, 400 MHz) δ: 0.71 (s, 3H, —CH$_3$), 1.38-1.58 (m, 6H), 1.98-2.06 (m, 2H), 2.12-2.22 (m, 1H), 2.26-2.40 (m, 2H), 2.68 (dd, J=16.9, 6.6 Hz, 1H), 2.82-2.92 (m, 2H), 4.17 (d, J=9.4 Hz, 1H, H-17), 4.56 (s, 1H, —OH), 6.59 (d, J=2.3 Hz, 1H), 6.64 (dd, J=8.6, 2.3 Hz, 1H), 6.81 (d, J=2.3 Hz, 1H), 7.00-7.06 (m, 2H), 7.18 (d, J=8.6 Hz, 1H), 7.27 (d, J=4.7 Hz, 1H). LRMS (FAB+): 366.2 (100, [M]$^+$).

STX476 3-Hydroxy-13-methyl-16-(4-nitro-benzylidene)-6,7,8,9,11,12,13,14,15,16-decahydro-cyclopenta[a]phenanthren-17-one (CAB02142):

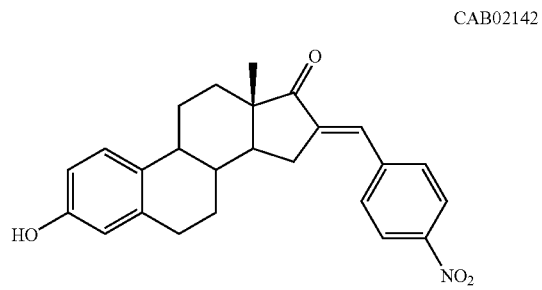

Potassium hydroxide (2.0 9) was added to a suspension of estrone (1.352 g, 5.0 mmol) and 4-nitro-benzaldehyde (755 mg, 5.0 mmol) in ethanol (80 mL). The resulting dark brown solution was stirred for 4 hours at room temperature, then acetic acid (5 mL) and water (5 ml) were added (colour changes to orange). The product precipitated and was filtered off, washed with water (50 mL), ethanol (50 mL) and diethyl ether (50 mL) and dried under high vacuum. Yield: 1.682 g (83%) yellow solid. $^1$H-NMR (DMSO-d6, 400 MHz), δ: 0.93 (s, 3H, —CH$_3$), 1.30-1.68 (m, 5H), 1.86-1.92 (m, 1H), 1.96-2.04 (m, 1H), 2.16-2.24 (m, 1H), 2.32-2.39 (m, 1H), 2.62-2.82 (m, 2H), 2.88-2.96 (m 1H), 6.46 (d, J=2.3 Hz, 1H), 6.52 (dd, J=8.6, 2.3 Hz, 1H), 7.06 (d, J=8.6 Hz, 1H), 7.42 (s, 1H), 7.92 (d, J=8.6 Hz, 2H), 8.27 (d, J=8.6 Hz, 2H), 9.04 (s, 1H, —OH). LRMS (FAB+): 404.1 (100, [M+H]$^+$).

STX478 4-(3-Hydroxy-13-methyl-17-oxo-6,7,8,9,11,12,13,14,15,17-decahydro-cyclopenta[a]phenanthren-16ylidenemethyl)-benzonitrile (CAB02144):

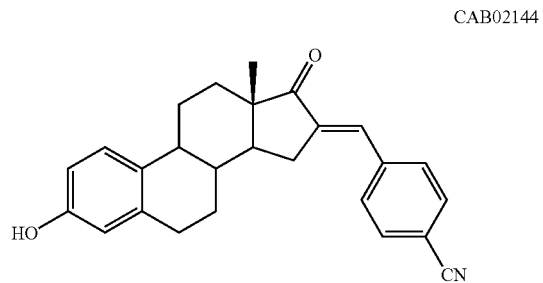

Potassium hydroxide (2.0 g) was added to a suspension of estrone (1:352 g, 5.0 mmol) and 4-cyano-benzaldehyde (655 mg, 5.0 mmol) in ethanol (40 mL). The resulting orange solution was stirred for 4 hours at room temperature, then acetic acid (5 mL) and water (5 ml) were added (colour changes to yellow). The product precipitated and was filtered off, washed with water (50 mL), ethanol (50 mL) and diethyl ether (50 mL) and dried under high vacuum. Yield: 1.795 g (94%) pale yellow solid. $^1$H-NMR (DMSO-d6, 400 MHz). δ: 0.91 (s, 3H, —CH$_3$), 1.30-1.66 (m, 5H), 1.82-1.90 (m, 1H), 1.94-2.02 (m, 1H), 2.14-2.22 (m, 1H), 2.30-2.38 (m, 1H), 2.58-2.92 (m, 3H), 6.45 (d, J=2.3 Hz, 1H), 6.51 (dd, J=8.6, 2.3 Hz, 1H), 7.04 (d, J=8.6 Hz, 1H), 7.36 (s, 1H), 7.82 (d, J=8.6 Hz, 2H), 7.90 (d, J=8.6 Hz, 2H), 9.03 (s, 1H, —OH). LRMS (FAB+): 384.1 (100, [M+H]$^+$). LRMS (FAB-): 383.2 (100, [M]$^-$).

STX508 13-Methyl-16-(4-nitro-benzylidene)-7,8,9,11,12,13,14,15,16,17-decahydro-6H-cyclopenta[a]phenanthrene-3,17-diol (CAB02155):

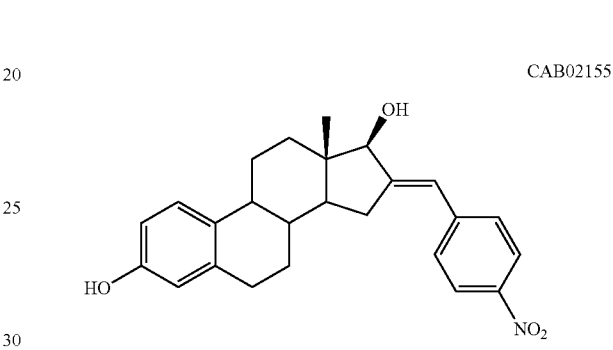

Sodium borohydride (100 mg) was added to a solution of 16-(4'-nitrophenyl)methylene estrone (404 mg, 1.0 mmol, CAB02142) in THF (20 mL) and ethanol (20 mL) at 0° C. The solution was stirred overnight at room temperature and concentrated under reduced pressure to ca 10 mL volume. Water (50 mL) was added to the mixture, the precipitate was filtered off, washed with water (50 mL), ethanol (50 mL) and diethyl ether (50 mL) and dried under high vacuum. Yield: 401 mg (99%) pale yellow solid. $^1$H-NMR (DMSO-d6, 400 MHz), δ: 0.60 (s, 3H, —CH$_3$), 1.22-1.46 (m, 5H), 1.84-1.96 (m, 2H), 2.16-2.32 (m, 3H), 2.62-2.80 (m, 3H), 4.02 (bs, 1H, H-17), 5.36 (d, J=5.9 Hz, 1H, —OH), 6.44 (d, J=2.3 Hz, 1H), 6.52 (dd, J=8.6, 2.3 Hz, 1H), 6.56 (d, J=2.3 Hz, 1H), 7.05 (d, J=8.6 Hz, 1H), 7.65 (d, J=9.0 Hz, 2H), 8.18 (d, J=9.0 Hz, 1H), 9.02 (s, 1H, —OH). LRMS (FAB+): 405.2 (100, [M]$^+$).

STX510 4-(3,17-Dihydroxy-13-methyl-6,7,8,9,11,12,13,14,15,17-decahydro-cyclopenta[a]phenanthren-16-ylidenemethyl)-benzonitrile (CAB02157):

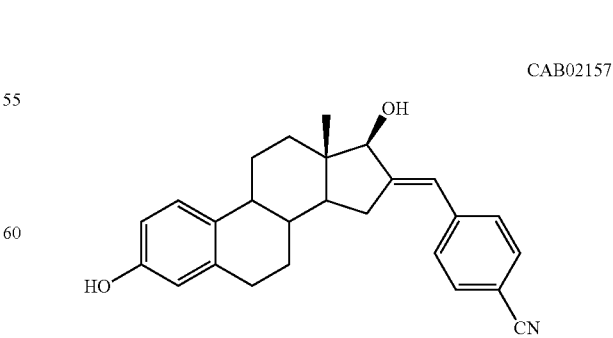

Sodium borohydride (100 mg) was added to a solution of 16-(4'-cyano-phenyl)methylene estrone (384 mg, 1.0 mmol, CAB02144) in THF (20 mL) and ethanol (20 mL) at 0° C. The solution was stirred overnight at room temperature and concentrated under reduced pressure to ca 10 mL volume. Water (50 mL) was added to the mixture, the precipitate was filtered off, washed with water (50 mL), ethanol (30 mL) and diethyl ether (50 mL) and dried under high vacuum. Yield: 366 mg (95%) white solid. $^1$H-NMR (DMSO-d6, 400 MHz), δ: 0.60 (s, 3H, —CH$_3$), 1.30-1.42 (m, 5H), 1.84-1.96 (m, 2H), 2.14-2.34 (m, 3H), 2.65-2.79 (m, 3H), 3.98-4.02 (m, 1H, H-17), 5.31 (d, J=5.9 Hz, 1H, —OH), 6.44 (d, J=2.3 Hz, 1H), 6.49-6.52 (m, 2H), 7.05 (d, J=8.6 Hz, 1H), 7.57 (d, J=9.0 Hz, 2H), 7.78 (d, J=9.0 Hz, 1H), 9.01 (s, 1H, —OH). LRMS (FAB+): 385.2 (100, [M]$^+$).

[3-(tert-Butyl-dimethyl-silanyloxy)-13-methyl-17-oxo-6,7,8,9,11,12,13,14,15,17-decahydro-cyclopenta [a]phenanthren-16-ylidene]-hydroxy-acetic acid ethyl ester (CAB01072).

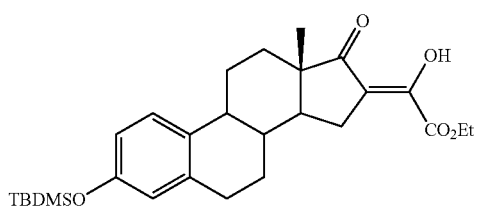

CAB01072

Sodium ethoxide (340 mg, 5.0 mmol) was added to a solution of 3-O-TBDMS-estrone (700 mg, 1.82 mmol) and diethyl oxalate (1.0 ml) in toluene (20 ml). The resulting yellow solution was stirred for 2 hours at room temperature (TLC-control). The solution was transferred into a separation funnel and ethyl acetate (50 ml) and 6N hydrochloric acid (20 ml) were added. Intensive shaking resulted in a nearly colourless organic layer, which was separated and dried over sodium sulphate and concentrated under reduced pressure. The residue was crystallised from ethanol. Yield: 737 mg (83%) colourless crystals. $^1$H-NMR (CDCl$_3$, 400 MHz) δ: 0.19 (s, 6H), 0.98 (s, 9H, —C(CH$_3$)$_3$), 1.00 (s, 3H), 1.40 (t, J=7.2 Hz, 3H), 1.43-1.71 (m, 5H), 1.98-2.06 (m, 2H), 2.24-2.34 (m, 1H), 2.38-2.46 (m, 2H), 2.82-2.90 (m, 2H), 3.08 (dd, J=16.0, 6.0 Hz, 1H), 4.36 (q, J=7.2 Hz, 2H), 6.57 (d, J=2.3 Hz, 1H), 6.63 (dd, J=8.6, 2.3 Hz, 1H), 7.11 (d, J=8.6 Hz, 1H), 12.47 (bs, 1H). LRMS (FAB+): 73.1 (61), 485.3 (100, [M+H]$^+$). LRMS (FAB−): 483.2 (100, [M−H]$^-$). HRMS (FAB+) 484.263771 C$_{28}$H$_{40}$O$_5$Si requires 484.264503

Hydroxy-(3-hydroxy-13-methyl-17-oxo-6,7,8,9,11,12,13,14,15,17-decahydro-cyclopenta[a]phenanthren-16-ylidene)-acetic acid ethyl ester (CAB01096, STX330).

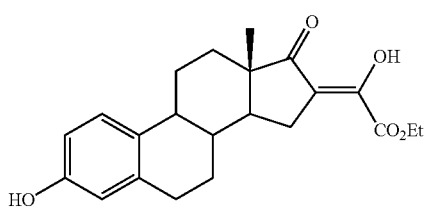

CAB01096

Tetrabutylammonium fluoride (1.5 ml, 1.5 mmol, 1M solution in THF) was added to a solution of [3-(tert-Butyl-dimethyl-silanyloxy)-13-methyl-17-oxo-6,7,8,9,11,13,14,15,17-decahydro-cyclopenta[a]phenanthren-16-ylidene-hydroxy-acetic acid ethyl ester (485 mg, 1.0 mmol, CAB01072) in THF (25 ml) at 0° C. (icebath). The resulting yellow solution was stirred for 1 h at this temperature, and then glacial acetic acid (1 ml) and ethyl acetate (75 ml) were added. The mixture was transferred into a separation funnel, washed with water (3×25 ml) and brine (25 ml), dried over sodium sulphate and concentrated under reduced pressure. The residue was crystallised from ethyl acetate/hexane. Yield: 303 mg (82%) colourless crystals. $^1$H-NMR (CDCl$_3$, 400 MHz) δ: 1.00 (s, 3H), 1.40 (t, J=7.2 Hz, 3H), 1.42-1.70 (m, 2H), 2.22-2.32 (m, 1H), 2.36-2.48 (m, 2H), 2.83-2.91 (m, 2H), 3.09 (dd, J=16.0, 6.0 Hz, 4.36 (q, J=7.2 Hz, 2H), 4.61 (bs, 1H, —OH), 6.59 (d, J=2.3 Hz, 1H), 6.64 (dd, J=8.2, 2.3 Hz, 1H), 7.14 (d, J=8.2 Hz, 1H), 12.47 (bs, 1H, —OH). $^{13}$C-NMR (CDCl$_3$, 100 MHz), δ: 14.2, 15.0, 25.9, 26.7, 27.5, 29.4, 31.1, 37.7, 43.9, 48.8, 49.4, 62.2, 112.8, 115.2, 116.5, 126.2, 131.6, 134.0, 137.7, 152.4, 153.4, 162.6, 216.7. LRMS (FAB+): 370.2 (100, [M+H]$^+$).

16-Benzylidene-3-hydroxy-13-methyl-6,7,8,9,11,12,13,14,15,16-decahydro-cyclopenta[a]phenanthren-17-one (CAB01122, STX312).

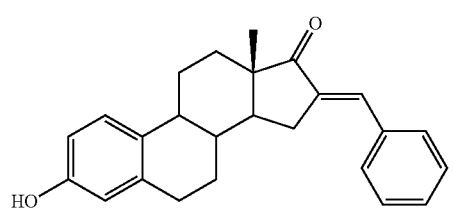

CAB01122

Potassium hydroxide (1.0 g) was added to a solution of estrone (1.350 g, 5.0 mmol) and benzaldehyde (1.0 g, 9.4 mmol) in methanol (50 ml) at room temperature. The resulting orange solution was stirred at this temperature for 4 h. Then glacial acetic acid (ca. 5 ml) was added with stirring. The colour changed to light yellow and a white solid precipitated. The solid was filtered off and washed with water (50 ml), methanol (20 ml), diethyl ether (50 ml) and hexane and dried under high vacuum. Yield 1.578 g (88%). H-NMR (CDCl$_3$, 400 MHz), δ: 1.00 (s, 3H), 1.40-1.77 (m, 5H), 2.04-2.12 (m, 2H), 2.26-2.34 (m, 1H), 2.38-2.45 (m, 1H), 2.50-2.60 (m, 1H) 2.86-3.03 (m, 3H), 4.76 (s, 1H, —OH), 6.60 (d, J=2.3 Hz, 1H), 6.66 (dd, J=8.2, 2.3 Hz, 1H), 7.17 (d, J=8.2 Hz, 1H), 7.34-7.45 (m, 3H), 7.48 (s, 1H), 7.54-7.59 (m, 2H). LRMS (FAB+): 359.2 (100, [M+H]$^+$). LRMS (FAB−): 357.2 (100, [M−H]$^-$). HRMS (FAB+) 359.202332 C$_{25}$H$_{27}$O$_2$ requires 359.201105

3-Hydroxy-13-methyl-16-(3,4,5-trimethoxy-benzylidene)-6,7,8,9,11,12,13,14,15,16-decahydro-cyclopenta[a]phenanthren-17-one (CAB01124, STX328).

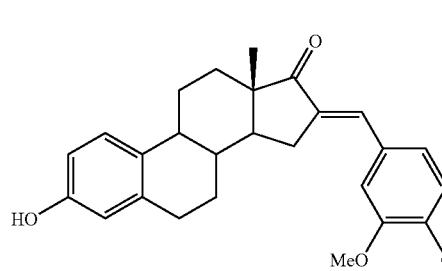

CAB01124

Potassium hydroxide (1.0 g) was added to a solution of estrone (1.350 g, 2.0 mmol) and 3,4,5-trimethoxybenzaldehyde (1.00 g, 5.10 mmol) in ethanol (50 ml) at room temperature. The resulting dark brown solution was stirred at this temperature for 4 h, then glacial acetic acid (ca. 2.5 ml) was added with stirring. The colour changed to yellow and a white solid precipitated. The solid was filtered off and washed with water (50 ml), ethanol (20 ml), diethyl ether (50 ml) and hexane and recrystallised from ethanol. Yield: 2.063 g (92%) light yellow crystals. $^1$H-NMR (CDCl$_3$, 400 MHz), δ: 1.00 (s, 3H), 1.40-1.78 (m, 5H), 2.00-2.11 (m, 2H), 2.26-2.34 (m, 1H), 2.38-2.56 (m, 2H), 2.84-3.04 (m, 3H), 3.90 (s, 3H), 3.91 (s, 6H), 4.93 (s, 1H, —OH), 6.60 (d, J=2.3 Hz, 1H), 6.66 (dd, J=8.2, 2.3 Hz, 1H), 6.80 (s, 2H), 7.17 (d, J=8.2 Hz, 1H), 7.40 (s, 1H). $^{13}$C-NMR (CDCl$_3$, 100 MHz), δ: 15.0, 26.4, 27.2, 29.4, 32.1, 38.4, 44.4, 48.2, 49.0, 56.6, 61.3, 108.2, 113.2, 115.6, 126.6, 131.3, 131.9, 133.9, 135.2, 137.9, 139.7, 153.4, 154.0, 209.9. LRMS (FAB+): 449.3 (100, [M+H]$^+$). LRMS (FAB−): 447.3 (100, [M−H]$^-$). HRMS (FAB+): 448.223763.

C$_{28}$H$_{32}$O$_5$ requires 448.224974 C$_{28}$H$_{32}$O$_5$ (448.6)

calculated: C 74.97% H 7.19% found: C 75.05% H 7.18%

13-Methyl-16-(3,4,5-trimethoxy-benzylidene)-7,8,9,11,12,13,14,15,16,17-decahydro-6H-cyclopenta[a]phenanthrene-3,17-diol (CAB02001, STX329).

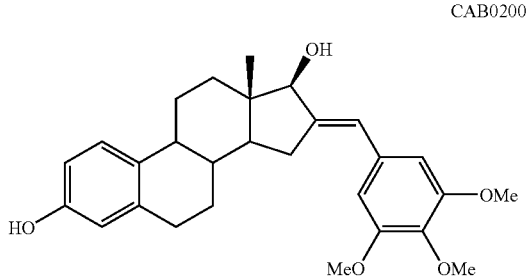

CAB02001

A solution of 3-Hydroxy-13-methyl-16-(3,4,5-trimethoxy-benzylidene)-6,7,8,9,11,12,13,14,15,16-decahydro-cyclopenta[a]phenanthren-17-one (448 mg, 1.0 mmol, CAB01124) in THF/methanol (1:1, 40 ml) was cooled to 0° C. (ice bath) and sodium borohydride (100 mg, 2.64 mmol) was added. The reaction mixture was stirred for 2 h at this temperature, while it was turning from slightly yellow to colourless. The solution was transferred into a separation funnel and ethyl acetate (100 ml) and water (100 ml) were added. The organic layer was separated, washed with water (50 ml) and brine (50 ml), dried over sodium sulphate and concentrated under reduced pressure. Yield 445 mg (99%) white solid. $^1$H-NMR (CDCl$_3$, 400 MHz), δ: 0.74 (s, 3H), 1.20-1.60 (m, 6H), 1.90-1.98 (m, 1H), 2.01-2.08 (m, 1H), 2.21-2.41 (m, 3H), 2.74-2.90 (m, 3H), 3.86 (s, 3H), 3.89 (s, 6H), 4.15 (d, J=9.4 Hz, 1H, H-17), 4.62 (s, 1H, —OH), 6.49-6.51 (m, 1H), 6.59 (d, J=2.3 Hz, 1H), 6.63-6.68 (m, 3H), 7.18 (d, J=8.2 Hz, 1H). LRMS (FAB+): 451.3 (100, [M+H]$^+$).

16-Benzylidene-13-methyl-7,8,9,11,12,13,14,15,16,17-decahydro-6H-cyclopenta[a]phenanthrene-3,17-diol (CAB01128, STX313).

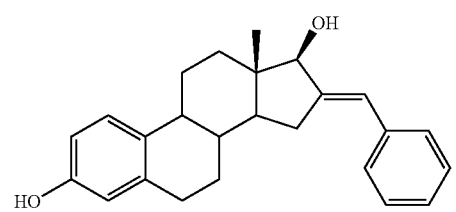

CAB01128

16-Benzylidene-3-hydroxy-13-methyl-6,7,8,9,11,12,13,14,15,16-decahydro-cyclopenta[a]phenanthren-17-one (179 mg, 0.50 mmol, CAB01122) was dissolved in ethanol (10 ml) and THF (10 ml). The resulting light yellow solution was cooled to 0° C. (ice bath) and sodium borohydride (100 mg, 2.64 mmol) was added. The reaction mixture was stirred overnight at room temperature, the solvents were removed under reduced pressure and the residue was dissolved in ethyl acetate (40 ml). The organic solution was washed with water (2×25 ml) and brine (25 ml), dried over sodium sulphate and concentrated under reduced pressure. The residue was dissolved in a small amount of ethyl acetate and precipitated by addition of hexane. The white solid was filtered off and dried under high vacuum. Yield 175 mg (97%). $^1$H-NMR (d6-DMSO, 270 MHz), δ: 0.61 (s, 3H), 1.20-1.50 (m, 5H), 1.82-0.98 (m, 2H), 2.20-2.35 (m, 3H), 2.58-2.82 (m, 3H), 3.95-4.05 (m, 1H, H-17), 5.15 (d, J=6.2 Hz, 1H), 6.43 (s, 1H), 6.46 (d, J=2.3 Hz, 1H), 6.52 (dd, J=8.2, 2.3 Hz, 1H), 7.06 (d, J=8.2 Hz, 1H), 7.15-7.20 (m, 1H), 7.31-7.41 (m, 4H). LRMS (FAB+): 343.2 (80), 360.2 (100, [M]$^+$). LRMS (FAB−): 359.3 (100, (M−H]$^-$). HRMS (FAB+) 360.209709 C$_{25}$H$_{28}$O$_2$ requires 360.208930

Sulfamic acid 16-benzylidene-13-methyl-17-oxo-7,8,9,11,12,13,14,15,16,17-decahydro-6H-cyclopenta[a]phenanthren-3-yl ester (CAB01148, STX314).

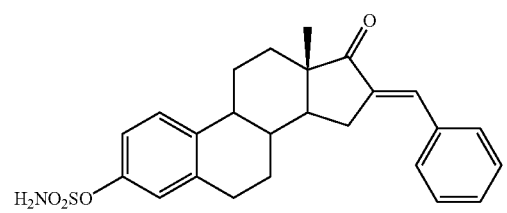

CAB01148

5 ml of a 0.7 M sulphamoyl chloride solution in toluene (3.5 mmol) were concentrated under reduced pressure (30° C. water bath temperature). The residue was cooled to 0° C. (ice bath) and DMA (10 ml) and 16-Benzylidene-3-hydroxy-13-methyl-6,7,8,9,11,12,13,14,15,16-decahydro-cyclopenta[a]phenanthren-17-one (717 mg, 2.0 mmol, CAB01122) were added. The resulting clear solution was stirred for 1 h at 0° C., then allowed to warm up to room temperature and stirred overnight. Ethyl acetate (50 ml) was added and the solution was washed with water (2×30 ml) and brine. The organic layer was dried over sodium sulphate and concentrated under reduced pressure. The resulting off-white solid was dissolved in a small amount of ethyl acetate and precipitated by addition of hexane. Yield: 683 mg (78%) off-white solid. $^1$H-NMR (CDCl$_3$, 400 MHz), δ: 0.96 (s, 3H), 1.20-2.60 (m, 11H), 2.80-3.02 (m, 3H), 5.38 (s, 2H, —NH$_2$), 7.06 (d, J=2.3 Hz, 1H), 7.11 (dd, J=8.0, 2.3 Hz, 1H), 7.30 (d, J=8.2 Hz, 1H), 7.34-7.47 (m, 2H), 7.52-7.65 (m, 2H). LRMS (FAB+): 438.2 (100, [M]$^+$).

Sulfamic acid 16-benzylidene-17-hydroxy-13-methyl-7,8,9,11,12,13,14,15,16,17-decahydro-6H-cyclopenta[a]phenanthren-3-yl ester (CAB01152, STX315).

CAB01152

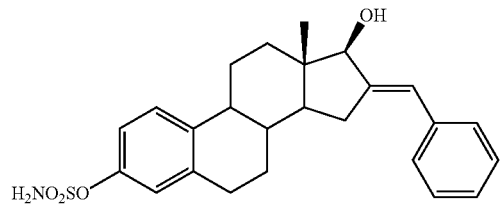

Sodium borohydride (100 mg, 2.64 mmol) was added to a solution of sulfamic acid 16-benzylidene-13-methyl-17-oxo-7,8,9,11,12,13,14,15,16,17-decahydro-6H-cyclopenta[a]phenanthren-3-yl ester (438 mg, 1.0 mmol, CAB01148) in THF (20 ml) and ethanol (20 ml) at 0° C. The mixture was stirred for 1 h at this temperature (TLC-control) and ethyl acetate (100 ml) and water (50 ml) were added. The organic layer was separated and washed with water (50 ml) and brine (50 ml), dried over sodium sulphate and concentrated under reduced pressure. The residue was dissolved in a small amount of ethyl acetate and precipitated by addition of diethyl ether. Yield: 440 mg (quant.) white powder. $^1$H-NMR (CDCl$_3$, 400 MHz), δ: 0.67 (s, 3H), 1.36-1.62 (m, 6H), 2.00-2.10 (m, 2H), 2.22-2.41 (m, 3H), 2.78 (dd, J=17.4, 7.2 Hz, 1H), 2.90-2.96 (m, 2H), 4.15 (d, J=9.4 Hz, 1H, H-17), 4.86 (s, 2H, —NH$_2$), 6.55 (d, J=2.3 Hz, 1H), 7.06 (d, J=2.3 Hz, 1H), 7.10 (dd, J=8.2, 2.3 Hz, 1H), 7.19-7.42 (m, 6H). LRMS (FAB+): 439.2 (100, [M]$^+$).

Sulfamic acid 13-methyl-17-oxo-16-(3,4,5-trimethoxy-benzylidene)7,8,9,11,12,13,14,15,16,17-decahydro-6H-cyclopenta[a]phenanthren-3-yl ester (CAB02069, STX692).

CAB02069

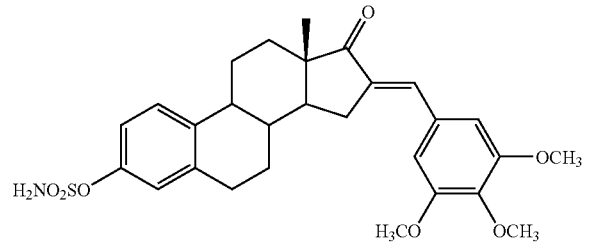

5 ml of a 0.59 M sulphamoyl chloride solution in toluene (2.95 mmol) were concentrated under reduced pressure (30° C. water bath temperature). The residue was cooled to 0° C. (ice bath) and DMA (10 ml) and 3-Hydroxy-13-methyl-16-(3,4,5-trimethoxy-benzylidene)-6,7,8,9,11,12,13,14,15,16-decahydro-cyclopenta[a]phenanthren-17-one (899 mg, 2.0 mmol, CAB01124) were added. The resulting clear solution was stirred for 1 h at 0° C., then allowed to warm up to room temperature and stirred overnight. Ethyl acetate (50 ml) was added and the solution was washed with water (2×30 ml) and brine. The organic layer was dried over sodium sulphate and concentrated under reduced pressure. The resulting off-white solid was dissolved in a small amount of acetone and precipitated by addition of hexane. Yield: 913 mg (86%) light yellow solid. $^1$H-NMR (d$_6$-DMSO, 400 MHz), δ: 0.91 (s, 3H), 1.35-1.74 (m, 4H), 1.86-1.92 (m, 1H), 2.02-2.10 (m, 1H), 2.26-2.34 (m, 1H), 2.40-2.46 (m, 1H), 2.60-2.70 (m, 1H), 2.84-2.96 (m, 3H), 3.32 (s, 9H), 6.95 (s, 2H), 6.98 (d, J=2.3 Hz, 1H), 7.02 (dd, J=8.2, 2.3 Hz, 1H), 7.29 (s, 1H), 7.35 (d, J=8.2 Hz, 1H), 7.90 (s, 2H, —NH$_2$). LRMS (FAB+): 528.2 (100, [M+H]$^+$). LRMS (FAB−): 526.2 (100, [M−H]$^-$).

Sulfamic acid 17-hydroxy-13-methyl-16-(3,4,5-trimethoxy-benzylidene)-7,8,9,11,12,13,14,15,16,17-decahydro-6H-cyclopenta[a]phenanthren-3-yl ester (CAB02084, STX693).

CAB02084

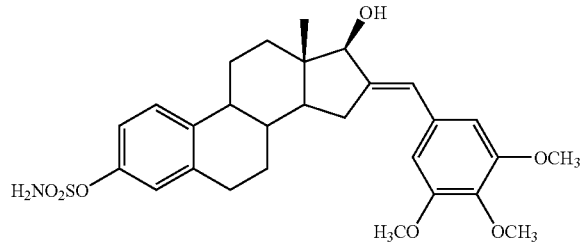

Sodium borohydride (100 mg, 2.64 mmol) was added to a solution of acid 13methyl-17-oxo-16-(3,4,5-trimethoxy-benzylidene)-7,8,9,11,12,13,14,15,16,17decahydro-6H-cyclopenta[a]phenanthren-3-yl ester (528 mg, 1.0 mmol, CAB02069) in THF (20 ml) and ethanol (20 ml) at 0° C. The mixture was stirred for 1 h at this temperature (TLC-control) and ethyl acetate (100 ml) and water (50 ml) were added. The organic layer was separated and washed with water (50 ml) and brine (50 ml), dried over sodium sulphate and concentrated under reduced pressure. The residue was dissolved in a small amount of ethyl acetate and precipitated by addition of diethyl ether. Yield: 527 mg (99%) white powder. $^1$H-NMR (CDCl$_3$, 400 MHz), δ: 0.72 (s, 3H), 1.20-1.60 (m, 4H), 1.64-1.72 (m, 2H), 1.88-1.96 (m, 1H), 2.02-2.10 (m, 1H), 2.21-2.40 (m, 3H), 2.71-2.94 (m, 3H), 3.83 (s, 3H), 3.86 (s, 6H), 4.13 (d, J=9.4 Hz, 1H, H-17), 5.17 (s, 2H, —NH$_2$), 6.48 (d, J=2.3 Hz, 1H), 6.61 (s, 2H), 7.02 (d, J=2.3 Hz, 1H), 7.09 (dd, J=8.2, 2.3 Hz, 1H), 7.30 (d, J=8.2 Hz, 1H). LRMS (FAB+): 529.2 (100, [M]$^+$). LRMS (FAB−): 528.2 (100, [M−H]$^-$).

Section 6

General Procedure for Debenzylation of Protected Phenol Intermediates Using a Radleys GreenHouse Synthesiser.

Starting materials were dissolved/suspended in THF (1 cm$^3$) and to each suspension was added ethanol (1 cm$^3$). Each suspension was degassed by bubbling nitrogen through for a few minutes before Pd/C (5% wt., catalytic) was added and each solution/suspension was degassed for a further few minutes. Hydrogen gas (balloon) was then passed over the reactions and they were stirred under a hydrogen atmosphere at room temperature for 24 h. ¹H NMR of one of the reactions at this stage showed that the debenzylation had not gone to completion therefore all were degassed again and more Pd added, followed by stirring under hydrogen for a further 21 h. Each reaction was then filtered through celite and the celite washed with ethyl acetate and methanol. The solutions were concentrated in vacuo and the products purified by flash chromatography.

2-Hydroxy-6a-methyl-4b,5,6,6a,8,10,10a,10b,11,12-decahydro-7,8-diaza-pentaleno[2,1-a]phenanthrene-9-carboxylic acid (tetrahydro-furan-2-ylmethyl)-amide STX 892 (GMA02058-2)

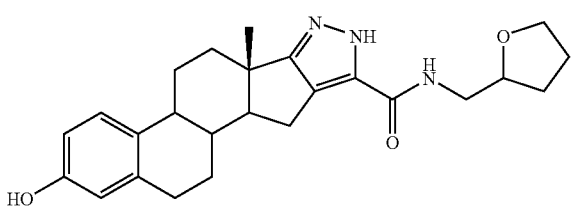

$R_f$ 0.36 (EtOAc). ¹H NMR (270 MHz, CD$_3$OD) δ: 0.92 (s, 3H), 1.25-1.95 (multiplets, 9H), 2.01-2.58 (m, 5H), 2.72-2.82 (m, 3H), 3.25-3.45 (m, 2H), 3.59-3.71 (m, 1H), 3.74-3.85 (m, 1H), 3.89-4.00 (m, 1H), 6.40 (d, J=2.5 Hz, 1H), 6.45 (dd, J=8.4, 2.7 Hz, 1H), 6.99 (d, J=8.4 Hz, 1H); HPLC 100% (Rt 1.70, 4:96 H$_2$O:MeOH); LCMS (APCI) 422.27 (M+H$^+$)

2-Hydroxy-6a-methyl-4b,5,6,6a,8,10,10a,10b,11,12-decahydro-7,8-diaza-pentaleno[2,1-a]phenanthrene-9-carboxylic acid methylamide STX 893 (GMA02058-4)

Yield 57%. $R_f$ 0.40 (EtOAc); ¹H NMR (270 MHz, CD$_3$OD) δ: 1.03 (s, 3H), 1.39-2.45 (multiplets, 10H), 2.83-2.88 (m, 3H), 2.89 (s, 3H), 6.50 (d, J=2.5 Hz, 1H), 6.54 (appdd, J=8.4 Hz, 1H), 7.09 (d, J=8.2 Hz, 1H); HPLC 99% (Rt=1.66, 4:96 H$_2$O:MeOH); LCMS (APCI), 350.21 (M−H$^+$)

2-Hydroxy-6a-methyl-4b,5,6,6a,8,10,10a,10b,11,12-decahydro-7,8-diaza-pentaleno[2,1-a]phenanthrene-9-carboxylic acid ethyl-methyl-amide STX894 (GMA02058-5)

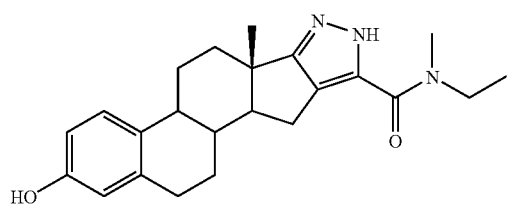

Yield 76%. $R_f$ 0.33 (EtOAc); ¹H NMR (270 MHz, CD$_3$OD) δ: 0.96 (s, 3H), 1.12 (t, J=7.2 Hz, 3H), 1.25-2.36 (multiplets, 10H), 2.60-2.79 (m, 3H), 2.95 and 3.09 (singlets, comb. 3H), 3.44-3.54 (m, 2H), 6.40 (d, J=2.5 Hz, 1H), 6.46 (dd, J=8.4, 2.7 Hz, 1H), 7.00 (d, J=8.4 Hz, 1H); HPLC 93% (Rt=1.69, 4:96 H$_2$O:MeOH); Acc. Mass (FAB$^+$) calcd 380.233803, obsd. 380.232979 (M+H$^+$)

2-Hydroxy-6a-methyl-4b,5,6,6a,8,10,10a,10b,11,12-decahydro-7,8-diaza-pentaleno[2,1-a]phenanthrene-9-carboxylic acid (1-methyl-1H-pyrrol-2-ylmethyl)-amide STX 895 (GMA02058-8)

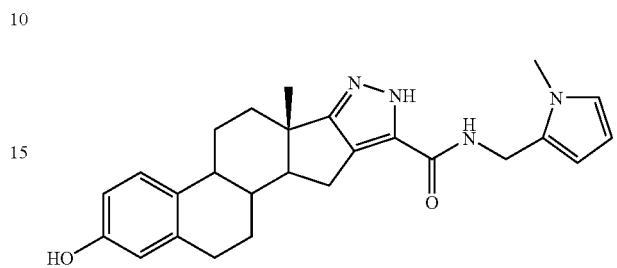

Yield 36%. $R_f$ 0.75 (EtOAc); ¹H NMR (270 MHz, CD$_3$OD) δ: 0.94 (s, 3H), 1.05-1.90 (multiplets, 6H), 2.15-2.36 (m, 4H), 2.72-2.79 (m, 3H), 3.52 (s, 3H), 4.43 (s, 2H), 5.85-5.86 (m, 1H), 5.96-5.98 (m, 1H), 6.40 (d, J=2.7 Hz, 1H), 6.45 (dd, J=8.4, 2.7 Hz, 1H), 6.51-6.53 (m, 1H), 7.01 (d, J=8.4 Hz, 1H); HPLC 100% (Rt=2.11, 4:96 H$_2$O:MeOH); Acc. Mass (FAB+) calcd. 431.244702, obsd. 431.244164 (M+H$^+$)

2-Hydroxy-6a-methyl-4b,5,6,6a,8,10,10a,10b,11,12-decahydro-7,8-diaza-pentaleno[2,1-a]phenanthrene-9-carboxylic acid (5-methyl-pyrazin-2-ylmethyl)-amide STX 896 (GMA02058-9)

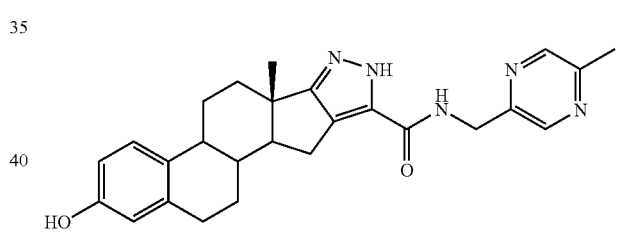

Yield 82%. $R_f$ 0.26 (EtOAc); ¹H NMR (400 MHz, CD$_3$OD) δ: 1.04 (s, 3H), 1.06-2.50 (multiplets, 10H), 2.54 (s, 3H), 2.78-2.90 (m, 3H), 4.66 (s, 2H), 6.50 (d, J=2.3 Hz, 1H), 6.55 (dd, J=8.2, 2.7 Hz, 1H), 7.09 (d, J=8.6 Hz, 1H), 8.48 (s, 1H), 8.49 (s, 1H); HPLC 89% (Rt=1.67, 4:96 H$_2$O:MeOH); LCMS (APCI) 442.30 (M−H$^+$)

(2-Hydroxy-6a-methyl-4b,5,6,6a,8,10,10a,10b,11,12-decahydro-7,8-diaza-pentaleno[2,1-a]phenanthren-9-yl)-(4-methyl-piperazin-1-yl)-methanone STX 897 (GMA02058-12)

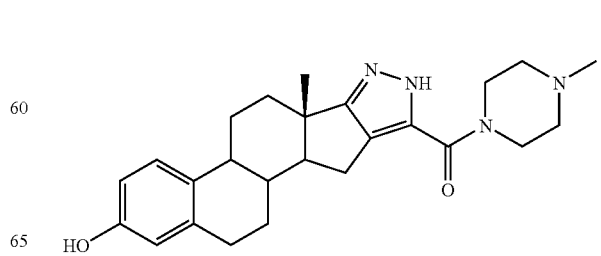

Yield 96%. $R_f$ 0.1 (10% MeOH in DCM); $^1$H NMR (270 MHz, CD$_3$OD) δ: 1.05 (s, 3H), 1.28-2.02 (m, 5H), 2.09-2.50 (m, 8H), 2.33 (s, 3H), 2.67-2.94 (m, 3H), 3.52-3.90 (m, 4H), 6.50 (d, J=2.5 Hz, 1H), 6.55 (dd, J=8.3, 2.6 Hz, 1H), 7.10 (d, J=8.7 Hz, 1H); HPLC 94% (Rt=1.68, 4:96 H$_2$O:MeOH); LCMS (APCI) 421.36 (M+H$^+$)

2-Hydroxy-6a-methyl-4b,5,6,6a,8,10,10a,10b,11,12-decahydro-7,8-diaza-pentaleno[2,1-a]phenanthrene-9-carboxylic acid (pyridin-2-ylmethyl)-amide STX 915 (GMA02070-1)

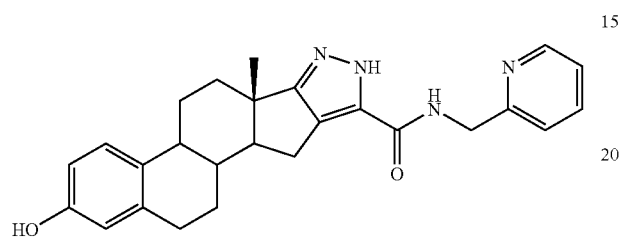

To a suspension of the acid starting material (0.095 g, 0.28 mmol) in dry DCM (6 cm3) was added DMAP (catalytic), EDC (0.065 g, 0.3 mmol) and triethylamine (0.04 cm$^3$, 0.37 mmol). The starting material did not dissolve therefore dry DMF (2 cm$^3$) was added and the resulting solution stirred at rt for 15 min. To this solution was added 2-(aminomethyl) pyridine and the reaction was stirred at rt for 4 d. The solution was washed with sat. aq. NaHCO$_3$ and the organic layer separated and concentrated in vacuo. Flash chromatography using DCM followed by 10% MeOH in DCM as eluents gave a solution of the product in DMF. Addition of hexane to this followed by a small amount of DCM gave a white powder. $^1$H NMR (270 MHz, DMSO-d$_6$) δ: 0.94 (s, 3H), 1.72-1.95 (m, 5H), 2.00-2.49 (m, 4H), 2.55-2.97 (m, 4H), 4.45-4.55 (m, 2H), 6.45 (d, 1H), 6.51 (dd, J=8.4 Hz, 1H), 7.05 (d, J=8.9 Hz, 1H), 7.22-7.33 (m, 1H), 7.74 (m, 1H), 8.28 (m, NH), 8.52 (apps, 1H), 9.03 (s, 1H); HPLC 99.8% (Rt=1.67, 4:96 H$_2$O:MeOH)

2-Hydroxy-6a-methyl-4b,5,6,6a,8,10,10a,10b,11,12-decahydro-7,8-diaza-pentaleno[2,1-a]phenanthrene-9-carboxylic acid (2-pyridin-3-yl-ethyl)-amide STX 916 (GMA02070-2)

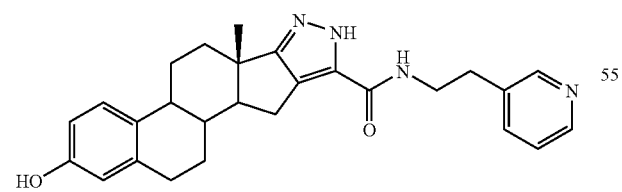

Procedure as for STX 915. Precipitation gave a cream-coloured powder. $^1$H NMR (270 MHz, DMSO-d$_6$) δ: 0.93 (s, 3H), 1.36-3.5 (multiplets, 17H), 6.47 (appd, 1H), 6.52 (appdd, 1H), 7.07 (d, J=8.2 Hz, 1H), 7.31-7.36 (m, 1H), 7.67 (appd, J~0.7 Hz, 1H), 8.45 (m, 2H), 9.07 (s, 1H); LCMS (APCI) 441.48 (M−H$^+$)

Alkylation Reactions

2-Benzyloxy-6a-methyl-7-phenethyl-4b,5,6,6a,7,10,10a,10b,11,12-decahydro-7,8-diaza-pentaleno[2,1-a] phenanthren-9-ol, GMA02076

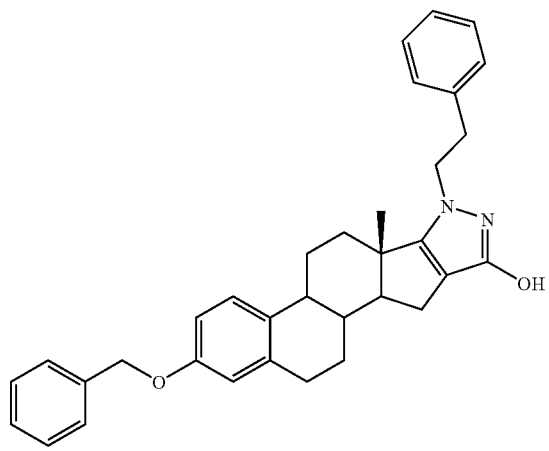

To a stirred, cooled (ice bath) solution of the benzyl protected hydroxypyrazole starting material (0.050 g, 0.12 mmol) in dry DMF (3 cm$^3$) was added sodium hydride (0.006 g of 60% dispersion, 0.14 mmol) and the reaction was stirred at 0° C. for 15 min. To this was added 2-bromoethyl benzene (0.024 cm$^3$, 0.18 mmol) and the reaction was allowed to warm to room temperature and stirred overnight. Water (5 cm$^3$) was added and the product extracted with ethyl acetate. Flash chromatography using hexane followed by ethyl acetate as eluents gave an alkylated product as the second fraction, $R_f$ 0.8 (EtOAc). $^1$H NMR (270 MHz, CDCl$_3$) δ: 1.01 (s, 3H), 1.29-2.41 (multiplets, 10H), 2.60 (dd, J=12.6, 5.9 Hz, 1H), 2.82-2.95 (m, 2H), 3.07 (t, J=2.7 Hz, 2H), 4.36 (t, J=7.2 Hz, 2H), 5.04 (s, 2H), 6.73 (d, J=2.7 Hz, 1H), 6.79 (appdd, J=8.5, 2.6 Hz, 1H), 7.18-7.45 (m, 11H); LCMS (APCI) 505.37 (M+H$^+$)

A: 2-Benzyloxy-9-methoxy-6a,7-dimethyl-4b,5,6,6a,7,10,10a,10b,11,12-decahydro-7,8-diaza-pentalano[2,1-a]phenanthrene B: 2-Benzyloxy-6a,7,8-trimethyl-5,6,6a,7,8,10,10a,10b,11,12-decahydro-4bH-7,8-diaza-pentaleno[2,1-a]phenanthren-9-one, GMA02107

A

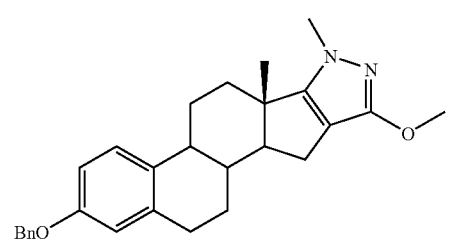

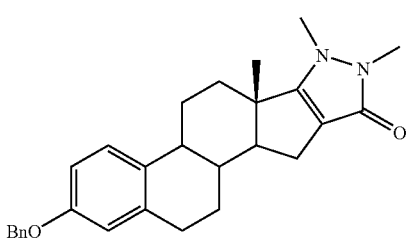

To a stirred solution of the benzyl protected hydroxypyrazole starting material (0.200 g, 0.5 mmol) in dry THF (2.3 cm$^3$) was added sodium hydride (0.06 g of 60% dispersion, 1.5 mmol) and the reaction was stirred at room temperature for 30 min. To this was added iodomethane (0.1 cm$^3$, 1.5 mmol) and stirring under nitrogen at room temperature was continued for 6 h. Water was added and the products extracted into ethyl acetate. The combined extracts were concentrated in vacuo. Chromatography on a 20 g flash column (flashmaster) using a hexane to ethyl acetate gradient followed by a methanol wash gave the title compounds as the second fraction, $R_f$ 0.7 (EtOAc) and fifth fraction, $R_f$-baseline (EtOAc) and 0.65 (10% MeOH in DCM), respectively. Yield of A: 0.046 g, 21%; $^1$H NMR (270 MHz, CDCl$_3$) δ: 1.01 (s, 3H), 1.38-1.54 (m, 1H), 1.56-1.75 (m, 2H), 1.83-1.97 (m, 2H), 2.15-2.44 (m, 5H), 2.50-2.62 (m, 1H), 2.82-2.93 (m, 2H), 3.65 (s, 3H), 3.87 (s, 3H), 5.03 (s, 2H), 6.74 (d, J=2.5 Hz, 1H), 6.79 (dd, J=8.4, 2.7 Hz, 1H), 7.19 (d, J=8.4 Hz, 1H), 7.29-7.45 (m, 5H); NOESY (400 MHz, CDCl$_3$) showed interaction between methyl peaks at 1.01 and 3.65 ppm; HPLC 98% (Rt=4.70, 4:96 H$_2$O:MeOH); LCMS (ES$^-$) 427.48 (M–H$^+$); Acc. Mass (FAB+) calcd. 429.254204, obsd. 429.254517 (M+H$^+$)

Yield of B: 0.031 g, 14%; $^1$H NMR (270 MHz, CDCl$_3$) δ: 1.02 (s, 3H), 1.36-1.52 (m, 1H), 1.55-1.74 (m, 2H), 1.82-1.96 (m, 2H), 2.03-2.20 (m, 3H), 2.28-2.43 (m, 2H), 2.47-2.57 (m, 1H), 2.83-2.91 (m, 2H), 3.24 (s, 3H), 3.28 (s, 3H), 5.01 (s, 2H), 6.72 (d, J=2.5 Hz, 1H), 6.77 (dd, J=8.5, 2.6 Hz, 1H), 7.15 (d, J=8.4 Hz, 1H), 7.27-7.69 (m, 5H); LCMS (ES$^-$) 427.42 (M–H$^+$)

9-Methoxy-6a,7-dimethyl-4b,5,6,6a,7,10,10a,10b,11,12-decahydro-7,8-diaza-penteleno[2,1-a]phenanthren-2-ol, GMA 02114

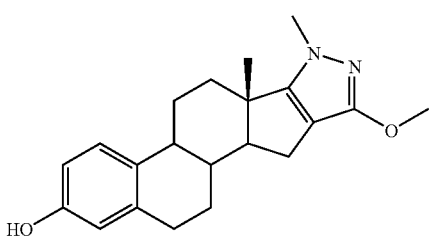

To a stirred solution of the benzylated starting material (0.025 g, 0.06 mmol) in dry DCM (2 cm$^3$) under nitrogen, cooled to −78° C. (dry ice/acetone) was added boron tribromide (0.065 cm$^3$ of a 1M solution in DCM, 0.065 mmol) and stirring at −78° C. was continued for 2.5 h. Water was added, the reaction was allowed to warm to room temperature and the resulting white precipitate was collected by filtration. This was shown by $^1$H NMR and LCMS to consist of a 3:1 mixture of dimethylated and monomethylated products. The dichloromethane layer of the filtrate was found to contain starting material and this was redissolved in DCM and reacted further with boron tribromide at −78° C. for 1.5 h before quenching with water as before. The white precipitate formed in this case was solely the dimethylated product. $^1$H NMR (270 MHz, CD$_3$OD) δ: 1.09 (s, 3H), 1.40-1.77 (m, 3H), 1.87-2.01 (m, 2H), 2.23-2.51 (m, 5H), 2.69-2.89 (m, 3H), 3.71 (s, 3H), 3.94 (s, 3H), 6.50 (d, J=2.5 Hz, 1H), 6.55 (appdd, J~8.3, 2.6 Hz, 1H), 7.09 (d, J=8.2 Hz, 1H); LCMS (ES$^-$) 337.35 (M–H$^+$)

2-Hydroxy-6a,7,8-trimethyl-5,6,6a,7,8,10,10a,10b,11,12-decahydro-4bH-7,8-diaza-pentaleno[2,1-a]phenanthren-9-one, STX942, GMA02116

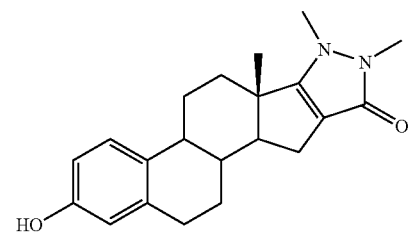

To a stirred solution of the benzylated starting material (0.031 g, 0.07 mmol) in dry DCM (3 cm$^3$) under nitrogen, cooled to −78° C., was added boron tribromide (0.15 cm$^3$ of a 1M solution in DCM (0.15 mmol) and the reaction was stirred at −78° C. for 2 h. The reaction was then quenched with water and the resulting white precipitate was collected by filtration and washed with water and DCM. Recrystallisation from methanol gave a pale orange powder which was collected by filtration and washed with DCM and hexane, yield 0.0125 g, 53%; $^1$H NMR (270 MHz, CD$_3$OD) δ: 1.15 (s, 3H), 1.40-1.80 (m, 3H), 1.93-2.04 (m, 2H), 2.21-2.53 (m, 5H), 2.70 (dd, J=13.1, 5.7 Hz, 1H), 2.80-2.95 (m, 2H), 3.34 (s, 1H), 3.71 (s, 3H), 3.84 (s, 3H), 6.51 (s, 1H), 6.56 (dd, J=8.4, 2.7 Hz, 1H), 7.09 (d, J=8.4 Hz, 1H); LCMS (ES–): 337.16 (M–H$^+$); HPLC 99.6% (Rt=2.46, 10:90 H$_2$O:MeOH)

Biological Data

The following assay for determining 17B-HSD Type I and Type II activities was performed.

17B-HSD Type I and Type II Assay

Purpose
  To determine 17β-hydroxysteroid dehydrogenase activity (types I and II) in human breast cancer cells (T-47D and MDA) in the absence or presence of regulatory agents.
Safety Notes
  Wear gloves and a lab coat when working with human cell lines.
  $^3$H-E$_1$, $^3$H-E$_2$, $^{14}$C-E$_1$, and $^{14}$C-E$_2$ are radioactive.
  Assume E$_1$, E$_2$ and inhibitors to be carcinogenic and/or teratogenic.
  DMSO promotes absorption through the skin and so when used as a solvent the solute may be easily absorbed—avoid bodily contact.
  THF can form potentially explosive peroxides upon long standing in air.

Diethyl ether has extremely flammable liquid and vapour. It is harmful when swallowed, inhaled or absorbed through skin. Causes irritation to skin, eyes and respiratory tract and affects the central nervous system.

Solid $CO_2$—contact with the product may cause frostbite or freeze burns in exposed tissues.

Methanol is highly flammable.

Dichloromethane must be handled with caution—causes respiratory tract, skin and eye irritation and may be a carcinogen.

Ethyl acetate—flammable liquid and vapour which is harmful if swallowed or inhaled. Causes irritation to skin, eyes and respiratory tract and affects the central nervous system.

Ecoscint A—contact hazard—will irritate skin and eyes.

Procedure

| | Materials | Supplier | Cat. No. | Comments |
|---|---|---|---|---|
| a. | [6,7-$^3$H(N)]-$E_1$ | NEN | NET-051 | 40.40 Ci/mmol |
| b. | [6,7-$^3$H(N)]-$E_2$ | NEN | NET-013 | 41.30 Ci/mmol |
| c. | [4-$^{14}$C]-$E_1$ | NEN | NEC-512 | 51.30 mCi/mmol |
| d. | [4-$^{14}$C]-$E_2$ | NEN | NEC-127 | 52.00 mCi/mmol |
| e. | T-47D human breast cancer cells | | | |
| f. | MDA-MB-231 human breast cancer cells | | | |
| g. | Oestrone | Sigma | E-9750 | |
| h. | β-Oestradiol | Sigma | E-8875 | |
| i. | DMSO | ICN Biomedicals | 196055 | |
| j. | Diethyl Ether | Fisher | D/2450/PB15 | |
| k. | Solid $CO_2$ | BOC | | |
| l. | Methanol | Fisher | M/4000/17 | |
| m. | Dichloromethane 'AnalaR' | BDH Lab. Supplies | 103406N | |
| n. | Ethyl Acetate 'AnalaR' | BDH Lab. Supplies | 101086J | |
| o. | Ecsocint A | National Diagnostics | LS-273 | |
| p. | Test Tubes | Fisher | TES-200-151G | 125 × 16 mm soda glass |
| q. | Test Tubes | Fisher | TES-200-089Y | 75 × 12 mm soda glass |
| r. | Scintillation Vials | Starstedt | 73.662 | 20 ml, polypropylene |

Equipment

Beckman LS6000SC Scintillation Spectrometer.

SMI Multi-tube Vortexer—model 2601.

Fume Hood.

TLC Aluminium Sheets Silica Gel 60 $F_{254}$ MERCK

Purification of $^3$H-$E_1$/$^3$H-$E_2$.

Set up a TLC plate with a lane at either end and a large lane in the middle for streaking.

Streak 100 μCi (100 μl or rather 5×20 μl) $^3$H-$E_1$/$^3$H-$E_2$ in the middle lane.

Spot 20 μl cold $E_1$/$E_2$ in the outer lanes.

Leave the plate in the TLC tank for 1-1½ hours.

Visualise the spots of $E_1$/$E_2$ (in the outer lanes) under UV light and circle.

Cut out the area where the labelled $E_1$/$E_2$ should be (according to the position of the cold $E_1$/$E_2$ on the TLC plate) and place in a glass vial.

Elute in 5.0 ml of diethyl ether.

Vortex mix the contents of the vial and leave for 12 hours at 4° C.

Vortex the vial again and allow the contents to settle down.

Add 1 ml of distilled water (to cover all the bits of plate) and freeze the aqueous phase in a solid carbon dioxide/methanol mixture.

Decant the diethyl ether phase into another glass vial and evaporate to dryness under an airstream at 40° C.

Dissolve the residue in 1 ml ethanol and count a 5 μl aliquot for radioactivity using a liquid scintillation counter.

Calculations

Use Specific Activity of $^3$H-$E_1$/$^3$H-$E_2$ to calculate how much $^3$H-$E_1$/$^3$H-$E_2$ needs to be added to each flask for physiological concentration (5 pmol) per flask. Also calculate how much needs to be added to each well for physiological concentration (3 pmol) per well when carrying out the assay in 24-well plate format.

Assay of 17β-hydroxysteroid Dehydrogenase Activity in T-47D cells ($E_1 \rightarrow E_2$).

Remove the growth medium from all flasks.

Add 2.5 ml of substrate [(assay medium+$^3$H-$E_1$)+appropriate inhibitor] to each flask.

Incubate the flasks at 37° C. for 0.5 hours.

Take 2 ml from each flask and add directly to tubes containing $^{14}$C-oestradiol (5000 cpm).

Extract the steroids from the medium with 4 ml diethyl ether.

Mechanically shake the tubes for 3 minutes to get a good partition.

Separate the ether phase by freezing the aqueous phase in a solid carbon dioxide/methanol mixture and decant the ether into tubes containing 50 μg (20 μl of 10 mM solution) unlabelled product to help visualise the labelled product upon TLC.

Evaporate the ether phase to dryness under an airstream at 40° C.

Dissolve the residue in 6-8 drops of diethyl ether and spot onto a TLC plate containing a fluorescent indicator.

Separate the oestrone and oestradiol by TLC using dichloromethane/ethyl acetate (4:1 v/v) as solvents.

Visualise the spots of product steroid ($^3$H-$E_2$) under UV light, cut them out, and place them in scintillation vials.

Add 0.5 ml methanol to the vials to elute the pieces of TLC.

Add 0.5 ml assay medium to each vial to correct for volume.

Add 10 ml Ecoscint A to each vial.

Measure the total activity of the $^3$H isotope by counting 0.5 ml substrate solution containing the $^3$H isotope ($^3$H-$E_1$), 0.5 ml methanol and 10 ml Ecoscint A. Measure the total activity of the $^{14}$C isotope by counting $^{14}$C-oestradiol (5000 cpm), 0.5 ml assay medium, 0.5 ml methanol and 10 ml Ecoscint A.

Count product and recovery radioactivity in a liquid scintillation counter using a program for dual [$^3$H/$^{14}$C] isotopes.

Calculations

Overall, four corrections are applied to the raw data:

Crossover Correction.

Recovery Correction.

Blank Correction.

Dilution Correction.

Use Microsoft Excel.

B & C represent columns of $^3$H & $^{14}$C raw data respectively:

D. C×0.14=Crossover
E. B−D=Crossover Corrected
F. C/Mean Total Activity $^{14}$C=Recovery
G. E/F=Recovery Corrected
H. G−Blank (mean)=Blank Corrected
I. H×Constant (see below)=fmol/flask/0.5 hrs
J. $[((x_1+x_2)\times 272)/1,000,000]$=cells/flask (millions)
K. I/J=fmol/0.5 hrs/million cells
L. K×2=fmol/hr/million cells
M. Mean of each triplicate=Mean Activity
N. Standard Deviation of each triplicate=Standard Deviation Activity
O. [(100/Mean activity of control)×L]=% Activity
P. 100−O=% Inhibition
Q. Mean % Inhibition of each triplicate=Mean % Inhibition
R. SD % Inhibition of each triplicate=Standard Deviation % Inhibition
S. Label Treatments and Concentrations=Inhibitor Codes & Concentrations Graphs and statistics as required.

$$\text{Dilution}(2.5/2)$$
$$\downarrow$$
$$\text{Constant} = [1.25 \times (pmol\,^3H - E_1/\text{total } cpm\,^3H - E_1/\text{flask})]$$

Assay of 17β-hydroxysteroid dehydrogenase activity in MDA-MB-231 cells ($E_2 \rightarrow E_1$)

Remove the growth medium from all flasks.

Add 2.5 ml substrate medium [(assay medium+$^3$H-$E_2$)+ appropriate inhibitor] to each flask.

Incubate the flasks at 37° C. for 3 hours.

Take 2 ml from each flask and add directly to tubes containing $^{14}$C-oestrone (5000 cpm).

Extract the steroids from the medium with 4 ml diethyl ether.

Mechanically shake the tubes for 3 minutes to get a good partition.

Separate the ether phase by freezing the aqueous phase in a solid carbon dioxide/methanol mixture and decant the ether into tubes containing 50 µg (20 µl of 10 mM solution) unlabelled product to help visualise the labelled product upon TLC.

Evaporate the ether phase to dryness under and airstream at 40° C.

Dissolve the residue in 6-8 drops of diethyl ether and spot onto a TLC plate containing a fluorescent indicator.

Separate the oestrone and oestradiol by TLC using dichloromethane/ethyl acetate (4:1 v/v) as solvents.

Visualise the spots of product steroid ($^3$H-$E_1$) under UV light, cut them out, and place into scintillation vials.

Add 0.5 ml methanol to the vials to elute the pieces of TLC.

Add 0.5 ml assay medium to each vial to correct for volume.

Add 10 ml Ecoscint A to each vial.

Measure the total activity of the $^3$H isotope by counting 0.5 ml substrate solution containing the $^3$H isotope ($^3$H-$E_2$), 0.5 ml methanol and 10 ml Ecoscint A. Measure the total activity of the $^{14}$C isotope by counting $^{14}$C-oestrone (5000 cpm), 0.5 ml assay medium, 0.5 ml methanol and 10 ml Ecoscint A.

Count product and recovery radioactivity in a liquid scintillation counter using a program for dual [$^3$H/$^{14}$C] isotopes.

Calculations

Overall, four corrections are applied to the raw data:

Crossover Correction.

Recovery Correction.

Blank Correction.

Dilution Correction.

Use Microsoft Excel.

B & C represent columns of $^3$H and $^{14}$C raw data respectively.

D. C×0.14=Crossover
E. B−D=Crossover Corrected
F. C/Mean Total Activity $^{14}$C=Recovery
G. E/F=Recovery Corrected
H. G−Blank (Mean)=Blank Corrected
I. H×Constant=fmol/flask/3 hrs
J. $[((x_1+x_2)\times 272)/1,000,000]$=cells/flask (millions)
K. I/J=fmol/3 hrs/million cells
L. K/3=fmol/hr/million cells
M. Mean of each triplicate=Mean Activity
N. Standard Deviation of each triplicate=Standard Deviation Activity
O. (100×Mean Activity of Control)×L=% Activity
P. 100−O=% Inhibition
Q. Mean % Inhibition of each triplicate=Mean % Inhibition
R. SD % Inhibition of each triplicate=SD % Inhibition
S. Label Treatments and Concentrations=Inhibitor Codes & Concentrations Graphs and statistics as required.

Ther Notes:

$$\text{Dilution}(2.5/2)$$
$$\downarrow$$
$$\text{Constant} = [1.25 \times (pmol\,^3H - E_1/\text{total } cpm\,^3H - E_1/\text{flask})]$$

Account for all radioactive isotope usage.

The assay of 17β-HSD Type I activity in T-47D cells is often carried out in 24-well plate format (rather than $T_{25}$ flasks). Under these circumstances only 1.5 ml substrate solution (±inhibitor) is used and the incubation time is increased to 3 hours. After incubation only 1 ml is taken from each well.

Examples of Expected Mean % Inhibition Values for the Positive Control:

$E_1 \rightarrow E_2$ Typical % inhibitions obtained with 10 µM $E_1$ are between 97% and 99% inhibition.

$E_2 \rightarrow E_1$ Typical % inhibitions obtained with 10 µM $E_2$ are between 37% and 43% inhibition.

RESULTS

| Compound STX No. | Structure | % inhibition of 17β-HSD1 @ 10 μM | % inhibition of 17β-HSD2 @ 10 μM |
| --- | --- | --- | --- |
| 207 | 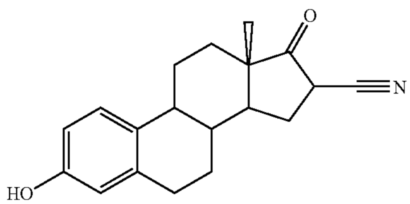 | 83, 71, IC$_{50}$ = 10 μM | 17 |
| 208 | 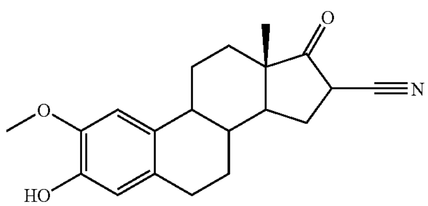 | 35, 31 | 4 |
| 209 | 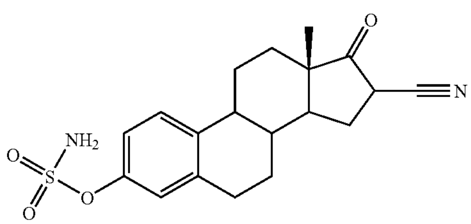 | 71, 73, IC$_{50}$ = 10 μM | 18 |
| 210 | 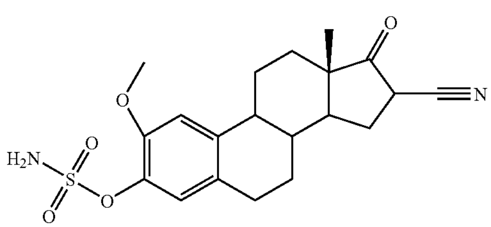 | 95, 95, IC$_{50}$ = 2.1 μM | 8 |
| 313 | 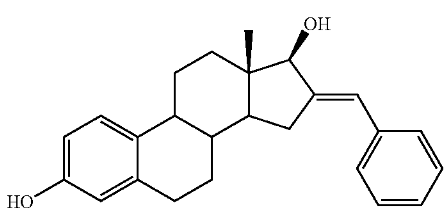 | 26 | 5 |
| 314 | 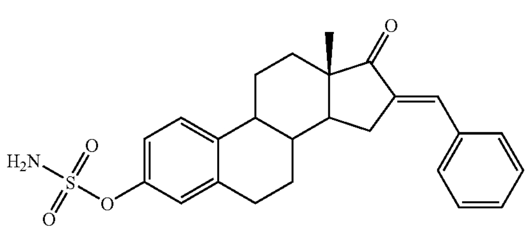 | −1 | 1 |

-continued

RESULTS

| Compound STX No. | Structure | % inhibition of 17β-HSD1 @ 10 μM | % inhibition of 17β-HSD2 @ 10 μM |
|---|---|---|---|
| 315 | 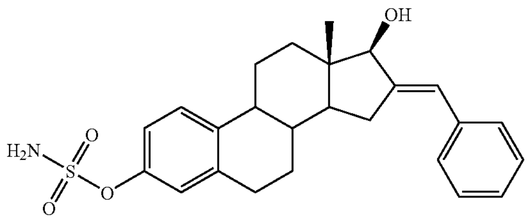 | 4 | 1 |
| 319 | 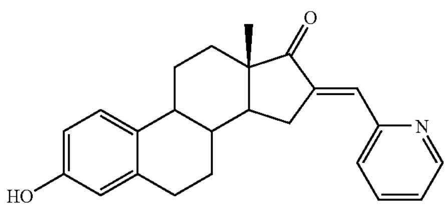 | 23 | 16 |
| 320 | 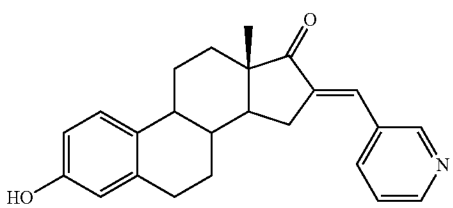 | 44 | 10 |
| 321 | 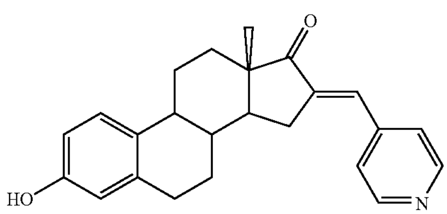 | 34 | 25 |
| 322 | 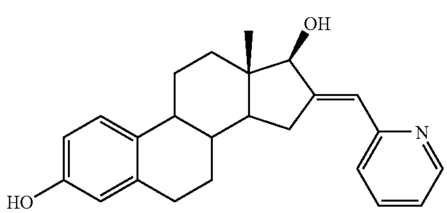 | 55 | 17 |
| 323 | 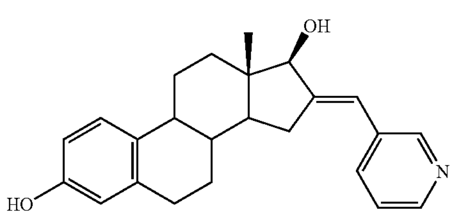 | 52 | 43 |
| 324 | 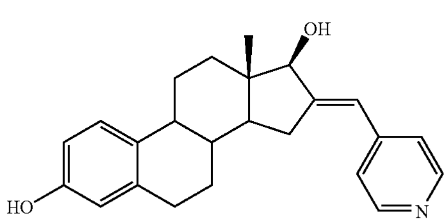 | 81, 72, IC$_{50}$ = 4.1 μM | 3 |

-continued

| | | RESULTS | |
|---|---|---|---|
| Compound STX No. | Structure | % inhibition of 17β-HSD1 @ 10 μM | % inhibition of 17β-HSD2 @ 10 μM |
| 327 | | 96, 94, IC$_{50}$ = 1.1 μM | 5 |
| 328 | | 24 | −12 |
| 329 | | 63, 33 | 3 |
| 330 | | 72, 77 | 7 |
| 337 | | 47 | 8 |
| 338 | | 55 | −2 |

-continued

RESULTS

| Compound STX No. | Structure | % inhibition of 17β-HSD1 @ 10 μM | % inhibition of 17β-HSD2 @ 10 μM |
|---|---|---|---|
| 416 | 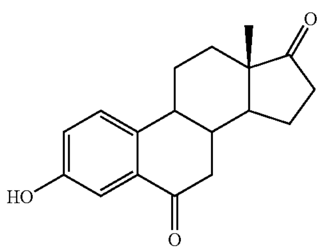 | 98, IC$_{50}$ = 0.34 μM | 8 |
| 452 | 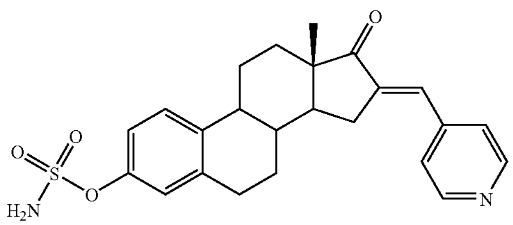 | 28 | 11 |
| 453 | 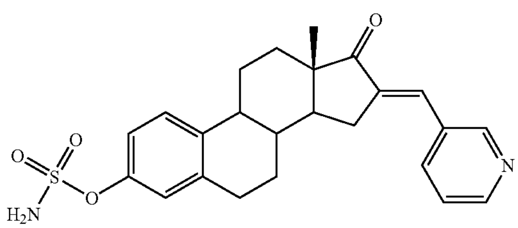 | 22 | 10 |
| 454 | 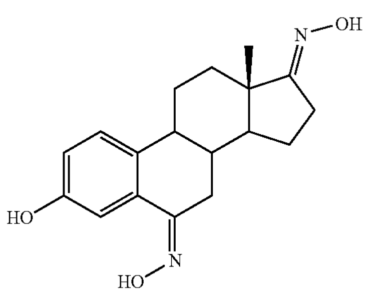 | IC$_{50}$ = 1.9 μM | 27 |
| 474 | 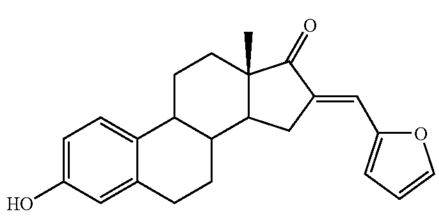 | 26 | 17 |
| 475 | 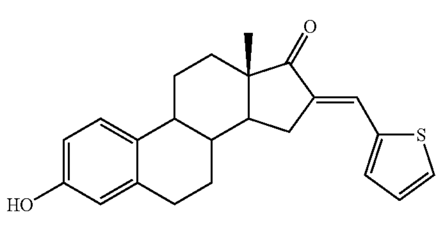 | 67 | 14 |

-continued

RESULTS

| Compound STX No. | Structure | % inhibition of 17β-HSD1 @ 10 μM | % inhibition of 17β-HSD2 @ 10 μM |
| --- | --- | --- | --- |
| 476 | 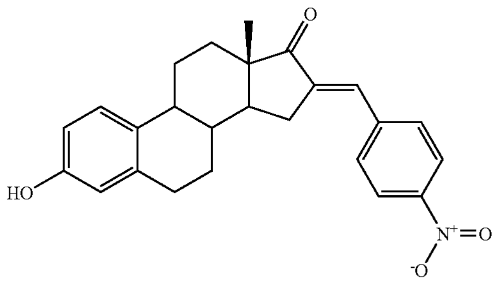 | 15 | 15 |
| 477 | 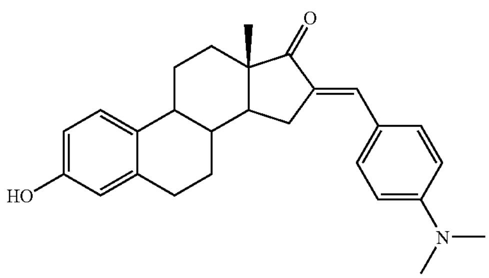 | 72 | 13 |
| 478 | 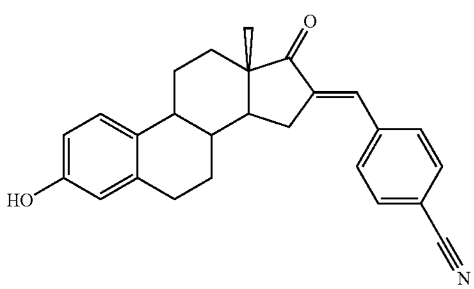 | 39 | 18 |
| 486 | 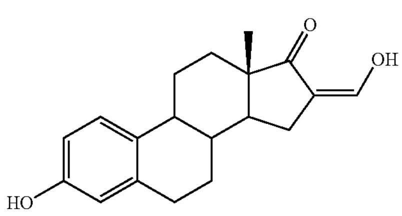 | 97, IC$_{50}$ = 0.11 μM | 15 |
| 507 | 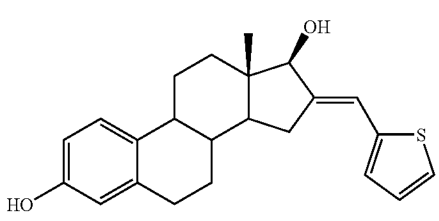 | 41 | 25 |

-continued

RESULTS

| Compound STX No. | Structure | % inhibition of 17β-HSD1 @ 10 μM | % inhibition of 17β-HSD2 @ 10 μM |
|---|---|---|---|
| 508 | 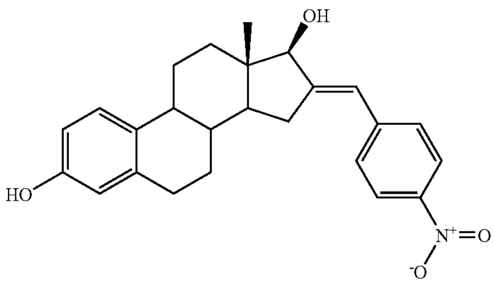 | 33 | 38 |
| 510 | 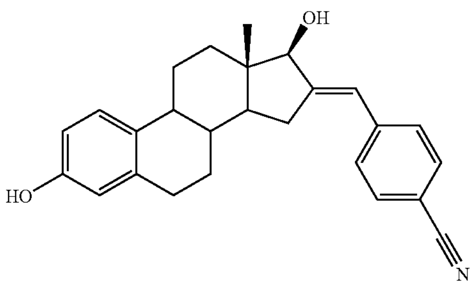 | 57 | 31 |
| 511 | 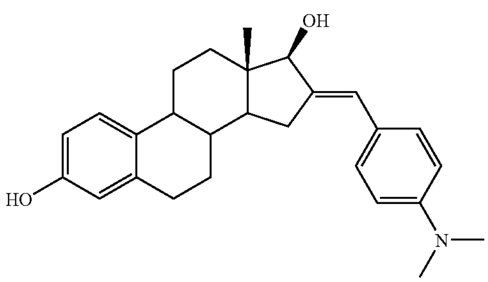 | 72 | 81, IC$_{50}$ = 5.4 μM |
| 515 | 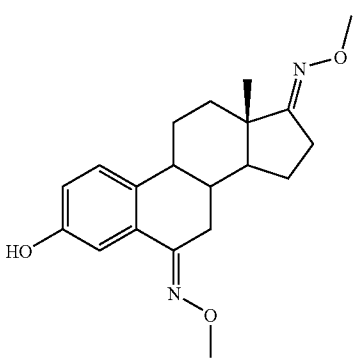 | 15 | 31 |
| 542 | 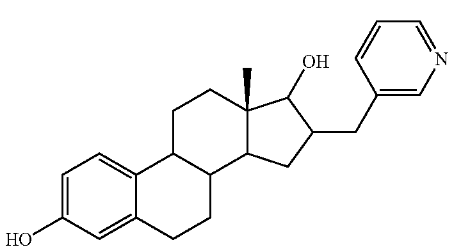 | 87 | 11 |

-continued
RESULTS
| Compound STX No. | Structure | % inhibition of 17β-HSD1 @ 10 μM | % inhibition of 17β-HSD2 @ 10 μM |
|---|---|---|---|
| 543 | 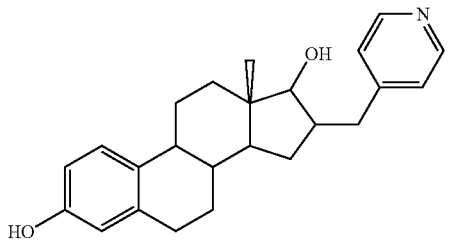 | 84 | 37 |
| 561 | 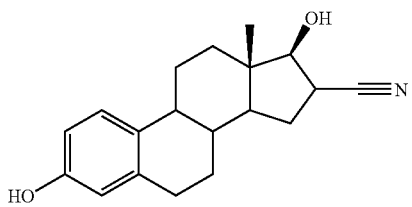 | 56 | 4 |
| 567 | 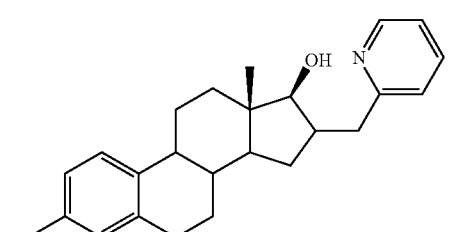 | 88 | 11 |
| 568 | 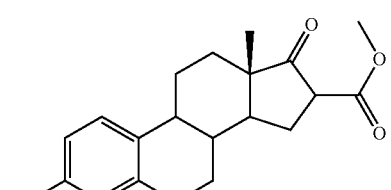 | 69 | 9 |
| 571 | 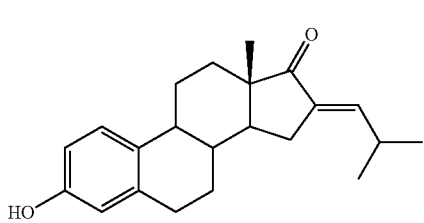 | 71 | 18 |
| 572 | 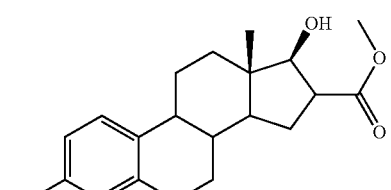 | 63 | 2 |

-continued

RESULTS

| Compound STX No. | Structure | % inhibition of 17β-HSD1 @ 10 μM | % inhibition of 17β-HSD2 @ 10 μM |
|---|---|---|---|
| 573 | 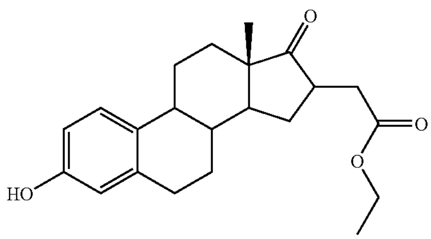 | 97, $IC_{50} = 0.30 \mu M$ | 18 |
| 574 | 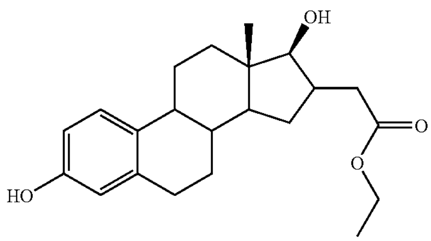 | 67 | 18 |
| 594 | 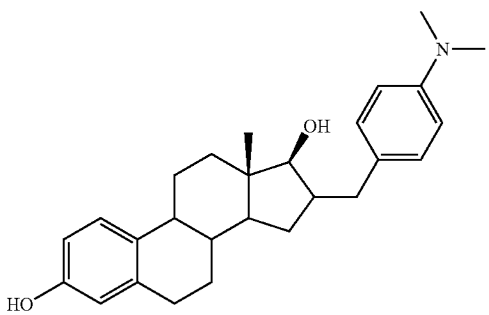 | 41 | 25 |
| 603 | 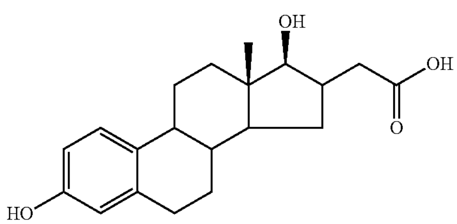 | 58 | 0 |
| 604 | 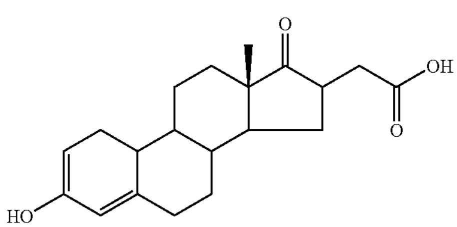 | 13 | −5 |
| 610 | 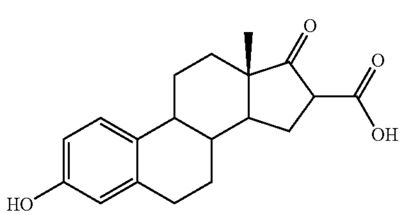 | 95, $IC_{50} = 0.94 \mu M$ | 1 |

-continued

RESULTS

| Compound STX No. | Structure | % inhibition of 17β-HSD1 @ 10 μM | % inhibition of 17β-HSD2 @ 10 μM |
|---|---|---|---|
| 611 | 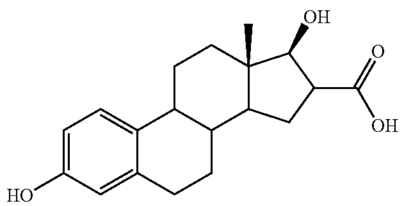 | 39 | 4 |
| 612 | 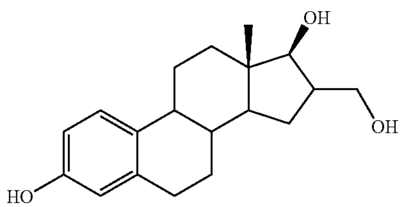 | 86 | 17 |
| 614 | 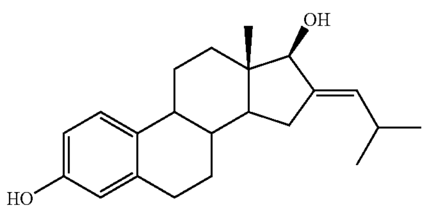 | 68 | 7 |
| 663 | 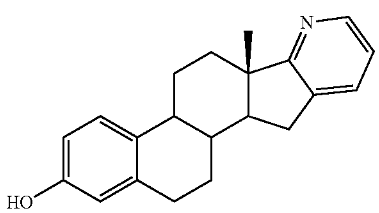 | 78 | 34 |
| 664 | 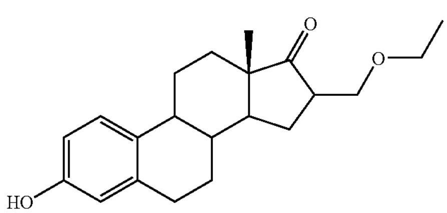 | 92, $IC_{50}$ = 0.32 μM | 19 |
| 665 | 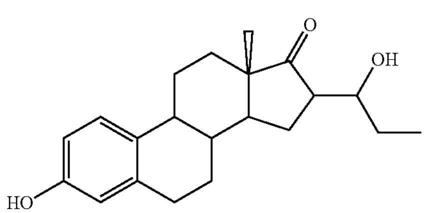 | 80 | −18 |
| 667 | 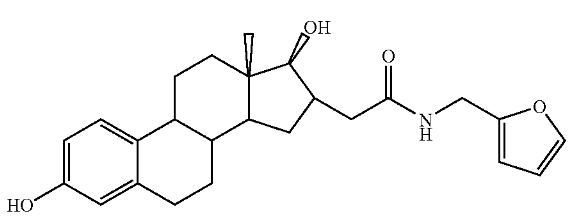 | 35 | 14 |

-continued

RESULTS

| Compound STX No. | Structure | % inhibition of 17β-HSD1 @ 10 μM | % inhibition of 17β-HSD2 @ 10 μM |
| --- | --- | --- | --- |
| 668 | 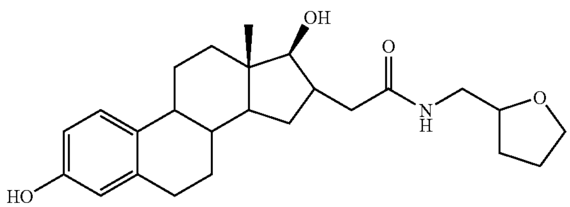 | 63 | 25 |
| 669 | 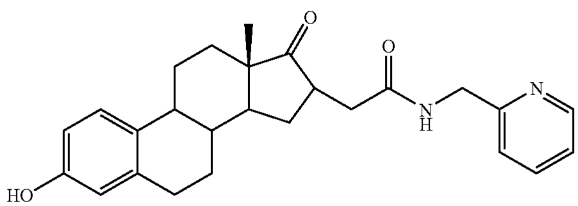 | 82 | 7 |
| 670 | 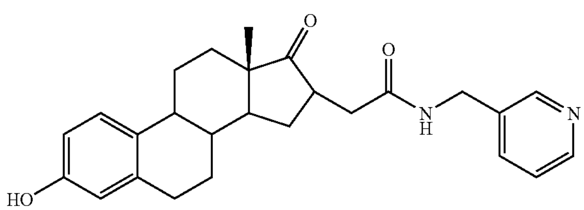 | 95, IC$_{50}$ = 0.033 μM | 26 |
| 671 | 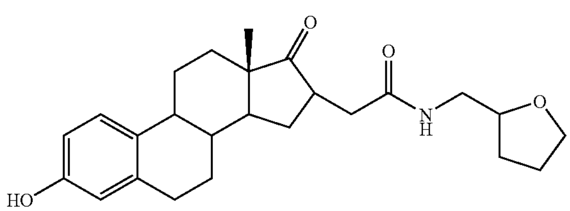 | 91, IC$_{50}$ = 0.38 μM | 21 |
| 672 | 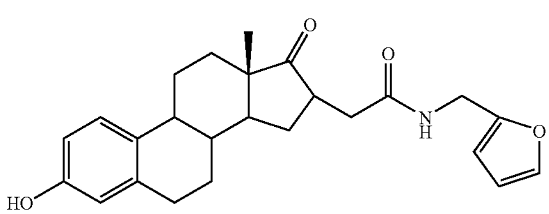 | 85 | 3 |
| 679 | 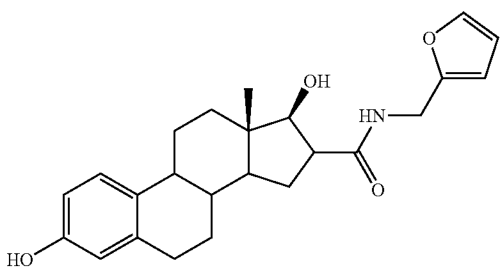 | 87 | −9 |

-continued

RESULTS

| Compound STX No. | Structure | % inhibition of 17β-HSD1 @ 10 μM | % inhibition of 17β-HSD2 @ 10 μM |
|---|---|---|---|
| 688 | 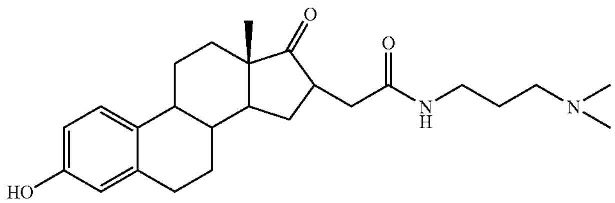 | 36 | 13 |
| 689 | 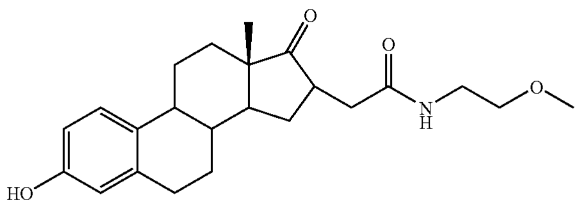 | 53 | 8 |
| 690 | 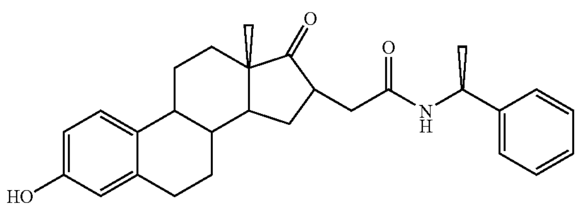 | 83 | 10 |
| 691 | 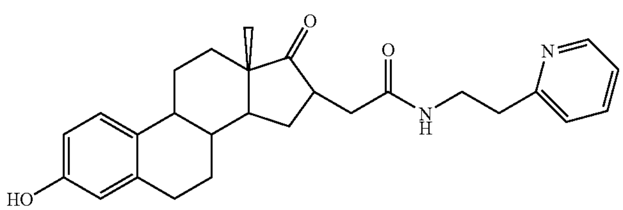 | 58 | 14 |
| 692 | 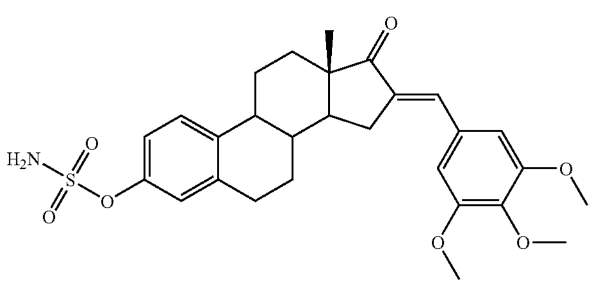 | 4 | 17 |
| 693 | 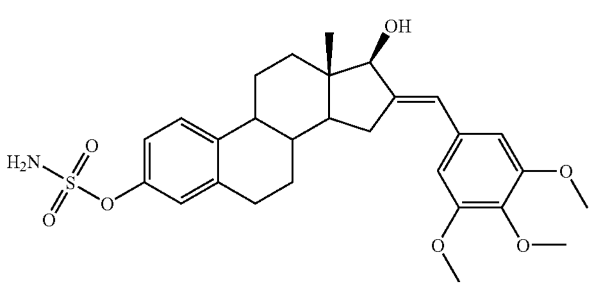 | 13 | 10 |

-continued

RESULTS

| Compound STX No. | Structure | % inhibition of 17β-HSD1 @ 10 μM | % inhibition of 17β-HSD2 @ 10 μM |
|---|---|---|---|
| 737 | 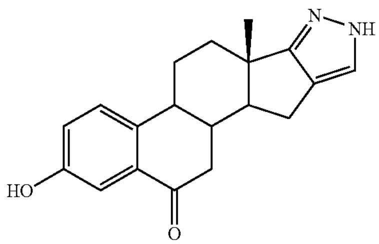 | 96<br>$IC_{50} = 0.46\ \mu M$ | −9 |
| 741 | 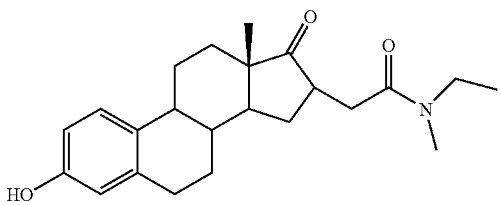 | 79 | 5 |
| 742 | 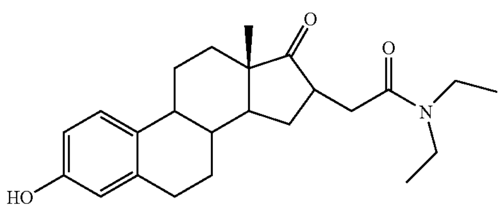 | 82 | 2 |
| 743 | 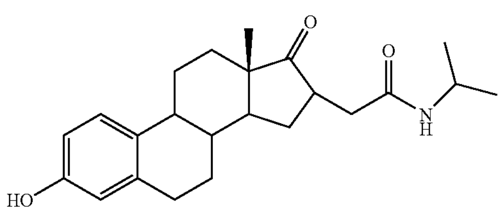 | 75 | 6 |
| 744 | 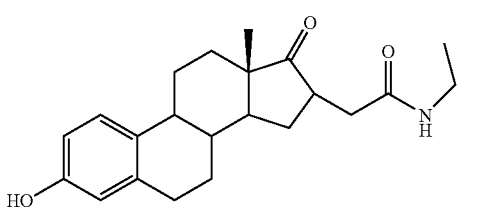 | 84 | 2 |
| 745 | 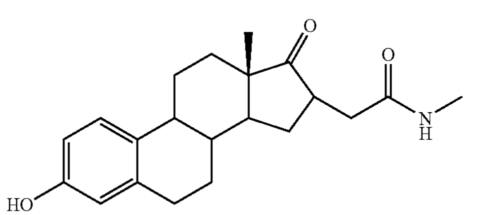 | 90<br>$IC_{50} = 1.5\ \mu M$ | 3.5 |
| 746 | 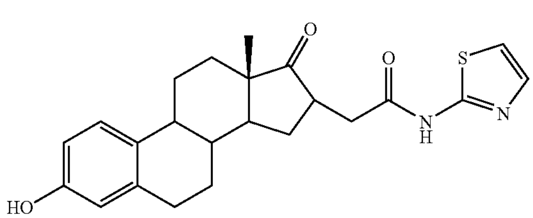 | 30 | 16 |

-continued
RESULTS
| Compound STX No. | Structure | % inhibition of 17β-HSD1 @ 10 μM | % inhibition of 17β-HSD2 @ 10 μM |
|---|---|---|---|
| 748 | 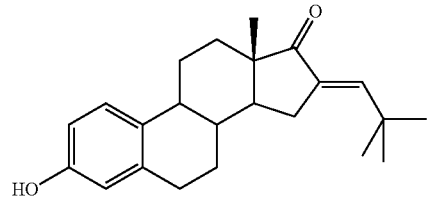 | 82 | 31 |
| 749 | 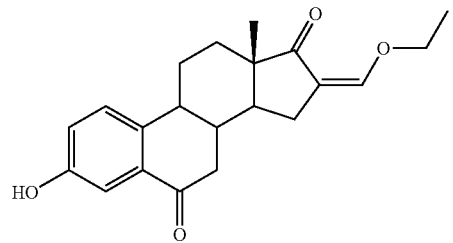 | 85 | 8 |
| 771 | 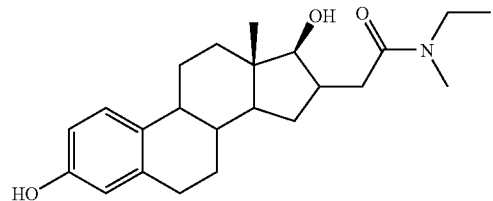 | 78 | 16 |
| 772 | 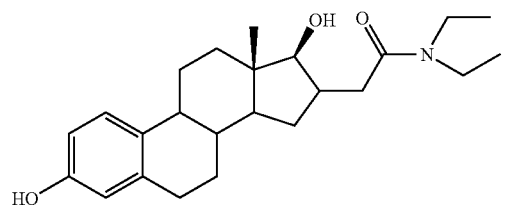 | 79 | 14 |
| 773 | 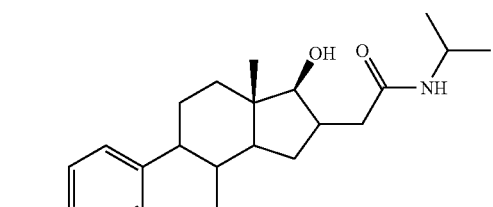 | 67 | 11 |
| 774 | 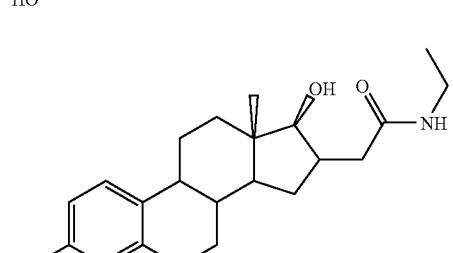 | 76 | 13 |

-continued

RESULTS

| Compound STX No. | Structure | % inhibition of 17β-HSD1 @ 10 μM | % inhibition of 17β-HSD2 @ 10 μM |
|---|---|---|---|
| 775 | 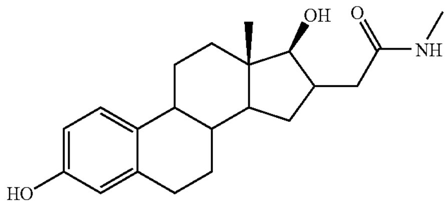 | 63 | 11 |
| 779 | 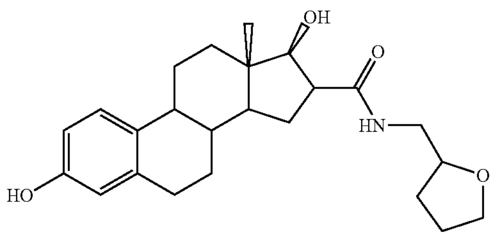 | 82 | 11 |
| 780 | 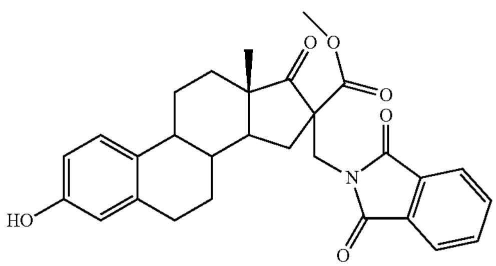 | 71 | 17 |
| 782 | 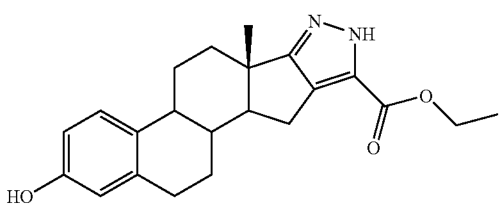 | 94<br>IC$_{50}$ = 1.85 μM | 7 |
| 783 | 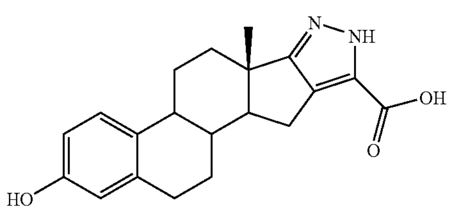 | 32 | −6 |
| 784 | 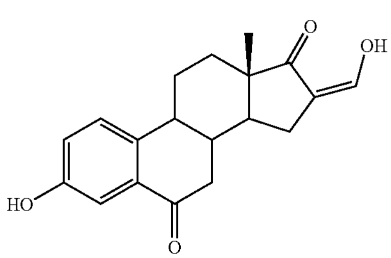 | 97<br>IC$_{50}$ = 0.7 μM | −7 |

-continued

RESULTS

| Compound STX No. | Structure | % inhibition of 17β-HSD1 @ 10 μM | % inhibition of 17β-HSD2 @ 10 μM |
|---|---|---|---|
| 785 | 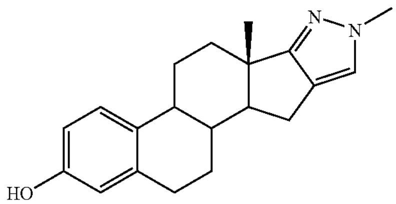 | 94<br>IC$_{50}$ = 2.75 μM | 24 |
| 786 | 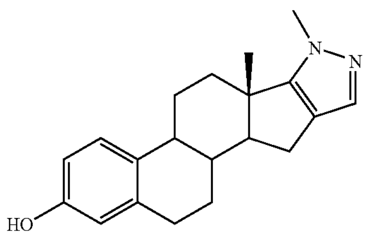 | 43 | 32 |
| 798 | 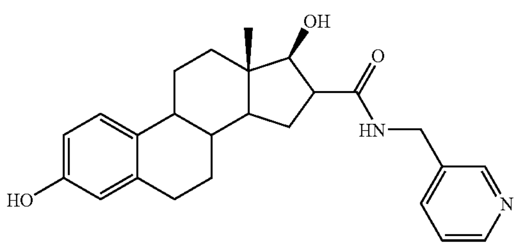 | 91<br>IC$_{50}$ = 510 nM | −12 |
| 799 | 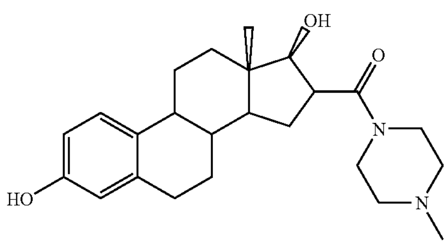 | 74 | −16 |
| 800 | 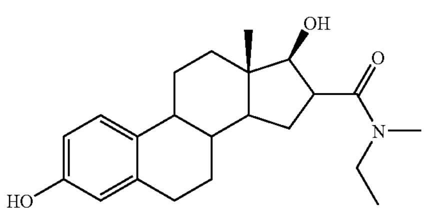 | 79 | −6 |
| 801 | 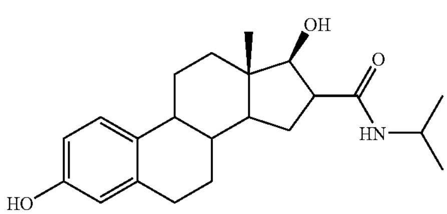 | 70 | −15 |

-continued

RESULTS

| Compound STX No. | Structure | % inhibition of 17β-HSD1 @ 10 μM | % inhibition of 17β-HSD2 @ 10 μM |
|---|---|---|---|
| 802 | 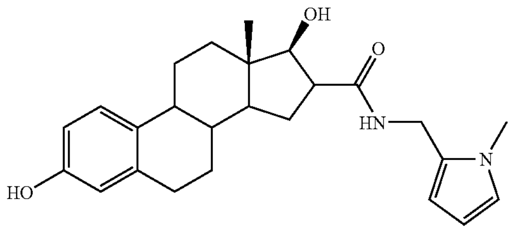 | 86 | −7 |
| 803 | 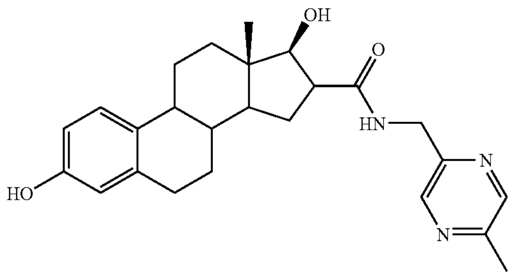 | 85 | −18 |
| 804 | 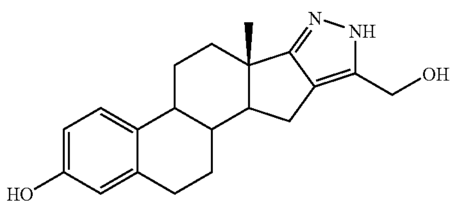 | 94<br>IC$_{50}$ = 0.95 μM | −1 |
| 806 | 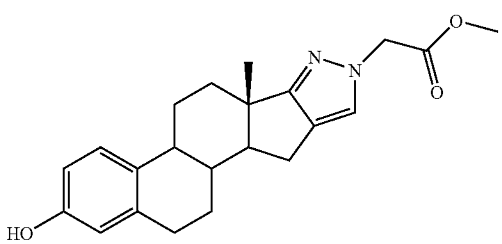 | 95<br>IC$_{50}$ = 920 nM | 19 |
| 807 | 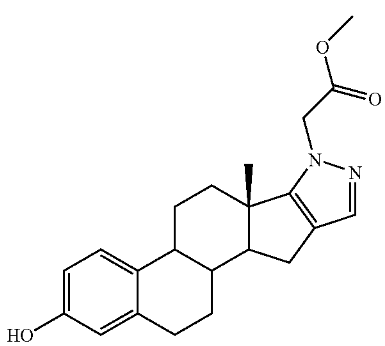 | 79 | 30 |
| 808 | 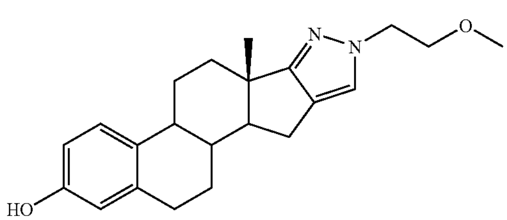 | 95<br>IC$_{50}$ = 530 nM | 48 |

-continued

RESULTS

| Compound STX No. | Structure | % inhibition of 17β-HSD1 @ 10 μM | % inhibition of 17β-HSD2 @ 10 μM |
|---|---|---|---|
| 809 | 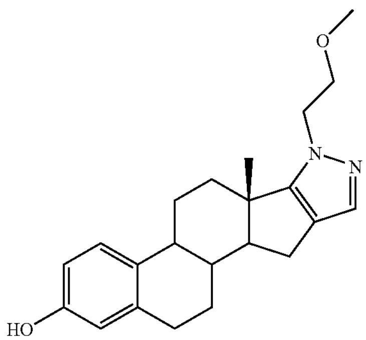 | 83 | 55 |
| 812 | 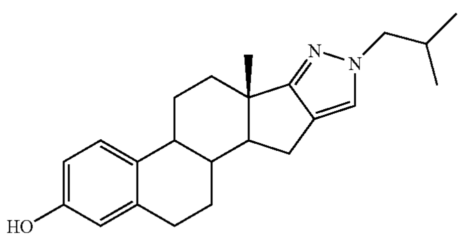 | 77 | 61 |
| 813 | 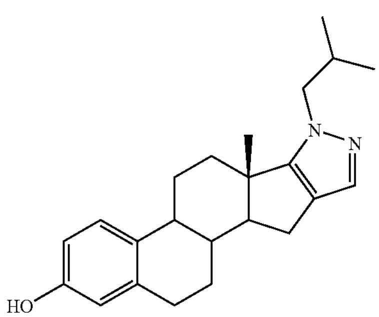 | 70 | 44 |
| 820 | 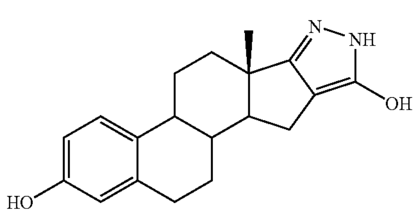 | 86 | 7 |
| 844 | 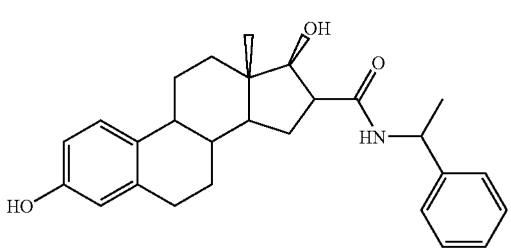 | 90<br>IC$_{50}$ = 810 nM | 12 |

-continued

RESULTS

| Compound STX No. | Structure | % inhibition of 17β-HSD1 @ 10 μM | % inhibition of 17β-HSD2 @ 10 μM |
|---|---|---|---|
| 845 | 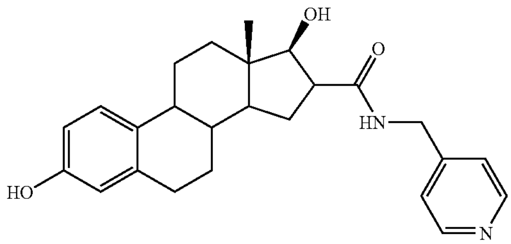 | 87 | 2.5 |
| 857 | 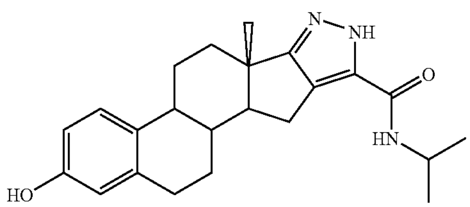 | 57 | 0.3 |
| 860 | 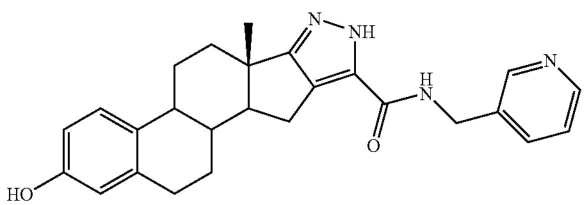 | 92<br>IC$_{50}$ = 780 nM | 28 |
| 892 | 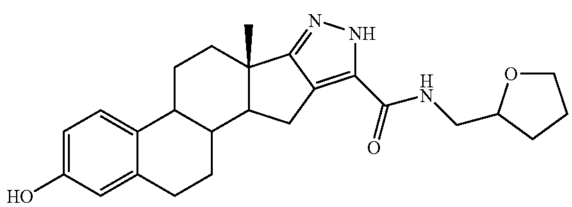 | 87 | −4 |
| 893 | 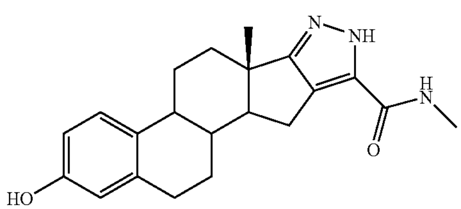 | 62 | 14 |
| 894 | 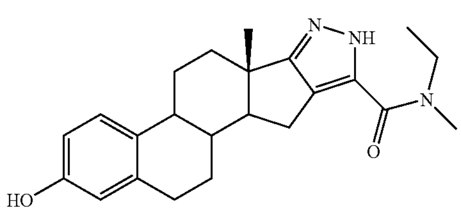 | 88 | 6 |
| 895 | 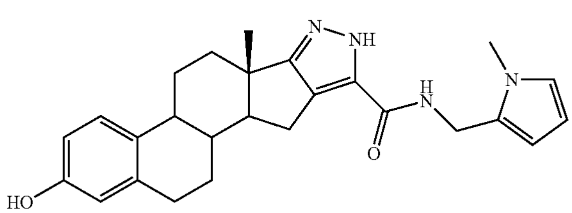 | 89<br>IC$_{50}$ = 2.3 μM | −4 |

-continued
RESULTS
| Compound STX No. | Structure | % inhibition of 17β-HSD1 @ 10 μM | % inhibition of 17β-HSD2 @ 10 μM |
|---|---|---|---|
| 896 | 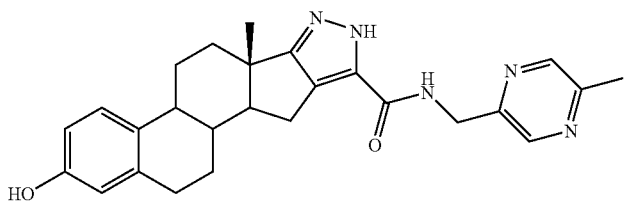 | 80 | 61 |
| 897 | 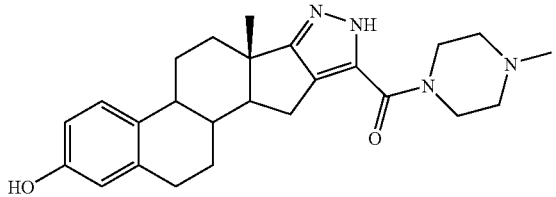 | 50 | −0.7 |
| 915 | 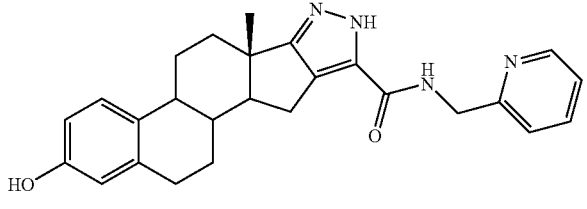 | 93<br>IC$_{50}$ = 880 nM | 9 |
| 916 | 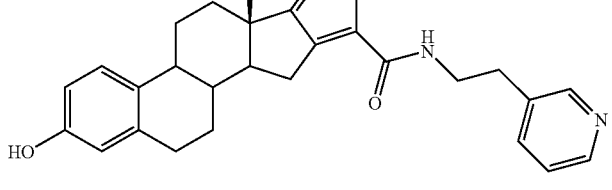 | 98.5<br>IC$_{50}$ = 300 nM | 3 |
| 921 | 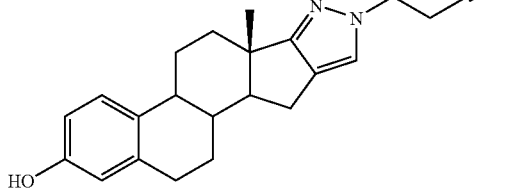 | 95<br>IC$_{50}$ = 730 nM | 44 |
| 924 | 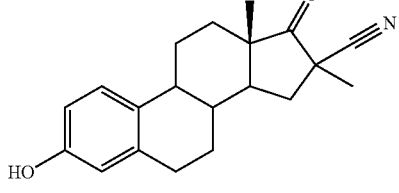 | 85 | 12 |

-continued

RESULTS

| Compound STX No. | Structure | % inhibition of 17β-HSD1 @ 10 μM | % inhibition of 17β-HSD2 @ 10 μM |
|---|---|---|---|
| 942 | 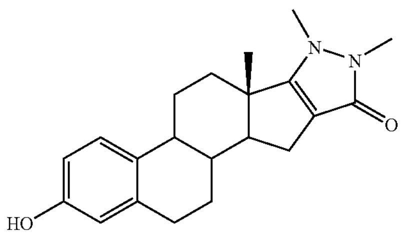 | 32 | 15 |
| 946 | 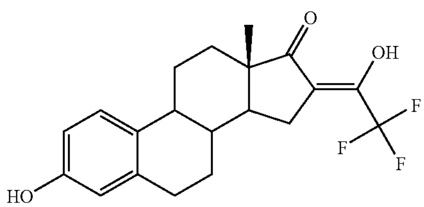 | 69, 87 | −1.5 |
| 947 | 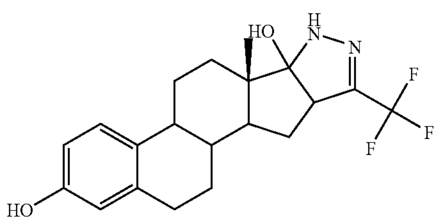 | 83 | 2 |
| 948 | 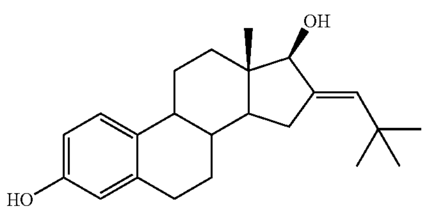 | 84 | 27 |
| 949 | 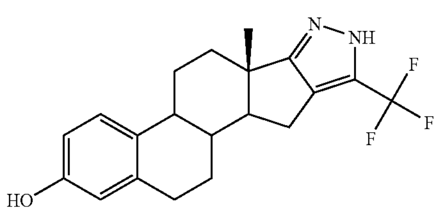 | 75 | 36 |
| 1039 | 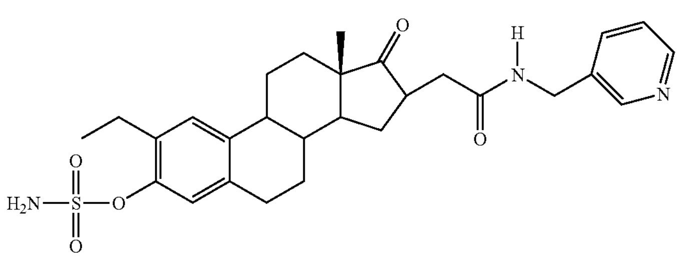 | IC$_{50}$ = 5.1 μM | −4 |

-continued

RESULTS

| Compound STX No. | Structure | % inhibition of 17β-HSD1 @ 10 µM | % inhibition of 17β-HSD2 @ 10 µM |
|---|---|---|---|
| 1040 | 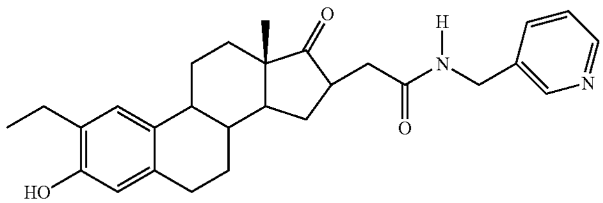 | $IC_{50}$ = 27 nM | −5 |
| 1191 | 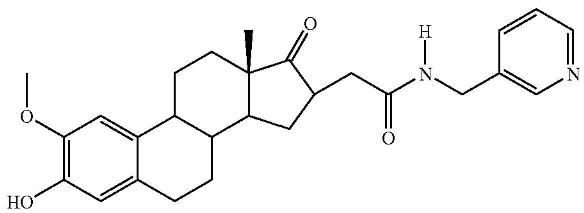 | 96<br>$IC_{50}$ = 0.29 µM | 1.2 |

All publications and patents and patent applications mentioned in the above specification are herein incorporated by reference.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

References (1) Saunders, C. M.; Baum, M. Management of early breast cancer. *Oncol. in Pract.* 1994, 3, 4-8
(2) Nicholls P. J. Breast cancer management: science and care together. *Pharm. J.* 1997, 259, 459-470
(3) Miller, B. A.; Kolonel, L. N.; Bernstein, L.; Young, Jr. J. L.; Swanson, G. M.; West, D.; Key, C. R.; Liff, J. M.; Glover, C. S.; Alexander, G. A.; et al. (eds). Racial/Ethnic patterns of cancer in the United States 1988-1992. *National Cancer Institute* 1996
(4) (a) Kaae, S. and Johansen, H. Does simple mastectomy followed by irradiation offer the survival comparable to radical procedures? *International Journal of Radiation Oncology, Biology, Physics.* 1977, 2, 1163-1166 (b) Holli, K.; Saaristo, R.; Isola, J.; Joensuu, H. and Hakama, M. Lumpectomy with or without postoperative radiotherapy for breast cancer with favourable prognostic features: results of a randomised study. *Br. J. Cancer* 2001, 84(2), 164-169
(5) Early Breast Cancer Trialists' Collaborative Group. Effects of adjuvant Tamoxifen and of cytotoxic therapy on mortality in early breast cancer. *N. Eng. J. Med.* 1988, 319, 1681-1692
(6) Gorski, J.; Toft, D.; Shyamala, G.; Smith, D.; Notides, A. Hormones receptors: studies on the interaction of estrogens with the uterus. *Recent Prog. Horm. Res.* 1968, 24, 45-80

(7) Gorski, J. and Gannon F. Current models of steroid hormone action: a critique. *Ann. Rev. Physiol.* 1976, 36, 425-450
(8) Coulson, C. J. Steroid biosynthesis and action, $2^{nd}$ edition. *Molecular Mechanism of Drug Action.* 1994, 95-122
(9) (a) Horwitz, K. B. and McGuire, W. L. Nuclear mechanism of estrogen action: effects of oestradiol and antiestrogens on estrogens receptors and nuclear receptor processing. *J. Biol. Chem.* 1978, 253, 8185-8191 (b) Horwitz, K. B.; Koseki, Y. and McGuire, W. L. Oestrogen control of progesterone receptor in human breast cancer: role of oestradiol and antiestrogen. *Endocrinology* 1978, 103, 1742-1751
(10) (a) Jordan, V. C. The strategic use of antiestrogens to control the development and growth of breast cancer. *Cancer.* 1992, 70, 977-982 (b) Powles, T. J. Breast cancer prevention *Breast Cancer Res.* 2000, 2, 10-12
(11) Wakeling, A. E.; Bowler, J. Steroidal pure antiestrogens. *J. Endocrinol.* 1987, 112, R7-R10
(12) Sexton, M. J.; Gherman, R. B. Selective estrogen receptor modulators: the ideal estrogen replacement? *Prim. Care. Update Ob/Gyns* 2001, 8(1), 25-30
(13) Agnusdei, D.; Liu-Leage, S.; Augendre-Ferrante, B. *Ann. Endocrinol.* 1999, 60(3), 242-246
(14) John Smith, H.; Nicholls, P. J.; Simons, C.; Le Lain, R. Inhibitors of steroidogenesis as agents for the treatment of hormone-dependent breast cancer. *Exp. Opin. Ther. Patents* 2001, 11, 789-824
(15) (a) Castiglione-Gertsch, M. New aromatase inhibitors: more selectivity, less toxicity, unfortunately, the same activity. *Eur. J. Cancer* 1996, 32A, 393-395 (b) Miller, W. R. Aromatase inhibitors—where are we now? *Br. J. Cancer* 1996, 73, 415-417
(16) Santner, S. J.; Feil, P. D and Santen, R. J. In situ estrogen production via the oestrone sulphatase pathway in breast tumour: relative importance vs the aromatase pathway. *J. Clin. Endocrin. Metab.* 1984, 59, 29-33
(17) Purohit, A. Williams, G. J.; Howarth, N. M.; Potter, B. V. L. and Reed, M. J. Inactivation of steroid sulphatase by an active site-directed inhibitor, estrone-3-O-sulfamate. *Biochem.* 1995, 34, 11508-11514

(18) Purohit, A.; Williams, G. J.; Roberts, C. J.; Potter, B. V. L.; Reed, M. J. In vivo inhibition of oestrone sulphatase and dehydroepiandrosterone sulphatase by estrone-3-O-sulfamate. *Int. J. Cancer* 1995, 62, 106-111

(19) Woo, L. W. L.; Howarth, N. M.; Purohit, A.; Hejaz, H. A. M.; Reed, M. J. and Potter, B. V. L. Steroidal and nonsteroidal sulfamates as potent inhibitors of steroid sulphatase. *J. Med. Chem.* 1998, 41, 1068-1083

(20) Purohit, A.; Woo, L. W. L.; Singh, A.; Winterborn, C. J.; Potter,. B. V. L. and Reed, M. J. In vivo activity of 4-methylcoumarin-7-O-sulfamate, a non steroidal, non estrogenic steroid sulphatase inhibitor. *Cancer Res.* 1996, 56, 4950-4955

(21) (a) Woo, L. W. L.; Purohit, A.; Malini, B.; Reed, M. J. and Potter, B. V. L. Potent active site-directed inhibition of steroid sulphatase by tricyclic coumarin-based sulfamates. *Chemistry & Biology* 2000, 7, 773-791 (b) Malini, B.;. Purohit, A.; Ganeshapillai, D.; Woo, L. W. L.; Potter, B. V. L.; Reed, M. J. Inhibition of steroid sulphatase activity by tricyclic coumarin sulfamates. *J. Steroid Biochem. Molec. Biol.* 2000, 75, 253-25 (c) Purohit, A.; Woo, L. W. L.; Barrow, D.; Hejaz, H. A. M.; Nicholson, R. I.; Potter, B. V. L.; Reed, M. J. Non-steroidal and steroidal sulfamates: new drugs for cancer therapy. *Mol. Cell. Endocrinol.* 2001, 171, 129-135

(22) Purohit, A.; Woo, L. W. L.; Potter, B. V. L.; Reed, M. J. In vivo inhibition of oestrone sulphatase activity and growth of nitrosomethylurea-induced mammary tumours by 667 COUMATE. *Cancer Res.* 2000, 60, 3394-3396

(23) Claussner, A.; Nédelec, L.; Nique, F.; Philibert, D.; Teush, G.; Van de Velde, P. 11β-Amidoalkylestradiols as new series of pure anti-estrogens. *J. Steroid. Biochem.* 1992, 41, 609-614

(24) Li, P.-K.; Chu, G-C.; Guo, J. P.; Selcer, K. W. Development of potent non-estrogenic oestrone sulphatase inhibitors. *Steroids* 1998, 63, 425-432

(25) (a) Jin, J-Z.; Lin, S-X. Human estrogenic 17β-hydroxysteroid dehydrogenase: predominance of oestrone reduction and its induction by NADPH. *Biochem. Biophys. Res.* 1999, 259, 489-493 (b) Penning, T. M. Molecular endocrinology of hydroxysteroid dehydrogenases. *Endocrine Reviews* 1997, 18, 281-305

(26) (a) Labrie, F. At the cutting edge. Intracrinology. *Mol. Cell. Endocrinol.* 1991, 78, C113-C118 (b) Poulin, R.; Labrie, F. Stimulation of cell proliferation and estrogenic response by adrenal $C_{19}$-?$^5$-steroids in the ZR-75-1 Human Breast Cancer Cell Line. *Cancer Res.* 1986, 46, 4933-4937

(27) (a) Peltoketo, H.; Luu-The, V.; Simard, J.; Adamski, J. 17β-hydroxysteroid dehydrogenase (HSD)/17-ketosteroid reductase (KSR) family; nomenclature and main characteristics of the 17 HSD/KSR enzymes. *J. Mol. Endocrinol.* 1999, 23, 1-11 (b) Peltoketo, H.; Isomaa, V.; Maentausta, O.; Vihko, R. Complete amino acid sequence of human placental 17β-hydroxysteroid dehydrogenase deduced from cDNA. *FEBS Lett.* 1988, 239, 73-77 (c) Wu, L.; Einstein, M.; Geissler, W. M.; Chan, H. K.; Elliston, K. O.; Andersson, S. Expression cloning and characterization of human 17β-hydroxysteroid dehydrogenase type 2, a microsomal enzyme possessing 20α-hydroxysteroid dehydrogenase activity. *J. Biol. Chem.* 1993, 268, 12964-12969 (d) Geissler, W. M.; Davis, D. L.; Wu, L.; Bradshaw, K. D.; Patel, S.; Mendonca, B. B.; Elliston, K. O.; Wilston, J. D.; Russell, D. W.; Andersson, S. Male pseudohermaphroditism caused by mutation of testicular 17β-hydroxysteroid dehydrogenase 3. *Nat. Genet.* 1994, 7, 34-39 (e) Adamski, J.; Normand, T.; Leenders F.; Monte, D.; Begue, A.; Stehelin, D.; Jungblut, P. W.; de Launoit, Y. Molecular cloning of a novel widely expressed human 80 kDa 17β-hydroxysteroid dehydrogenase IV. *Biochem. J.* 1995, 311, 437-443 (f) Deyashiki, Y.; Ohshima, K.; Nakanishi, M.; Sato, K.; Matsuura, K.; Hara, A. Molecular cloning and characterization of mouse oestradiol 17β-dehydrogenase (A-specific), a member of the aldoketoreductase family. *J. Biol. Chem.* 1995, 270, 10461-10467

(28) Tremblay, M. R.; Auger, S. and Poirier, D. Synthesis of 16-(bromoalkyl)-estradiols having inhibitory effect on human placental oestradiol 17β-hydroxysteroid dehydrogenase (17β-HSD type 1). *Bioorg. Med. Chem.* 1995, 3, 505-523

(29) Tremblay, M. R.; Poirier, D. Overview of a rational approach to design type I 17β-hydroxysteroid dehydrogenase inhibitors without estrogenic activity: chemical synthesis and biological evaluation. *J. Steroid. Biochem.* 1998, 66, 179-191

(30) Collins, B. M.; Mac Lachlan, J. A.; Arnold, S. F. The estrogenic and anti-oestrogenic activities of phytochemicals with the human estrogen receptor expressed in yeast. *Steroids* 1997, 62, 365-372

(31) (a) Makela, S.; Poutanen, M.; Kostian, M. L.; Lehtimaki, N.; Strauss, L.; Santti, R.; Vihko, R. Inhibition of 17 beta-hydroxysteroid oxidoreductase by flavonoids in breast and prostate cancer cells. *Proc. Soc. Exp. Biol. Med.* 1998, 217, 310-316

(32) LeBail, J. C.; Laroche, T.; Marre-Fournier, F.; Habrioux, G. Aromatase and 17β-hydroxysteroid dehydrogenase inhibition by flavonoids. *Cancer Lett.* 1998, 133, 101-106

(33) Coldham, N. G.; James, V. H. T. A possible mechanism for increased breast cell proliferation by progestins through increased reductive 17β-hydroxysteroid dehydrogenase activity. *Int. J. Cancer* 1990, 45, 174-178

(34) Purohit, A.; Hejaz, H. A. M.; Walden, J.; MacCarthy-Marrogh, L.; Packam, G.; Potter, B. V. L.; Reed, M. J. The effect of 2-methoxyestrone-3-O-sulphamate on the growth of breast cancer cells and induced mammary tumours. *Int. J. Cancer* 2000, 85, 584-589

(35) Heer, J.; Miescher, K. Über Steroide. Marrianol-und Doisynolsäure. Über oestrogene carbonsäuren II. *Helv. Chim. Acta* 1945, 28, 156-165

(36) (a) Matkovics, B.; Taródi, B.; Baláspiri, L. Rearrangement of steroids, VII. Schmidt reaction and Beckmann rearrangement of oestrone and its derivatives. *Acta Chim. Acad. Scien. Hung.* 1974, 80, 79-87 (b) Regan, B. M.; Newton Hayes, F. 17- and 17-Aza-D-homosteroids. *J. Am. Chem. Soc.* 1956, 78, 639-643

(37) Gupta, R. and Jindal, D. P. Synthesis and biological activity of some D-ring modified oestrone derivatives. *Ind. J. Chem.* 1999, 38B, 563-571

(38) Love, B. and Dawson, C. R. Alkylphenols related to the poison ivy principle. An improved method of synthesis involving the Na-Butanol cleavage of benzyl ethers. *J. Am. Chem. Soc.* 1956, 78, 6095-6101

(39) Okada, M.; Iwashita, S.; Koizumi, N. Efficient general method for sulfamoylation of a hydroxyl group. *Tet. Lett.* 2000, 41, 7047-7051.

(40) C. A. Hioruchi & J. Y. Satoh, Regioselective 2-Iodination of Estradiol, Estriol & Oestrone, J. Chem. Soc., Chem. Commun., 1982, 671-672.

(41) M. Numazawa and Y. Ogura, J. Chem. Soc., Chem. Commun. 1983, 9, 533.

(42) Williams, G. J.; Woo, L. W. L.; Mahon, M. F.; Purohit, A.; Reed, M. J.; Potter, B. V. L. X-ray crystal structure and mechanism of action of oestrone 3-O sulphamate, a synthetic active site-directed inhibitor of oestrone sulphatase. *Pharm. Sci.* 1996, 2, 11-16

(43) Ghosh, D.; Pletnev, V. Z.; Zhu, D-W. et al. Structure of the human estrogenic 17 beta-hydroxysteroid dehydrogenase at 2.20 Å resolution. *Structure*, 1995, 3, 503-513

(44) (a) Lin, S. X.; Han, Q.; Azzi, A.; Zhu, D-W.; Gongloff, A.; Campbell, R. L. 3D structure of human estrogenic 17β-HSD: binding with various steroids. *J. Steroid Biochem. Mol. Biol.* 1999, 69, 425-429 (b) Puranen, T.; Poutanen, M.; Ghosh, D.; Vihko, R. and Vihko, P. Origin of substrate specificity of human and rat 17β-hydroxysteroid dehydrogenase Type 1, using chimeric enzymes and site-directed substitutions. *Endocrinology* 1997, 138, 3532-3539

(45) Breton, R.; Housset, D.; Mazza, C.; Fontecilla-Camps, J. C. The structure of a complex of human 17β-hydroxysteroid dehydrogenase with oestradiol and NADP+ identifies two principal targets for the design of inhibitors. *Structure (Lond)* 1996, 4, 905-915

(46) Apel, R.; Berger, G. Über das hydrazidosulfamid *Chem. Ber.* 1958, 91, 1339-1341

(47) Woo, L. W. W.; Lightowler, M.; Purohit, A.; Reed, M. J.; Potter, B. V. L. Heteroatom-substituted analogues of the active-site directed inhibitor estra-1,3,5(10)-trien-17-one-3-sulphamate inhibit oestrone sulphatase by different mechanism. *J. Steroid Biochem Mol. Biol.* 1996, 57, 79-88

(48) Duncan, L.; Purohit, A.; Howarth, N. M.; Potter, B. V. L.; Reed, M. J. Inhibition of oestrone sulphatase activity by estrone-3-methyl-thiophosphonate: a potential therapeutic agent in breast cancer *Cancer Res.* 1993, 53, 298-303

The invention will now be further described by the following numbered paragraphs:

1. A compound of Formula I

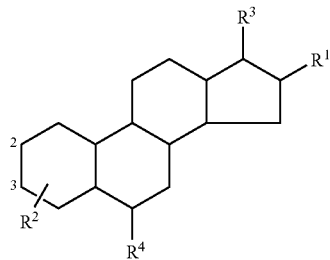

Formula I wherein (I) $R^1$ is a selected from
(i) an alkyloxyalkyl group
(ii) a nitrile group, and wherein $R^2$ is capable of forming a hydrogen bond
(iii) alkylaryl group, wherein the aryl group is substituted by other than a C1-10 group
(iv) alkenylaryl group wherein the aryl group is substituted
(v) alkylheteroaryl group, wherein when heteroaryl group comprises only C and N in the ring, the aryl group is substituted by other than a methyl group
(vi) alkenylheteroaryl group
(vii) =N—O-alkyl or =N—O—H group
(viii) branched alkenyl
(ix) alkyl-alcohol group
(x) amide or alkylamide wherein (a) the alkyl of the alkylamide is —$CH_2$— or —$CH_2CH_2$—, (b) the amide is di-substituted and/or (c) the amide is substituted with at least one of alkylheterocycle group, alkenylheterocycle group, alkylheteroaryl group, alkenylheteroaryl group, heteroaryl group, alkylamine group, alkyloxyalkyl group, alkylaryl group, straight or branched alkyl group, (xi) —CHO so that $R_1$ together with $R_3$ provide the enol tautomer

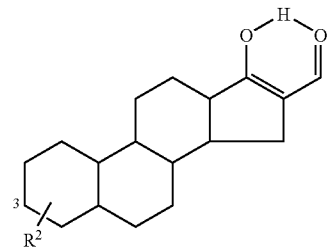

OR, $R_1$ together with $R^3$ form (xii) a pyrazole wherein (a) $R^4$ is =N—O-alkyl or =N—O—H group, (b) the pyrazole is substituted with one of alkyl-OH group, alkyl ester group, alkyloxyalkyl group, branched alkyl group, and an amide and/or (c) the 2 position is substituted with a group selected from —OH and —O-hydrocarbyl (xiii) a heteroaryl ring to provide a compound of the formula

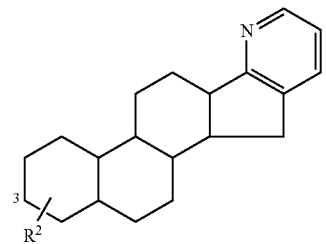

(II) $R^2$ is selected from
groups capable of forming a hydrogen bond, a sulphamate group, a phosphonate group, a thiophosphonate group, a sulphonate group and a sulphonamide group; and (III) $R^3$ is selected from
—OH, =O, or a —C(=O)— mimetic.

2. Use of a compound in the manufacture of a medicament for use in the therapy of a condition or disease associated with 17β-hydroxysteroid dehydrogenase (17β-HSD), wherein the compound is of formula I

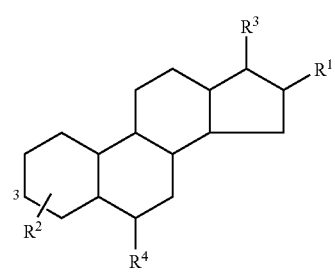

Formula I wherein (I) $R^1$ is a selected from
(i) an alkyloxyalkyl group
(ii) a nitrile group (iii) alkylaryl group, wherein the aryl group is substituted by other than a methyl group
(iv) alkenylaryl group
(v) alkylheteroaryl group, wherein when heteroaryl group comprises only C and N in the ring, the aryl group is substituted by other than a methyl group
(vi) alkenylheteroaryl group
(vii) =N—O-alkyl or =N—O—H group
(viii) carboxylic acid esters wherein (a) $R^3$ is =O and/or (b) the ester is selected from —$CO_2X$, —$CH_2CO_2X$, and —$CH_2CH_2CO_2X$, wherein X is a hydrocarbyl group
(ix) $CO_2H$ or alkyl-$CO_2H$ group, wherein alkyl is $CH_2$ or $CH_2CH_2$ group
(x) branched alkenyl
(xi) alkyl-alcohol group or alkenyl-alcohol group
(xii) amide or alkylamide wherein (a) the alkyl of the alkylamide is —$CH_2$— or —$CH_2CH_2$—, (b) the amide is di-substituted and/or (c) the amide is substituted with at least one of alkylheterocycle group, alkenylheterocycle group, alkylheteroaryl group, alkenylheteroaryl group, heteroaryl group, alkylamine group, alkyloxyalkyl group, alkylaryl group, straight or branched alkyl group,
(xiv) —CHO so that $R_1$ together with $R_3$ provide the enol tautomer

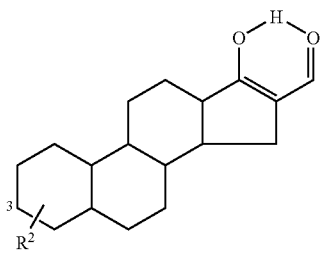

OR, $R_1$ together with $R^3$ form
(xii) a pyrazole wherein (a) $R^4$ is =N—O-alkyl or =N—O—H group, (b) the pyrazole is substituted and/or (c) the 2 position is substituted with a group selected from —OH and —O— hydrocarbyl
(xiii) a heteroaryl ring to provide a compound of the formula

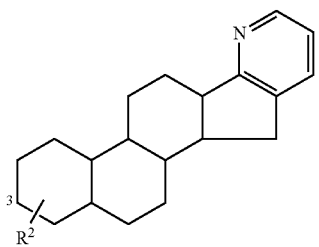

(II) R2 is selected from
groups capable of forming a hydrogen bond, a sulphamate group, a phosphonate group, a thiophosphonate group, a sulphonate group and a sulphonamide group; and
(III) R3 is selected from
—OH, =O, or a —C(=O)— mimetic.
3. Use according to paragraph 2 wherein the aryl group of the alkenylaryl group is substituted.
4. Use according to paragraph 2 or 3 wherein the carboxylic acid ester is selected from —$CO_2X$, —$CH_2CO_2X$, and —$CH_2CH_2CO_2X$, wherein X is a hydrocarbyl group.
5. Use according to paragraph 2 or 3 wherein X is a hydrocarbon group alkyl.
6. Use according to any one of paragraphs 2 to 5 wherein the pyrazole is substituted with one of alkyl-OH group, alkyl ester group, alkyloxyalkyl group, branched alkyl group, and an amide.
7. Use of a compound in the manufacture of a medicament for use in the therapy of a condition or disease associated with 17β-hydroxysteroid dehydrogenase (17β-HSD), wherein the compound is a compound as defined in paragraph 1.
8. The invention of any one of the preceding paragraphs wherein when $R^1$ is a nitrile group, $R^2$ is —OH.
9. The invention of any one of the preceding paragraphs wherein the aryl group of the alkylaryl group is substituted by a group selected from N,N-dialkyl, alkoxy, nitro (—$NO_2^-$), nitrile, and azaalkyl groups.
10. The invention of paragraph 9 wherein the N,N-dialkyl is $NMe_2$.
11. The invention of paragraph 9 or 10 wherein the alkoxy group is methoxy.
12. The invention of any one of the preceding paragraphs wherein the alkylaryl group is —$CH_2$-Ph.
13. The invention of any one of the preceding paragraphs wherein the aryl group of the alkenylaryl group is substituted by a group selected from N,N-dialkyl, alkoxy, nitro (—$NO_2^-$), and nitrile groups.
14. The invention of paragraph 13 wherein the N,N-dialkyl is $NMe_2$.
15. The invention of paragraph 13 or 14 wherein the alkoxy group is methoxy.
16. The invention of any one of the preceding paragraphs wherein the alkenylaryl group is =CH-Ph.
17. The invention of any one of the preceding paragraphs wherein the aryl group of the alkylheteroaryl group is substituted by a group selected from N,N-dialkyl, alkoxy, nitro (—$NO_2^-$), and nitrile groups.
18. The invention of paragraph 17 wherein the N,N-dialkyl is $NMe_2$.
19. The invention of paragraph 17 or 18 wherein the alkoxy group is methoxy.
20. The invention of any one of the preceding paragraphs wherein the alkylheteroaryl group is selected from

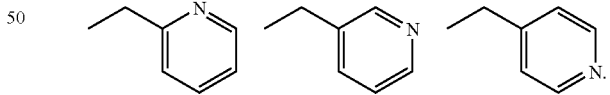

21. The invention of any one of the preceding paragraphs wherein the aryl group of the alkenylheteroaryl group is substituted.
22. The invention of any one of the preceding paragraphs wherein the aryl group of the alkenylheteroaryl group is substituted by a group selected from N,N-dialkyl, alkoxy, nitro (—$NO_2^-$), and nitrile groups.
23. The invention of paragraph 22 wherein the N,N-dialkyl is $NMe_2$.
24. The invention of paragraph 22 or 23 wherein the alkoxy group is methoxy.
25. The invention of any one of the preceding paragraphs wherein the alkenylheteroaryl group is selected from 26. The invention of any one of the preceding paragraphs wherein the =N—O-alkyl or =N—O—H group is a =N—O-alkyl group.

27. The invention of any one of the preceding paragraphs wherein when $R^1$ is selected from =N—O-alkyl and =N—O—H groups and $R^3$ is a =N—O-alkyl group or =N—O—H group.

28. The invention of any one of the preceding paragraphs wherein when $R^1$ and $R^3$ form a pyrazole the 2 position is substituted with a group selected from —OH and —O-hydrocarbyl.

29. The invention of any one of the preceding paragraphs wherein when $R^1$ and $R^3$ form a pyrazole the 2 position is substituted with a group selected from —OH and —O-alkyl.

30. The invention of any one of the preceding paragraphs wherein the amide is of the formula —C(=O)NR$^5$R$^6$ or —N(CO—R$^7$)R$^8$, wherein $R^5$, $R^6$, $R^7$ and $R^8$ are independently selected from H and hydrocarbyl groups.

31. The invention of any one of the preceding paragraphs wherein the amide or alkylamide is an alkylamide.

32. The invention of any one of the preceding paragraphs wherein the substituents of the di-substituted amide together form a cyclic structure.

33. The invention of paragraph 32, wherein the substituents of the di-substituted amide together form an aryl ring.

34. The invention of paragraph 32 or 33 wherein the substituents of the di-substituted amide together form a heterocyclic ring.

35. The invention of any one of the preceding paragraphs wherein $R^2$ is selected from groups capable of forming a hydrogen bond and a sulphamate group.

36. The invention of paragraph 35 wherein the group capable of forming a hydrogen bond are selected from —OH.

37. The invention of any one of the preceding paragraphs wherein the —C(=O)— mimetic is selected from —CN, =N—O-alkyl group, =N—O—H group, pyridine, pyrimidine, and groups of the formula 38. The invention of any one of the preceding paragraphs wherein $R^3$ is selected from —OH, and =O.

39. The invention of any one of the preceding paragraphs wherein $R^3$ is =O.

40. The invention of any one of the preceding paragraphs wherein the compound is of Formula II 41. The invention of any one of the preceding paragraphs wherein the compound is of Formula III 42. The invention of any one of the preceding paragraphs wherein the compound is of Formula IV 43. The invention of any one of the preceding paragraphs wherein the compound is of Formula IX wherein $R^{11}$ is an alkoxy group or an alkyl group.

44. The invention of paragraph 43 wherein $R^{11}$ is an alkoxy group.

45. The invention of paragraph 44 wherein $R^{11}$ is methoxy.

46. The invention of paragraph 43 wherein $R^{11}$ is an alkyl group.

47. The invention of paragraph 46 wherein $R^{11}$ is a $C_1$-$C_{10}$ alkyl group, preferably a $C_1$-$C_6$ alkyl group, preferably a $C_1$-$C_3$ alkyl group.

48. The invention of paragraph 46 or 47 wherein $R^{11}$ is —$CH_3$ or —$CH_2CH_3$.

49. The invention of any one of the preceding paragraphs wherein the sulphamate group is of the formula wherein $R^9$ and $R^{10}$ are independently selected from H; alkyl, cycloalkyl, alkenyl and aryl, or combinations thereof, or together represent alkylene, wherein the or each alkyl or cycloalkyl or alkenyl optionally contain one or more hetero atoms or groups.

50. The invention of paragraph 49 wherein at least one of $R^9$ and $R^{10}$ is H.

51. The invention of paragraph 49 wherein $R^9$ and $R^{10}$ is H.

52. A pharmaceutical composition comprising a compound according to any one of paragraphs 1 and 8 to 51 optionally admixed with a pharmaceutically acceptable carrier, diluent, excipient or adjuvant.

53. A compound according to any one of paragraphs 1 and 8 to 51 for use in medicine.

54. A compound as substantially hereinbefore described with reference to any one of the Examples.

55. A composition as substantially hereinbefore described with reference to any one of the Examples.

56. A use as substantially hereinbefore described with reference to any one of the Examples.

The invention claimed is:

1. A compound of Formula III

Formula III wherein
(I) $R^1$ is an alkylamide wherein the alkyl of the alkylamide is —$CH_2$— or —$CH_2CH_2$—, wherein the amide of the alkylamide is substituted with an alkylheteroaryl group, wherein the alkyl has from 1 to 5 carbon atoms;
(II) $R^2$ is selected from —OH and a sulphamate group; and
(III) $R^3$ is selected from —OH or =O;
(IV) $R^4$ is absent;
wherein the ring system may contain one or more hydroxyl, alkyl, alkoxy, alkinyl or halo substituents.

2. The invention of claim 1 wherein the compound is of Formula IV

Formula IV

3. The invention of claim 1 wherein the compound is of Formula IX

Formula IX wherein $R^{11}$ is an alkoxy group or an alkyl group.

4. The invention of claim 3 wherein $R^{11}$ is an alkoxy group.

5. The invention of claim 4 wherein $R^{11}$ is methoxy.

6. The invention of claim 3 wherein $R^{11}$ is an alkyl group.

7. The invention of claim 6 wherein $R^{11}$ is a $C_1$-$C_{10}$ alkyl group.

8. The compound of claim 7 wherein $R^{11}$ is a $C_1$-$C_6$ alkyl group.

9. The compound of claim 8 wherein $R^{11}$ is a $C_1$-$C_3$ alkyl group.

10. The invention of claim 6 wherein $R^{11}$ is —$CH_3$ or —$CH_2CH_3$.

11. The invention of claim 1 wherein $R^2$ is a sulphamate group of the formula wherein $R^9$ and $R^{10}$ are independently selected from H; alkyl, cycloalkyl, alkenyl and aryl, or combinations thereof, or together represent alkylene, wherein the or each alkyl or cycloalkyl or alkenyl optionally contain one or more hetero atoms or groups.

12. The invention of claim 11 wherein at least one of $R^9$ and $R^{10}$ is H.

13. The invention of claim 11 wherein $R^9$ and $R^{11}$ are independently H.

14. A pharmaceutical composition comprising a compound of claim 1 optionally admixed with a pharmaceutically acceptable carrier, diluent, excipient or adjuvant.

15. A compound according to claim 1 for use in medicine.

16. The invention of claim 1 wherein $R^3$ is =O.

17. The invention of claim 10, wherein the compound is selected from

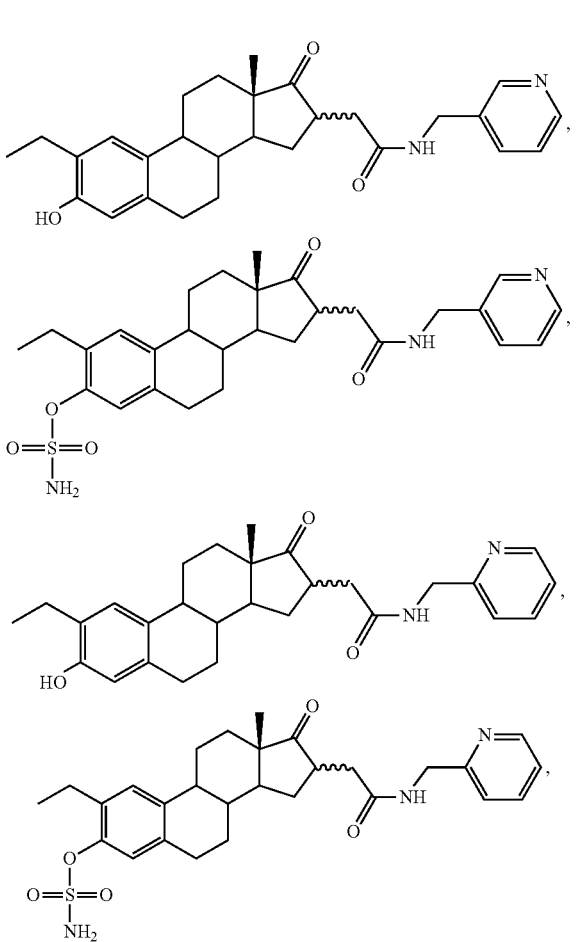
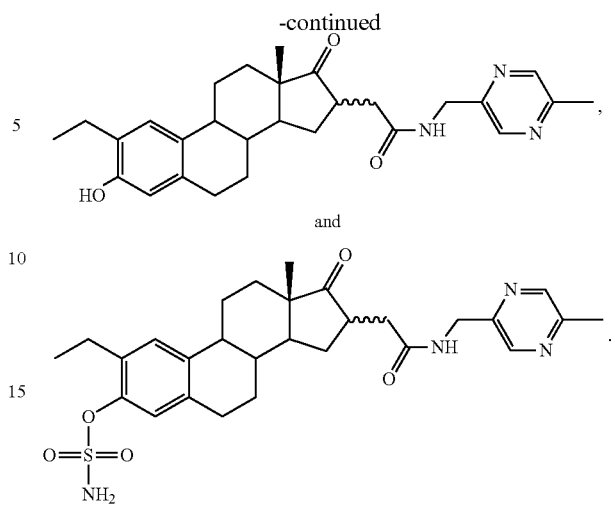
and
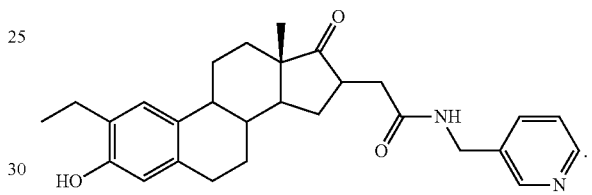
18. The invention of claim 17, wherein the compound is
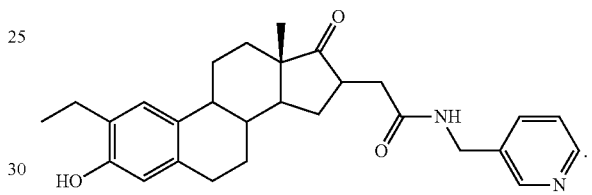
19. A method of treating breast cancer, comprising administering to a patient in need thereof a compound as defined in any one of claim 1-3, 6, 10, 11, 15, or 16.
* * * * *